(12) United States Patent
Tokumasu et al.

(10) Patent No.: US 10,562,898 B2
(45) Date of Patent: Feb. 18, 2020

(54) SUBSTITUTED BENZENESULFONAMIDES AS INHIBITORS OF ALPHA-4 BETA-7 INTEGRIN ACTIVITY

(71) Applicant: EA PHARMA CO., LTD., Chuo-ku (JP)

(72) Inventors: Munetaka Tokumasu, Chuo-ku (JP); Masatsugu Noguchi, Chuo-ku (JP); Mizuki Kawahira, Chuo-ku (JP); Kana Iwasaki, Chuo-ku (JP); Nobuhiko Hayakawa, Chuo-ku (JP); Wataru Miyanaga, Chuo-ku (JP); Yuki Saitou, Chuo-ku (JP); Yui Yamaura, Chuo-ku (JP); Ayatoshi Ando, Chuo-ku (JP); Atsushi Tsuruta, Chuo-ku (JP); Misato Noguchi, Chuo-ku (JP)

(73) Assignee: EA PHARMA CO., LTD., Chuo-ku (JP)

( * ) Notice: Subject to any disclaimer, the term of this patent is extended or adjusted under 35 U.S.C. 154(b) by 0 days.

(21) Appl. No.: 16/075,415

(22) PCT Filed: Feb. 6, 2017

(86) PCT No.: PCT/JP2017/004278
§ 371 (c)(1),
(2) Date: Aug. 3, 2018

(87) PCT Pub. No.: WO2017/135472
PCT Pub. Date: Aug. 10, 2017

(65) Prior Publication Data
US 2019/0040059 A1    Feb. 7, 2019

(30) Foreign Application Priority Data

Feb. 5, 2016 (JP) ................... 2016-021053

(51) Int. Cl.

| | |
|---|---|
| *A61K 31/18* | (2006.01) |
| *C07D 307/02* | (2006.01) |
| *C07D 471/04* | (2006.01) |
| *C07D 401/14* | (2006.01) |
| *C07D 405/14* | (2006.01) |
| *C07D 401/04* | (2006.01) |
| *C07D 401/12* | (2006.01) |
| *C07D 405/12* | (2006.01) |
| *C07D 239/54* | (2006.01) |
| *C07D 409/12* | (2006.01) |
| *C07D 491/052* | (2006.01) |
| *A61P 1/00* | (2006.01) |
| *C07D 473/04* | (2006.01) |

(52) U.S. Cl.
CPC ............ *C07D 471/04* (2013.01); *A61P 1/00* (2018.01); *C07D 239/54* (2013.01); *C07D 401/04* (2013.01); *C07D 401/12* (2013.01); *C07D 401/14* (2013.01); *C07D 405/12* (2013.01); *C07D 405/14* (2013.01); *C07D 409/12* (2013.01); *C07D 473/04* (2013.01); *C07D 491/052* (2013.01)

(58) Field of Classification Search
CPC .............................. A61K 31/18; C07D 307/02
USPC ............................................ 514/601; 564/80
See application file for complete search history.

(56) References Cited

U.S. PATENT DOCUMENTS

| | | |
|---|---|---|
| 6,388,084 B1 | 5/2002 | Kaplan et al. |
| 2002/0133015 A1 | 9/2002 | Kaplan et al. |
| 2003/0220268 A1 | 11/2003 | Makino et al. |
| 2004/0127706 A1 | 7/2004 | Kaplan et al. |
| 2005/0065192 A1 | 3/2005 | Yednock et al. |
| 2005/0074451 A1 | 4/2005 | Yednock et al. |
| 2005/0101779 A1 | 5/2005 | Sagi et al. |
| 2005/0192279 A1 | 9/2005 | Barbay et al. |

(Continued)

FOREIGN PATENT DOCUMENTS

| | | |
|---|---|---|
| EP | 2 842 945 A1 | 3/2015 |
| JP | 2003-321358 A | 11/2003 |

(Continued)

OTHER PUBLICATIONS

International Search Report dated May 16, 2017 in PCT/JP2017/004278 filed Feb. 6, 2017.

(Continued)

*Primary Examiner* — Douglas M Willis
(74) *Attorney, Agent, or Firm* — Oblon, McClelland, Maier & Neustadt, L.L.P.

(57) ABSTRACT

Provided is a compound having α4 integrin inhibitory action.

The compound is a sulfonamide derivative represented by the following formula (I), or pharmaceutically acceptable salt thereof:

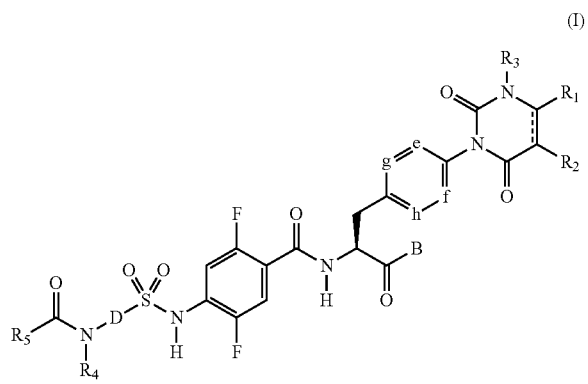

(I)

where $R_1$ to $R_5$, e to h, D, and B represent those as described in the specification.

20 Claims, No Drawings

(56) References Cited

U.S. PATENT DOCUMENTS

| | | |
|---|---|---|
| 2005/0222141 A1 | 10/2005 | Sagi et al. |
| 2005/0276803 A1 | 12/2005 | Chan et al. |
| 2006/0223836 A1 | 10/2006 | Makino et al. |
| 2007/0037804 A1 | 2/2007 | Stappenbeck et al. |
| 2008/0075719 A1 | 3/2008 | Chan et al. |
| 2008/0108634 A1 | 5/2008 | Sagi et al. |
| 2011/0065918 A1 | 3/2011 | Makino et al. |
| 2012/0253041 A1 | 10/2012 | Makino et al. |
| 2015/0051395 A1 | 2/2015 | Ueno et al. |
| 2016/0244451 A1 | 8/2016 | Ueno et al. |

FOREIGN PATENT DOCUMENTS

| | | |
|---|---|---|
| JP | 2007-524626 A | 8/2007 |
| WO | WO 01/42215 A1 | 6/2001 |
| WO | WO 01/56994 A1 | 8/2001 |
| WO | WO 02/16329 A1 | 2/2002 |
| WO | WO 03/070709 A1 | 8/2003 |
| WO | WO 2005/000246 A2 | 1/2005 |
| WO | WO 2005/000246 A3 | 1/2005 |
| WO | WO 2005/061466 A1 | 7/2005 |
| WO | WO 2005/077915 A1 | 8/2005 |
| WO | WO 2005/113003 A2 | 12/2005 |
| WO | WO 2006/127584 A1 | 11/2006 |
| WO | WO 2013/161904 A1 | 10/2013 |
| WO | WO 2015/064580 A1 | 5/2015 |

OTHER PUBLICATIONS

Byrareddy, S.N. et al., "Targeting α-4β7 integrin reduces mucosal transmission of SIV and protects GALT from infection," Nat. Med., vol. 20, No. 12, Dec. 2014, pp. 1-14.

Extended European Search Report dated Jun. 13, 2019 in Patent Application No. 17747622.3, citing documents AO and AP therein, 7 pages.

Eurasian office action dated May 28, 2019 issued in corresponding patent application No. 201891780 (with English translation).

SUBSTITUTED BENZENESULFONAMIDES AS INHIBITORS OF ALPHA-4 BETA-7 INTEGRIN ACTIVITY

CROSS REFERENCE TO RELEATED APPLICATIONS

This application is a 371 of International Patent Application No. PCT/JP/2017/004278, filed on Feb. 6, 2017, and claims priority to Japanese Patent Application No. 2016-021053, filed on Feb. 5, 2016, both of which are incorporated herein by reference in their entireties.

BACKGROUND OF THE INVENTION

Field of the Invention

The present invention relates to a sulfonamide derivative or a pharmaceutically acceptable salt thereof and a pharmaceutical composition containing any of these compounds as an active ingredient. In particular, the present invention relates to a compound being possibly usable as a therapeutic agent or prophylactic agent for inflammatory diseases in which an α4 integrin-dependent adhesion process is involved in the disease states.

Discussion of the Background

Orally administrable compounds having α4 integrin inhibitory activity have been already known which are effective as a therapeutic agent or prophylactic agent for inflammatory diseases in which an α4 integrin-dependent adhesion process is involved in the disease states. For example, Patent Literature 1 discloses a phenylalanine derivative represented by the following formula or a pharmaceutically acceptable salt thereof, and a representative compound thereof has the following chemical structure.

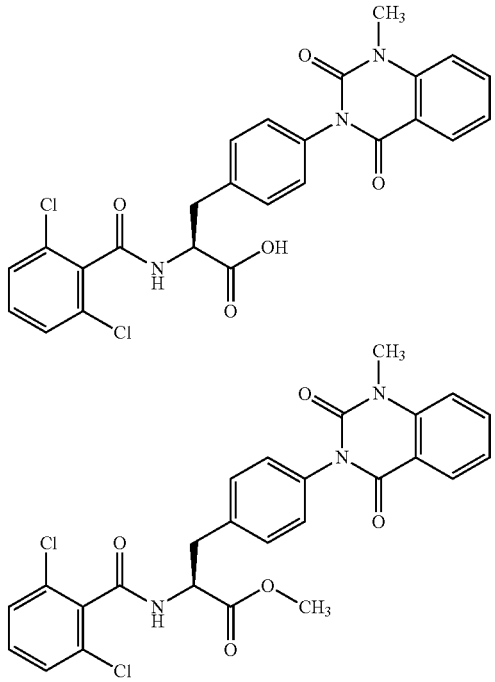

Then, Patent Literature 1 shows the results of VCAM inhibitory activity (VCAM-1/α4β1 binding assay) and (VCAM-1/α4β7 binding assay).

In addition, Patent Document 2 also discloses a phenylalanine derivative having an R12(R13)N—X1-group at its terminus as represented by the following formula, or a pharmaceutically acceptable salt thereof.

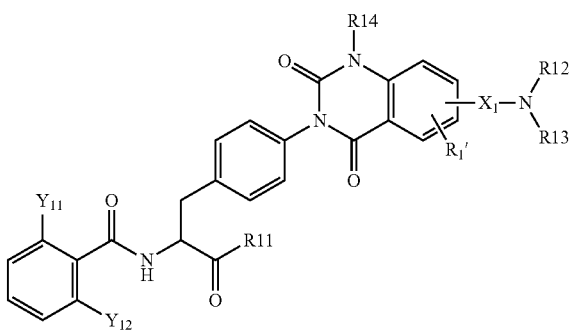

This compound is demonstrated having a higher VCAM-1/α4β1 integrin inhibitory activity in the presence of serum than the compound of Example 1 of Patent Literature 1 has. Also, Patent Literature 3 discloses a compound having an α4 integrin inhibitory action.

Patent Literature 4 (WO2005/077915) describes phenylalanine derivatives each having an α4 integrin inhibitory action and represented by the following formula, in which a 2,6-dichlorobenzoyl group, an amino acid residue, or the like is bonded to the N-terminus of phenylalanine.

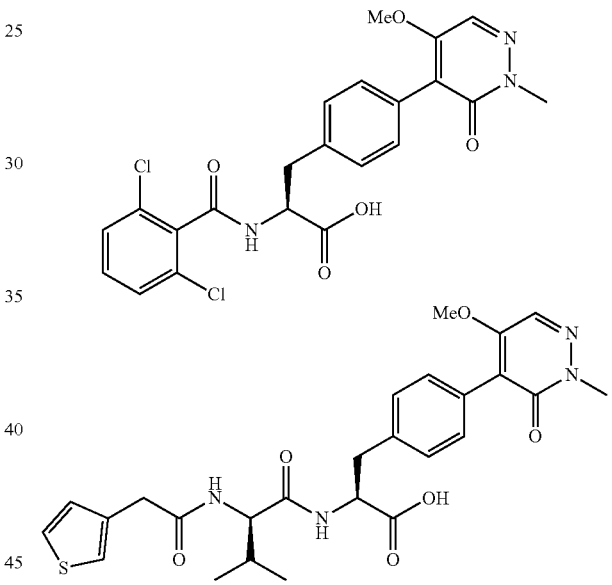

Patent Literature 5 (Japanese Patent Application Publication No. 2003-321358) describes a phenylalanine derivative having an α4 integrin inhibitory action and represented by the following formula, in which a 2,6-dichlorobenzoyl group or the like is bonded to the N-terminus of phenylalanine.

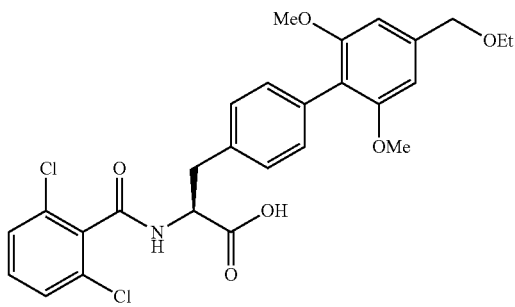 [SMILES: CCOCc1cc(OC)c(-c2ccc(C[C@H](NC(=O)c3c(Cl)cccc3Cl)C(=O)O)cc2)c(OC)c1]

Patent Literature 6 (WO01/56994) describes a phenylalanine derivative having an α4 integrin inhibitory action and represented by the following formula, in which proline or the like is boned to the N-terminus of phenylalanine.

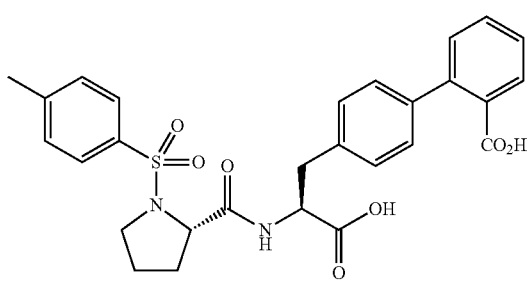 [SMILES: Cc1ccc(S(=O)(=O)N2CCC[C@H]2C(=O)N[C@@H](Cc2ccc(-c3ccccc3C(=O)O)cc2)C(=O)O)cc1]

Patent Literature 7 (WO2006/127584) describes a phenylalanine derivative having an α4 integrin inhibitory action and represented by the following formula, in which a pyrimidine ring or the like is boned to the N-terminus of phenylalanine.

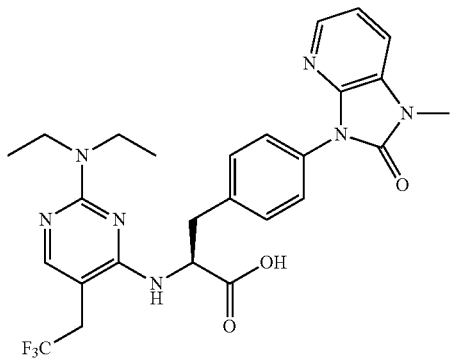 [SMILES: CCN(CC)c1ncc(CC(F)(F)F)c(N[C@@H](Cc2ccc(-n3c(=O)n(C)c4cccnc43)cc2)C(=O)O)n1]

Patent Literature 8 (WO01/42215) describes a phenylalanine derivative having an α4 integrin inhibitory action and represented by the following formula, in which a 2-chloro-6-methylbenzoyl group or the like is boned to the N-terminus of phenylalanine.

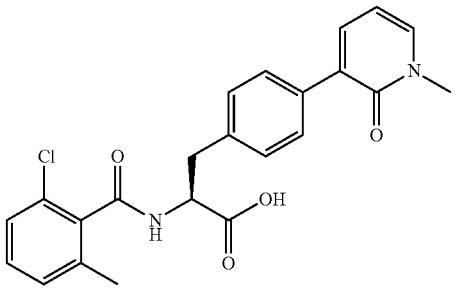 [SMILES: Cc1cccc(Cl)c1C(=O)N[C@@H](Cc1ccc(-c2cccn(C)c2=O)cc1)C(=O)O]

Patent Literature 9 (WO2013/161904) describes a phenylalanine derivative having an α4β7 integrin inhibitory action and represented by the following formula.

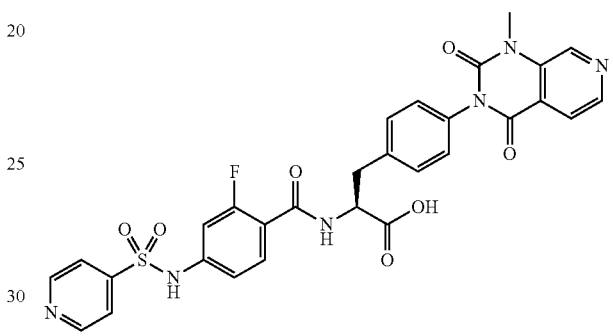

This literature demonstrates the results of the evaluation tests of the specific phenylalanine derivatives in terms of a VCAM-1/α4β1 integrin binding inhibitory activity and a MAdCAM-1/α4β7 integrin binding inhibitory activity in the presence of serum, and concludes that the effect on the α4β1 integrin was low, whereas the effect on the α4β7 integrin was high.

Patent Literature 10 (WO2015/064580) describes a phenylalanine derivative having an α4β7 integrin inhibitory action and represented by the following formula.

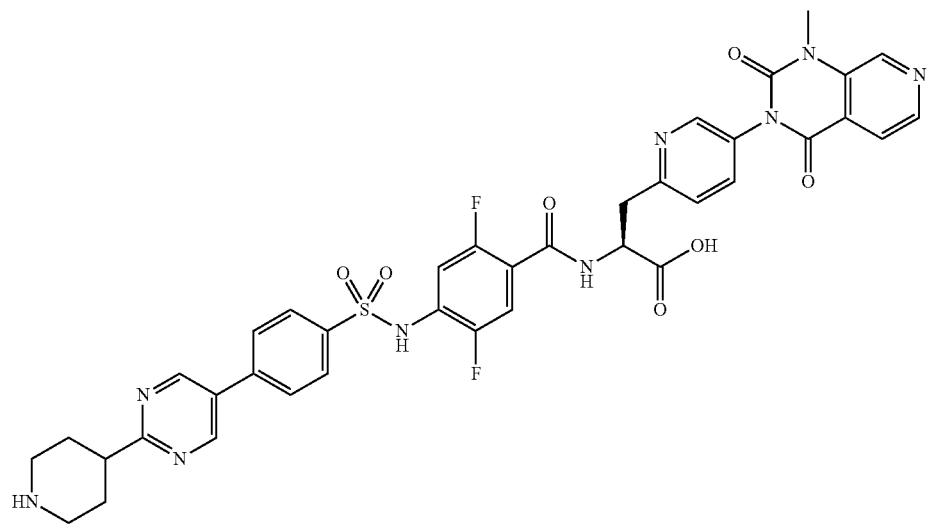 [SMILES: Cn1c(=O)n(-c2ccc(C[C@H](NC(=O)c3cc(F)c(NS(=O)(=O)c4ccc(-c5cnc(C6CCNCC6)nc5)cc4)cc3F)C(=O)O)nc2)c(=O)c2ccncc21]

This literature also demonstrates the results of the evaluation tests of the specific phenylalanine derivatives in terms of a VCAM-1/α4β1 integrin binding inhibitory activity and a MAdCAM-1/α4β7 integrin binding inhibitory activity in the presence of serum, and concludes that the effect on the α4β1 integrin was low, whereas the effect on the α4β7 integrin was high.

CITATION LIST

Patent Literatures

Patent Literature 1:
Patent Literature 1: WO02/16329
Patent Literature 2: WO05/061466
Patent Literature 3: WO03/070709
Patent Literature 4: WO2005/077915
Patent Literature 5: JP2003-321358A
Patent Literature 6: WO01/56994
Patent Literature 7: WO2006/127584
Patent Literature 8: WO01/42215
Patent Literature 9: WO2013/161904
Patent Literature 10: WO2015/064580

Non Patent Literature

Non Patent Literature 1: Nat Med. 2014 December; 20(12): 1397-1 400.

BRIEF SUMMARY OF THE INVENTION

The present invention has an object to provide a novel compound which has a chemical structure having been unknown so far, and which has an α4 integrin inhibitory action.

In particular, the present invention has an object to provide a novel compound which has an α4 integrin inhibitory action with selectivity which produces low effect on α4β1 but produces high effect on α4β7.

The present invention also has an object to provide an orally-administrable compound which has an α4 integrin inhibitory action.

The present invention also has an object to provide a safe compound which has an α4 integrin inhibitory action.

The present invention also has an object to provide a long-acting compound which has an α4 integrin inhibitory action.

The present invention also has an object to provide a novel compound which has an α4 integrin inhibitory action in whole human blood.

The present invention also has an object to provide a pharmaceutical composition containing the above novel compound and a pharmaceutically acceptable carrier.

The present invention also has an object to provide a drug containing the above novel compound.

The present invention also has an object to provide a therapeutic agent or prophylactic agent for inflammatory diseases in which an α4β7 integrin-dependent adhesion process is involved in the disease states.

The present invention also has an object to provide an α4 integrin inhibitor.

The inventors of the present application examined the α4 integrin inhibitory activity of compounds having various structures. As a result, the inventors of the present application found that sulfonamide derivatives each having a specific chemical structure that contains a sulfonamide group to which a heterocyclic group or a phenyl group containing an acylamino group as a substituent is bonded, or a pharmaceutically acceptable salt thereof has an α4β7 integrin inhibitory activity in whole human blood, and that the above objects can be achieved by using these compounds.

Specifically, the present invention includes the following matters.

[1] A sulfonamide derivative represented by the following general formula (I) or a pharmaceutically acceptable salt thereof:

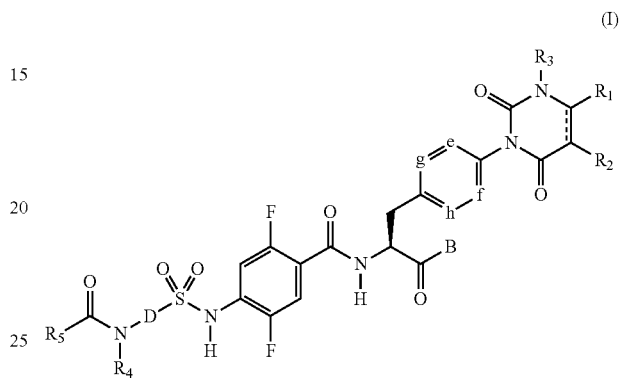

(I)

where

---- represents a single bond or double bond, $R_1$ and $R_2$ each independently represent a hydrogen atom, a halogen atom, a lower alkyl group, a lower alkenyl group, a lower alkoxy group, a lower alkoxy lower alkyl group, a halogeno lower alkyl group, a hydroxy group, or a hydroxy lower alkyl group, and $R_1$ and $R_2$ may be bonded together to form a benzene ring which may have a substituent, an alicyclic hydrocarbon which has 4 to 7 carbon atoms and which may have a substituent, a heteroaryl ring which may have a substituent, or a hetero ring which may have a substituent, $R_3$ represents a lower alkyl group, e, f, g, and h each independently represent C—H or a nitrogen atom, B represents a hydroxy group, an alkoxy group having 1 to 10 carbon atoms, an —O— heterocyclic group, a cilexetiloxy group, or a medoxomiloxy group, D represents any of a benzene ring and a heteroaryl ring each of which may have a substituent, $R_4$ represents a hydrogen atom or a lower alkyl group, $R_5$ represents a lower alkyl group which may have a substituent, a lower alkenyl group which may have a substituent, a lower alkynyl group which may have a substituent, a lower alkylamino group, a phenyl group which may have a substituent, a heteroaryl group which may have a substituent, or a heterocyclic group which may have a substituent, and $R_4$ and $R_5$ may be bonded together to form a hetero ring which may have a substituent.

[2]

The sulfonamide derivative or the pharmaceutically acceptable salt thereof according to the [1], wherein $R_1$ and $R_2$ each independently represent a hydrogen atom, a halogen atom, a lower alkyl group, a lower alkenyl group, a lower alkoxy group, a lower alkoxy lower alkyl group, a hydroxy group, or a hydroxy lower alkyl group, where $R_1$ and $R_2$ may be bonded together to form a benzene ring which may have a substituent, an alicyclic hydrocarbon which has 4 to 7 carbon atoms and which may have a substituent, a heteroaryl ring which may have a substituent, or a hetero ring which may have a substituent, and $R_5$ represents a lower alkyl group which may have a substituent, a lower alkenyl group which may have a substituent, a lower alkylamino group, a phenyl group which may have a substituent, a heteroaryl group which may have a substituent, or a heterocyclic group which may have a substituent.

[3]

The sulfonamide derivative or the pharmaceutically acceptable salt thereof according to the [1] or [2], wherein ═══ represents a double bond.

[4]

The sulfonamide derivative or the pharmaceutically acceptable salt thereof according to any one of the [1] to [3], wherein $R_1$ and $R_2$ are bonded together to form a benzene ring which may have a substituent, an alicyclic hydrocarbon which has 4 to 7 carbon atoms and which may have a substituent, a heteroaryl ring which may have a substituent, or a hetero ring which may have a substituent, and the substituent is selected from a lower alkyl group, a lower alkoxy group, a hydroxy lower alkyl group, an amino group, a lower alkylamino group, and a lower alkylamino lower alkyl group.

[5]

The sulfonamide derivative or the pharmaceutically acceptable salt thereof according to any one of the [1] to [3], wherein $R_1$ and $R_2$ each independently represent a hydrogen atom, a lower alkyl group, or a hydroxy lower alkyl group, $R_1$ and $R_2$ may be bonded together to form an alicyclic hydrocarbon which has 4 to 7 carbon atoms and which may have a substituent, a heteroaryl ring which may have a substituent, or a hetero ring which may have a substituent, and the substituent is selected from a lower alkyl group and a lower alkoxy group.

[6]

The sulfonamide derivative or the pharmaceutically acceptable salt thereof according to the [1], wherein $R_1$ and $R_2$ each independently represent a hydrogen atom, a lower alkyl group, a halogeno lower alkyl group, or a hydroxy lower alkyl group, $R_1$ and $R_2$ may be bonded together to form an alicyclic hydrocarbon which has 4 to 7 carbon atoms and which may have a substituent, a heteroaryl ring which may have a substituent, or a hetero ring which may have a substituent, and the substituent is selected from a lower alkyl group and a lower alkoxy group.

[7]

The sulfonamide derivative or the pharmaceutically acceptable salt thereof according to any one of the [1] to [3], wherein $R_1$ and $R_2$ each independently represent a hydrogen atom, a lower alkyl group, or a hydroxy lower alkyl group.

[8]

The sulfonamide derivative or the pharmaceutically acceptable salt thereof according to any one of the [1] to [3], wherein $R_1$ and $R_2$ are bonded together to form a pyridine which may have a substituent, a cyclohexene which may have a substituent, a dihydropyran which may have a substituent, a tetrahydropyridine which may have a substituent, or an imidazole which may have a substituent, and the substituent is selected from a lower alkyl group, a lower alkoxy group, a hydroxy lower alkyl group, an amino group, a lower alkylamino group, and a lower alkylamino lower alkyl group.

[9]

The sulfonamide derivative or the pharmaceutically acceptable salt thereof according to any one of the [1] to [8], wherein e represents a nitrogen atom, and f, g, and h each represent C—H.

[10]

The sulfonamide derivative or the pharmaceutically acceptable salt thereof according to anyone of the [1] to [9], wherein B represents a hydroxy group or an alkoxy group having 1 to 6 carbon atoms.

[11]

The sulfonamide derivative or the pharmaceutically acceptable salt thereof according to any one of the [1] to [10], wherein the substituent in D is selected from a halogen atom, a lower alkyl group, a lower alkoxy group, and a hydroxy group.

[12]

The sulfonamide derivative or the pharmaceutically acceptable salt thereof according to any one of the [1] to [11], wherein D represents a benzene ring which may have a substituent, a pyridine ring which may have a substituent, or a thiophene ring which may have a substituent, and the substituent is selected from a halogen atom, a lower alkyl group, a lower alkoxy group, and a hydroxy group.

[13]

The sulfonamide derivative or the pharmaceutically acceptable salt thereof according to any one of the [1] to [11], wherein D represents a benzene ring which may have a substituent, a pyridine ring which may have a substituent, or a thiophene ring which may have a substituent, and the substituent represents a halogen atom.

[14]

The sulfonamide derivative or the pharmaceutically acceptable salt thereof according to any one of the [1] to [13], wherein $R_4$ represents a hydrogen atom.

[15]

The sulfonamide derivative or the pharmaceutically acceptable salt thereof according to any one of the [1] to [14], wherein when $R_5$ contains a substituent, the substituent is selected from a halogen atom, a cyano group, a hydroxy group, a lower alkyl group, a lower alkoxy group, a trifluoromethyl group, a phenyl group, and a heterocyclic group.

[16]

The sulfonamide derivative or the pharmaceutically acceptable salt thereof according to any one of the [1] to [14], wherein $R_4$ and $R_5$ are bonded together to form a hetero ring which may have a substituent, and the substituent is selected from a lower alkyl group, a lower alkoxy group, a hydroxy group, and a heterocyclic group.

[17]

The sulfonamide derivative or the pharmaceutically acceptable salt thereof according to any one of the [1] to [14], wherein $R_5$ represents a lower alkyl group which may have a substituent, a lower alkylamino group, or a heterocyclic group which may have a substituent, and the substituent is selected from a halogen atom, a cyano group, a hydroxy group, a lower alkoxy group, a trifluoromethyl group, and a phenyl group.

[18]

The sulfonamide derivative or the pharmaceutically acceptable salt thereof according to the [1] or [2], wherein $R_1$ and $R_2$ each independently represent a hydrogen atom, a lower alkyl group, a lower alkoxy group, or a hydroxy lower alkyl group, $R_1$ and $R_2$ may be bonded together to form an alicyclic hydrocarbon which has 4 to 7 carbon atoms and which may be substituted with a lower alkyl group, a heteroaryl ring which may be substituted with a lower alkyl group, or a hetero ring which may be substituted with a lower alkyl group, D represents a benzene ring which may be substituted with a halogen atom or represents a heteroaryl ring selected from the following formulas:

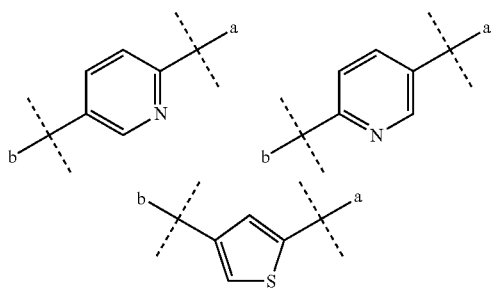

where a represents a bonding position with S and b represents a bonding position with N, $R_4$ represents a hydrogen atom, and $R_5$ represents: an alkyl group which has 2 to 5 carbon atoms, and which may have a substituent selected from the group consisting of a lower alkoxy group, a halogen atom, a hydroxy group, and an aryl group; a heteroaryl group; or a heterocyclic group containing O as a ring atom, wherein when D is a benzene ring which may be substituted with a halogen atom, D is bonded to S and N at para positions, when D is a heteroaryl ring represented by the following formula

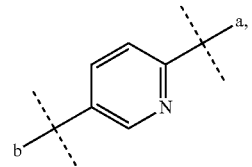

e represents a nitrogen atom, when $R_5$ is a heterocyclic group containing O as a ring atom, $R_1$ and $R_2$ are bonded together to form a heteroaryl ring, and when $R_5$ is an alkyl group which has 2 to 5 carbon atoms and is substituted with a hydroxyl group, $R_5$ is represented by the following formula.

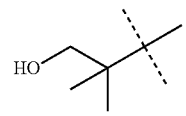

[19]

The sulfonamide derivative or the pharmaceutically acceptable salt thereof according to the [1] or [2], represented by the following formula.

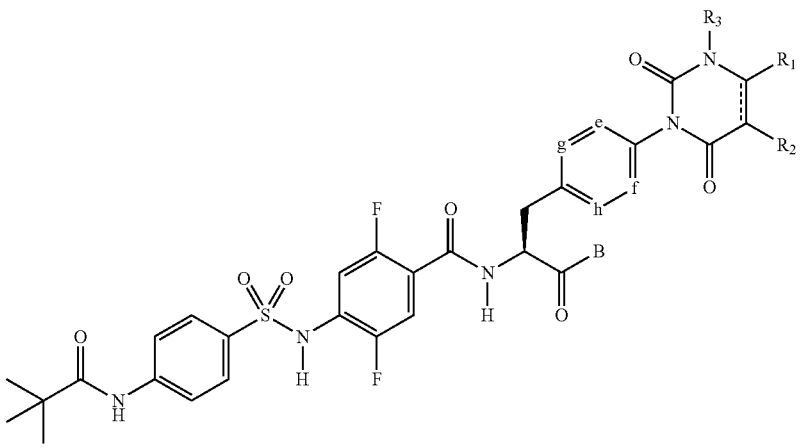

[20] The sulfonamide derivative or the pharmaceutically acceptable salt thereof according to the [19], represented by the following formula.

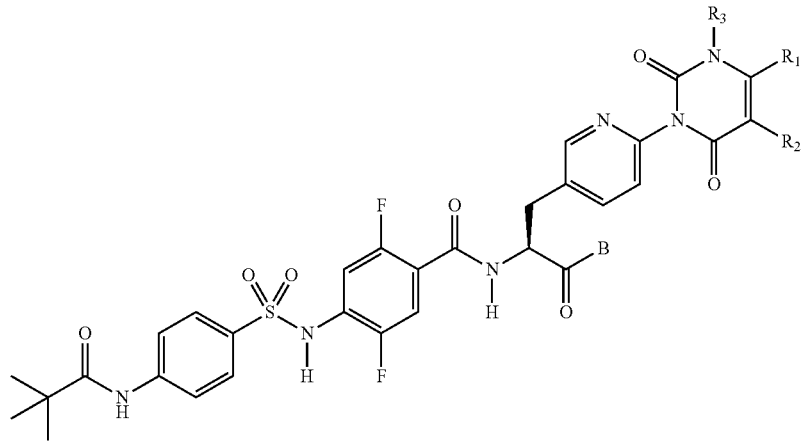

[21] The sulfonamide derivative or the pharmaceutically acceptable salt thereof according to the [19], represented by the following formula.

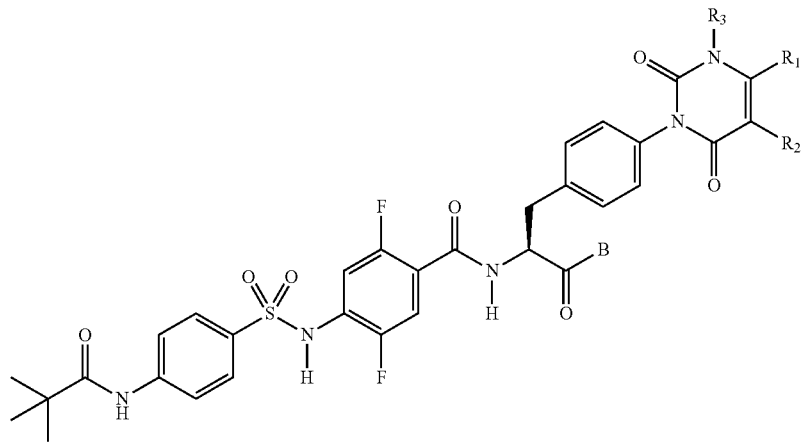

[22] The sulfonamide derivative or the pharmaceutically acceptable salt thereof according to the [19], represented by any one of the following formulas.

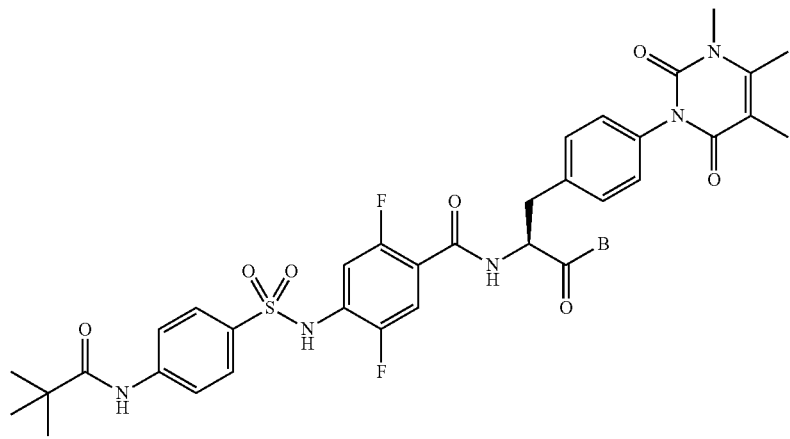

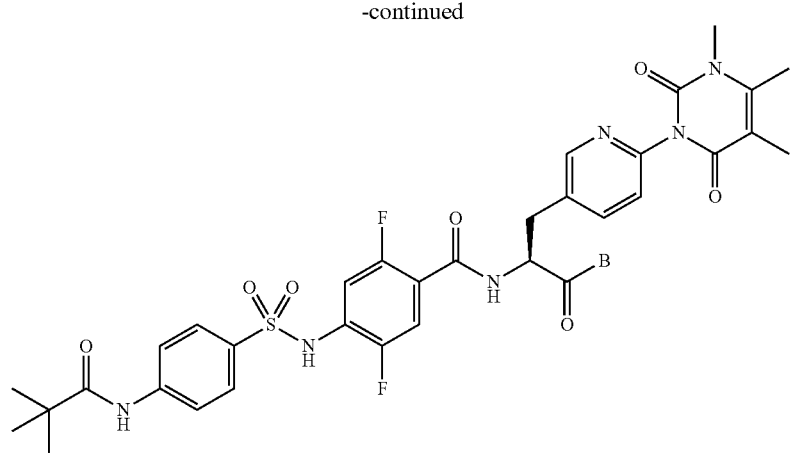
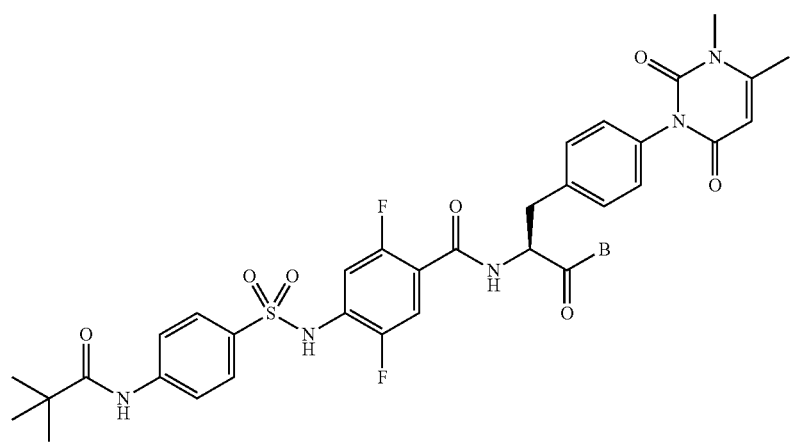
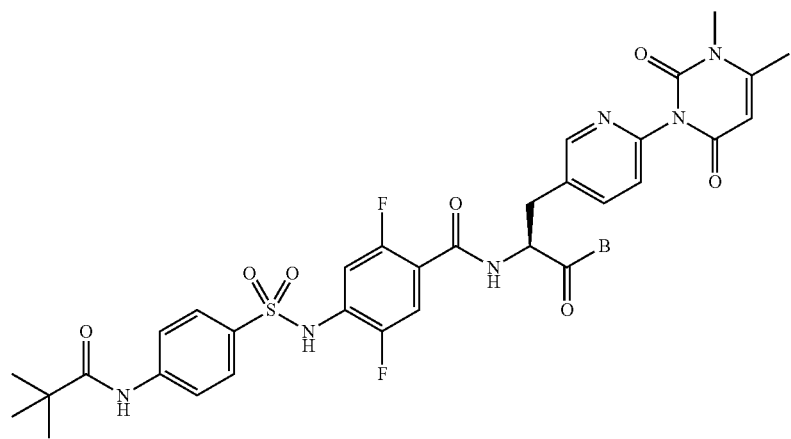

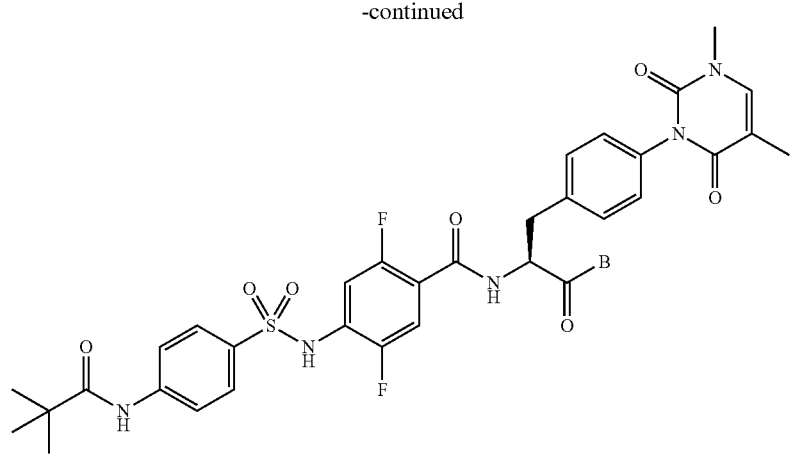
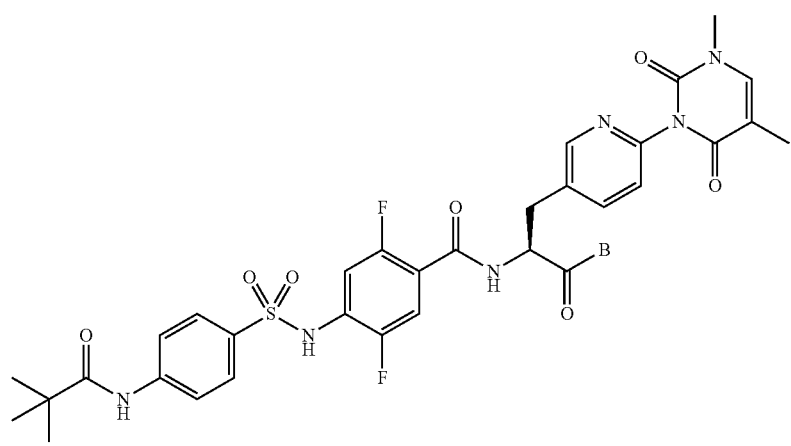
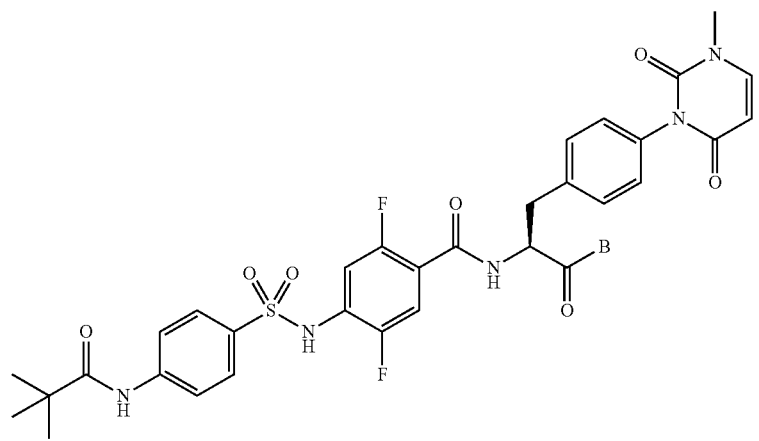

-continued
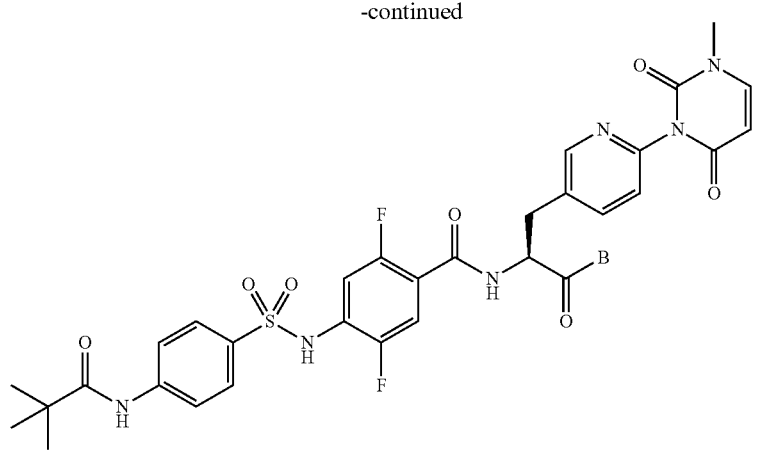
[23] The sulfonamide derivative or the pharmaceutically acceptable salt thereof according to the [22], represented by any one of the following formulas.
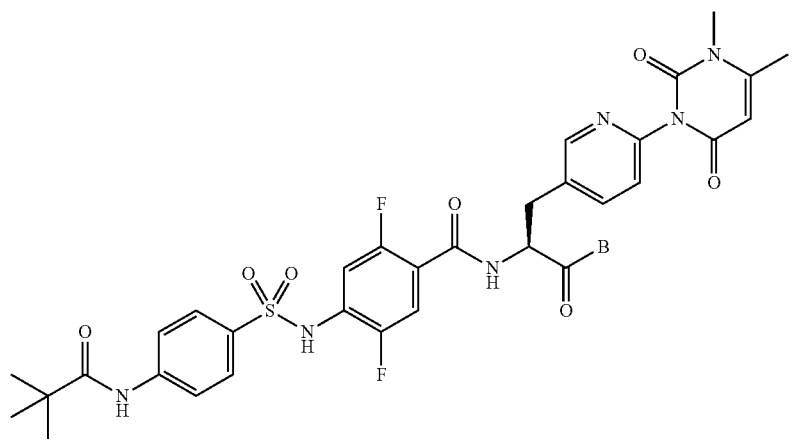
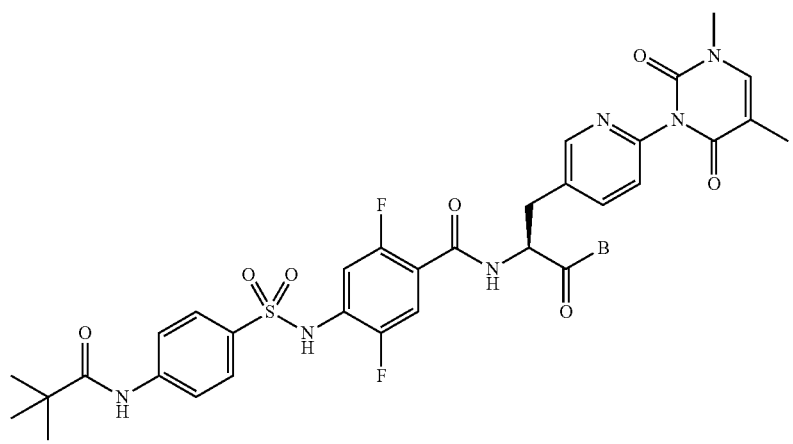

-continued

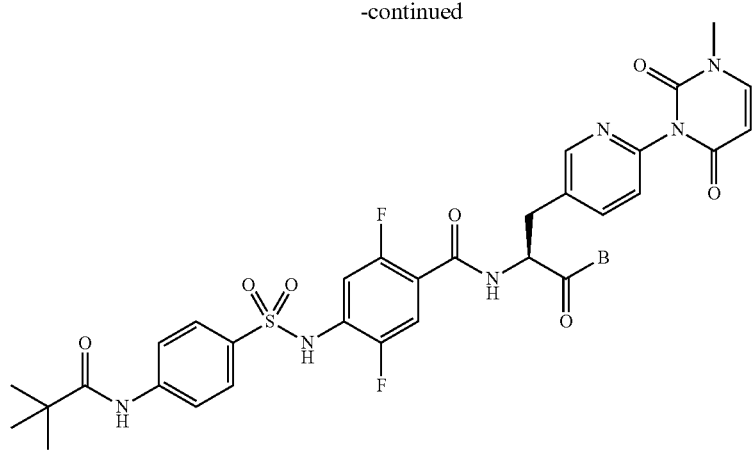

[24]

The sulfonamide derivative or the pharmaceutically acceptable salt thereof according to any of the [1] to [23], wherein B is a hydroxy group, a methoxy group, an ethoxy group, an isopropoxy group, or an isobutyloxy group.

[25]

A pharmaceutical composition containing the sulfonamide derivative or the pharmaceutically acceptable salt thereof according to any of the [1] to [24].

[26]

A therapeutic agent or prophylactic agent for an inflammatory disease in which an α4β7 integrin-dependent adhesion process is involved in a disease state, the agent containing the sulfonamide derivative or the pharmaceutically acceptable salt thereof according to any of the [1] to [24].

[27]

An α4β7 integrin inhibitor containing the sulfonamide derivative or the pharmaceutically acceptable salt thereof according to any of the [1] to [24].

According to the present invention, provided is a novel compound having a chemical structure which has been unknown so far and has an α4 integrin inhibitory action.

According to the present invention, in particular, provided is a novel compound having an α4 integrin inhibitory action with selectivity which produces low effect on α4β1 but produces high effect on α4β7.

According to the present invention, also provided is an orally-administrable compound having an α4 integrin inhibitory action.

According to the present invention, also provided is a safe compound which has an α4 integrin inhibitory action.

According to the present invention, also provided is a long-acting compound which has an α4 integrin inhibitory action.

According to the present invention, also provided is a novel compound having an α4 integrin inhibitory action in human blood.

According to the present invention, also provided is a pharmaceutical composition containing the above novel compound and a pharmaceutically acceptable carrier.

According to the present invention, also provided is a drug containing the above novel compound.

According to the present invention, also provided is a therapeutic agent or prophylactic agent for an inflammatory disease in which an α4β7 integrin-dependent adhesion process is involved in the disease state.

According to the present invention, provided is an α4 integrin inhibitor.

DETAILED DESCRIPTION OF THE INVENTION

In the present specification, "which may have a substituent" means "which is substituted or is not substituted". Unless otherwise specified, the number and positions of substituents are any number and positions, which are not particularly limited. In the case of substitutions with two or more substituents, these substituents may be the same or may be different from each other. Example of the substituents include a halogen atom, a nitro group, a cyano group, a hydroxyl group, a lower alkyl group, a lower alkenyl group, a lower alkynyl group, a lower alkoxy group, a lower alkylthio group, a hydroxy lower alkyl group, a hydroxy lower alkenyl group, a hydroxy lower alkoxy group, a lower alkoxy alkyl group, a halogeno lower alkyl group, a halogeno lower alkenyl group, a halogeno lower alkoxy group, a halogeno lower alkylthio group, an amino group, a lower alkylamino group, a lower alkylaminocarbonyl group, a carboxy group, a lower alkyloxycarbonyl group, a carbamoyl group, a lower alkanoyl group, an aroyl group, a lower alkylsulfinyl group, a lower alkylsulfonyl group, a sulfamoyl group, an ammonium group, an aryl group, a heterocyclic group, an aryl lower alkyl group, a heterocyclic lower alkyl group, an aryloxy group, a heterocyclic oxy group, an arylsulfonyl group, a heterocyclic sulfonyl group, a dihydroxyboryl group, a lower alkylamino lower alkyl group, an aryl lower alkoxycarbonyl group, a lower alkenyloxy group, a lower acyloxy group, a lower acylamino group, and the like.

In the present specification, the term "lower" means a group having 1 to 6 carbon atoms, and "a lower alkyl group" means a linear, branched, or cyclic alkyl group having 1 to 6 carbon atoms. For example, there are a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a tert-pentyl group, a neopentyl group, a 2-pentyl group, a 3-pentyl group, an n-hexyl group, a 2-hexyl group, a cyclopropyl group, a cyclobutyl group, a cyclopentyl group, a cyclohexyl group, a cyclopropylmethyl group, a cyclopropylethyl group, and the like. Preferable groups are a methyl group, an ethyl group, and an n-propyl group.

"A lower alkenyl group" means any of linear or branched alkenyl groups having 2 to 6 carbon atoms including isomers. For example, there are a vinyl group, an allyl group, a propenyl group, a butenyl group, a pentenyl group, a hexenyl group, and the like. Preferable groups are a vinyl group, an allyl group, and a propenyl group.

"A lower alkynyl group" means any of linear or branched alkynyl groups having 2 to 6 carbon atoms including isomers. For example, there are an ethynyl group, a propynyl group, a butynyl group, a pentynyl group, a hexynyl group, and the like. Preferable groups are an ethynyl group and a propynyl group.

As "a halogen atom", there are, for example, a fluorine atom, a chlorine atom, a bromine atom, an iodine atom, and the like. The fluorine atom and the chlorine atom are preferable atoms.

"A lower alkoxy group" means an alkoxy group containing a linear, branched, or cyclic alkyl group having 1 to 6 carbon atoms. For example, there are a methoxy group, an ethoxy group, an n-propoxy group, an n-butoxy group, an n-pentyloxy group, an n-hexyloxy group, an isopropoxy group, an isobutoxy group, a sec-butoxy group, a tert-butoxy group, a cyclopropyloxy group, a cyclobutoxy group, a cyclopentyloxy group, and a cyclohexyloxy group. The methoxy group, the ethoxy group, and the n-propoxy group are preferable groups.

"A lower alkoxymethyl group" means a methyl group substituted with one or more of the aforementioned "lower alkoxy groups". For example, there are a methoxymethyl group, an ethoxymethyl group, an isopropoxymethyl group, a tert-butoxymethyl group, and the like. The methoxymethyl group and the ethoxymethyl group are preferable groups.

"A halogeno lower alkyl group" means a lower alkyl group substituted with one or more of the aforementioned "halogen atoms". For example, there are a trifluoromethyl group, a difluoromethyl group, a monofluoromethyl group, a trichloromethyl group, a dichloromethyl group, a monochloromethyl group, a trifluoroethyl group, a pentafluoroethyl group, and the like. The trifluoromethyl group is a preferable group.

"A hydroxy lower alkyl group" means a lower alkyl group substituted with a hydroxyl group. For example, there are a hydroxymethyl group, a hydroxyethyl group, and the like. The hydroxymethyl group is a preferable group.

"A lower alkylamino group" means an amino group substituted with one or more of the aforementioned "lower alkyl groups". For example, there are a methylamino group, an ethylamino group, a propylamino group, a tert-butylamino group, an isopropylamino group, a dimethylamino group, a diethylamino group, a dipropylamino group, a diisopropylamino group, a methylethylamino group, and the like. The methylamino group, the ethylamino group, the propylamino group, the isopropylamino group, and the dimethylamino group are preferable groups.

"A lower alkylamino lower alkyl group" means a lower alkyl group substituted with an amino group substituted with one or two of the aforementioned "lower alkyl groups". For example, there are a methylaminomethyl group, an ethylaminomethyl group, a propylaminomethyl group, an isopropylaminomethyl group, a methylaminoethyl group, an ethylaminoethyl group, a dimethylaminomethyl group, a methylethylaminomethyl group, and the like. The methylaminomethyl group, the ethylaminomethyl group, and the methylaminoethyl group are preferable groups.

"An alicyclic hydrocarbon" means any of cyclic structures composed of carbon atoms and hydrogen atoms, which include a cycloalkane, all the bonds of which are single bonds, a cycloalkene which may contain a double bond, and so on. For example, there are a cyclobutane, a cyclopentane, a cyclohexane, a cycloheptane, a cyclohexene, and the like. The cyclohexane and the cyclohexene are preferable rings.

"A heteroaryl ring" means a 4- to 10-membered aromatic ring containing, as ring atoms, 1 to 4 hetero atoms selected from an oxygen atom, a sulfur atom, and a nitrogen atom. For example, there are a pyridine ring, a pyridazine ring, a pyrimidine ring, a pyrazine ring, a furan ring, a thiophene ring, a pyrrole ring, an isooxazole ring, an oxazole ring, an isothiazole ring, a thiazole ring, a pyrazole ring, an imidazole ring, an oxadiazole ring, a thiadiazole ring, a triazole ring, a tetrazole ring, a benzofuran ring, a benzothiophene ring, an indole ring, an isoindole ring, a benzoxazole ring, a benzisoxazole ring, a benzthiazole ring, a benzisothiazole ring, a benzimidazole ring, an indazole ring, a purine ring, a quinoline ring, an isoquinoline ring, a cinnoline ring, a phthalazine ring, a quinazoline ring, a quinoxaline ring, a pteridine ring, and the like. The pyridine ring and the pyrimidine ring are preferable rings.

"A hetero ring" means a 4- to 10-membered monocyclic or bicyclic hetero ring containing, as ring atoms, 1 to 4 hetero atoms selected from an oxygen atom, a sulfur atom, and a nitrogen atom. Here, any carbon atom as a ring atom may be substituted with an oxo group, and the sulfur atom or the nitrogen atom may be oxidized to form an oxide. The hetero ring may be condensed with a benzene ring. For example, there are an oxetane ring, a tetrahydrofuran ring, a dihydropyran ring, a tetrahydropyran ring, a dioxolane ring, a tetrahydrothiophene ring, a tetrahydrothiopyran ring, a thiazolidine ring, an azetidine ring, a pyrrolidine ring, a piperidine ring, a piperadine ring, a homopiperidine ring, a homopiperadine ring, a pyrazolidine ring, an imidazolidine ring, a tetrahydropyridine ring, a tetrahydropyrimidine ring, a morpholine ring, a thiomorpholine ring, an indoline ring, an isoindoline ring, a chroman ring, an isochroman ring, an azaindoline ring, a piperidinone ring, an imidazooxadine ring, an imidazothiazoline ring, a pyrimidone ring, a hydantoin ring, a quinuclidine ring, and the like. The piperidine ring, the piperadine ring, the tetrahydropyran ring, and the morpholine ring are preferable rings.

"A heteroaryl group" means a 4- to 10-membered aromatic ring group containing, as ring atoms, 1 to 4 hetero atoms selected from an oxygen atom, a sulfur atom, and a nitrogen atom. For example, there are a pyridyl group, a pyridazinyl group, a pyrimidinyl group, a pyrazinyl group, a furyl group, a thienyl group, a pyrrolyl group, an isooxazolyl group, an oxazolyl group, an isothiazolyl group, a thiazolyl group, a pyrazolyl group, an imidazolyl group, an oxadiazolyl group, a thiadiazolyl group, a triazolyl group, a tetrazolyl group, a benzofuranyl group, a benzothienyl group, an indolyl group, an isoindolyl group, a benzoxazolyl group, a benzisoxazolyl group, a benzthiazolyl group, a benzisothiazolyl group, a benzimidazolyl group, an indazolyl group, a purinyl group, a quinolinyl group, a isoquinolinyl group, a cinnolinyl group, a phthalazinyl group, a quinazolinyl group, a quinoxalinyl group, a pteridinyl group, and the like. The pyridyl group and the pyrimidinyl group are preferable groups.

"A heterocyclic group" means a 4- to 10-membered monocyclic or bicyclic heterocyclic group containing, as ring atoms, 1 to 4 hetero atoms selected from an oxygen atom, a sulfur atom, and a nitrogen atom. Here, any carbon atom as a ring atom may be substituted with an oxo group, and the sulfur atom or the nitrogen atom may be oxidized to form an oxide. Moreover, the heterocyclic group may be condensed with a benzene ring. There are an oxetanyl group, a tetrahydrofuranyl group, a dihydropyranyl group, a tetrahydropyranyl group, a dioxolanyl group, a tetrahydrothiophenyl group, a tetrahydrothiopyranyl group, a thiazolidinyl group, an azetidinyl group, a pyrrolidinyl group, a piperidinyl group, a piperazinyl group, a homopiperidinyl group, a homopiperazinyl group, a pyrazolidinyl group, an imidazolidinyl group, a tetrahydropyridyl group, a tetrahydropyrimidyl group, a morpholinyl group, a thiomorpholinyl group, an indolinyl group, an isoindolinyl group, a chromanyl group, an isochromanyl group, an azaindolyl group, a piperidinonyl group, an imidazooxazolyl group, an imidazothiazolyl group, a pyrimidonnyl group, a hydantoinyl group, a quinuclidinyl group, and the like. The piperidinyl group, the piperazinyl group, the tetrahydropyranyl group, the morpholinyl group, the piperidinonyl group, and the hydantoinyl group are preferable groups.

In the present invention, for a sulfonamide derivative represented by the general formula (I) or a pharmaceutically acceptable salt thereof, the following substances are preferred in the formula.

In the general formula (I), $R_1$ and $R_2$ each independently represent: preferably a hydrogen atom, a lower alkyl group, a halogeno lower alkyl group, or a hydroxy lower alkyl group; more preferably a hydrogen atom or a lower alkyl group; and particularly preferably a hydrogen atom and a methyl group. Instead, it is preferable that $R_1$ and $R_2$ each independently represent a hydrogen atom, a lower alkyl group, or a hydroxy lower alkyl group.

In the general formula (I), a ring formed by $R_1$ and $R_2$ bonded together is preferably any of a pyridine, a cyclohexene, a dihydropyran, and a tetrahydropyridine, more preferably any of a cyclohexene, a dihydropyran, and a tetrahydropyridine, and particularly preferably any of a dihydropyran and a tetrahydropyridine.

In the general formula (I), $R_3$ is preferably a lower alkyl group, more preferably any of an isopropyl group and a methyl group, and particularly preferably a methyl group.

In the general formula (I), it is preferable that e, f, g, and h each be C—H or a nitrogen atom, it is more preferable that any one of e, f, g, and h be a nitrogen atom, and it is particularly preferable that e or f be a nitrogen atom.

In the general formula (I), B is: preferably a hydroxy group or a lower alkoxy group; more preferably a hydroxy group, a methoxy group, an ethoxy group, an isopropoxy group, an isobutyloxy group, or a cyclohexyloxy group; particularly preferably a hydroxy group, a methoxy group, an ethoxy group, an isopropoxy group, or an isobutyloxy group; and most preferably an isobutyloxy group. Instead, B is more preferably a hydroxy group, a methoxy group, an ethoxy group, an isopropoxy group, or a cyclohexyloxy group, and particularly preferably a hydroxy group, a methoxy group, an ethoxy group, or an isopropoxy group.

In the general formula (I), D is: preferably a benzene ring which may have a substituent or a heteroaryl ring which may have a substituent; more preferably a benzene ring, a pyridine ring, or a thiophene ring; and particularly preferably a benzene ring.

In the general formula (I), the substituent in D is: preferably a halogen atom, a lower alkyl group, a lower alkoxy group, or a hydroxy group; and more preferably a fluorine atom.

In the general formula (I), when D represents a benzene ring, the substitution positions of an aminosulfonyl group and an aminocarbonyl group bound to D are preferably para or meta positions, and particularly preferably the para positions.

In the general formula (I), $R_4$ is preferably a hydrogen atom or a lower alkyl group, more preferably a hydrogen atom or a methyl group, and particularly preferably a hydrogen atom.

In the general formula (I), $R_5$ is: preferably a lower alkyl group which may have a substituent, a lower alkynyl group which may have a substituent, a lower alkylamino group, a phenyl group which may have a substituent, a heteroaryl group which may have a substituent, or a heterocyclic group which may have a substituent; more preferably a lower alkyl group which may have a substituent, a lower alkylamino group, a phenyl group which may have a substituent, a heteroaryl group which may have a substituent, or a heterocyclic group which may have a substituent; further preferably a methyl group, an ethyl group, a tert-butyl group, a 3-pentyl group, a cyclopropyl group, a tert-butylamide group, a pyridyl group, a piperidyl group, or a tetrahydropyranyl group; and particularly preferably a tert-butyl group or a cyclopropyl group.

In the general formula (I), the substituent in $R_5$ is: preferably a halogen atom, a hydroxy group, a lower alkoxy group, a trifluoromethyl group or a phenyl group; and particularly preferably a fluorine atom, a hydroxy group, a methoxy group, or a trifluoromethyl group.

In the general formula (I), a ring formed by $R_4$ and $R_5$ bonded together is preferably a hetero ring which may have a substituent, and particularly preferably a pyrimidone or a hydantoin.

In the general formula (I), the substituent in a ring formed by $R_4$ and $R_5$ bonded together is preferably a lower alkyl group or a heterocyclic group, and particularly preferably a methyl group or a tetrahydropyranyl group.

Moreover, a particularly preferable compound is represented by the general formula (I), where $R_1$ and $R_2$ each independently represent a hydrogen atom, a lower alkyl group, a lower alkoxy group, or a hydroxy lower alkyl group, and $R_1$ and $R_2$ may be bonded together to form an alicyclic hydrocarbon which has 4 to 7 carbon atoms and which may be substituted with a lower alkyl group, a heteroaryl ring which may be substituted with a lower alkyl group, or a hetero ring which may be substituted with a lower alkyl group, D represents a benzene ring which may be substituted with a halogen atom or represents a heteroaryl ring selected from the following formulas:

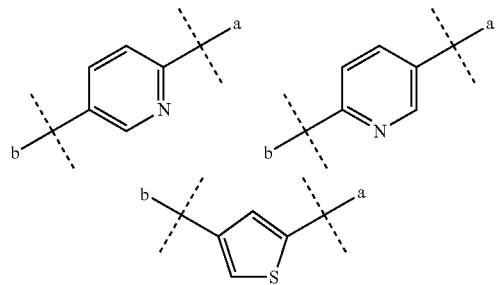

where a represents a bonding position with S and b represents a bonding position with N, $R_4$ represents a hydrogen atom, $R_5$ represents: an alkyl group which has 2 to 5 carbon atoms, and which may have a substituent selected from the group consisting of a lower alkoxy group, a halogen atom, a hydroxy group, and an aryl group; a heteroaryl group; or a heterocyclic group containing O as a ring atom, wherein when D is a benzene ring which may be substituted with a halogen atom, D is bonded to S and N at para positions, when D is a heteroaryl ring represented by the following formula

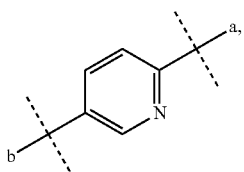

e represents a nitrogen atom, when $R_5$ is a heterocyclic group containing O as a ring atom, $R_1$ and $R_2$ are bonded together to form a heteroaryl ring, and when $R_5$ is an alkyl group which has 2 to 5 carbon atoms and is substituted with a hydroxyl group, $R_5$ is represented by the following formula.

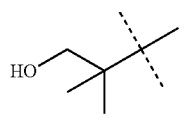

If the compound represented by the general formula (I) of the present invention is in the form of a salt, the compound may be any pharmaceutically acceptable salt. As salts for an acidic group such as a carboxyl group in the formula, there are ammonium salts, salts with alkali metals such as sodium and potassium, salts with alkaline earth metals such as calcium and magnesium, aluminum salts, zinc salts, salts with organic amines such as triethylamine, ethanolamine, morpholine, piperidine, and dicyclohexylamine, and salts with basic amino acids such as arginine and lysine. As salts for a basic group in the case where the basic group is present in the formula, there are salts with inorganic acids such as hydrochloric acid, sulfuric acid, and phosphoric acid; salts with organic carboxylic acids such as acetic acid, citric acid, benzoic acid, maleic acid, fumaric acid, tartaric acid, and succinic acid; and salts with organic sulfonic acids such as methanesulfonic acid and p-toluenesulfonic acid. As a method of forming a salt, it is possible to mix a compound of the general formula (I) with a necessary acid or base at an appropriate content ratio in a solvent or a dispersant, or to obtain a salt by cation exchange or anion exchange from a salt in another form.

The compounds of the present invention may include solvates of the compound represented by the general formula (I), for example hydrates, alcohol adducts, and so on.

The compounds of the present invention may include ones in the forms of prodrugs of the compound represented by the general formula (I). The prodrug of the compound of the present invention means a compound which can be converted into the compound represented by the general formula (I) by reaction with an enzyme, gastric acid or the like under physiological conditions in the living body, that is, a compound which can change to the compound of the general formula (I) by enzymatic oxidation, reduction, hydrolysis or the like, or a compound which can change to the compound represented by the general formula (I) by hydrolysis or the like with gastric acid or the like. Examples of prodrugs of the compound represented by the general formula (I) may include, but not particularly limited to, compounds in Examples. For example, in the case where the compound represented by the general formula (I) contains an amino group, prodrugs thereof include compounds in each of which the amino group is acylated, alkylated, or phosphorylated (such for example as a compound in which the amino group in the compound represented by the general formula (I) is eicosanoylated, alanylated, pentylaminocarbonylated, (5-methyl-2-oxo-1,3-dioxolen-4-yl)methoxycarbonylated, tetrahydrofuranylated, pyrrolidyl methylated, pivaloyloxymethylated, or tert-butylated. In the case where the compound represented by the general formula (I) contains a hydroxy, prodrugs thereof include compounds in each of which the hydroxy is acylated, alkylated, phosphorylated, or borated (such for example as a compound in which the hydroxy of the compound represented by the general formula (I) is acetylated, palmitoylated, propanoylated, pivaloylated, succinylated, fumarylated, alanylated, or dimethylaminomethylcarbonylated. In the case where the compound represented by the general formula (I) contains a carboxy group, prodrugs thereof include compounds in each of which the carboxy group is esterified or amidated (such for example as a compound in which the carboxyl of the compound represented by the general formula (I) is methyl-esterified, ethyl-esterified, normal propyl-esterified, phenyl-esterified, isopropyl-esterified, isobutyl-esterified, cyclobutyl-esterified, cyclopentyl-esterified, cyclohexyl-esterified, cycloheptyl-esterified, cyclobutylmethyl-esterified, cyclohexylmethyl-esterified, normal hexyl-esterified, sec-butyl-esterified, tert-butyl-esterified, (4-tetrahydropyranyl)methyl-esterified, (4-tetrahydropyranyl)-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolene-4-yl)methyl-esterified, cyclohexyl oxycarbonylethyl-esterified, or methyl-amidated. In particular, in the case where the compound represented by the general formula (I) contains a carboxyl group, a preferable prodrug thereof is a compound in which the carboxy group is esterified with a linear, branched or cyclic alkyl group having 1 to 10 carbon atoms. These compounds may be manufactured from the compound represented by the general formula (I) in accordance with any of the publicly known methods.

In addition, the prodrug of the compound (I) may be a compound that can change to the compound (I) under physiological conditions as described in *Iyakuhin no Kaihatsu* (*Development of Drugs*), Vol. 7, *Bunshi Sekkei* (*Molecular Design*), Hirokawa-Shoten, 1990, pp. 163 to 198.

The present invention includes all the isotopes of any compound represented by the formula (I). The isotope of the compound of the present invention is one in which at least one atom is substituted with an atom having the same atomic number (proton number) and different mass number (the sum of the numbers of protons and neutrons). Examples of the isotopes included in the compounds of the present invention include a hydrogen atom, a carbon atom, a nitrogen atom, an oxygen atom, a phosphorus atom, a sulfur atom, a fluorine atom, a chlorine atom and the like, which include $^2H$, $^3H$, $^{13}C$, $^{14}C$, $^{15}N$, $^{17}O$, $^{18}O$, $^{31}P$, $^{32}P$, $^{35}S$, $^{18}F$, $^{36}Cl$, and the like. Particularly, unstable radioisotopes emitting neutrons by emitting radioactivity, such as $^3H$ and $^{14}C$, are useful in the in vivo tissue distribution tests of a pharmaceutical or compound. A stable isotope does not cause disintegration, keeps its abundance almost unchanged, and has no radioactivity, so that the stable isotope can be safely used. An isotope of the compound of the present invention can be obtained by conversion according to a conventional method using a reagent containing the corresponding isotope instead of using a reagent usually used in the synthesis.

The compound represented by the general formula (I) or a salt thereof is administered as it is or as any of various kinds of pharmaceutical compositions. The dosage form of such a pharmaceutical composition may be, for example, a tablet, a powder, a pill, a granule, a capsule, a suppository, a solution, a sugar coated tablet, a debauge, or a syrup, which can be manufactured according to a conventional method by using usual formulation auxiliaries.

For example, the tablet can be prepared by mixing a phenylalanine derivative as the active ingredient of the present invention with known auxiliary substances, for example, including: an inert diluent such as lactose, calcium carbonate, or calcium phosphate; a binder such as gum arabic, corn starch or gelatin; a bulking agent such as alginic acid, corn starch or pregelatinized starch; a sweetener such as sucrose, lactose or saccharin; a flavoring agent such as peppermint, akamono (*gaultheria adenothrix*) oil or cherry extract; a lubricant such as magnesium stearate, talc or carboxymethyl cellulose; any of excipients for a soft gelatin capsule and suppository such as fat, wax, semisolid or liquid polyol, natural oil, and hydrogenated oil; and any of excipients for a solution such as such as water, alcohol, glycerol, polyol, sucrose, invert sugar, glucose, and vegetable oil.

An inhibitor containing the compound represented by formula (I) or a salt thereof as an active ingredient may be used as a therapeutic agent or prophylactic agent for inflammatory diseases in which an α4 integrin-dependent adhesion process is involved in disease states. Such inflammatory diseases include, for example, rheumatoid arthritis, inflammatory bowel disease, systemic lupus erythematosus, multiple sclerosis, Sjogren's syndrome, asthma, psoriasis, allergy, diabetes, cardiovascular disease, arteriosclerosis, restenosis, tumor growth, tumor metastasis, transplant rejection, and/or human immunodeficiency virus infection (see Non Patent Literature 1).

The dose to be used for the above purpose is determined depending on the targeted therapeutic effect, administration method, treatment period, age, body weight and the like. In general, preferred doses for an adult per day by administration via an oral route and a parenteral route are 1 μg to 5 g in the case of oral administration and 0.01 μg to 1 g in the case of parenteral administration.

In the sulfonamide derivative represented by the general formula (I), an acylamino group is provided as a substituent in D. By employing such a structure, α4β7 integrin inhibitory activity can be obtained in whole human blood. In addition, the sulfonamide derivative of the present invention is transferred into the portal vein and is increased in exposure in circulating blood, thereby producing the effect. Also from this point of view, the sulfonamide derivative of the present invention may be used as a therapeutic agent or prophylactic agent for inflammatory diseases in which an α4β7 integrin-dependent adhesion process is involved in the disease states.

Furthermore, in the sulfonamide derivative of the general formula (I), the 2-position and the 5-position of the phenyl of the phenylalanine moiety are substituted with fluorine atoms. As a result, the sulfonamide derivative can have an inhibitory activity which produces low effect on α4β1 integrin, but produces high effect on α4β7 integrin.

The compound represented by the general formula (I) of the present invention can be produced, for example, by amidation reaction of an intermediate having a carboxyl group at the terminus as represented by a general formula (M-I) with an intermediate having an amino group at the terminus as represented by a general formula (M-II).

The amidation reaction is publicly known, and examples thereof include (1) method using a condensing agent, (2) method using an acid halide, and so on.

The (1) method using a condensing agent is carried out by reacting a carboxylic acid with an amine or a salt thereof, for example, in a solvent which does not adversely affect this reaction, such as dichloromethane, tetrahydrofuran (THF), 1,4-dioxane, N,N-dimethylformamide (DMF) or acetonitrile, for example, in the presence or absence of a base such as pyridine, triethylamine or N,N-diisopropylethylamine, for example, in the presence or absence of a condensation aid such as 1-hydroxybenzotriazole (HOBt), 1-hydroxy-7-azabenzotriazole (HOAt) or N-hydroxysuccinimide (HOSu), for example, using a condensing agent such as 1-ethyl-3-(3'-dimethylaminopropyl) carbodiimide (WSC), 1,3-dicyclohexylcarbodiimide (DCC) or (7-azabenzotriazol-1-yl)-N,N,N',N'-tetramethyluronium hexafluorophosphate (HATU), for example.

The (2) method using an acid halide is carried out by: obtaining an acid halide by reacting a carboxylic acid with a thionyl chloride, oxalyl chloride, thionyl bromide, or the like, for example, in the presence or absence of a catalyst such as DMF, for example, in a solvent which does not adversely affect this reaction, such as dichloromethane, for example, or without using the solvent; and reacting the acid halide with an amine or a salt thereof in a solvent which does not adversely affect this reaction such as dichloromethane or THF, for example, in the presence of a base such as pyridine, triethylamine, or N,N-diisopropylethylamine, for example.

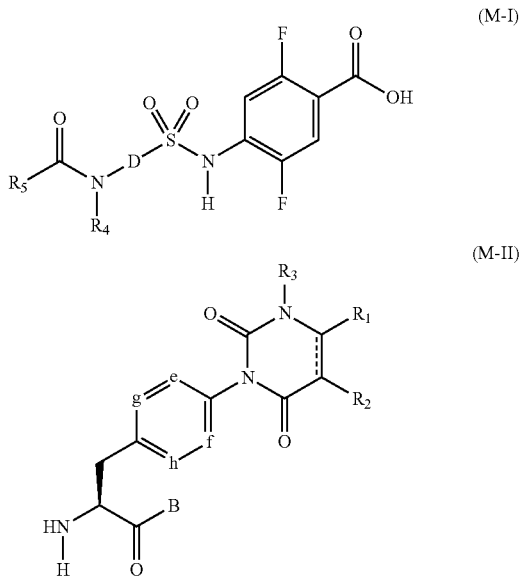

Out of them, the intermediate having a carboxyl group at the terminus as represented by the general formula (M-I) can be produced, for example, by the following method.

Description is provided for a method for producing a representative compound among intermediates, each of which is a compound of the present invention and has a carboxyl group at the terminus as represented by the formula (M-I). In the following description, the symbols in the formulas are defined as having the same meanings as those in the formula (I) unless otherwise noted.

It is possible to synthesize an intermediate (S7) having a carboxyl group at the terminus as represented by the general formula (M-I) where D is a phenyl group or a heteroaryl group which may have a substituent selected from the group consisting of a lower alkyl group, a lower alkoxy group, and a halogen atom, and $R_4$ is a hydrogen atom, by using a method (production method A) described below or the like.

<Production Method A>

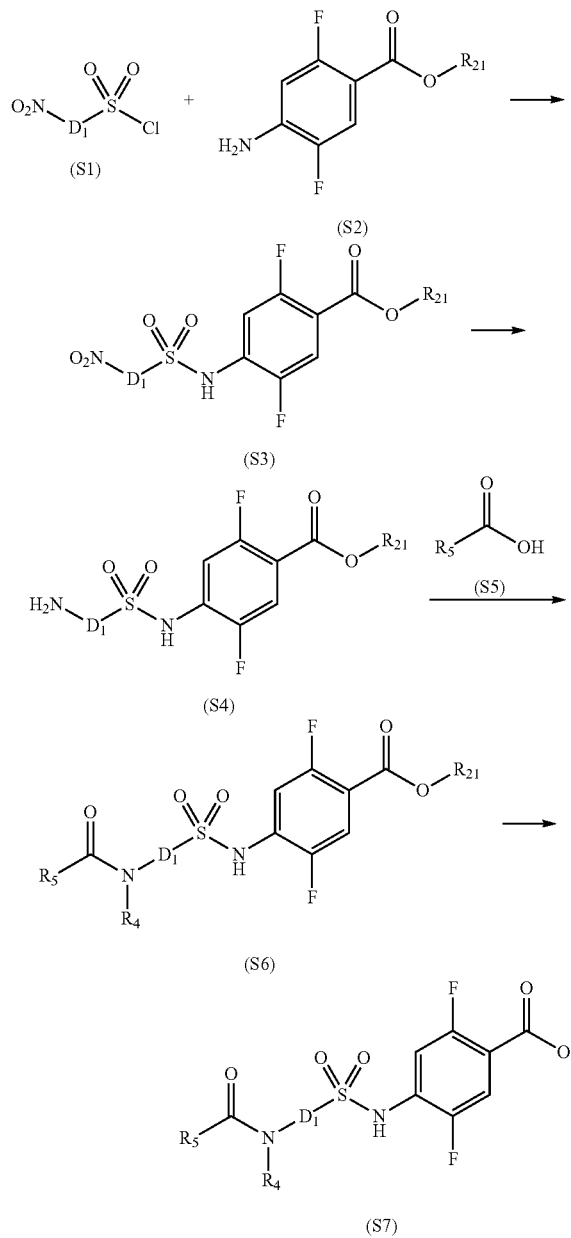

$D_1$ in the formulas represents a substituent represented by the above D or a substituent that can be easily converted to D by an operation such for example as deprotection, and $R_{21}$ in the formulas represents a general ester substituent such for example as a lower alkyl group.

A sulfonamide derivative (S3) can be synthesized by reacting a sulfonyl chloride derivative (S1) and an aniline derivative (S2) with each other in a solvent that does not adversely affect the reaction such as dichloromethane, acetonitrile, THF, or DMF, for example, in the presence of a base such as pyridine or trimethylamine, for example. From the sulfonamide derivative (S3) obtained, an amine derivative (S4) can be synthesized: by catalytic reduction reaction using a metal catalyst such for example as palladium carbon, palladium hydroxide, or Raney nickel in a solvent that does not adversely affect this reaction such for example as methanol, ethanol, or isopropyl alcohol; or by an action of a metal such for example as zinc under an acidic condition (for example, hydrochloric acid, acetic acid, ammonium chloride, or the like). The amine derivative (S4) thus obtained and a carboxylic acid derivative (S5) are transformed into the corresponding amide derivative (S6) by reacting with each other using a condensing agent such for example as WSC, DCC, or HATU in a solvent that does not adversely affect the reaction such for example as dichloromethane, THF, 1,4-dioxane, DMF, or acetonitrile, in the presence or absence of a base such for example as pyridine, triethylamine, or N,N-diisopropylethylamine, in the presence or absence of a condensation aid such for example as HOBt, HOAt, or HOSu. Subsequently, in a solvent that does not adversely affect the reaction such for example as THF, 1,4-dioxane, methanol or ethanol, the amide derivative (S6) is subjected to hydrolysis such as alkaline hydrolysis using a base such as a sodium hydroxide or lithium hydroxide, for example, or acid hydrolysis using a hydrochloric acid or trifluoroacetic acid, for example, thereby producing a desired carboxylic acid derivative (S7).

It is possible to synthesize an intermediate (S7) having a carboxyl group at the terminus as represented by the general formula (M-I) where D is a phenyl group or a heteroaryl group which may have a substituent selected from the group consisting of a lower alkyl group, a lower alkoxy group, and a halogen atom, by using, for example, a method (production method B or C) described below or the like.

<Production Method B>

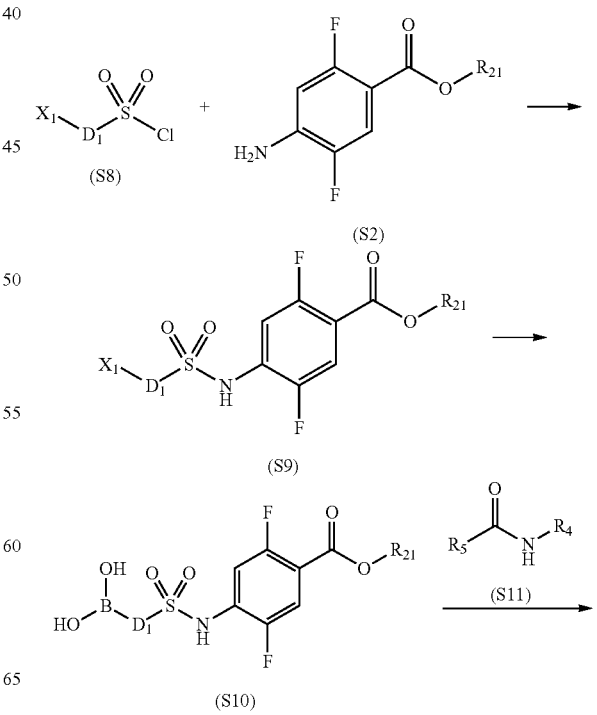

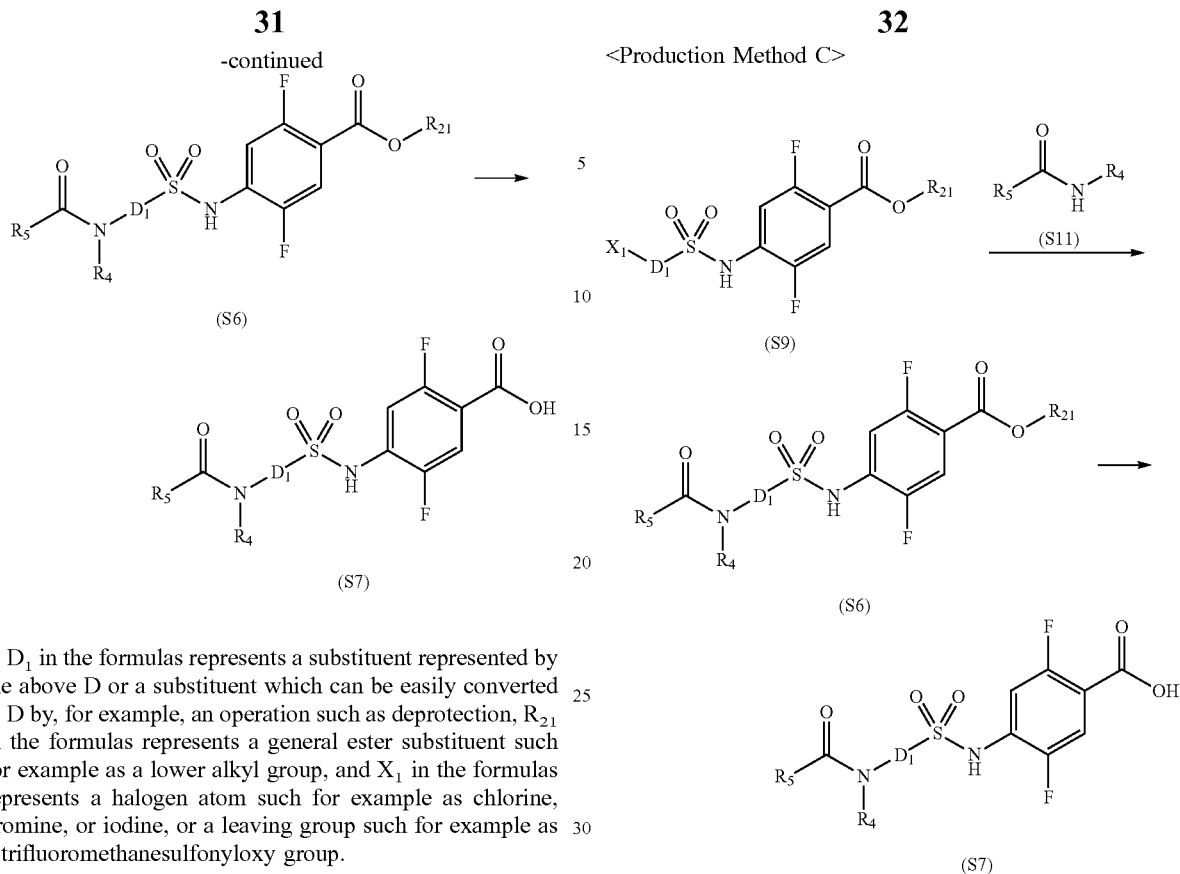

$D_1$ in the formulas represents a substituent represented by the above D or a substituent which can be easily converted to D by, for example, an operation such as deprotection, $R_{21}$ in the formulas represents a general ester substituent such for example as a lower alkyl group, and $X_1$ in the formulas represents a halogen atom such for example as chlorine, bromine, or iodine, or a leaving group such for example as a trifluoromethanesulfonyloxy group.

A sulfonyl chloride derivative (S8) and an aniline derivative (S2) are reacted with each other in a solvent that does not adversely affect the reaction such for example as dichloromethane, acetonitrile, THF, or DMF, for example, in the presence of a base such as pyridine or triethylamine, thereby synthesizing a sulfonamide derivative (S9). The sulfonamide derivative (S9) thus obtained and a borane derivative such for example as bis(pinacolato)diborane are transformed into the corresponding boronic acid ester derivative by coupling reaction using a metal catalyst such for example as 1,1'-bis(diphenylphosphinoferrocene)dichloropalladium(II) in a solvent that does not adversely affect this reaction such for example as DMF in the presence of a base such for example as potassium acetate. Then, the boronic acid ester derivative thus obtained is treated in a solvent that does not adversely affect the reaction such for example as acetone by adding, for example, sodium periodate or ammonium acetate and water, so that the boronic acid ester is deprotected to synthesize the corresponding boronic acid derivative (S10). The obtained boronic acid derivative (S10) and the amide derivative (S11) are subjected to coupling reaction using a metal catalyst such for example as copper(II) acetate or copper(II) trifluoromethanesulfonate in a solvent that does not adversely affect the reaction such for example as dichloromethane, dimethylsulfoxide (DMSO) or DMF in the presence of a base such for example as pyridine or triethylamine, so that a compound (S6) can be synthesized. Subsequently, in a solvent that does not adversely affect the reaction such as THF, 1,4-dioxane, methanol, or ethanol, the compound (S6) is subjected to hydrolysis such as alkaline hydrolysis using a base such as a sodium hydroxide or lithium hydroxide, for example, or acid hydrolysis using a hydrochloric acid or trifluoroacetic acid, for example, thereby producing a desired carboxylic acid derivative (S7).

$D_1$ in the formulas represents a substituent represented by the above D or a substituent which can be easily converted to D by, for example, an operation such as deprotection, $R_{21}$ in the formulas represents a general ester substituent such as a lower alkyl group, for example, and $X_1$ in the formulas represents a halogen atom such for example as chlorine, bromine, or iodine, or a leaving group such for example as a trifluoromethanesulfonyloxy group.

A halogenated aryl derivative (S9) and an amide derivative (S11) are subjected to coupling reaction using a metal catalyst such for example as copper(I) iodide, copper(I) bromide, or copper(I) chloride, in a solvent that does not adversely affect the reaction such for example as DMSO, NMP, or DMF, in the presence of a base such for example as triethylamine, N,N-diisopropylethylamine, or diazabicycloundecene (DBU), so that a compound (S6) can be synthesized. Then, in a solvent that does not adversely affect the reaction such for example as THF, 1,4-dioxane, methanol, or ethanol, the compound (S6) is subjected to hydrolysis such as alkaline hydrolysis using a base such as a sodium hydroxide or lithium hydroxide, for example, or acid hydrolysis using a hydrochloric acid or trifluoroacetic acid, for example, thereby producing a desired carboxylic acid derivative (S7).

It is possible to synthesize an intermediate (S16) that is a compound of the present invention and has an amino group at the terminus as represented by the general formula (M-II) by using, for example, a method (any of production methods D, E, and F) described below or the like. In the following description, the symbols in the formulas are defined as having the same meanings as those in the formula (I) unless otherwise noted.

<Production Method D>

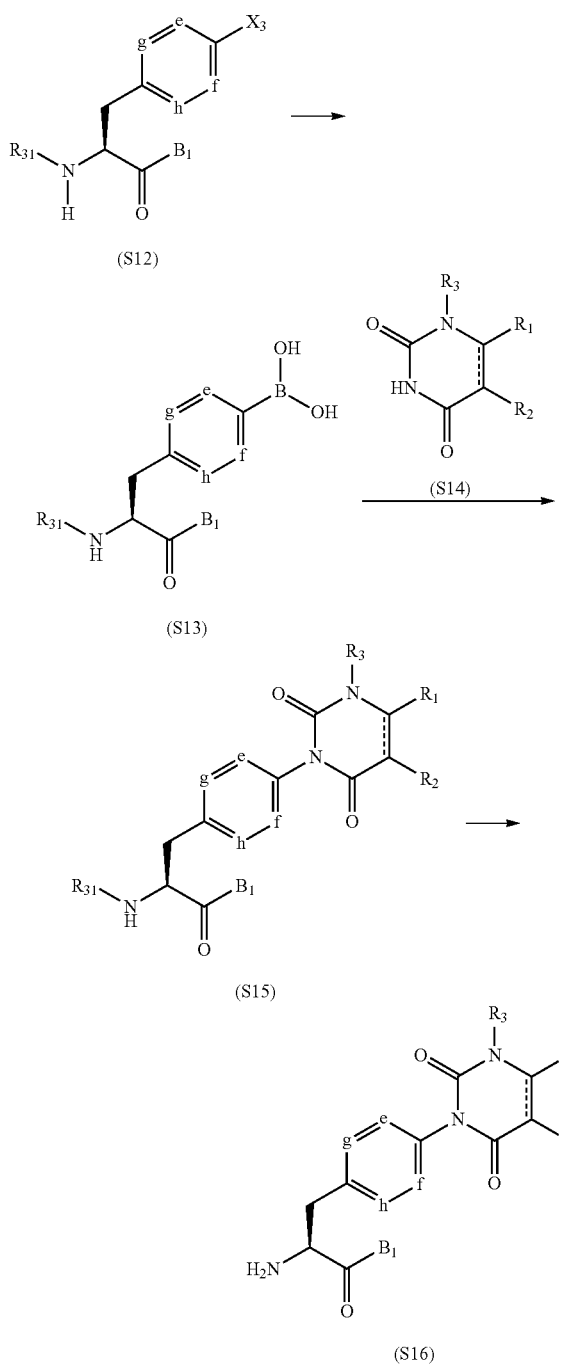

formed into the corresponding boronic acid ester derivative by coupling reaction using a metal catalyst such for example as 1,1'-bis(diphenylphosphinoferrocene)dichloropalladium (II) in a solvent which does not adversely affect the reaction such for example as DMF in the presence of a base such for example as potassium acetate. Then, the obtained boronic acid ester derivative is treated in a solvent that does not adversely affect the reaction such for example as acetone by adding, for example, a sodium periodate or ammonium acetate and water, so that the boronic acid ester is deprotected to synthesize the corresponding boronic acid derivative (S13). The boronic acid derivative (S13) thus obtained and an uracil derivative (S14) are subjected to coupling reaction using a metal catalyst such for example as copper (II) acetate or copper(II) trifluoromethanesulfonate in a solvent that does not adversely affect the reaction such for example as dichloromethane, dimethylsulfoxide (DMSO) or DMF, in the presence of a base such for example as pyridine or triethylamine, so that an amino acid derivative (S15) can be synthesized. Thereafter, the amino acid derivative (S14) is deprotected by acid hydrolysis using for example, a hydrochloric acid or trifluoroacetic acid, by hydrogenation, or by the like, so that a desired carboxylic acid derivative (S16) can be produced.

<Production Method E>

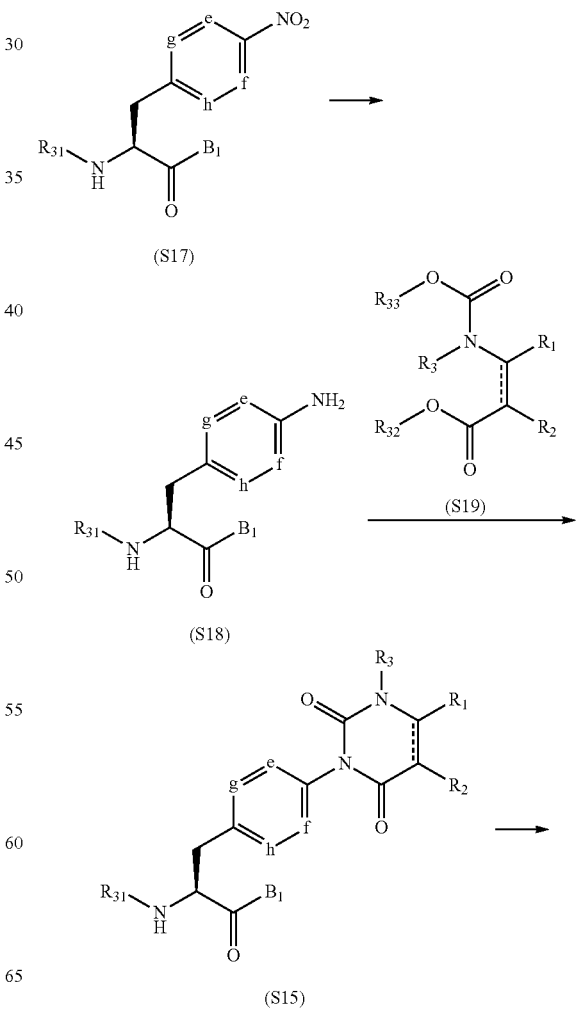

$R_{31}$ in the formulas represents a general amine substituent which can be removed by an operation such for example as deprotection, such for example as a tert-butoxycarbonyl group or a benzyloxycarbonyl group, $X_3$ in the formulas represents a halogen atom such for example as chlorine, bromine or iodine, or a leaving group such for example as a trifluoromethanesulfonyloxy group, and $B_1$ in the formulas represents a substituent which can be easily converted to B by an operation such as deprotection.

A halogenated aryl derivative (S12) and a borane derivative such for example as bis(pinacolato)diborane are trans-

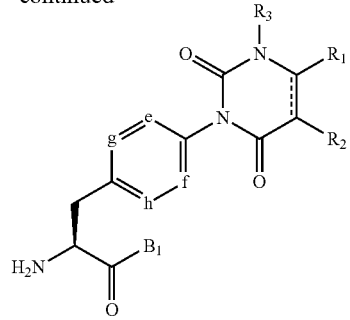

(S16)

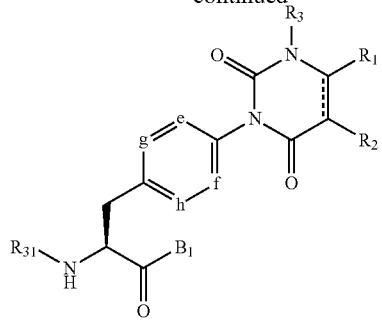

(S15)

R$_{31}$ in the formulas represents a general amine substituent which can be removed by an operation such for example as deprotection, such for example as a tert-butoxycarbonyl group or a benzyloxycarbonyl group, R$_{32}$ and R$_{33}$ in the formulas each independently represent a general ester substituent such for example as a lower alkyl group or a benzene ring which may have a substituent, and B$_1$ in the formulas represents a substituent which can be easily converted to B by an operation such as deprotection.

From a nitro derivative (S17), an aniline derivative (S18) can be synthesized: by catalytic reduction reaction using a metal catalyst such for example as palladium carbon, palladium hydroxide, or Raney nickel in a solvent that does not adversely affect this reaction such for example as methanol, ethanol, or isopropyl alcohol; or by an action of a metal such for example as zinc under an acidic condition (for example, hydrochloric acid, acetic acid, ammonium chloride, or the like). The aniline derivative (S18) thus obtained and a carbamate derivative (S19) are reacted with each other by using a base such as triethylamine, pyridine, or DBU in a solvent that does not adversely affect the reaction such for example as dichloromethane, 1,4-dioxane, THF, or DMF, so that an amino acid derivative (S15) can be synthesized. Subsequently, the amino acid derivative (S15) is deprotected by acid hydrolysis using, for example, hydrochloric acid or trifluoroacetic acid, by hydrogenation, or by the like, so that a desired carboxylic acid derivative (S16) can be produced.

<Production Method F>

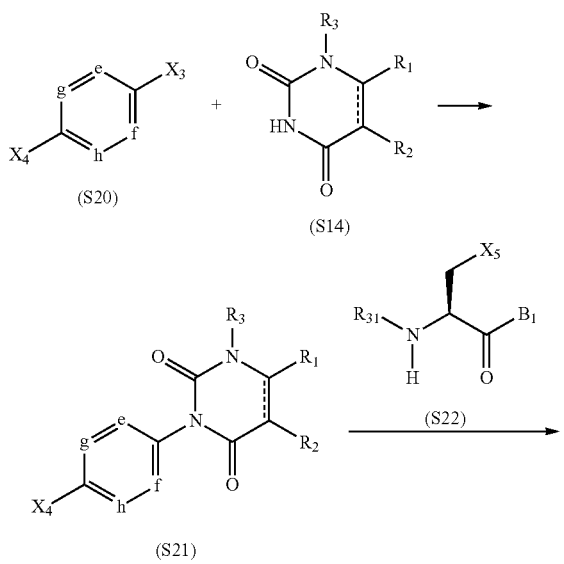

(S20) (S14) (S21) (S22)

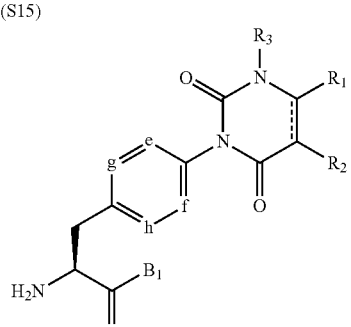

(S16)

R$_{31}$ in the formulas represents a general amine substituent which can be removed by an operation such for example as deprotection, such for example as a tert-butoxycarbonyl group or a benzyloxycarbonyl group, X$_3$, X$_4$ and X$_5$ in the formulas each independently represent a halogen atom such for example as chlorine, bromine, or iodine, or a leaving group such for example as a trifluoromethanesulfonyloxy group, and B$_1$ in the formulas represents a substituent which can be easily converted to B by an operation such as deprotection.

A halogenated aryl derivative (S20) and a uracil derivative (S14) are subjected to coupling reaction using a metal catalyst such for example as copper(I) iodide, copper(I) bromide, or copper(I) chloride in a solvent that does not adversely affect the reaction such for example as DMSO, NMP, or DMF, in the presence of a base such for example as triethylamine, N,N-diisopropylethylamine, or DBU, so that a compound (S21) can be synthesized. The compound (S21) thus obtained and a halide (S22) are subjected to Negishi coupling reaction using a metal catalyst such for example as tris(dibenzylideneacetone)dipalladium(0) and a ligand commonly used in organic synthesis such for example as 2-dicyclohexyl-2',6'-dimethoxybiphenyl (SPhos) in a solvent that does not adversely affect the reaction such for example as DMF in the presence of, for example, zinc powder activated by iodine or the like, so that an amino acid derivative (S15) can be synthesized. Subsequently, the amino acid derivative (S15) is deprotected by acid hydrolysis using, for example, a hydrochloric acid or trifluoroacetic acid, by hydrogenation, or by the like, so that a desired carboxylic acid derivative (S16) can be produced.

The present invention is described in more detail based on Synthesis Examples, Examples and Test Examples presented below. These examples are just preferable embodiments of the present invention, and the present invention should not be limited to Synthesis Examples, Examples, and Test Examples, but may be altered without deviating from the scope of the present invention. In addition, reagents, apparatuses, and materials used in the present invention are commercially available unless otherwise noted.

A common intermediate, specifically, methyl 4-amino-2,5-difluoro-benzoate can be synthesized in accordance with the method described in Patent Literature (WO2013/161904).

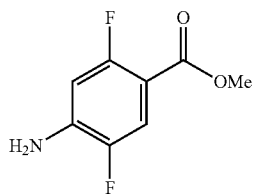

Synthesis Examples for the intermediate to be used to synthesize compounds in Examples are described below.

SYNTHESIS EXAMPLE 1

4-[[4-(2,2-dimethylpropanoylamino)phenyl]sulfonylamino]-2,5-difluoro-benzoic acid

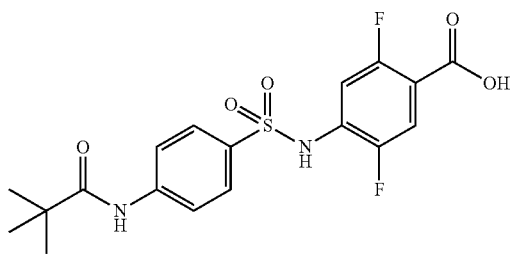 [SMILES: CC(C)(C)C(=O)Nc1ccc(S(=O)(=O)Nc2cc(F)c(C(=O)O)cc2F)cc1]

(Step 1)

Synthesis of Methyl 2,5-difluoro-4-[(4-nitrophenyl)sulfonylamino]benzoate

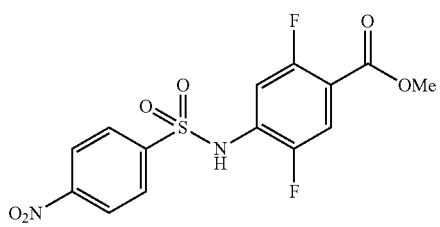 [SMILES: COC(=O)c1cc(F)c(NS(=O)(=O)c2ccc([N+](=O)[O-])cc2)cc1F]

A 4-nitro benzene sulfonyl chloride (8.9 g, 40.1 mmol) was added to a pyridine solution (30 ml) of methyl 4-amino-2,5-difluoro-benzoate (3.0 g, 16.0 mmol), followed by stirring at 50° C. for 18 hours. The resultant mixture was concentrated under reduced pressure, and the residue was slurry washed using acetonitrile to obtain methyl 4-[bis[(4-nitrophenyl)sulfonyl]amino]-2,5-difluoro-benzoate (11.6 g). To the obtained substance, THF (30 mL) was added, a 1 M tetrabutylammonium fluoride/THF solution (8.4 mL) was added, and the mixture was stirred at room temperature for 30 minutes. The mixture was concentrated under reduced pressure, diluted with ethyl acetate, and washed sequentially with 0.5 M hydrochloric acid and a saturated saline solution. After the resultant was dried with anhydrous magnesium sulfate and was concentrated under reduced pressure, the residue was slurry washed with hexane/ethyl acetate (7/3) to give the title compound (5.3 g, 89%).

$^1$H NMR (400 MHz, Chloroform-d) δ 8.39-8.32 (m, 2H), 8.09-8.02 (m, 2H), 7.62 (dd, J=10.5, 6.2 Hz, 1H), 7.46 (dd, J=11.0, 6.3 Hz, 1H), 7.08 (s, 1H), 3.90 (s, 3H); MS (ESI) m/z 373 [M+H]$^+$ (Step 2)

Synthesis of Methyl 4-[(4-aminophenyl)sulfonylamino]-2,5-difluoro-benzoate

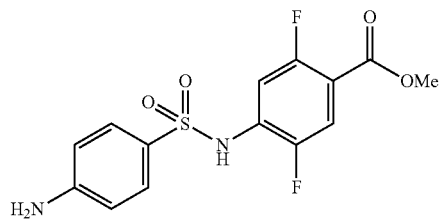

10% palladium carbon (0.4 g) and methanol (2.0 mL) were added to an ethyl acetate suspension (10.5 mL) of the compound (2.4 g, 6.4 mmol) obtained in (step 1), and the mixture was stirred under a hydrogen atmosphere at room temperature for 18 hours. After filtration through celite and concentration under reduced pressure, the residue was purified by silica gel column chromatography to give the title compound (1.9 g, 84%).

$^1$H NMR (400 MHz, Chloroform-d) δ 7.69-7.61 (m, 2H), 7.58 (dd, J=10.7, 6.3 Hz, 1H), 7.38 (dd, J=11.6, 6.5 Hz, 1H), 6.98 (d, J=12.5 Hz, 1H), 6.63 (d, J=8.8 Hz, 2H), 3.89 (s, 3H); MS (ESI) m/z 343[M+H]$^+$ (Step 3)

Synthesis of Methyl 4-[[4-(2,2-dimethylpropanoylamino)phenyl]sulfonylamino]-2,5-difluoro-benzoate

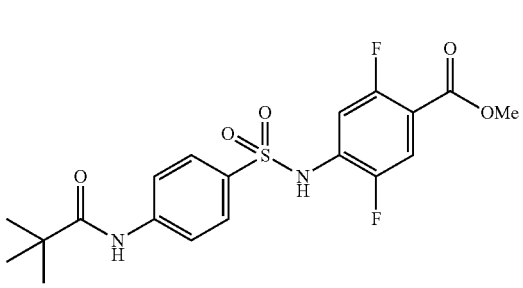 [SMILES: COC(=O)c1cc(F)c(NS(=O)(=O)c2ccc(NC(=O)C(C)(C)C)cc2)cc1F]

Triethylamine (1.6 mL, 12 mmol) and pivaloyl chloride (0.70 mL, 5.7 mmol) were added sequentially to a dichloromethane suspension (30 mL) of the compound (1.9 g, 5.4 mmol) obtained in (step 2), and the mixture was stirred at room temperature for 1 hour. Water was added to the mixture, followed by extraction with dichloromethane and washing with a saturated ammonium chloride aqueous solution and a saturated saline solution in turn. After the resultant was dried with anhydrous magnesium sulfate and was concentrated under reduced pressure, the residue was slurry washed with acetonitrile to give the title compound (2.1 g, 91%).

MS (ESI) m/z 427 [M+H]⁺

(Step 4)

Synthesis of 4-[[4-(2,2-dimethylpropanoylamino) phenyl]sulfonylamino]-2,5-difluoro-benzoic acid

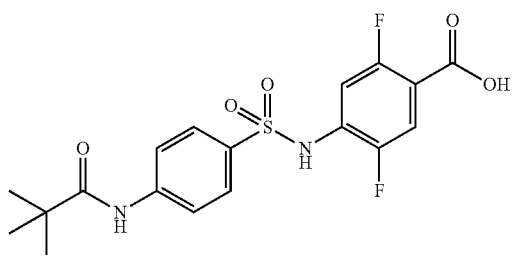 [SMILES: CC(C)(C)C(=O)Nc1ccc(S(=O)(=O)Nc2cc(F)c(C(=O)O)cc2F)cc1]

A 1 M sodium hydroxide aqueous solution (12 mL) was added to a 1,4-dioxane solution (36 mL) of the compound (2.1 g, 4.9 mmol) obtained in (step 3) and the mixture was stirred at room temperature for 18 hours. After the resultant mixture was neutralized with 1 M hydrochloric acid and was concentrated under reduced pressure, ethyl acetate and a saturated ammonium chloride aqueous solution were added to the mixture. The mixture was subjected to extraction with ethyl acetate, followed by washing with a saturated saline solution, and then drying with anhydrous magnesium sulfate. The resultant was concentrated under reduced pressure, and the residue was slurry washed with ethyl acetate/hexane (7/3) to give the title compound (1.8 g, 88%).

¹H NMR (400 MHz, DMSO-d₆) δ 10.86 (s, 1H), 9.59 (s, 1H), 7.91-7.83 (m, 2H), 7.81-7.71 (m, 2H), 7.56 (dd, J=10.7, 6.5 Hz, 1H), 7.18 (dd, J=12.0, 6.3 Hz, 1H), 1.22 (s, 8H); MS (ESI) m/z 413 [M+H]⁺

Compounds in [Synthesis Example 2], [Synthesis Example 3], [Synthesis Example 5], [Synthesis Example 6], [Synthesis Example 8] to [Synthesis Example 10], [Synthesis Example 12], [Synthesis Example 13], and [Synthesis Example 15] can be synthesized in a method similar to that of the compound in [Synthesis Example 1] by condensing the compound obtained in (step 2) in [Synthesis Example 1] with the corresponding carboxylic acid or acid chloride.

SYNTHESIS EXAMPLE 2

4-[(4-acetamidophenyl)sulfonylamino]-2,5-difluoro-benzoic acid

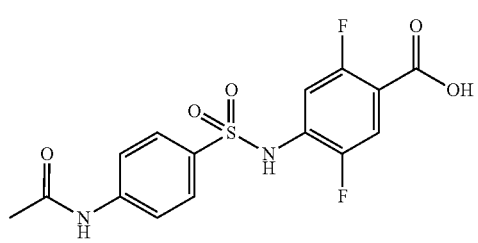 [SMILES: CC(=O)Nc1ccc(S(=O)(=O)Nc2cc(F)c(C(=O)O)cc2F)cc1]

MS (ESI) m/z 371 [M+H]⁺

SYNTHESIS EXAMPLE 3

4-[[4-(2-ethylbutanoylamino)phenyl]sulfonylamino]-2,5-difluoro-benzoic acid

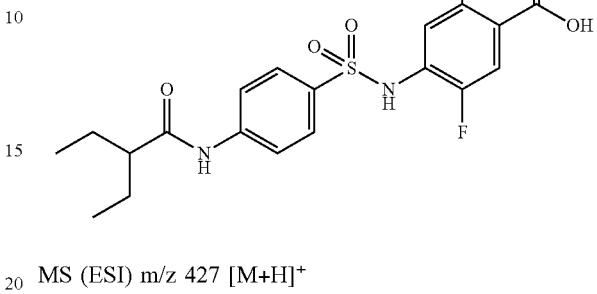

MS (ESI) m/z 427 [M+H]⁺

SYNTHESIS EXAMPLE 4

4-[[4-(tert-butylcarbamoylamino)phenyl]sulfonylamino]-2,5-difluoro-benzoic acid

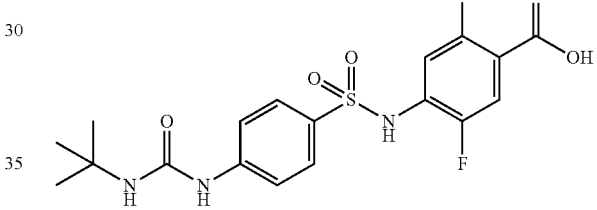

(Step 1)

Synthesis of Methyl 4-[[4-(tert-butylcarbamoylamino)phenyl]sulfonylamino]-2,5-difluoro-benzoate

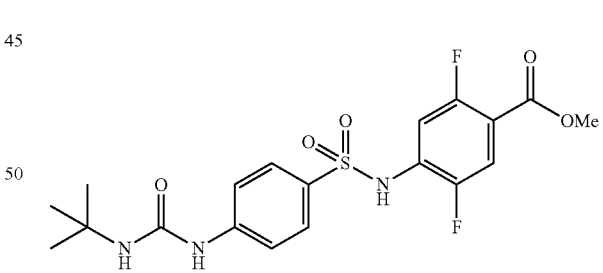

To a dichloromethane solution (3 ml) of the compound (100 mg, 0.29 mmol) obtained in (step 1) in [Synthesis Example 1], 4-nitrophenyl chloroformate (118 mg, 0.58 mmol) and N,N-diisopropylethylamine (298 µl, 1.75 mmol) were added sequentially, and the mixture was stirred at room temperature for 30 minutes. Then, tert-butylamine (124 µl, 1.17 mmol) was added to the mixture, followed by stirring at room temperature for 3 hours. After the reaction solution was concentrated under reduced pressure, the residue was subjected to reverse phase HPLC using ODS as a packing material for elution with a mixed solution of water and acetonitrile containing 0.1% (v/v) of trifluoroacetic acid, and the targeted fraction was freeze-dried to give a trifluoroacetate salt of the title compound (15 mg, 10%).
MS (ESI) m/z 442 [M+H]+
(Step 2)

Synthesis of 4-[[4-(tert-butylcarbamoylamino)phenyl]sulfonylamino]-2,5-difluoro-benzoic acid

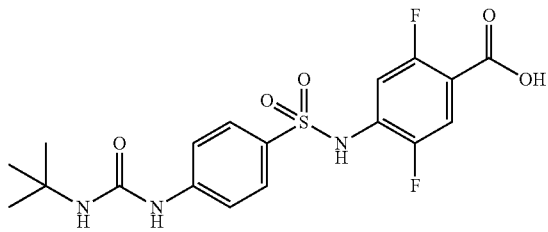 [SMILES: CC(C)(C)NC(=O)Nc1ccc(S(=O)(=O)Nc2cc(F)c(C(=O)O)cc2F)cc1]

A 1 M lithium hydroxide aqueous solution (204 µl) was added to a 1,4-dioxane solution (1 ml) of the compound (15 mg, 0.034 mmol) obtained in (step 1), and the mixture was stirred at room temperature for 2 hours. After the reaction solution was concentrated under reduced pressure, the residue was subjected to reverse phase HPLC using ODS as a packing material and was purified in the same method as (step 1) to give the title compound (9.5 mg, 65%).
MS (ESI) m/z 428 [M+H]+

SYNTHESIS EXAMPLE 5

4-[[4-[(1-tert-butoxycarbonylpiperidine-4-carbonyl)amino]phenyl]sulfonylamino]-2,5-difluoro-benzoic acid

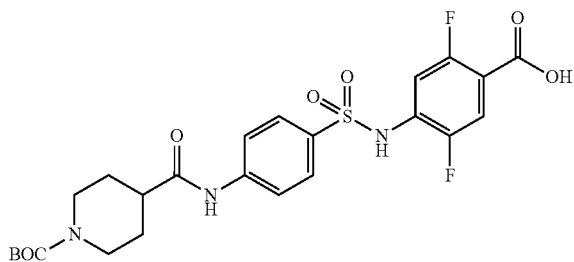 [SMILES: CC(C)(C)OC(=O)N1CCC(C(=O)Nc2ccc(S(=O)(=O)Nc3cc(F)c(C(=O)O)cc3F)cc2)CC1]

MS (ESI) m/z 540 [M+H]+

SYNTHESIS EXAMPLE 6

2,5-difluoro-4-[[4-(pyridine-4-carbonylamino)phenyl]sulfonylamino]benzoic acid

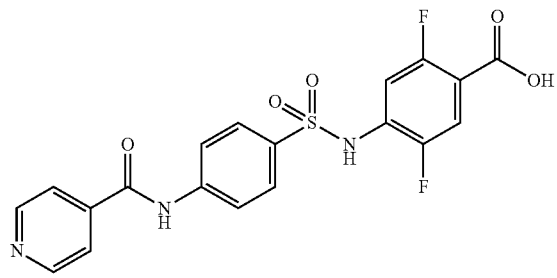 [SMILES: O=C(Nc1ccc(S(=O)(=O)Nc2cc(F)c(C(=O)O)cc2F)cc1)c1ccncc1]

MS (ESI) m/z 434 [M+H]+

Compounds in [Synthesis Example 7], [Synthesis Example 11], [Synthesis Example 14], [Synthesis Example 19], [Synthesis Example 20], and [Synthesis Example 21] can be synthesized in a method similar to that of the compound in [Synthesis Example 1] by causing the corresponding nitro aryl sulfonyl chloride reagent to act on methyl 4-amino-2,5-difluoro-benzoate in (step 1) in [Synthesis Example 1].

SYNTHESIS EXAMPLE 7

4-[[4-(2,2-dimethylpropanoylamino)-3-fluoro-phenyl]sulfonylamino]-2,5-difluoro-benzoic acid

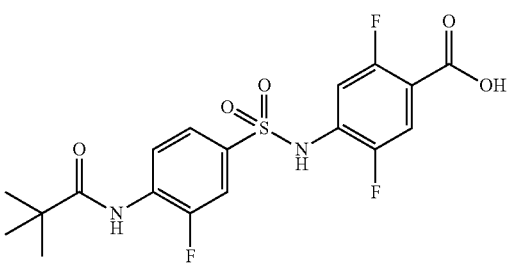 [SMILES: CC(C)(C)C(=O)Nc1ccc(S(=O)(=O)Nc2cc(F)c(C(=O)O)cc2F)cc1F]

MS (ESI) m/z 431 [M+H]+

SYNTHESIS EXAMPLE 8

2,5-difluoro-4-[[4-(tetrahydropyran-4-carbonylamino)phenyl]sulfonylamino]benzoic acid

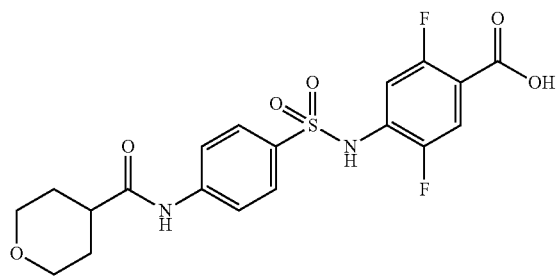 [SMILES: O=C(O)c1cc(F)c(NS(=O)(=O)c2ccc(NC(=O)C3CCOCC3)cc2)cc1F]

MS (ESI) m/z 441 [M+H]+

SYNTHESIS EXAMPLE 9

2,5-difluoro-4-[[4-[(1-methoxycyclopropanecarbonyl)amino]phenyl]sulfonylamino]benzoic acid

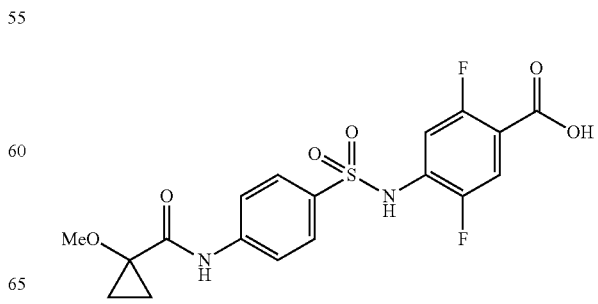

MS (ESI) m/z 427 [M+H]+

SYNTHESIS EXAMPLE 10

2,5-difluoro-4-[[4-[(3-hydroxy-2,2-dimethyl-propanoyl)amino]phenyl]sulfonylamino]benzoic acid

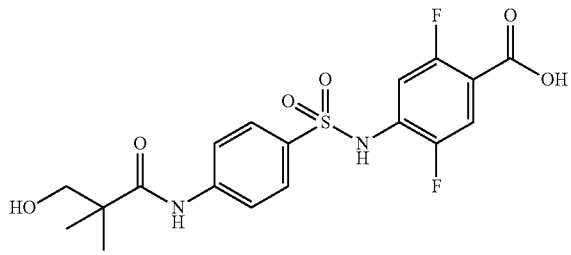 [SMILES: CC(C)(CO)C(=O)Nc1ccc(S(=O)(=O)Nc2cc(F)c(C(=O)O)cc2F)cc1]

MS (ESI) m/z 429 [M+H]$^+$

SYNTHESIS EXAMPLE 11

4-[[5-(2,2-dimethylpropanoylamino)-2-pyridyl]sulfonylamino]-2,5-difluoro-benzoic acid

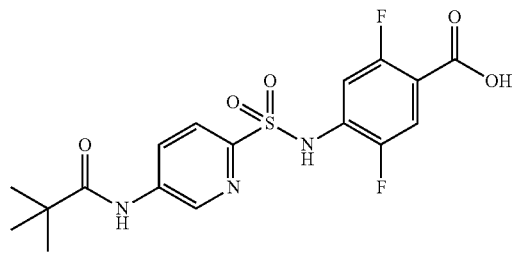

MS (ESI) m/z 414 [M+H]$^+$

SYNTHESIS EXAMPLE 12

2,5-difluoro-4-[[4-[[1-(trifluoromethyl)cyclopropanecarbonyl]amino]phenyl]sulfonylamino]benzoic acid

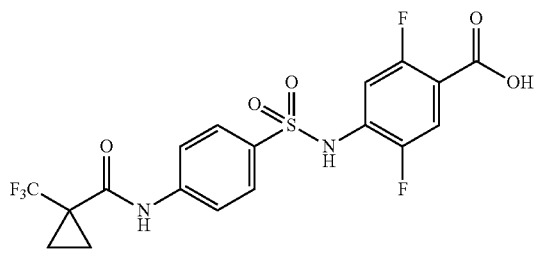 [SMILES: O=C(O)c1cc(F)c(NS(=O)(=O)c2ccc(NC(=O)C3(C(F)(F)F)CC3)cc2)cc1F]

MS (ESI) m/z 465 [M+H]$^+$

SYNTHESIS EXAMPLE 13

2,5-difluoro-4-[[4-[(1-hydroxycyclopropanecarbonyl)amino]phenyl]sulfonylamino]benzoic acid

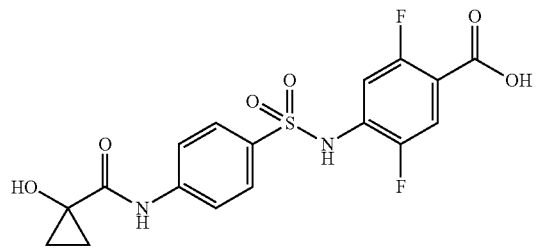 [SMILES: O=C(O)c1cc(F)c(NS(=O)(=O)c2ccc(NC(=O)C3(O)CC3)cc2)cc1F]

MS (ESI) m/z 413 [M+H]$^+$

SYNTHESIS EXAMPLE 14

4-[[6-(2,2-dimethylpropanoylamino)-3-pyridyl]sulfonylamino]-2,5-difluoro-benzoic acid

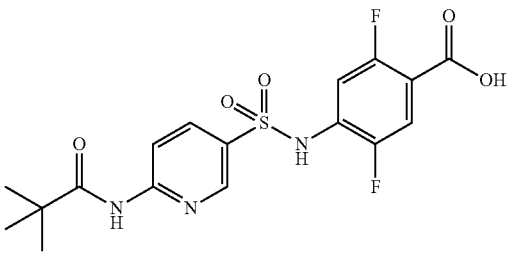 [SMILES: CC(C)(C)C(=O)Nc1ccc(S(=O)(=O)Nc2cc(F)c(C(=O)O)cc2F)cn1]

MS (ESI) m/z 414 [M+H]$^+$

SYNTHESIS EXAMPLE 15

2,5-difluoro-4-[[4-[(1-phenylcyclopropanecarbonyl)amino]phenyl]sulfonylamino]benzoic acid

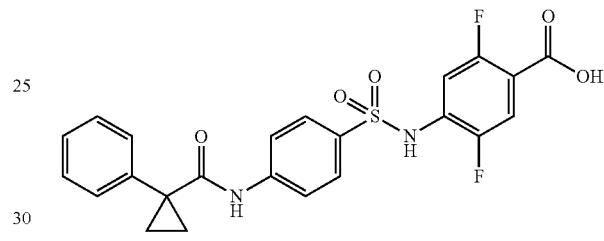

MS (ESI) m/z 473 [M+H]$^+$

SYNTHESIS EXAMPLE 16

2,5-difluoro-4-[[4-(2-oxo-4-tetrahydropyran-4-yl-1-pyridyl)phenyl]sulfonylamino]benzoic acid

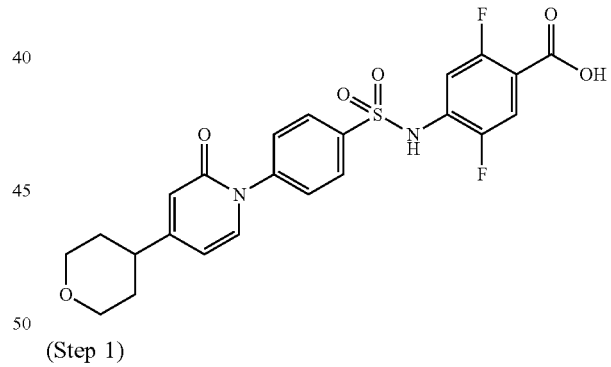

(Step 1)

Synthesis of Methyl 4-[[4-(4-bromo-2-oxo-1-pyridyl)-4-methylene-cyclohexa-1,5-dien-1-yl]sulfonylamino]-2,5-difluoro-benzoate

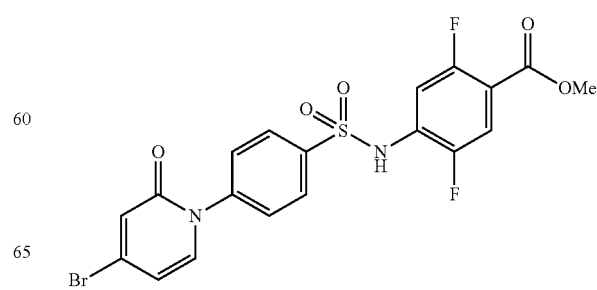

[4-[(2,5-difluoro-4-methoxycarbonyl-phenyl)sulfamoyl]-1-methylene-cyclohexa-2,4-dien-1-yl]boronic acid (0.11 g, 0.30 mmol), a preparation method of which is described in Patent Document (WO2015/064580), copper(II) acetate (52 mg, 0.29 mmol), and N,N-diisopropylethylamine (98 µl) were sequentially added to a DMF solution (2.0 ml) of 4-bromo-1H-pyridin-2-one (50 mg, 0.29 mmol), and the mixture was stirred at 60° C. for 18 hours. The reaction solution was concentrated under reduced pressure, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (33 mg, 23%).
MS (ESI) m/z 499 [M+H]+
(Step 2)

Synthesis of Methyl 4-[[4-[4-(3,6-dihydro-2H-pyran-4-yl)-2-oxo-1-pyridyl]-4-methylene-cyclohexa-1,5-dien-1-yl]sulfonylamino]-2,5-difluorobenzoate

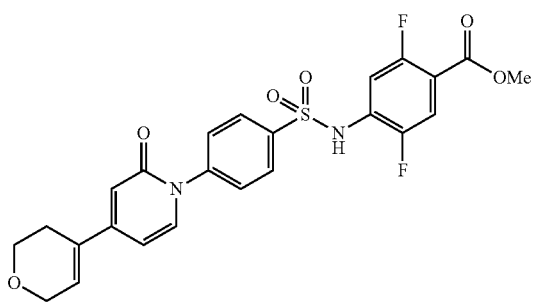 [SMILES: COC(=O)c1cc(F)c(NS(=O)(=O)c2ccc(-n3ccc(C4=CCOCC4)cc3=O)cc2)cc1F]

A 1 M sodium carbonate aqueous solution (0.5 ml) was added to an acetonitrile solution (1.5 ml) of the compound (33 mg, 0.066 mmol) obtained in (step 1). Then, 2-(3,6-dihydro-2H-pyran-4-yl)-4,4,5,5-tetramethyl-1,3,2-dioxaborolane (21 mg, 0.10 mmol) and bistriphenylphosphine dichloropalladium(II) (2.3 mg, 0.0032 mmol) were sequentially added to the mixture to cause the reaction to proceed in a microwave device (at 130° C., for 10 minutes). The reaction solution was concentrated under reduced pressure, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (27 mg, 82%).
MS (ESI) m/z 503 [M+H]+
(Step 3)

Synthesis of 2,5-difluoro-4-[[4-(2-oxo-4-tetrahydropyran-4-yl-1-pyridyl)phenyl]sulfonylamino]benzoic acid

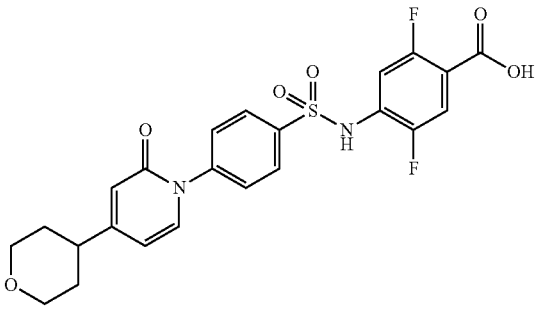 [SMILES: O=C(O)c1cc(F)c(NS(=O)(=O)c2ccc(-n3ccc(C4CCOCC4)cc3=O)cc2)cc1F]

10% of palladium carbon was added to a methanol solution (3.0 ml) of the compound (27 mg, 0.054 mmol) obtained in (step 2), and the mixture was stirred under a hydrogen atmosphere at room temperature for 2 hours. The reaction solution was concentrated under reduced pressure, and the residue was dissolved in methanol (2.0 ml). A 4 M lithium hydroxide aqueous solution (0.6 ml) was added to the resultant, and the obtained mixture was stirred at room temperature for 18 hours. Then, the mixture was neutralized with 1 M hydrochloric acid and was concentrated under reduced pressure. After that, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (13 mg, 50%).
MS (ESI) m/z 491 [M+H]+

Compounds in [Synthesis Example 17] and [Synthesis Example 18] can be synthesized in a method similar to that of the compound in [Synthesis Example 16] by causing N-Methyltrimethylacetamide or 1,5,5-trimethylhydantoin to act in (step 1) in [Synthesis Example 16].

SYNTHESIS EXAMPLE 17

4-[[4-[2,2-dimethylpropanoyl(methyl)amino]phenyl]sulfonylamino]-2,5-difluoro-benzoic acid

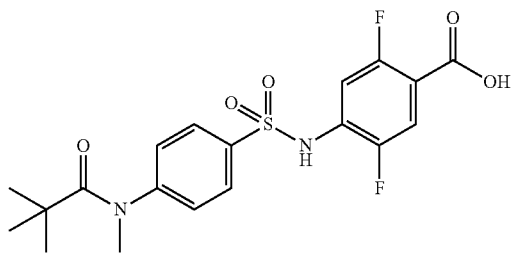 [SMILES: CN(C(=O)C(C)(C)C)c1ccc(S(=O)(=O)Nc2cc(F)c(C(=O)O)cc2F)cc1]

MS (ESI) m/z 427 [M+H]+

SYNTHESIS EXAMPLE 18

2,5-difluoro-4-[[4-(3,4,4-trimethyl-2,5-dioxo-imidazolidin-1-yl)phenyl]sulfonylamino]benzoic acid

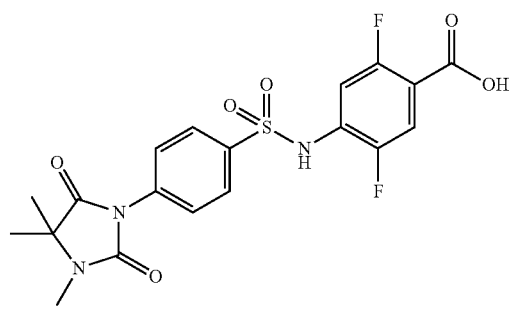 [SMILES: CN1C(=O)N(c2ccc(S(=O)(=O)Nc3cc(F)c(C(=O)O)cc3F)cc2)C(=O)C1(C)C]

MS (ESI) m/z 454 [M+H]+

SYNTHESIS EXAMPLE 19

4-[[3-(2,2-dimethylpropanoylamino)phenyl]sulfonylamino]-2,5-difluoro-benzoic acid

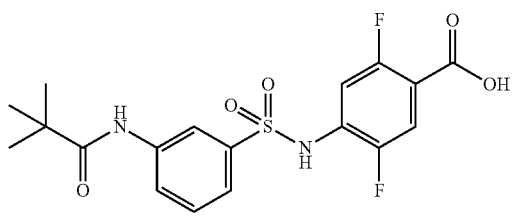 [SMILES: CC(C)(C)C(=O)Nc1cccc(S(=O)(=O)Nc2cc(F)c(C(=O)O)cc2F)c1]

MS (ESI) m/z 413 [M+H]$^+$

SYNTHESIS EXAMPLE 20

4-[[5-(2,2-dimethylpropanoylamino)-2-thienyl]sulfonylamino]-2,5-difluoro-benzoic acid

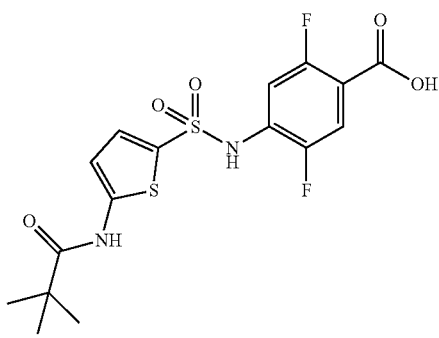 [SMILES: CC(C)(C)C(=O)Nc1ccc(S(=O)(=O)Nc2cc(F)c(C(=O)O)cc2F)s1]

MS (ESI) m/z 419 [M+H]$^+$

SYNTHESIS EXAMPLE 21

4-[[4-(2,2-dimethylpropanoylamino)-2-thienyl]sulfonylamino]-2,5-difluoro-benzoic acid

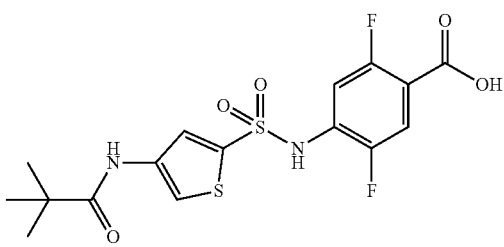 [SMILES: CC(C)(C)C(=O)Nc1csc(S(=O)(=O)Nc2cc(F)c(C(=O)O)cc2F)c1]

MS (ESI) m/z 419 [M+H]$^+$

Compounds in [Synthesis Example 22], [Synthesis Example 26], [Synthesis Example 28], [Synthesis Example 29], [Synthesis Example 32], [Synthesis Example 33], and [Synthesis Example 36] can be synthesized in accordance with a method described in Patent Literature (WO2013/161904).

SYNTHESIS EXAMPLE 22

Methyl (2S)-2-amino-3-[4-(1-methyl-2,4-dioxo-pyrido[3,4-d]pyrimidin-3-yl)phenyl]propanoate

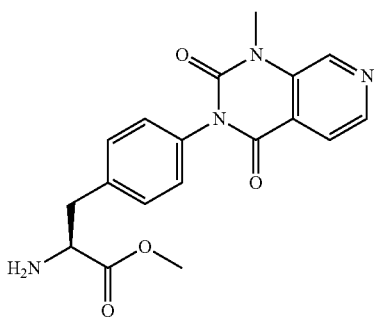 [SMILES: COC(=O)[C@@H](N)Cc1ccc(-n2c(=O)c3ccncc3n(C)c2=O)cc1]

SYNTHESIS EXAMPLE 23

Methyl (2S)-2-amino-3-[4-(3,4,5-trimethyl-2,6-dioxo-pyrimidin-1-yl)phenyl]propanoate

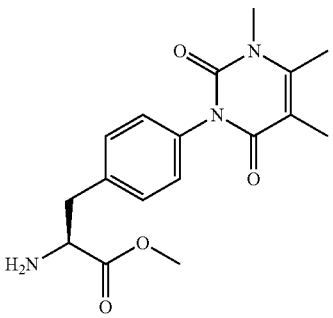 [SMILES: COC(=O)[C@@H](N)Cc1ccc(-n2c(=O)c(C)c(C)n(C)c2=O)cc1]

(Step 1)

Synthesis of Methyl (2S)-2-(tert-butoxycarbonylamino)-3-[4-(5,6-dimethyl-2,4-dioxo-1H-pyrimidin-3-yl)phenyl]propanoate

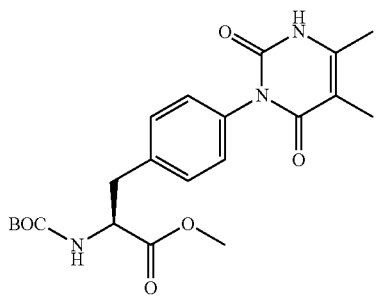 [SMILES: COC(=O)[C@H](Cc1ccc(-n2c(=O)[nH]c(C)c(C)c2=O)cc1)NC(=O)OC(C)(C)C]

Copper acetate (5.2 g, 29 mmol), 5,6-dimethyluracil (4.0 g, 29 mmol), and triethylamine (10 ml) were sequentially added to a dichloromethane solution (100 ml) of [4-[(2S)-2-(tert-butoxycarbonylamino)-3-methoxy-3-oxo-propyl]phenyl]boronic acid (9.2 g, 29 mmol), a production method of which is described in Patent Literature (WO2013/161904), and the mixture was stirred at room temperature for 18 hours. The reaction solution was filtered through celite, followed by concentration under reduced pressure. Thereafter, the residue was purified by silica gel column chromatography (petroleum ether: ethyl acetate=5:1 to 1:1) to give the title compound (0.83 g, 7%).

1H NMR (CDCl$_3$, 400 MHz) δ 8.90 (s, 1H), 7.26 (d, J=8.4 Hz, 2H), 7.17 (d, J=7.8 Hz, 2H), 5.06 (d, J=8.7 Hz, 1H), 4.64-4.59 (m, 1H), 3.72 (s, 3H), 3.15 (d, J=6.3 Hz, 2H), 2.16 (s, 3H), 1.95 (s, 3H), 1.44 (s, 9H).; MS (ESI) m/z 418 [M+H]+

(Step 2)

Synthesis of Methyl (2S)-2-(tert-butoxycarbonylamino)-3-[4-(3,4,5-trimethyl-2,6-dioxo-pyrimidin-1-yl)phenyl]propanoate

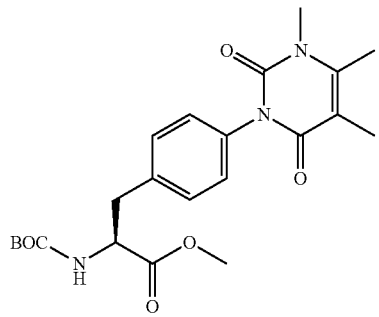 [SMILES: COC(=O)[C@H](Cc1ccc(-n2c(=O)c(C)c(C)n(C)c2=O)cc1)NC(=O)OC(C)(C)C]

Potassium carbonate (0.85 g, 6.0 mmol) and methyl iodide (0.4 ml) were sequentially added to a DMF solution (15 ml) of the compound (0.83 g, 2.0 mmol) obtained in (step 1), and the mixture was stirred at room temperature for 1 hour 30 minutes. The reaction solution was concentrated under reduced pressure, and water (20 ml) and ethyl acetate (30 ml) were added thereto. The resultant mixture was subjected to three times of extractions with ethyl acetate, and the organic layer was dried with sodium sulfate. Then, the resultant was concentrated under reduced pressure to give the title compound (0.64 g, 75%).

1H NMR (CDCl$_3$, 400 MHz) δ 8.02 (s, 1H), 7.24 (d, J=8.4 Hz, 2H), 7.13 (d, J=8.4 Hz, 1H), 5.05 (d, J=8.0 Hz, 1H), 4.63-4.58 (m, 1H), 3.71 (s, 3H), 3.47 (s, 3H), 3.13 (d, J=6.0 Hz, 2H), 2.33 (s, 3H), 2.02 (s, 3H), 1.43 (s, 9H).; MS (ESI) m/z 432 [M+H]+

(Step 3)

Synthesis of Methyl (2S)-2-amino-3-[4-(3,4,5-trimethyl-2,6-dioxo-pyrimidin-1-yl)phenyl]propanoate

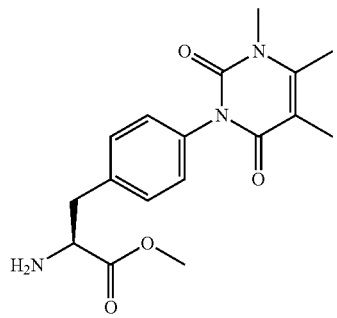 [SMILES: COC(=O)[C@@H](N)Cc1ccc(-n2c(=O)c(C)c(C)n(C)c2=O)cc1]

The compound (0.64 g, 1.5 mmol) obtained in (Step 2) was dissolved in a 4 M hydrochloric acid/ethyl acetate solution (40 ml), and the mixture was stirred at room temperature for 1 hour. The reaction solution was concentrated under reduced pressure, and ethyl acetate (30 ml) was added thereto. After stirring at room temperature for 30 minutes, the solid was collected by filtration to give a hydrochloride salt of the title compound (0.46 g, 93%).

1H NMR (CD$_3$OD, 400 MHz) δ 7.31 (d, J=8.0 Hz, 2H), 7.13 (d, J=8.4 Hz, 2H), 4.31-4.27 (m, 1H), 3.78 (s, 3H), 3.38 (s, 3H), 3.37-3.32 (m, 1H), 3.09-3.03 (m, 1H), 2.30 (s, 3H), 1.91 (s, 3H).; MS (ESI) m/z 332[M+H]+

SYNTHESIS EXAMPLE 24

Isopropyl (2S)-2-amino-3-[4-(1,7-dimethyl-2,4-dioxo-6,8-dihydro-5H-pyrido[3,4-d]pyrimidin-3-yl)phenyl]propanoate

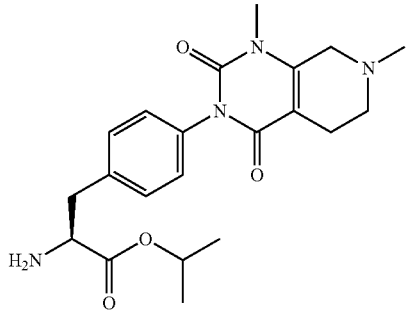 [SMILES: CC(C)OC(=O)[C@@H](N)Cc1ccc(-n2c(=O)c3c(n(C)c2=O)CN(C)CC3)cc1]

(Step 1)

Synthesis of Ethyl 1-benzyl-5-[(4-nitrophenoxy)carbonylamino]-3,6-dihydro-2H-pyridine-4-carboxylate

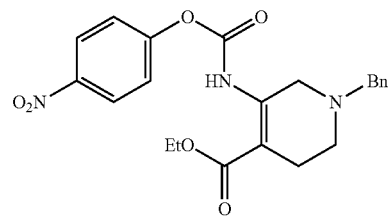 [SMILES: CCOC(=O)C1=C(NC(=O)Oc2ccc([N+](=O)[O-])cc2)CN(Cc2ccccc2)CC1]

Ammonium acetate (5.2 g, 67 mmol) was added to an ethanol solution (20 ml) of a hydrochloride of ethyl 1-benzyl-3-oxo-piperidine-4-carboxylate (2.0 g, 6.7 mmol), and the mixture was stirred at room temperature for 18 hours. The reaction solution was concentrated under reduced pressure, and dichloromethane and saturated sodium bicarbonate water were added. After two times of extractions with dichloromethane, the organic layer was washed with a saturated sodium chloride aqueous solution. After drying with anhydrous magnesium sulfate, the resultant was concentrated under reduced pressure, and the residue was dissolved in dichloromethane (50 ml). Pyridine (0.6 ml) was added, and then 4-nitrophenyl chloroformate (1.4 g, 6.7 mmol) was added under ice cooling, followed by stirring at the same temperature for 5 hours. The reaction solution was concentrated under reduced pressure, and the residue was purified by silica gel column chromatography to give the title compound (0.49 g, 16%).
(Step 2)

Synthesis of Isopropyl (2S)-3-(4-aminophenyl)-2-(tert-butoxycarbonylamino)propanoate

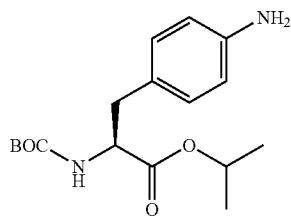 [SMILES: CC(C)OC(=O)[C@H](Cc1ccc(N)cc1)NC(=O)OC(C)(C)C]

Potassium carbonate (3 g, 22 mmol) and 2-iodopropane (2.0 ml) were sequentially added to a DMF solution (15 ml) of (2S)-2-(tert-butoxycarbonylamino)-3-(4-nitrophenyl)propanoic acid (2 g, 6.4 mmol), and the mixture was stirred at room temperature for 18 hours. Water was added to the reaction solution, the mixture was subjected to three times of extractions with a mixed solution of ethyl acetate and hexane (1:1), and the organic layer was washed with a saturated sodium chloride aqueous solution. After drying with anhydrous magnesium sulfate, the resultant was concentrated under reduced pressure, and the residue was dissolved in methanol (40 ml) and water (4.0 ml). Zinc powder (3.5 g, 54 mmol) and ammonium chloride (0.52 g, 9.7 mmol) were sequentially added, and the mixture was stirred at 70° C. for 1 hour 30 minutes. The reaction solution was filtered through celite, followed by concentration under reduced pressure. The residue was subjected to reverse phase HPLC using ODS as a packing material for elution with a mixed solution of water and acetonitrile containing 0.1% (v/v) of trifluoroacetic acid, and the targeted fraction was freeze-dried to give a trifluoroacetate of the title compound.
(Step 3)

Synthesis of Isopropyl (2S)-3-[4-(7-benzyl-2,4-dioxo-1,5,6,8-tetrahydropyrido[3,4-d]pyrimidin-3-yl)phenyl]-2-(tert-butoxycarbonylamino)propanoate

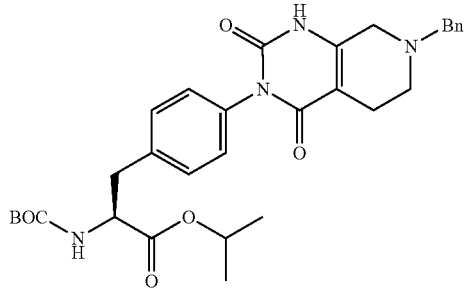 [SMILES: CC(C)OC(=O)[C@H](Cc1ccc(-n2c(=O)[nH]c3c(c2=O)CCN(Cc2ccccc2)C3)cc1)NC(=O)OC(C)(C)C]

The compound (0.50 g, 1.1 mmol) obtained in (step 2) and DBU (0.42 ml) were sequentially added to a 1,4-dioxane solution (20 ml) of the compound (0.49 g, 1.2 mmol) obtained in (step 1), and the mixture was stirred at 60° C. for 18 hours. The reaction solution was concentrated under reduced pressure, and ethyl acetate and water were added thereto. After two times of extractions with ethyl acetate, the organic layer was washed with a saturated sodium chloride aqueous solution and then was dried with anhydrous magnesium sulfate. After concentration under reduced pressure, the residue was subjected to reverse phase HPLC using ODS as a packing material, and was purified in the same method as (step 1) in [Synthesis Example 4] to give a trifluoroacetate of the title compound (0.40 g, 51%).
(Step 4)

Synthesis of Isopropyl (2S)-3-[4-(7-benzyl-1,7-dimethyl-2,4-dioxo-6,8-dihydro-5H-pyrido[3,4-d]pyrimidin-7-ium-3-yl)phenyl]-2-(tert-butoxycarbonylamino)propanoate

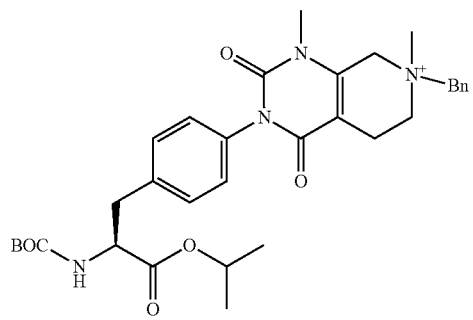 [SMILES: CC(C)OC(=O)[C@H](Cc1ccc(-n2c(=O)c3c(n(C)c2=O)C[N+](C)(Cc2ccccc2)CC3)cc1)NC(=O)OC(C)(C)C]

Potassium carbonate (0.30 g, 2.2 mmol) and methyl iodide (0.22 ml, 3.5 mmol) were sequentially added to a DMF solution (3.5 ml) of the compound (0.40 g, 0.59 mmol) obtained in (step 3), and the mixture was stirred at room temperature for 3 hours. The reaction solution was concentrated under reduced pressure, and then the residue was subjected to reverse phase HPLC using ODS as a packing material, and was purified in the same manner as in (Step 2) to give a trifluoroacetate of the title compound (0.30 g, 71%).
(Step 5)

Synthesis of Isopropyl (2S)-2-amino-3-[4-(1,7-dimethyl-2,4-dioxo-6,8-dihydro-5H-pyrido[3,4-d]pyrimidin-3-yl)phenyl]propanoate

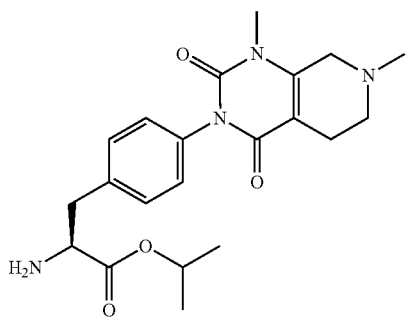 [SMILES: CC(C)OC(=O)[C@@H](N)Cc1ccc(-n2c(=O)c3c(n(C)c2=O)CN(C)CC3)cc1]

10% palladium carbon (50 mg) was added to an isopropyl alcohol solution (5.0 ml) of the compound (0.30 g, 0.43 mmol) obtained in (step 4), and the mixture was stirred under hydrogen atmosphere at room temperature for 18 hours. The reaction solution was filtered through celite, followed by concentration under reduced pressure. Then, the residue was dissolved in 1,4-dioxane (2.0 ml) and isopropyl alcohol (1.0 ml). A 4 M hydrochloric acid/1,4-dioxane solution (2.0 ml) was added, and the mixture was stirred at room temperature for 5 hours and thereafter concentrated under reduced pressure to give a hydrochloride of the title compound (0.15 g, 74%).
MS (ESI) m/z 401 [M+H]$^+$

SYNTHESIS EXAMPLE 25

Methyl (2S)-2-amino-3-[6-(1-methyl-2,4-dioxo-7,8-dihydro-5H-pyrano[4,3-d]pyrimidin-3-yl)-3-pyridyl]propanoate

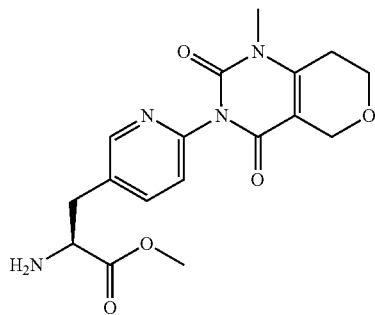

(Step 1)

Synthesis of Ethyl 4-amino-3,6-dihydro-2H-pyran-5-carboxylate

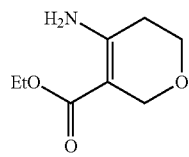

Ammonium acetate (2.4 g, 31 mmol) was added to an ethanol solution (10 ml) of ethyl 4-oxotetrahydropyran-3-carboxylate (0.54 g, 3.1 mmol), and the mixture was stirred at 60° C. for 18 hours. The reaction solution was concentrated under reduced pressure, and then dichloromethane and saturated sodium bicarbonate water were added thereto. After two times of extractions with dichloromethane, the organic layer was washed with a saturated sodium chloride aqueous solution, dried with anhydrous magnesium sulfate, and thereafter concentrated under reduced pressure to give the title compound (0.49 g, quant.).
(Step 2)

Synthesis of 1,5,7,8-tetrahydropyrano[4,3-d]pyrimidine-2,4-dione

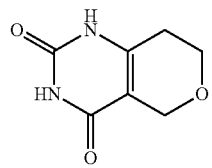 [SMILES: O=c1[nH]c2c(c(=O)[nH]1)COCC2]

Trichloroacetyl isocyanate (0.74 ml, 6.2 mmol) was added to an acetonitrile solution (6.0 ml) of the compound (0.49 g, 3.1 mmol) obtained in (step 1), and the mixture was stirred at room temperature for 30 minutes. The solid was collected by filtration and suspended in an 8 M ammonia/methanol solution (5.0 ml). The suspension was stirred at 70° C. for 18 hours, and the solid was collected by filtration to give the title compound (0.30 g, 57%).
(Step 3)

Synthesis of 3-(5-bromo-2-pyridyl)-1,5,7,8-tetrahydropyrano[4,3-d]pyrimidine-2,4-dione

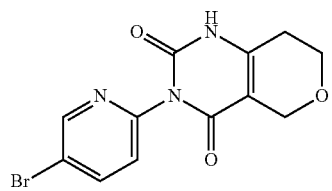 [SMILES: O=c1[nH]c2c(c(=O)n1-c1ccc(Br)cn1)COCC2]

5-Bromo-2-iodopyridine (1.1 g, 3.7 mmol), copper iodide (0.30 g, 1.6 mmol), and DBU (0.93 ml, 6.4 mmol) were sequentially added to an acetonitrile solution (10.0 ml) of the compound (0.53 g, 3.2 mmol) obtained in (step 2), and the mixture was stirred at 70° C. for 18 hours. The reaction solution was cooled to room temperature and then filtered through celite, followed by concentration under reduced pressure. The residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (0.26 g, 26%).
(Step 4)

Synthesis of 3-(5-bromo-2-pyridyl)-1-methyl-7,8-dihydro-5H-pyrano[4,3-d]pyrimidine-2,4-dione

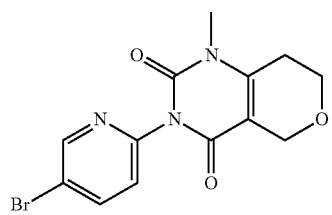 [SMILES: Cn1c2c(c(=O)n(-c3ccc(Br)cn3)c1=O)COCC2]

Potassium carbonate (0.33 g, 2.4 mmol) and methyl iodide (0.25 ml) were sequentially added to a DMF solution (2.0 ml) of the compound (0.26 g, 0.80 mmol) obtained in (step 3), and the mixture was stirred at room temperature for 5 hours. The reaction solution was concentrated under reduced pressure, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (0.20 g, 74%).

(Step 5)

Methyl (2S)-2-(tert-butoxycarbonylamino)-3-[6-(1-methyl-2,4-dioxo-7,8-dihydro-5H-pyrano[4,3-d]pyrimidin-3-yl)-3-pyridyl]propanoate synthesis of

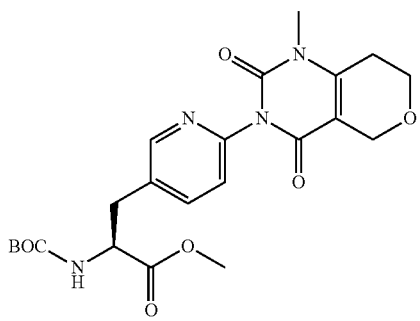 [SMILES: COC(=O)[C@H](Cc1ccc(-n2c(=O)c3c(n(C)c2=O)CCOC3)nc1)NC(=O)OC(C)(C)C]

Zinc powder (0.12 g, 1.8 mmol) was suspended in DMF (2.0 ml), and iodine (34 mg, 0.13 mmol) was added thereto. Then, the mixture was stirred at room temperature for 15 minutes. Methyl (2R)-2-(tert-butoxycarbonylamino)-3-iodo-propanoate (0.23 g, 0.70 mmol), and iodine (34 mg, 0.13 mmol) were sequentially added, and the mixture was stirred at room temperature for 30 minutes.

The compound (0.20 g, 0.59 mmol) obtained in (step 4) was placed in a separate vessel and dissolved in DMF (1.0 ml). Tris(dibenzylideneacetone)dipalladium (0) (14 mg, 0.015 mmol) and SPhos (24 mg, 0.058 mmol) were sequentially added, and the mixture was stirred for 10 minutes. This mixed solution was added to the previously prepared mixed solution. After three times of operations of degasification with argon substitution, the resultant mixed solution was stirred at 60° C. for 18 hours. The reaction solution was cooled to room temperature, and was concentrated under reduced pressure. Thereafter, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (0.12 g, 45%).

(Step 6)

Synthesis of Methyl (2S)-2-amino-3-[6-(1-methyl-2,4-dioxo-7,8-dihydro-5H-pyrano[4,3-d]pyrimidin-3-yl)-3-pyridyl]propanoate

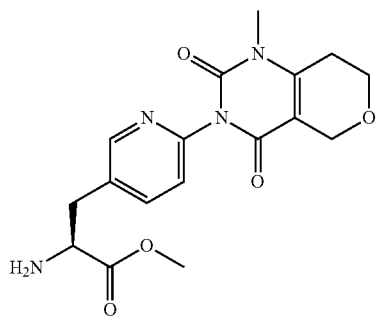

The compound (0.12 g, 0.26 mmol) obtained in (step 5) was dissolved in 1,4-dioxane (1.0 ml) and methanol (1.0 ml). A 4 M hydrochloric acid/1,4-dioxane solution (1.0 ml) was added and the mixture was stirred at room temperature for 5 hours and then concentrated under reduced pressure to give a hydrochloride of the title compound (0.10 mg, quant.). MS (ESI) m/z 361 [M+H]$^+$

SYNTHESIS EXAMPLE 26

Methyl (2S)-2-amino-3-[6-(1-methyl-2,4-dioxo-pyrido[3,4-d]pyrimidin-3-yl)-3-pyridyl]propanoate

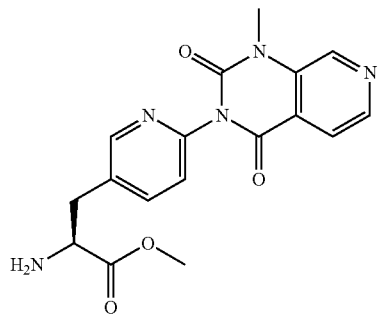 [SMILES: COC(=O)[C@@H](N)Cc1ccc(-n2c(=O)c3ccncc3n(C)c2=O)nc1]

Compounds in [Synthesis Example 27], [Synthesis Example 31], and [Synthesis Example 40] can be synthesized in a method similar to that of the compound in [Synthesis Example 25] by using the corresponding 1,2-ketoester reagent in (Step 1) in [Synthesis Example 25].

SYNTHESIS EXAMPLE 27

Isopropyl (2S)-2-amino-3-[4-(1-methyl-2,4-dioxo-7,8-dihydro-5H-pyrano[4,3-d]pyrimidin-3-yl)phenyl]propanoate

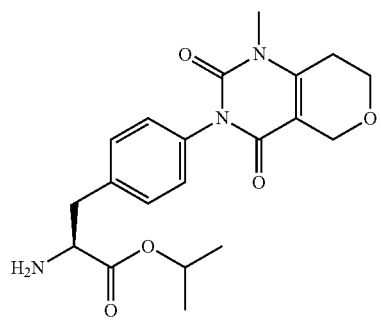 [SMILES: CC(C)OC(=O)[C@@H](N)Cc1ccc(-n2c(=O)c3c(n(C)c2=O)CCOC3)cc1]

MS (ESI) m/z 388 [M+H]$^+$

SYNTHESIS EXAMPLE 28

Methyl (2S)-2-amino-3-[4-(6-methoxy-1-methyl-2,4-dioxo-pyrido[3,4-d]pyrimidin-3-yl)phenyl]propanoate

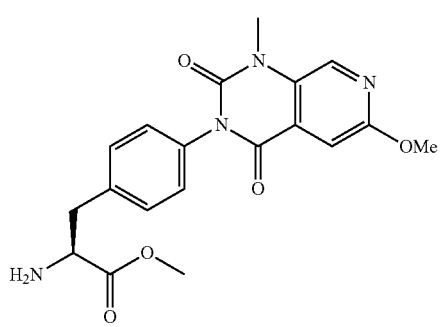 [SMILES: COC(=O)[C@@H](N)Cc1ccc(-n2c(=O)c3cc(OC)ncc3n(C)c2=O)cc1]

SYNTHESIS EXAMPLE 29

Methyl (2S)-2-amino-3-[4-(3,5-dimethyl-2,6-dioxo-pyrimidin-1-yl)phenyl]propanoate

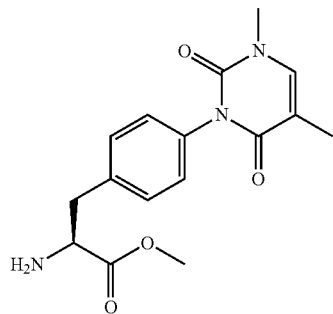 [SMILES: COC(=O)[C@@H](N)Cc1ccc(-n2c(=O)c(C)cn(C)c2=O)cc1]

A compound in [Synthesis Example 30] can be synthesized in a method similar to that of the compound in [Synthesis Example 25] by using ethyl 3-oxotetrahydropyran-4-carboxylate in (Step 1) in [Synthesis Example 25].

SYNTHESIS EXAMPLE 30

Methyl (2S)-2-amino-3-[6-(1-methyl-2,4-dioxo-6,8-dihydro-5H-pyrano[3,4-d]pyrimidin-3-yl)-3-pyridyl]propanoate

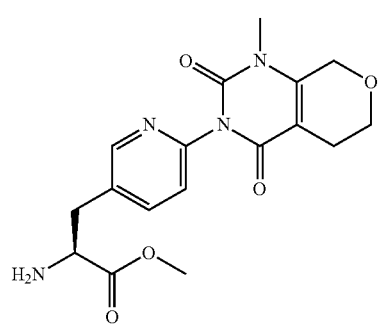

MS (ESI) m/z 361 [M+H]$^+$

SYNTHESIS EXAMPLE 31

Isopropyl (2S)-2-amino-3-[4-(1-methyl-2,4-dioxo-6,8-dihydro-5H-pyrano[3,4-d]pyrimidin-3-yl)phenyl]propanoate

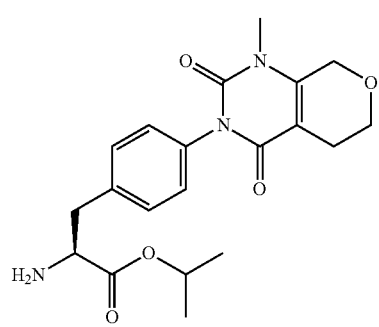 [SMILES: CC(C)OC(=O)[C@@H](N)Cc1ccc(-n2c(=O)c3c(n(C)c2=O)COCC3)cc1]

MS (ESI) m/z 388 [M+H]$^+$

SYNTHESIS EXAMPLE 32

Methyl (2S)-2-amino-3-[4-(3-methyl-2,6-dioxo-pyrimidin-1-yl)phenyl]propanoate

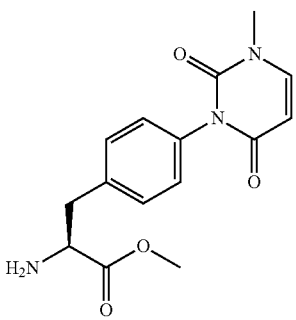 [SMILES: COC(=O)[C@@H](N)Cc1ccc(-n2c(=O)ccn(C)c2=O)cc1]

SYNTHESIS EXAMPLE 33

Methyl (2S)-2-amino-3-[4-(3,7-dimethyl-2,6-dioxo-purin-1-yl)phenyl]propanoate

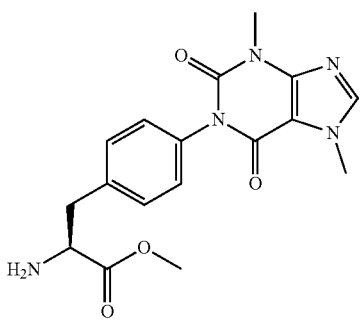 [SMILES: COC(=O)[C@@H](N)Cc1ccc(-n2c(=O)c3c(ncn3C)n(C)c2=O)cc1]

A compound in [Synthesis Example 34] can be synthesized in a method similar to that of the compound in [Synthesis Example 25] by using 6-methyluracil or 5,6-dimethyluracil in (Step 3) in [Synthesis Example 25].

SYNTHESIS EXAMPLE 34

Methyl (2S)-2-amino-3-[6-(3,4,5-trimethyl-2,6-dioxo-pyrimidin-1-yl)-3-pyridyl]propanoate

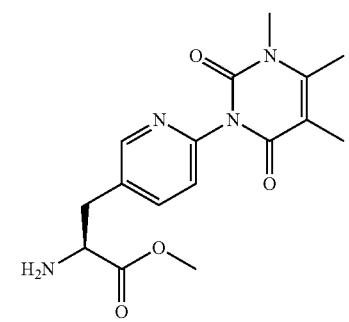 [SMILES: COC(=O)[C@@H](N)Cc1ccc(-n2c(=O)c(C)c(C)n(C)c2=O)nc1]

MS (ESI) m/z 333 [M+H]$^+$

SYNTHESIS EXAMPLE 35

Methyl (2S)-2-amino-3-[6-(3,4-dimethyl-2,6-dioxo-pyrimidin-1-yl)-3-pyridyl]propanoate

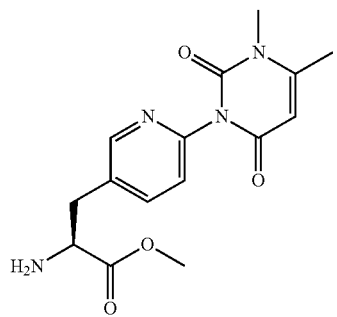 [SMILES: COC(=O)[C@@H](N)Cc1ccc(-n2c(=O)cc(C)n(C)c2=O)nc1]

(Step 1)

Synthesis of 3-(5-bromopyridin-2-yl)-6-methylpyrimidine-2,4(1H,3H)-dione

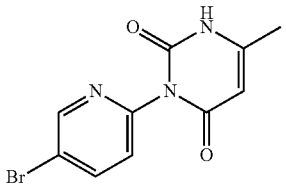 [SMILES: Cc1cc(=O)n(-c2ccc(Br)cn2)c(=O)[nH]1]

5-bromo 2-iodopyridine (1.1 g, 3.7 mmol), copper iodide (0.30 g, 1.6 mmol), and DBU (0.93 ml, 6.4 mmol) were sequentially added to an acetonitrile solution (10 ml) of 6-methyluracil (0.40 g, 3.2 mmol), and the mixture was stirred at 70° C. for 18 hours. The reaction solution was cooled to room temperature, and was filtered through celite, followed by concentration under reduced pressure. The residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (0.23 g, 26%).
MS (ESI) m/z 282 [M+H]$^+$
(Step 2)

Synthesis of 3-(5-bromopyridin-2-yl)-1,6-dimethyl-pyrimidine-2,4(1H,3H)-dione

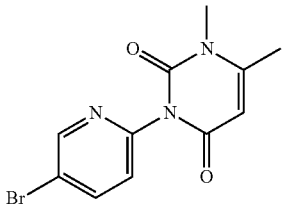 [SMILES: Cc1cc(=O)n(-c2ccc(Br)cn2)c(=O)n1C]

Potassium carbonate (0.33 g, 2.4 mmol) and methyl iodide (0.25 ml) were sequentially added to a DMF solution (2.0 ml) of the compound (0.23 g, 0.82 mmol) obtained in (step 1), and the mixture was stirred at room temperature for 5 hours. The reaction solution was concentrated under reduced pressure, and the residue was purified in the same method (reverse phase HPLC fractionation) as in (step 1) to give the title compound (0.18 g, 74%).
$^1$H NMR (400 MHz, DMSO-d$_6$) δ 8.72 (d, J=2.5 Hz, 1H), 8.23 (dd, J=8.4, 2.6 Hz, 1H), 7.40 (d, J=8.4 Hz, 1H), 5.76 (s, 1H), 3.32 (s, 3H), 2.32 (s, 3H); MS (ESI) m/z 296 [M+H]$^+$
(Step 3)

Synthesis of Methyl (2S)-2-((tert-butoxycarbonyl)amino)-3-(6-(3,4-dimethyl-2,6-dioxo-3,6-dihydropyrimidin-1(2H)-yl)pyridin-3-yl)propanoate

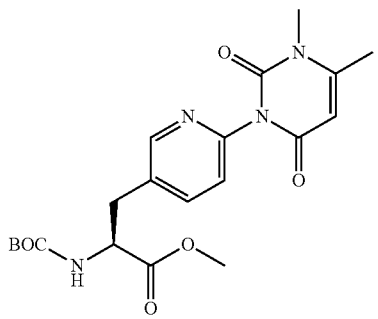 [SMILES: COC(=O)[C@H](Cc1ccc(-n2c(=O)cc(C)n(C)c2=O)nc1)NC(=O)OC(C)(C)C]

Zinc powder (0.12 g, 1.8 mmol) was suspended in DMF (2.0 ml), iodine (34 mg, 0.13 mmol) was added thereto, and the mixture was stirred at room temperature for 15 minutes. Methyl (2R)-2-(tert-butoxycarbonylamino)-3-iodo-propanoate (0.23 g, 0.70 mmol) and iodine (34 mg, 0.13 mmol) were sequentially added, and the resultant mixture was stirred at room temperature for 30 minutes.

The compound (0.18 g, 0.60 mmol) obtained in (step 2) was placed in another vessel, and was dissolved in DMF (1.0 ml). Tris(dibenzylideneacetone)dipalladium (14 mg, 0.015 mmol) and SPhos (24 mg, 0.058 mmol) were sequentially added, and the resultant mixture was stirred for 10 minutes. This mixed solution was added to the previously prepared mixed solution. After three times of operations of degasification with argon substitution, the resultant mixed solution was stirred at 60° C. for 18 hours. The reaction solution was cooled to room temperature, and was concentrated under reduced pressure. Thereafter, the residue was purified in the same method (reverse phase HPLC fractionation) as in (step 1) to give the title compound (0.11 g, 43%).
MS (ESI) m/z 419 [M+H]$^+$
(Step 4)

Synthesis of Methyl (2S)-2-amino-3-[6-(3,4-dimethyl-2,6-dioxo-pyrimidin-1-yl)-3-pyridyl]propanoate

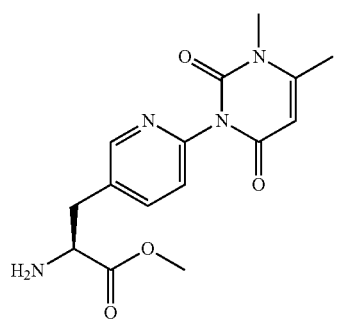 [SMILES: COC(=O)[C@@H](N)Cc1ccc(-n2c(=O)cc(C)n(C)c2=O)nc1]

The compound (0.11 g, 0.26 mmol) obtained in (step 3) was dissolved in 1,4-dioxane (1.0 ml) and methanol (1.0 ml). A 4M hydrochloric acid/1,4-dioxane solution (1.0 ml) was added thereto, and the resultant mixture was stirred at room temperature for 5 hours and then concentrated under reduced pressure to give a hydrochloride of the title compound (0.10 g, quant.).

MS (ESI) m/z 319 [M+H]$^+$

SYNTHESIS EXAMPLE 36

Methyl (2S)-2-amino-3-[4-(3,4-dimethyl-2,6-dioxo-pyrimidin-1-yl)phenyl]propanoate

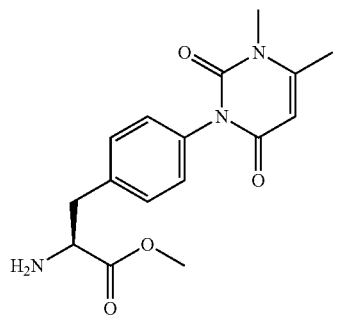 [SMILES: COC(=O)[C@@H](N)Cc1ccc(-n2c(=O)cc(C)n(C)c2=O)cc1]

SYNTHESIS EXAMPLE 37

Isopropyl (2S)-2-amino-3-[5-(1-methyl-2,4-dioxo-5,6,7,8-tetrahydroquinazolin-3-yl)-2-pyridyl]propanoate

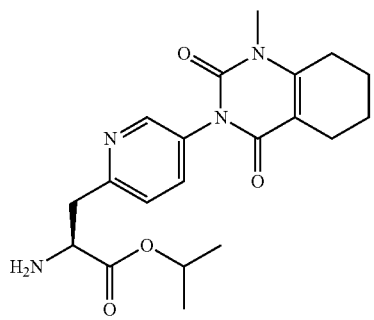 [SMILES: CC(C)OC(=O)[C@@H](N)Cc1ccc(-n2c(=O)c3c(n(C)c2=O)CCCC3)cn1]

(Step 1)

Synthesis of Ethyl 2-[(4-nitrophenoxy)carbonylamino]cyclohexene-1-carboxylate

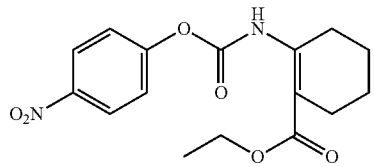 [SMILES: CCOC(=O)C1=C(NC(=O)Oc2ccc([N+](=O)[O-])cc2)CCCC1]

Ethyl 2-oxocyclohexanecarboxylate (1.5 mL, 8.823 mmol) was dissolved in methanol (90 mL). Ammonium acetate (6.80 g, 88.23 mmol) was added to the solution, and the mixture was stirred at 60° C. for 14 hours. After removal of the solvent of the reaction solution under reduced pressure, ethyl acetate was added to the residue, and the organic layer was washed with a saturated sodium hydrogen carbonate aqueous solution, water, and a saturated saline solution, and the obtained organic layer was dried with anhydrous sodium sulfate. After insoluble matters were filtered out, the residue was dissolved in dichloromethane (45 mL). Pyridine (0.86 mL, 10.65 mmol) was added to that solution, followed by cooling to 0° C. Then, (4-nitrophenyl) carbonochloridate (1.879 g, 9.322 mmol) was added thereto and the mixture was stirred for 14 hours while gradually returning to room temperature. After removal of the solvent of the reaction solution under reduced pressure, the obtained residue was purified using silica gel column chromatography (SiO$_2$, hexane/ethyl acetate) to give the title compound as a pale yellow solid (2.72 g, 94.0%).

MS (ESI) m/z 335 [M+H]$^+$ (Step 2)

Synthesis of 3-(6-bromo-3-pyridyl)-5,6,7,8-tetrahydro-1H-quinazoline-2,4-dione

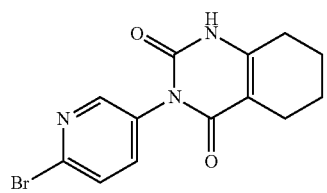 [SMILES: O=c1[nH]c2c(c(=O)n1-c1ccc(Br)nc1)CCCC2]

The compound (1.47 g, 4.401 mmol) obtained in (step 1) was dissolved in 1,4-dioxane (45 mL), 6-bromopyridin-3-amine (0.795 g, 4.621 mmol) and 1,8-diazabicyclo[5.4.0]undec-7-ene (1.31 mL, 8.802 mmol) were added, and the mixture was stirred at room temperature for 17 hours. After removal of the solvent of the reaction solution under reduced pressure, the residue obtained was subjected to reverse phase HPLC using ODS as a packing material, and was purified in the same method (reverse phase HPLC fractionation) as in (step 1) in [Synthesis Example 4] to give the title compound (719 mg, 30.2%).

MS (ESI) m/z 322 [M+H]$^+$ (Step 3)

Synthesis of 3-(6-bromo-3-pyridyl)-1-methyl-5,6,7,8-tetrahydroquinazoline-2,4-dione

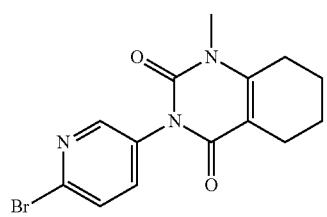 [SMILES: Cn1c2c(c(=O)n(-c3ccc(Br)nc3)c1=O)CCCC2]

The compound (719 mg, 2.232 mmol) obtained in (step 2) was dissolved in dimethylformamide (8 mL), potassium carbonate (770 mg, 5.580 mmol) and methyl iodide (207 uL, 3.348 mmol) were added, and the mixture was stirred at room temperature for 3 hours. Ethyl acetate was added to the reaction solution, and then the organic layer was washed with water and a saturated saline solution, and was dried with anhydrous sodium sulfate. After insoluble matters were filtered out, the solvent was removed under reduced pressure to obtain a residue. The residue obtained was subjected to reverse phase HPLC using ODS as a packing material, and was purified in the same method as in (Step 1) in [Synthesis Example 4] to give the title compound (269 mg, 35.9%).

MS (ESI) m/z 336 [M+H]$^+$ (Step 4)

Synthesis of Isopropyl (2S)-2-(tert-butoxycarbonylamino)-3-[5-(1-methyl-2,4-dioxo-5,6,7,8-tetrahydroquinazolin-3-yl)-2-pyridyl]propanoate

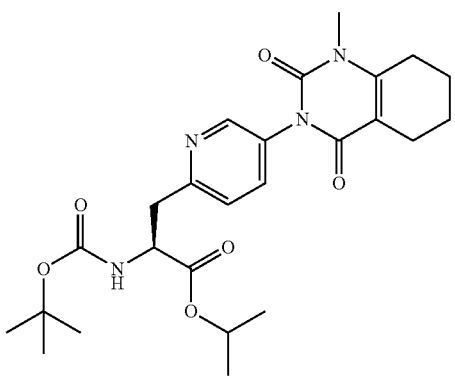 [SMILES: CC(C)OC(=O)[C@H](Cc1ccc(-n2c(=O)c3c(n(C)c2=O)CCCC3)cn1)NC(=O)OC(C)(C)C]

Zinc powder (157 mg, 2.40 mmol) was suspended in DMF (2.0 ml), iodine (46.3 mg, 0.18 mmol) was added, and the mixture was stirred at room temperature for 15 minutes. Methyl (2R)-2-(tert-butoxycarbonylamino)-3-iodo-propanoate (269 mg, 0.801 mmol) and iodine (46.3 mg, 0.18 mmol) were sequentially added, and the resultant mixture was stirred at room temperature for 30 minutes.

The compound (256 mg, 0.801 mmol) obtained in (step 3) was placed in another vessel, and was dissolved in DMF (2.0 ml). Tris(dibenzylideneacetone)dipalladium (0) (18.3 mg, 0.020 mmol) and SPhos (32.9 mg, 0.0801 mmol) were sequentially added, and the resultant mixture was stirred for 10 minutes. This mixed solution was added to the previously prepared mixed solution. After three times of operations of degasification with argon substitution, the resultant mixed solution was stirred at 60° C. for 15 hours. The reaction solution was cooled to room temperature, and then water (25 ml) and dichloromethane (25 ml) were added thereto. After filtration through celite and two times of extraction with dichloromethane, the organic layer was washed with a saturated sodium chloride aqueous solution. The resultant organic layer was dried with anhydrous sodium sulfate, and was concentrated under reduced pressure. The residue was purified by silica gel column chromatography to give the title compound (223 mg, 57.3%).
MS (ESI) m/z 487 [M+H]$^+$
(Step 5)

Synthesis of a hydrochloride of isopropyl (2S)-2-amino-3-[5-(1-methyl-2,4-dioxo-5,6,7,8-tetrahydroquinazolin-3-yl)-2-pyridyl]propanoate

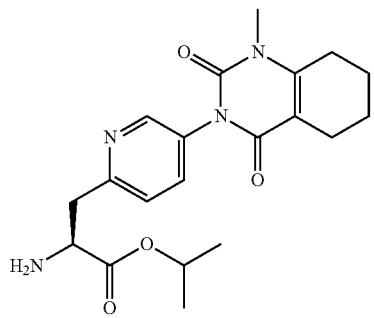 [SMILES: CC(C)OC(=O)[C@@H](N)Cc1ccc(-n2c(=O)c3c(n(C)c2=O)CCCC3)cn1]

The compound (223 mg, 0.459 mmol) obtained in (step 4) was dissolved in ethyl acetate (3 mL). A 4 N hydrochloric acid/ethyl acetate solution (1.2 mL) was added to that solution, followed by stirring at room temperature for 7 hours. After removal of the solvent of the reaction solution under reduced pressure, the residue was freeze-dried to give the title compound (219 mg, quant.).
MS (ESI) m/z 387 [M+H]$^+$ A compound in [Synthesis Example 38] can be synthesized in a method similar to that of the compound in [Synthesis Example 23] by causing 2-iodopropane to act in (Step 2) in [Synthesis Example 23].

SYNTHESIS EXAMPLE 38

Methyl (2S)-2-amino-3-[4-(3-isopropyl-4,5-dimethyl-2,6-dioxo-pyrimidin-1-yl)phenyl]propanoate

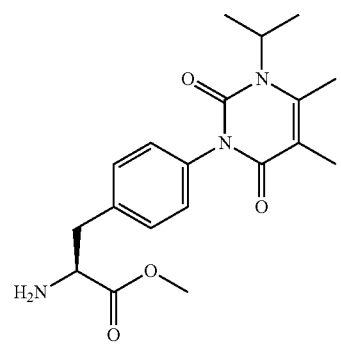 [SMILES: COC(=O)[C@@H](N)Cc1ccc(-n2c(=O)c(C)c(C)n(C(C)C)c2=O)cc1]

MS (ESI) m/z 360 [M+H]$^+$

SYNTHESIS EXAMPLE 39

Methyl (2S)-2-amino-3-[4-[5-(hydroxymethyl)-3,4-dimethyl-2,6-dioxo-pyrimidin-1-yl]phenyl]propanoate

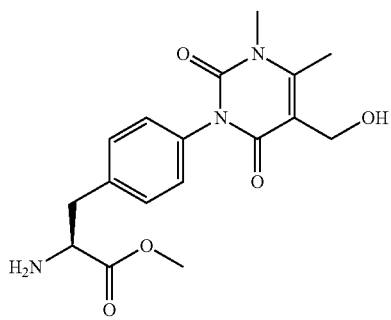 [SMILES: COC(=O)[C@@H](N)Cc1ccc(-n2c(=O)c(CO)c(C)n(C)c2=O)cc1]

(Step 1)

Synthesis of Methyl (2S)-2-(tert-butoxycarbonylamino)-3-[4-(5-(hydroxymethyl)-6-methyl-2,4-dioxo-1H-pyrimidin-3-yl)phenyl]propanoate

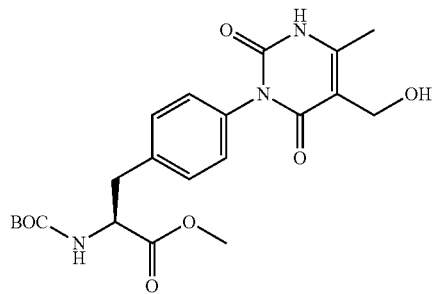 [SMILES: COC(=O)[C@H](Cc1ccc(-n2c(=O)[nH]c(C)c(CO)c2=O)cc1)NC(=O)OC(C)(C)C]

Copper acetate (90 mg, 0.47 mmol), 5-(hydroxymethyl)-6-methylpyrimidine-2,4-(1H,3H)-dione (78 mg, 0.5 mmol), and pyridine (0.08 ml) were sequentially added to a DMSO solution (1 ml) of [4-[(2S)-2-(tert-butoxycarbonylamino)-3-methoxy-3-oxo-propy l]phenyl]boronic acid (0.15 g, 0.47 mmol), a production method of which is described in Patent Literature (WO2013/161904), and the mixture was stirred at 60° C. for 18 hours. The reaction solution was filtered through celite, followed by concentration under reduced pressure. Thereafter, the residue obtained was subjected to reverse phase HPLC using ODS as a packing material, and was purified in the same method as in (step 1) in [Synthesis Example 4] to give the title compound (69 mg, 33.9%).

$^1$H NMR (400 MHz, DMSO-$d_6$) δ 11.17 (s, 1H), 7.39-7.26 (m, 3H), 7.13-7.03 (m, 2H), 4.26-4.10 (m, 3H), 3.63 (s, 3H), 3.04 (dd, J=14.0, 4.8 Hz, 1H), 2.91 (dd, J=13.8, 10.2 Hz, 1H), 2.20 (s, 3H), 1.35 (s, 9H); MS (ESI) m/z 434[M+H]$^+$ (Step 2)

Synthesis of Methyl (2S)-2-(tert-butoxycarbonylamino)-3-[4-{5-(hydroxymethyl)-3,4-dimethyl-2,6-dioxo-pyrimidin-1-yl}phenyl]propanoate

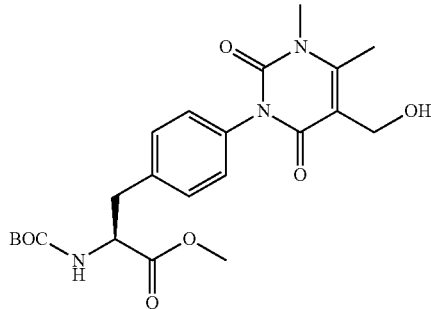 [SMILES: COC(=O)[C@H](Cc1ccc(-n2c(=O)c(CO)c(C)n(C)c2=O)cc1)NC(=O)OC(C)(C)C]

Potassium carbonate (24 mg, 0.17 mmol) and methyl iodide (0.012 ml) were sequentially added to a DMF solution (1 ml) of the compound (69 mg, 0.16 mmol) obtained in (step 1), and the mixture was stirred at room temperature for 1 hour 30 minutes. The reaction solution was concentrated under reduced pressure. Thereafter, the residue obtained was subjected to reverse phase HPLC using ODS as a packing material, and was purified in the same method as in (Step 1) in [Synthesis Example 4] to give the title compound (34 mg, 47.5%).
MS (ESI) m/z 448 [M+H]$^+$
(Step 3)

Synthesis of Methyl (2S)-2-amino-3-[4-[5-(hydroxymethyl)-3,4-dimethyl-2,6-dioxo-pyrimidin-1-yl]phenyl]propanoate

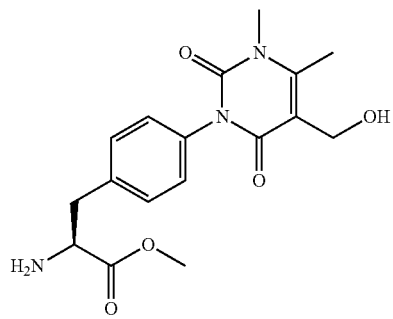 [SMILES: COC(=O)[C@@H](N)Cc1ccc(-n2c(=O)c(CO)c(C)n(C)c2=O)cc1]

The compound (14 mg, 0.031 mmol) obtained in (step 2) was dissolved in trifluoroacetic acid (1 ml), and the mixture was stirred at room temperature for 1 hour. The reaction solution was concentrated under reduced pressure to give a trifluoroacetate of the title compound (15 mg, quant.).
MS (ESI) m/z 348 [M+H]$^+$

SYNTHESIS EXAMPLE 40

Methyl (2S)-2-amino-3-[6-(1-methyl-2,4-dioxo-5,6,7,8-tetrahydroquinazolin-3-yl)-3-pyridyl]propanoate

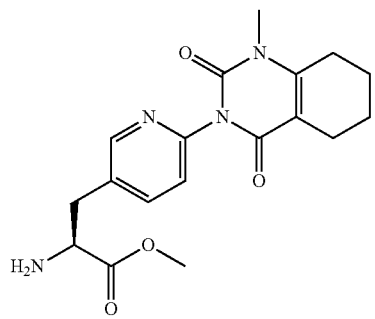 [SMILES: COC(=O)[C@@H](N)Cc1ccc(-n2c(=O)c3c(n(C)c2=O)CCCC3)nc1]

MS (ESI) m/z 359 [M+H]$^+$

SYNTHESIS EXAMPLE 41

Methyl (2S)-2-amino-3-[6-(3-methyl-2,6-dioxo-pyrimidin-1-yl)-3-pyridyl]propanoate

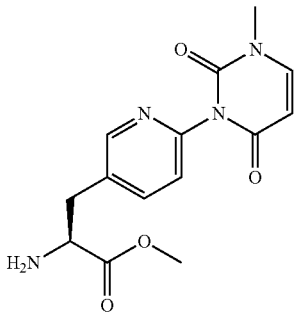 [SMILES: COC(=O)[C@@H](N)Cc1ccc(-n2c(=O)ccn(C)c2=O)nc1]

(Step 1)

Synthesis of tert-butyl 3-benzoyl-2,4-dioxo-pyrimidine-1-carboxylate

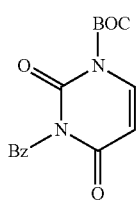

Di-tert-butyl dicarbonate (10.2 g, 47 mmol) and 4-dimethylaminopyridine (55 mg, 0.45 mmol) were sequentially added to an acetonitrile solution (50 ml) of uracil (5.0 g, 45 mmol), and the mixture was stirred at room temperature for 18 hours. The reaction solution was concentrated under reduced pressure, and the residue was slurry washed with ethyl acetate. The solid obtained was dissolved in dichloromethane (50 ml), and N,N-diisopropylethylamine (7.9 ml, 45 mmol) was added. Benzoyl chloride (5.3 g, 37 mmol) was added under ice cooling, and the mixture was stirred at room temperature for 12 hours. Water was added to the reaction solution, and the mixture was subjected to two times of extractions with dichloromethane. The organic layer was washed successively with 0.5 M hydrochloric acid and a saturated sodium chloride aqueous solution, and was dried with anhydrous magnesium sulfate. After concentration under reduced pressure, the residue was slurry washed with ethyl acetate to give the title compound (9.4 g, 66%).

$^1$H NMR (400 MHz, DMSO-d$_6$) δ 8.15 (dd, J=8.5, 1.6 Hz, 1H), 8.11-8.04 (m, 2H), 7.87-7.76 (m, 1H), 7.68-7.56 (m, 2H), 5.98 (dd, J=8.4, 1.7 Hz, 1H), 1.54 (d, J=1.6 Hz, 9H); MS (ESI) m/z 317[M+H]$^+$
(Step 2)

Synthesis of
3-benzoyl-1-methyl-pyrimidine-2,4-dione

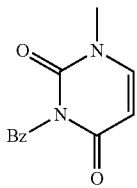

Trifluoroacetic acid (8.0 ml) was added to a dichloromethane solution (5.0 ml) of the compound (9.4 g, 30 mmol) obtained in (step 1), and the mixture was stirred at room temperature for 3 hours. The reaction solution was concentrated under reduced pressure, and the residue was dissolved in acetonitrile (50 ml). Potassium carbonate (4.5 g, 33 mmol) and methyl iodide (2.8 ml, 45 mmol) were sequentially added, and the mixture was stirred at room temperature for 12 hours. Water (30 ml) was added to the reaction solution, followed by stirring at room temperature for 30 minutes. The solid was collected by filtration to give the title compound (7.4 g, quant.).

$^1$H NMR (400 MHz, DMSO-d$_6$) δ 7.96 (dd, J=8.0, 1.3 Hz, 2H), 7.87 (d, J=7.9 Hz, 1H), 7.83-7.72 (m, 1H), 7.60 (dd, J=8.4, 7.2 Hz, 2H), 5.81 (dd, J=7.9, 0.6 Hz, 1H), 3.32 (s, 3H); MS (ESI) m/z 231[M+H]$^+$.
(Step 3)

Synthesis of 1-methyluracil

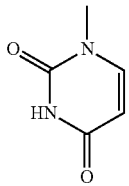

An 8 M ammonia/methanol solution (50 ml) was added to the compound (7.4 g, 30 mmol) obtained in (step 2), and the mixture was stirred at room temperature for 5 hours. The solid was collected by filtration (first crystal), and the filtrate was concentrated under reduced pressure. The residue was slurry washed with ethyl acetate (second crystal) and the solids obtained were collected to give the title compound (4.2 g, quant.).

$^1$H NMR (400 MHz, DMSO-d$_6$) δ 11.21 (s, 1H), 7.61 (d, J=7.8 Hz, 1H), 5.51 (d, J=7.8 Hz, 1H), 3.22 (s, 3H); MS (ESI) m/z 127 [M+H]$^+$
(Step 4)

Synthesis of a Mixture of 3-(5-bromo-2-pyridyl)-1-methyl-pyrimidine-2,4-dione and 3-(5-iodo-2-pyridyl)-1-methyl-pyrimidine-2,4-dione

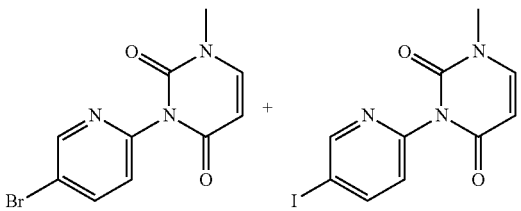 [SMILES: Cn1ccc(=O)n(-c2ccc(Br)cn2)c1=O ; Cn1ccc(=O)n(-c2ccc(I)cn2)c1=O]

5-Bromo-2-iodopyridine (0.74 g, 2.6 mmol), copper iodide (0.50 g, 2.6 mmol), and trimethylamine (1.0 ml, 6.9 mmol) were sequentially added to a DMF solution (5.0 ml) of the compound (0.22 g, 1.7 mmol) obtained in (step 3), and the mixture was stirred at 140° C. for 18 hours. The reaction solution was cooled to room temperature, and then water (25 ml) and dichloromethane (25 ml) were added thereto. After filtration through celite and two times of extractions with dichloromethane, the organic layer was washed with a saturated sodium chloride aqueous solution. The organic layer was dried with anhydrous magnesium sulfate, and then was concentrated under reduced pressure. The residue was purified by silica gel column chromatography to obtain the mixture (1:1) of the title compounds (0.29 g).
(Step 5)

Synthesis of Methyl (2S)-2-(tert-butoxycarbonylamino)-3-[6-(3-methyl-2,6-dioxo-pyrimidin-1-yl)-3-pyridyl]propanoate

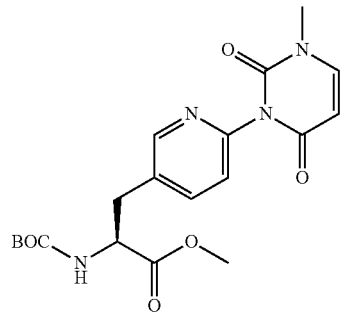 [SMILES: COC(=O)[C@H](Cc1ccc(-n2c(=O)ccn(C)c2=O)nc1)NC(=O)OC(C)(C)C]

Zinc powder (96 mg, 1.5 mmol) was suspended in DMF (2.0 ml), iodine (26 mg, 0.10 mmol) was added thereto, and the mixture was stirred at room temperature for 15 minutes. Methyl (2R)-2-(tert-butoxycarbonylamino)-3-iodo-propanoate (0.19 g, 0.59 mmol) and iodine (26 mg, 0.10 mmol) were sequentially added, and the mixture was stirred at room temperature for 30 minutes.

The mixture (0.29 g) obtained in (step 4) was placed in another vessel and dissolved in DMF (1.0 ml).

Tris(dibenzylideneacetone)dipalladium (0) (22 mg, 0.024 mmol) and SPhos (20 mg, 0.049 mmol) were sequentially added, followed by stirring for 10 minutes. This mixed solution was added to the previously prepared mixed solution. After three times of operations of degasification with argon substitution, the resultant mixed solution was stirred at 60° C. for 18 hours. The reaction solution was cooled to room temperature, and then water (25 ml) and dichloromethane (25 ml) were added. After filtration through celite and two times of extractions with dichloromethane, the organic layer was washed with a saturated sodium chloride aqueous solution. The organic layer was dried with anhydrous magnesium sulfate, and then was concentrated under reduced pressure. The residue was purified by silica gel column chromatography to give the title compound (0.21 g).

¹H NMR (400 MHz, DMSO-d₆) δ 8.42 (d, J=2.3 Hz, 1H), 7.92-7.72 (m, 2H), 7.44 (d, J=8.1 Hz, 1H), 7.30 (d, J=8.0 Hz, 1H), 5.77 (d, J=7.9 Hz, 1H), 4.35-4.20 (m, 1H), 3.64 (s, 3H), 3.31 (s, 3H), 3.11 (dd, J=13.9, 4.8 Hz, 1H), 2.94 (dd, J=14.1, 10.6 Hz, 1H), 1.34 (s, 9H); MS (ESI) m/z 405 [M+H]⁺.

(Step 6)

Synthesis of Methyl (2S)-2-amino-3-[6-(3-methyl-2,6-dioxo-pyrimidin-1-yl)-3-pyridyl]propanoate

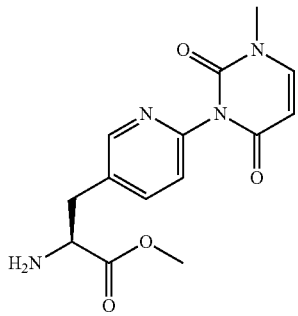 [SMILES: COC(=O)[C@@H](N)Cc1ccc(-n2c(=O)ccn(C)c2=O)nc1]

The compound (0.21 g, 0.52 mmol) obtained in (step 5) was dissolved in 1,4-dioxane (2.0 ml) and methanol (1.0 ml). A 4 M hydrochloric acid/1,4-dioxane solution (2.0 ml) was added thereto, and the mixture was stirred at room temperature for 5 hours and then was concentrated under reduced pressure to give a hydrochloride of the title compound (0.18 g, quant.).
MS (ESI) m/z 305 [M+H]⁺.

SYNTHESIS EXAMPLE 42

Isopropyl (2S)-2-amino-3-[6-(3,5-dimethyl-2,6-dioxo-pyrimidin-1-yl)-3-pyridyl]propanoate TFA salt

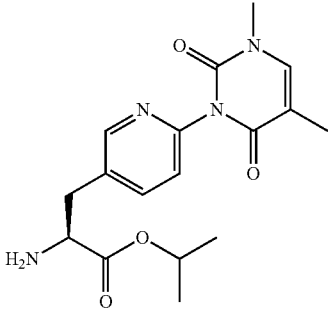 [SMILES: Cc1cn(C)c(=O)n(-c2ccc(C[C@H](N)C(=O)OC(C)C)cn2)c1=O]

(Step 1)

Synthesis of tert-butyl 3-benzoyl-5-methyl-2,4-dioxo-3,4-dihydropyrimidine-1(2H)-carboxylate

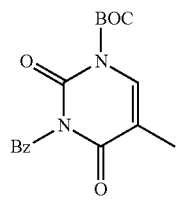

As similar to (Step 1) in [Synthesis Example 40], tert-butyl 5-methyl-2,4-dioxo-3,4-dihydropyrimidine-1(2H)-carboxylate (3.0 g, 13.3 mmol) derived from thymine was dissolved in dichloromethane (30 ml), and N,N-diisopropylethylamine (3.4 ml, 20 mmol) was added thereto. Benzoyl chloride (2.3 g, 16.4 mmol) was added under ice cooling, and the mixture was stirred at room temperature for 12 hours. Water was added to the reaction solution, and the mixture was subjected to extraction with dichloromethane. The organic layer was washed successively with water and a saturated sodium chloride aqueous solution, and was dried with anhydrous magnesium sulfate. After concentration under reduced pressure, the residue was slurry washed with ethyl acetate to give the title compound.

MS (ESI) m/z 331 [M+H]⁺

(Step 2)

Synthesis of 3-benzoyl-1,5-dimethylpyrimidine-2,4(1H,3H)-dione

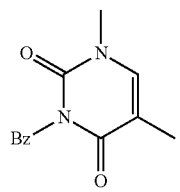

A 4 M hydrochloric acid/1,4-dioxane solution (15 ml) and 1,4-dioxane (15 ml) were added to the compound obtained in (step 1), and the mixture was stirred at room temperature. The reaction solution was concentrated under reduced pressure, and the residue was slurry washed with a mixed solution of ethyl acetate and hexane to obtain a white solid (2.87 g). The solid obtained was dissolved in acetonitrile (60 ml), potassium carbonate (2.6 g, 18.8 mmol) and methyl iodide (1.6 ml, 25.7 mmol) were sequentially added thereto, and the mixture was stirred at room temperature. The reaction solution was evaporated under reduced pressure, followed by addition of water and extraction with dichloromethane. The organic layer was washed with a saturated sodium chloride aqueous solution and then was dried with anhydrous magnesium sulfate.

MS (ESI) m/z 245 [M+H]⁺.

(Step 3)

Synthesis of 1-methyl-thymine

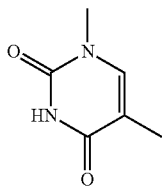

An 8 M ammonia/methanol solution (10 ml) and methanol (5 ml) were added to the compound obtained in (step 2), and the mixture was stirred at room temperature. The reaction solution was evaporated under reduced pressure, and the residue was slurry washed with methanol to give the title compound (1.25 g).
MS (ESI) m/z 141 [M+H]$^+$.
(Step 4)

Synthesis of 3-(5-bromopyridine-2-yl)-1,5-dimethylpyrimidine-2,4(1H,3H)-dione

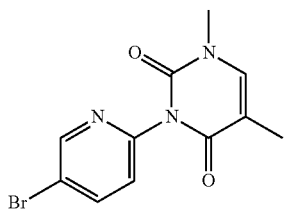 [SMILES: Cc1cn(C)c(=O)n(-c2ccc(Br)cn2)c1=O]

5-Bromo-2-iodopyridine (1.44 g, 5.08 mmol), copper iodide (967 mg, 5.15 mmol), and trimethylamine (0.71 ml, 5.48 mmol) were sequentially added to a DMF solution of the compound (712 mg, 5.08 mmol) obtained in (step 3), and the mixture was stirred at 140° C. overnight. The reaction solution was cooled to room temperature, and then water and dichloromethane were added thereto. After filtration through celite and two times of extractions with dichloromethane, the organic layer was washed with a saturated sodium chloride aqueous solution. The organic layer was dried with anhydrous magnesium sulfate and then was concentrated under reduced pressure. The residue was purified by silica gel column chromatography to obtain the mixture of the title compounds (350 mg, 23%).
$^1$H NMR (400 MHz, DMSO-d$_6$) δ 8.72 (d, J=2.5 Hz, 1H), 8.24 (dd, J=8.4, 2.6 Hz, 1H), 7.72 (d, J=1.4 Hz, 1H), 7.42 (d, J=8.4 Hz, 1H), 3.29 (s, 3H), 1.83 (s, 3H).
MS (ESI) m/z 296 [M+H]$^+$.
(Step 5)

Synthesis of Methyl (2S)-2-(tert-butoxycarbonylamino)-3-[6-(3,5-dimethyl-2,6-dioxo-pyrimidin-1-yl)-3-pyridyl]propanoate

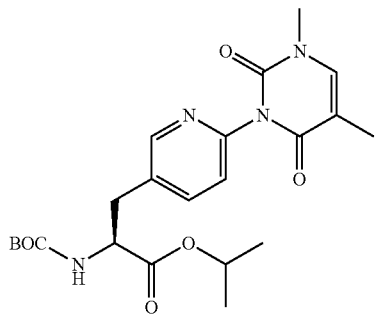 [SMILES: Cc1cn(C)c(=O)n(-c2ccc(C[C@H](NC(=O)OC(C)(C)C)C(=O)OC(C)C)cn2)c1=O]

Zinc powder (232 mg, 3.55 mmol) was suspended in DMF (5 ml), iodine (75 mg, 0.30 mmol) was added thereto, and then the mixture was stirred at room temperature for 15 minutes. Isopropyl (2R)-2-(tert-butoxycarbonylamino)-3-iodo-propanoate (422 mg, 1.18 mmol) and iodine (75 mg, 0.30 mmol) were sequentially added, and the mixture was stirred at room temperature for 30 minutes.

The compound (350 mg, 1.18 mmol) obtained in (step 4) was placed in another vessel and dissolved in DMF (5 ml). Tris(dibenzylideneacetone)dipalladium (0) (27 mg, 0.03 mmol) and SPhos (49 mg, 0.12 mmol) were sequentially added, and the mixture was stirred for 10 minutes. This mixed solution was added to the previously prepared mixed solution. After three times of operations of degasification with argon substitution, the resultant mixed solution was stirred at 60° C. for 18 hours. The reaction solution was cooled to room temperature, and water (25 ml) and dichloromethane (25 ml) were added. After filtration through celite and two times of extractions with dichloromethane, the organic layer was washed with a saturated sodium chloride aqueous solution. The organic layer was dried anhydrous magnesium sulfate, and was concentrated under reduced pressure. The residue was purified by silica gel column chromatography to give the title compound (404 mg, 77%).
MS (ESI) m/z 447 [M+H]$^+$.
(Step 6)

Synthesis of Isopropyl (2S)-2-amino-3-[6-(3,5-dimethyl-2,6-dioxo-pyrimidin-1-yl)-3-pyridyl]propanoate TFA salt

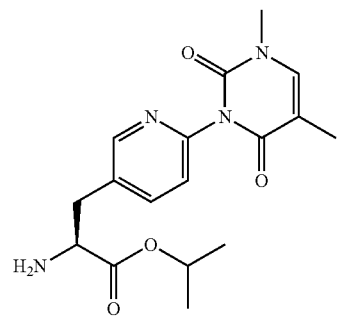 [SMILES: Cc1cn(C)c(=O)n(-c2ccc(C[C@H](N)C(=O)OC(C)C)cn2)c1=O]

The compound (93 mg, 0.21 mmol) obtained in (Step 5) was dissolved in trifluoroacetic acid (3 ml), and the mixture was stirred at room temperature for 30 minutes. The solvent was concentrated under reduced pressure, and then was freeze-dried with addition of water to give the title compound (96 mg, 81%).
$^1$H NMR (400 MHz, DMSO-d$_6$) δ 8.58 (s, 3H), 8.45 (d, J=2.4 Hz, 1H), 7.87 (dd, J=8.1, 2.4 Hz, 1H), 7.71 (d, J=1.3 Hz, 1H), 7.36 (d, J=8.1 Hz, 1H), 4.91 (p, J=6.2 Hz, 1H), 4.40 (s, 1H), 3.29 (s, 3H), 3.24 (dd, J=14.3, 5.9 Hz, 1H), 3.11 (dd, J=14.3, 8.6 Hz, 1H), 1.83 (d, J=1.0 Hz, 3H), 1.16 (d, J=6.2 Hz, 3H), 1.06 (d, J=6.2 Hz, 3H); MS (ESI) m/z 347 [M+H]$^+$.

SYNTHESIS EXAMPLE 43

4-((4-(4,4-dimethylpent-2-ynamido)phenyl)sulfonamido)-2,5-difluorobenzoic acid

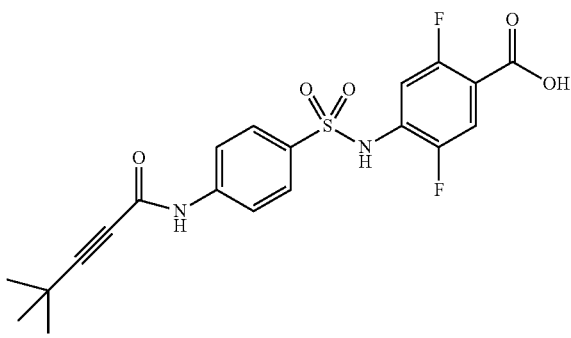 [SMILES: CC(C)(C)C#CC(=O)Nc1ccc(S(=O)(=O)Nc2cc(F)c(C(=O)O)cc2F)cc1]

(Step 1)

Synthesis of 4,4-dimethylpent-2-ynoic acid

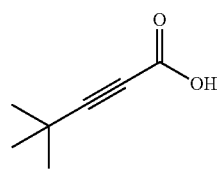

N-butyllithium (29 ml, 73.8 mmol, 2.5 M hexane solution) was added dropwise to a THF (100 ml) solution of 3,3-dimethyl-1-butyne (5.5 g, 67 mmol) under a nitrogen atmosphere at −65° C. The reaction solution was stirred at −78° C. for 30 minutes. After 20 minutes of bubbling with a carbon dioxide gas dried with concentrated sulfuric acid, the reaction solution was slowly heated to room temperature. The reaction was stopped by adding water (30 ml), acidified by adding 10% hydrochloric acid, and subjected to extraction with diethyl ether. The organic layer was washed successively with a 5% sodium hydrogen carbonate aqueous solution (50 ml, twice) and a saturated saline solution, dried with sodium sulfate, and was concentrated under reduced pressure to give a crude product of the title compound (9.5 g).

$^1$H NMR (300 MHz, CD$_3$OD) δ 7.70 (br, s, 1H), 1.26 (s, 9H).

(Step 2)

Synthesis of Methyl 4-((4-(4,4-dimethylpent-2-ynamido)phenyl)sulfonamido)-2,5-difluorobenzoate

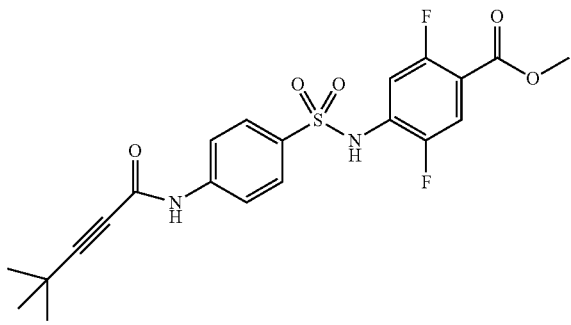 [SMILES: COC(=O)c1cc(F)c(NS(=O)(=O)c2ccc(NC(=O)C#CC(C)(C)C)cc2)cc1F]

HATU (267 mg, 0.702 mmol) and N,N-diisopropylamine (1 ml) were sequentially added to a DMF (10 ml) solution of the compound (74 mg, 0.585 mmol) obtained in (step 1) and the compound (200 mg, 0.585 mmol) obtained in (step 2) in [Synthesis Example 1], and the mixture was stirred at room temperature overnight. Water (50 ml) was added to the reaction solution, followed by extraction with ethyl acetate (50 ml, 3 times). The organic layer was washed with a saturated saline solution, dried with sodium sulfate, and the residue was purified by silica gel column chromatography (petroleum ether:ethyl acetate=2:1) to give the title compound (157 mg, 87%).

(Step 3)

Synthesis of 4-((4-(4,4-dimethylpent-2-ynamido)phenyl)sulfonamido)-2,5-difluorobenzoic acid

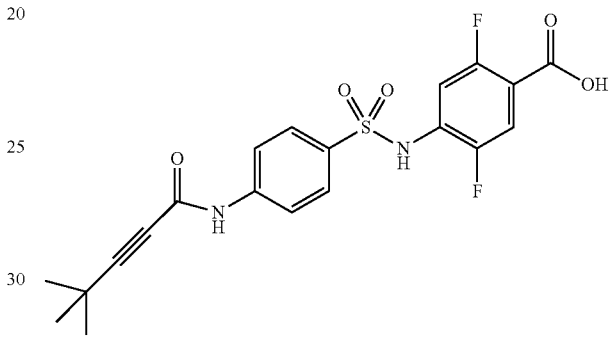

The compound (157 mg, 0.35 mmol) obtained in (step 2) was dissolved in methanol (6 ml) and water (2 ml), lithium hydroxide monohydrate (44 mg, 1.05 mmol) was added, and the mixture was stirred at room temperature overnight. After concentration under reduced pressure, the reaction solution was adjusted to a pH of 3 to 4 with 1 M hydrochloric acid, and the white solid was collected by filtration to give the title compound (132 mg, 87%).

$^1$H NMR (400 MHz, DMSO-d$_6$) δ 13.25 (br, s, 1H), 10.96-10.86 (m, 2H), 7.85-7.74 (m, 4H), 7.61-7.57 (m, 1H), 7.24-7.19 (m, 1H), 1.25 (m, 9H); MS (ESI) m/z 437 [M+H]$^+$.

SYNTHESIS EXAMPLE 44

2,5-difluoro-4-(((6-pivalamido-1H-indole)-3-sulfonamido)benzoic acid

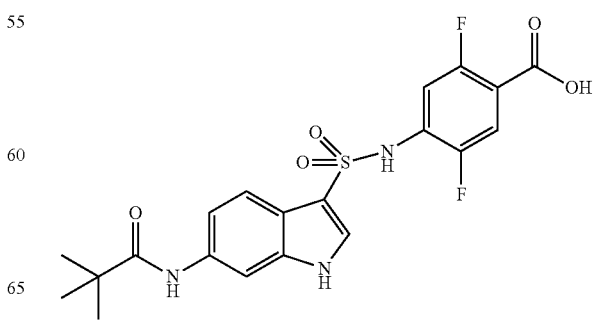

(Step 1)

Synthesis of 6-nitro-1H-indole-3-sulfonyl chloride

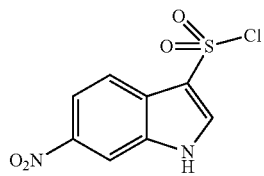 [SMILES: O=[N+]([O-])c1ccc2c(S(=O)(=O)Cl)c[nH]c2c1]

A chloroform (302 ml) solution of 6-nitro-1H-indole (3.0 g, 18.5 mmol) was added dropwise at 0° C. to a chloroform (454 ml) solution of sodium sulfate (74.6 g, 18.5 mmol) and chlorosulfuric acid (45.1 ml, 678.0 mmol), and the mixture was stirred for 1 hour. The reaction solution was slowly poured into water, followed by stirring, and the solid was collected by filtration and was dried to give a crude product of the title compound (13 g, 68%).

$^1$H NMR (400 MHz, CDCl$_3$) δ 9.60 (br, s 1H), 8.51 (d, J=8.8 Hz, 1H), 8.32 (q, J=10.8, 6.4 Hz, 1H), 8.24 (d, J=3.2 Hz, 1H), 8.18 (d, J=8.8 Hz, 1H).

(Step 2)

Synthesis of N-(4-bromo-2,5-difluorophenyl)-6-nitro-1H-indole-3-sulfonamide

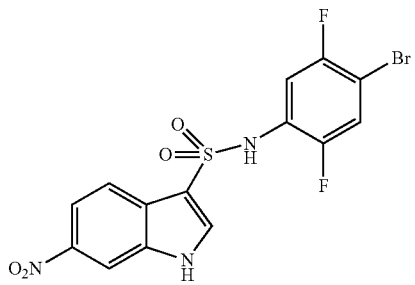 [SMILES: O=[N+]([O-])c1ccc2c(S(=O)(=O)Nc3cc(F)c(Br)cc3F)c[nH]c2c1]

The crude product (11.0 g) obtained in (step 1) and a pyridine (110 ml) solution of 4-bromo-2,5-difluoroaniline (8.76 g, 42.3 mmol) were stirred at 0° C. for 30 minutes, and then stirred at room temperature for 2 hours. After the reaction solution was concentrated under reduced pressure, the residue was purified by silica gel column chromatography (petroleum ether:ethyl acetate=3:1) to give the title compound (1.5 g, 8.3%).

$^1$H NMR (300 MHz, DMSO-d$_6$) δ 12.57 (s, 1H), 10.61 (s, 1H), 8.37 (q, J=6.4, 5.2 Hz, 1H), 8.10 (d, J=12.0 Hz, 1H), 7.97 (d, J=8.0 Hz, 1H), 7.59-7.65 (m, 1H), 7.31-7.37 (m, 1 H); MS (ESI) m/z 430 [M–H]$^-$.

(Step 3)

Synthesis of Methyl 4-((6-amino-1H-indole)-3-sulfonamido)-2,5-difluoro-benzoate

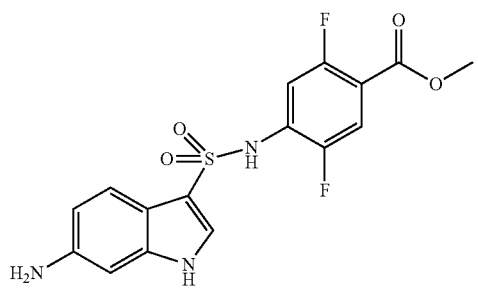 [SMILES: COC(=O)c1cc(F)c(NS(=O)(=O)c2c[nH]c3cc(N)ccc23)cc1F]

The compound (1.5 g, 3.5 mmol) obtained in (step 2), acetic acid palladium (313 mg, 1.4 mmol), 1,1'-bis(diphenylphosphino)ferrocene (1.15 g, 2.1 mmol) and trimethylamine (703 mg, 7.0 mmol) were suspended in DMSO (150 ml) and methanol (150 ml), and the suspension was stirred overnight under a carbon monoxide atmosphere at 100° C. and 4 Mpa. The reaction solution was concentrated under reduced pressure, followed by addition of water and extraction with ethyl acetate. The organic layer was washed with a saturated saline solution and was dried with sodium sulfate, and then the residue was purified by silica gel column chromatography (methanol:dichloromethane=20:1) to give the title compound (200 mg, 15%).

$^1$H NMR (400 MHz, DMSO-d$_6$) δ 7.72 (s, 1H), 7.59 (d, J=8.4 Hz, 1H), 7.48 (q, J=11.2, 6.8 Hz, 1H), 7.37 (q, J=6.4, 5.2 Hz, 1H), 6.70-6.76 (m, 2H), 3.82 (s, 3H); MS (ESI) m/z 380 [M–H]$^-$.

(Step 4)

Synthesis of Methyl 2,5-difluoro-4-((6-pivalamido-1H-indole)-3-sulfonamido)benzoate

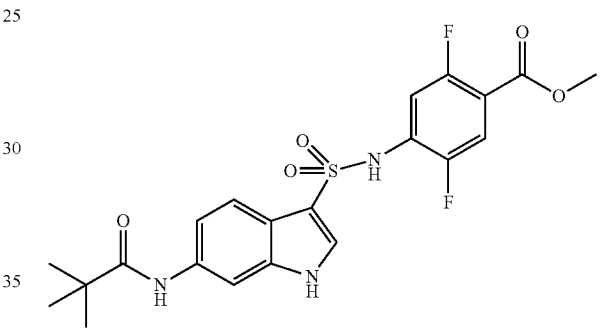

The compound (200 mg, 0.52 mmol) obtained in (step 3), pivalic acid chloride (76 mg, 0.63 mmol) and N,N-diisopropylethylamine (7 drops) were dissolved in dichloromethane (10 ml), and the mixture was stirred at room temperature for 4 hours. After the reaction solution was concentrated, the residue was purified by silica gel column chromatography (dichloromethane:methanol=20:1) to give the title compound (110 mg, 45%).

MS (ESI) m/z 466 [M+H]$^+$.

(Step 5)

Synthesis of 2,5-difluoro-4-((6-pivalamido-1H-indole)-3-sulfonamido)benzoic acid

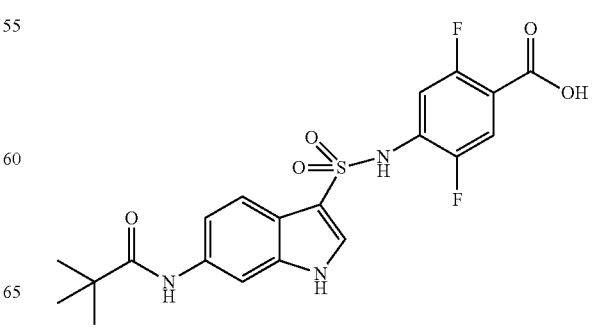

The compound (110 mg, 0.24 mmol) obtained in (step 4) was dissolved in THF (1 ml), a 2 M lithium hydroxide aqueous solution (0.5 ml) was added, and the mixture was stirred at room temperature for 5 hours. The reaction solution was concentrated and then purified by reverse phase HPLC to give the title compound (40 mg, 38%).

¹H NMR (400 MHz, CD₃OD) δ 7.91 (s, 1H), 7.85 (s, 1H), 7.82 (d, J=3.2 Hz, 1H), 7.47 (q, J=10.8, 6.8 Hz, 1H), 7.38 (q, J=12.0, 11.6 Hz, 1H), 7.21 (q, J=8.8, 8.8 Hz, 1H), 1.30 (s, 9H);

MS (ESI) m/z 452 [M+H]⁺.

SYNTHESIS EXAMPLE 45

2,5-difluoro-4-((5-pivalamido-1H-indole)-3-sulfonamido)benzoic acid

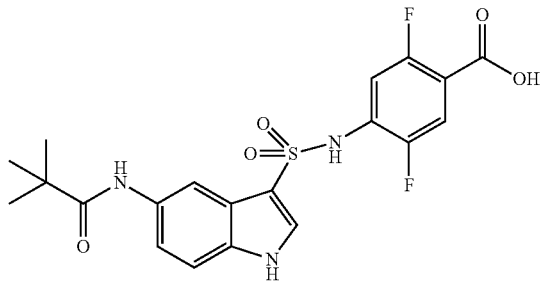 [SMILES: CC(C)(C)C(=O)Nc1ccc2[nH]cc(S(=O)(=O)Nc3cc(F)c(C(=O)O)cc3F)c2c1]

The title compound was obtained in the same method as in [Synthesis Example 44].

SYNTHESIS EXAMPLE 46

Synthesis of 2,5-difluoro-4-((3-pivalamido-1H-indole)-6-sulfonamido)benzoic acid

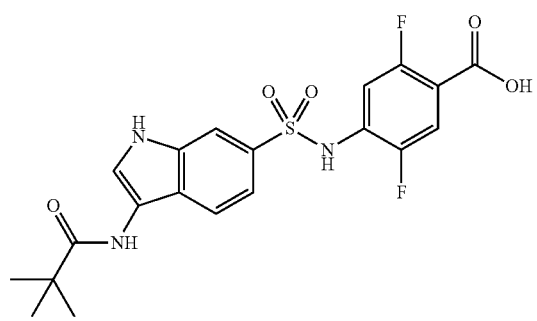 [SMILES: CC(C)(C)C(=O)Nc1c[nH]c2cc(S(=O)(=O)Nc3cc(F)c(C(=O)O)cc3F)ccc12]

(Step 1)

Synthesis of 6-bromo-1-(triisopropylsilyl)-1H-indole

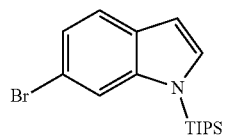

Sodium hydride (1.33 g, 33.2 mmol, 60% in mineral oil) was added at room temperature to a THF (100 ml) solution of 6-bromo-1H-indole (5.0 g, 25.5 mmol), and the mixture was stirred for 10 minutes. Then, triisopropylsilyl chloride (5.4 g, 28.05 mmol) was added slowly and the mixture was stirred at room temperature for 30 minutes. The reaction solution was poured into water, followed by extraction with ethyl acetate. The organic layer was washed with a saturated saline solution and was dried with sodium sulfate, and the residue was purified by silica gel column chromatography to give the title compound (8.6 g, 91%).

(Step 2)

Synthesis of 1-(triisopropylsilyl)-1H-indole-6-sulfonyl chloride

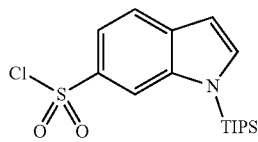

N-butyllithium (2.5 M, 6 ml, 15 mmol) was added at −65° C. to a THF (80 ml) solution of the compound (4.4 g, 12.5 mmol) obtained in (step 1), and the mixture was stirred for 1 hour. The reaction solution was bubbled with sulfur dioxide at −78° C. for 15 minutes. Next, N-chlorosuccinimide (2.0 g, 15 mmol) was added, and the mixture was returned to room temperature and stirred for 30 minutes. The reaction solution was poured into water, followed by extraction with ethyl acetate. The organic layer was washed with a saturated saline solution and was dried with sodium sulfate, and the residue was purified by silica gel column chromatography to give the title compound (1.48 g, 30%).

¹H NMR (400 MHz, CDCl₃) δ 8.21 (s, 1H), 7.78-7.77 (m, 2H), 7.56 (s, 1H), 6.77 (s, 1H), 1.76-1.69 (m, 3H), 1.17 (s, 9H), 1.15 (s, 9H).

(Step 3)

Synthesis of N-(4-bromo-2,5-difluorophenyl)-1-(triisopropylsilyl)-1H-indole-6-sulfonamide

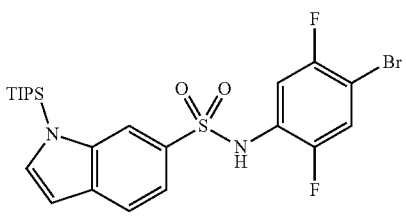

A pyridine (10 ml) solution of the compound (984 mg, 2.64 mmol) obtained in (step 2) and 4-bromo-2,5-difluoroaniline (500 mg, 2.4 mmol) was stirred at room temperature overnight. After the reaction solution was concentrated under reduced pressure, the residue was diluted with water (30 ml), followed by extraction with ethyl acetate (50 ml, twice). Purification by silica gel column chromatography (petroleum ether:ethyl acetate=3:1) gave the title compound (1.5 g, 8.3%). The organic layer was washed with a saturated saline solution and was dried with sodium sulfate. The residue was diluted with diethyl ether (20 ml), and the solid was collected by filtration and was dried to give the title compound (500 mg, 38%).

$^1$H NMR (300 MHz, DMSO-$d_6$): δ 10.51 (s, 1H), 7.85-7.77 (m, 2H), 7.65-7.25 (m, 4H), 6.77-6.59 (m, 1H), 1.73-1.57 (m, 3H), 1.09 (d, J=7.5 Hz, 6H), 1.00 (d, J=10.5 Hz, 12H).

(Step 4)

Synthesis of Methyl 2,5-difluoro-4-(1H-indole-6-sulfonamido)benzoate

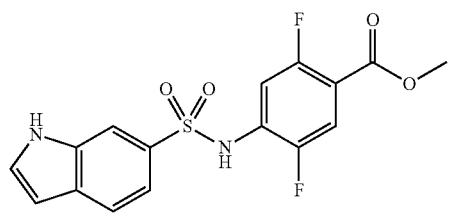 [SMILES: COC(=O)c1cc(F)c(NS(=O)(=O)c2ccc3cc[nH]c3c2)cc1F]

The title compound was obtained in the same method as in (step 3) in [Synthesis Example 44] by using the compound obtained in (step 3).

$^1$H NMR (300 MHz, DMSO-$d_6$): δ 11.65 (s, 1H), 10.91 (s, 1H), 7.97 (s, 1H), 7.74-7.56 (m, 3H), 7.48-7.45 (m, 1H), 7.33-7.28 (m, 1H), 6.56 (s, 1H), 3.78 (s, 3H).

(Step 5)

Synthesis of Methyl 2,5-difluoro-4-((3-nitro-1H-indole)-6-sulfonamido)benzoate

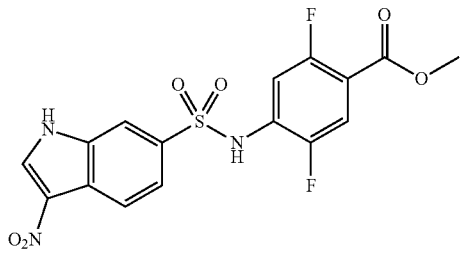 [SMILES: COC(=O)c1cc(F)c(NS(=O)(=O)c2ccc3c([N+](=O)[O-])c[nH]c3c2)cc1F]

An acetic anhydride (10 ml) solution of the compound (200 mg, 0.546 mmol) obtained in (step 4) was ice-cooled and nitric acid (1 ml) was added by a syringe, followed by stirring at room temperature for 30 minutes. The reaction solution was poured into water (20 ml), followed by extraction with ethyl acetate. The organic layer was washed with a saturated saline solution and was dried with sodium sulfate, and the residue was purified by silica gel column chromatography to give the title compound (140 mg, 63%).

$^1$H NMR (300 MHz, DMSO-$d_6$): δ 13.03 (br s, 1H), 11.10 (br s, 1H), 8.89-8.87 (m, 1H), 8.26 (d, J=8.7 Hz, 1H), 8.07 (s, 1H), 8.82 (dd, J=8.7 Hz, 1.5 Hz, 1H), 7.65-7.59 (m, 1H), 7.34-7.28 (m, 1H), 3.79 (s, 3H).

(Step 6)

Synthesis of Methyl 4-((3-amino-1H-indole)-6-sulfonamido)-2,5-difluoro-benzoate

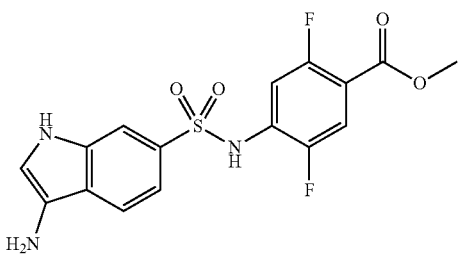

Palladium carbon (30 mg) and trimethylamine (3 drops) were added to a methanol (5 ml) solution of the compound obtained in (step 5), and the mixture was stirred under a hydrogen atmosphere for 1 hour. The reaction solution was filtered and the filtrate was concentrated to give the title compound (108 mg, 98%).

(Step 7)

Synthesis of 2,5-difluoro-4-((3-pivalamido-1H-indole)-6-sulfonamido)benzoic acid

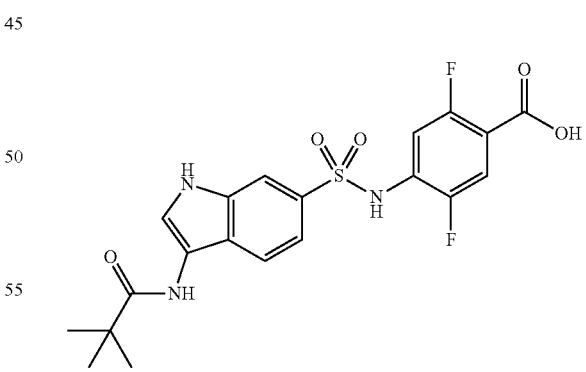

The title compound was obtained in the same method as in (step 4) and (step 5) in [Synthesis Example 44] by using the compound obtained in (step 6).

$^1$H NMR (400 MHz, CD$_3$OD): δ 7.94 (s, 1H), 7.66-7.63 (m, 2H), 7.53-7.45 (m, 2H), 7.40-7.36 (m, 1H), 1.37 (m, 9H); MS (ESI) m/z 452 [M+H]$^+$.

EXAMPLE 1

(2S)-2-[[4-[[4-(2,2-dimethylpropanoylamino)phenyl]sulfonylamino]-2,5-difluoro-benzoyl]amino]-3-[4-(1-methyl-2,4-dioxo-pyrido[3,4-d]pyrimidin-3-yl)phenyl]propanoic acid (A1)

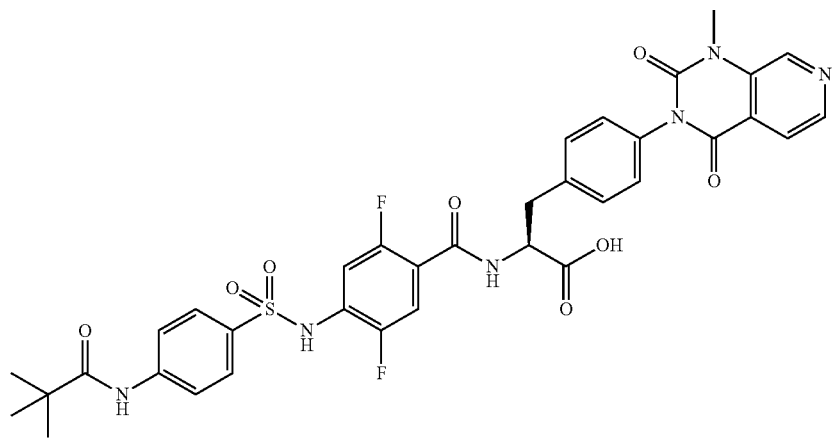 [SMILES: Cn1c(=O)n(-c2ccc(C[C@H](NC(=O)c3cc(F)c(NS(=O)(=O)c4ccc(NC(=O)C(C)(C)C)cc4)cc3F)C(=O)O)cc2)c(=O)c2ccncc21]

(Step 1)

Synthesis of Methyl (2S)-2-[[4-[[4-(2,2-dimethyl-propanoylamino)phenyl]sulfonylamino]-2,5-difluoro-benzoyl]amino]-3-[4-(1-methyl-2,4-dioxo-pyrido[3,4-d]pyrimidin-3-yl)phenyl]propanoate

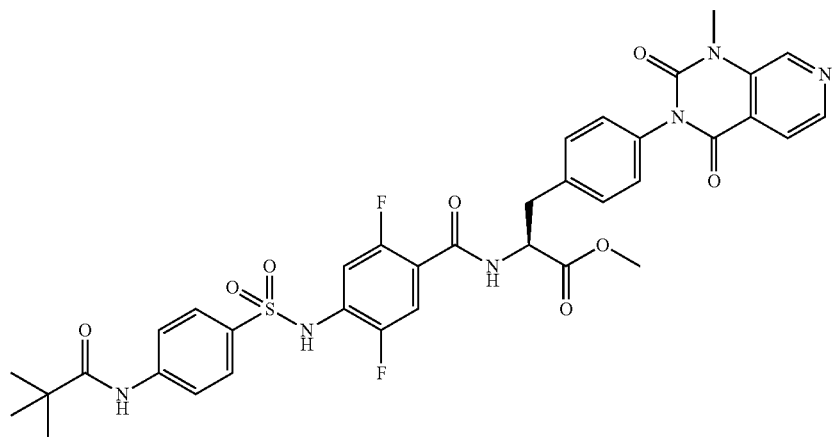 [SMILES: COC(=O)[C@H](Cc1ccc(-n2c(=O)c3ccncc3n(C)c2=O)cc1)NC(=O)c1cc(F)c(NS(=O)(=O)c2ccc(NC(=O)C(C)(C)C)cc2)cc1F]

HATU (55 mg, 0.15 mmol) and N,N-diisopropylamine (62 μl) were sequentially added to a DMF solution (2.0 mL) of the compound (50 mg, 0.12 mmol) in [Synthesis Example 1] and the hydrochloride (52 mg, 0.13 mmol) of the compound in [Synthesis Example 22], and the mixture was stirred at room temperature for 5 hours. The mixture was concentrated under reduced pressure, and the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (64 mg, 71%).

(Step 2)

Synthesis of (2S)-2-[[4-[[4-(2,2-dimethylpropanoylamino)phenyl]sulfonylamino]-2,5-difluoro-benzoyl]amino]-3-[4-(1-methyl-2,4-dioxo-pyrido[3,4-d]pyrimidin-3-yl)phenyl]propanoic acid

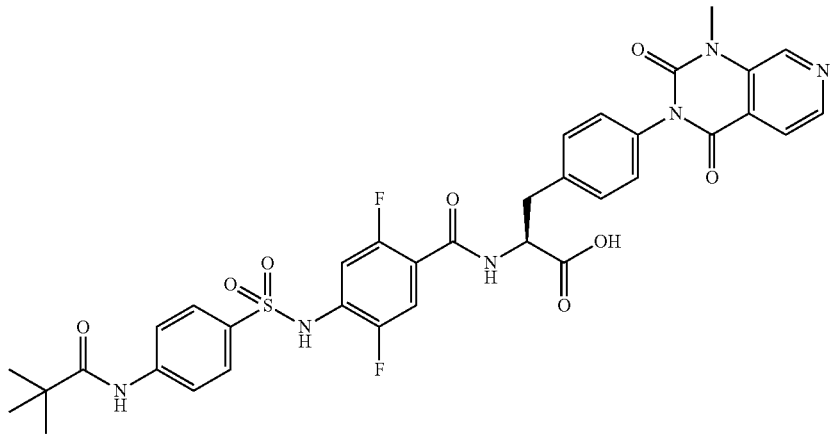 [SMILES: Cn1c(=O)n(-c2ccc(C[C@H](NC(=O)c3cc(F)c(NS(=O)(=O)c4ccc(NC(=O)C(C)(C)C)cc4)cc3F)C(=O)O)cc2)c(=O)c2ccncc21]

Water (2.0 ml) and a 1 M sodium hydroxide aqueous solution (0.26 ml) were sequentially added to a 1,4-dioxane solution (2.0 ml) of the compound (64 mg, 0.085 mmol) obtained in (step 1), and the mixture was stirred at room temperature for 5 hours. The resultant mixture was neutralized by adding 1 M hydrochloric acid thereto, and was concentrated under reduced pressure. Thereafter, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound (54 mg, 87%).

EXAMPLE 2

(2S)-2-[[2,5-difluoro-4-[[4-(piperidine-4-carbonylamino)phenyl]sulfonylamino]benzoyl]amino]-3-[4-(1-methyl-2,4-dioxo-pyrido[3,4-d]pyrimidin-3-yl)phenyl]propanoic acid (A6)

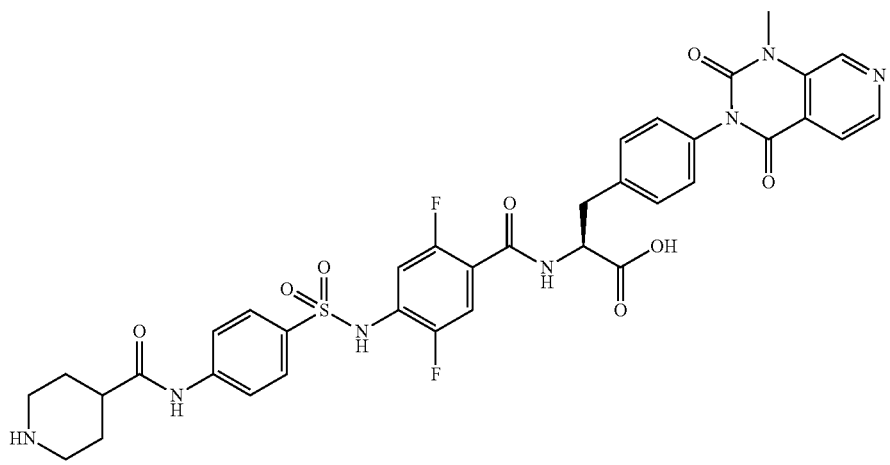 [SMILES: Cn1c(=O)n(-c2ccc(C[C@H](NC(=O)c3cc(F)c(NS(=O)(=O)c4ccc(NC(=O)C5CCNCC5)cc4)cc3F)C(=O)O)cc2)c(=O)c2ccncc21]

(Step 1)

Synthesis of tert-butyl 4-[[4-[[2,5-difluoro-4-[[(1S)-2-methoxy-1-[[4-(1-methyl-2,4-dioxo-pyrido[3,4-d]pyrimidin-3-yl)cyclohexa-2,4-dien-1-yl]methyl]-2-oxo-ethyl]carbamoyl]phenyl]sulfamoyl]phenyl]carbamoyl]piperidine-1-carboxylate

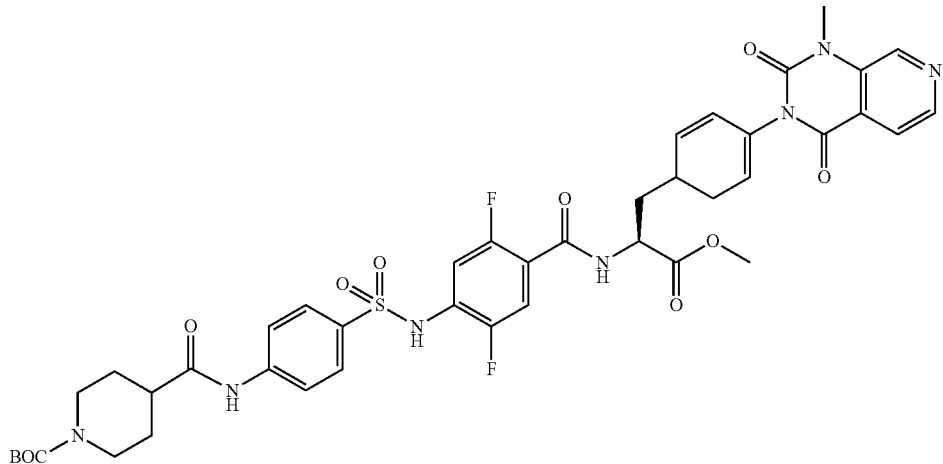 [SMILES: COC(=O)[C@H](CC1C=CC(n2c(=O)c3ccncc3n(C)c2=O)=CC1)NC(=O)c1cc(F)c(NS(=O)(=O)c2ccc(NC(=O)C3CCN(C(=O)OC(C)(C)C)CC3)cc2)cc1F]

HATU (34 mg, 0.089 mmol) and N, N-diisopropylamine (33 μl) were sequentially added to a DMF solution (2.0 ml) of the compound (40 mg, 0.074 mmol) in [Synthesis Example 5] and the hydrochloride of the compound (32 mg, 0.082 mmol) in [Synthesis Example 22], and the mixture was stirred at room temperature for 5 hours. The mixture was concentrated under reduced pressure, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound.

(Step 2)

Synthesis of (2S)-2-[[2,5-difluoro-4-[[4-(piperidine-4-carbonylamino)phenyl]sulfonylamino]benzoyl]amino]-3-[4-(1-methyl-2,4-dioxo-pyrido[3,4-d]pyrimidin-3-yl)phenyl]propanoic acid

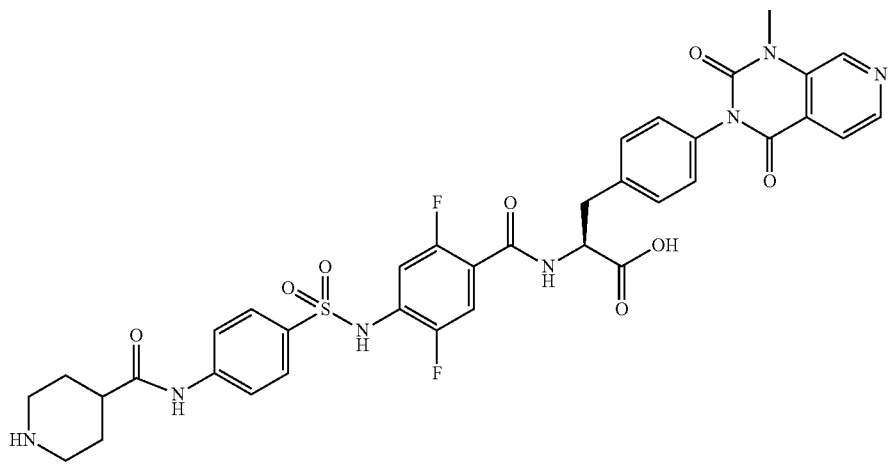 [SMILES: Cn1c(=O)n(-c2ccc(C[C@H](NC(=O)c3cc(F)c(NS(=O)(=O)c4ccc(NC(=O)C5CCNCC5)cc4)cc3F)C(=O)O)cc2)c(=O)c2ccncc21]

Water (2.0 ml) and 4 M hydrochloric acid/1,4-dioxane were added to the compound obtained in (step 1), and the mixture was stirred at 50° C. for 18 hours. The mixture was concentrated under reduced pressure, the residue was subjected to reverse phase HPLC using ODS as a packing material for elution with a mixed solution of water and acetonitrile containing 0.1% (v/v) of trifluoroacetic acid, and the targeted fraction was freeze-dried to give the trifluoroacetate of the title compound (4.5 mg, 8.0% for 2 steps).

EXAMPLE 3

(2S)-2-[2,5-difluoro-4-[(4-pivalamidophenyl)sulfonamide]benzamido]-3-[6-(3-methyl-2,6-dioxotetrahydropyrimidin-1(2H)-yl)pyridin-3-yl]propanoic acid (A75)

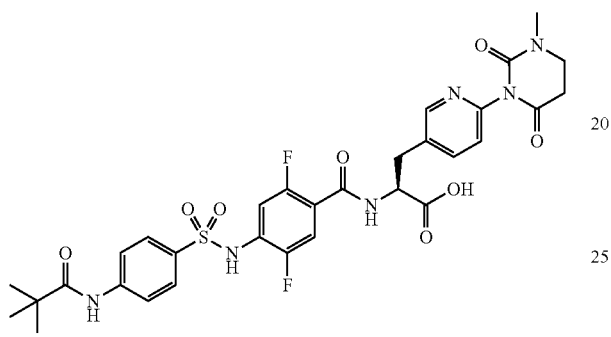

A catalytic amount of 5% rhodium carbon was added to a methanol solution of A53 (10.3 mg, 0.015 mmol) to cause a reaction to proceed at 70° C. and 60 bar. The solvent was evaporated under reduced pressure, the residue was subjected to reverse phase HPLC using ODS as a packing material for elution with a mixed solution of water and acetonitrile containing 0.1% (v/v) of trifluoroacetic acid, and the targeted fraction was freeze-dried to give the title compound.

Each of the compounds shown in Tables 1 was synthesized in the same method as in the compound in [Example 1] by using the corresponding one of any carboxylic acid intermediate selected from [Synthesis Examples 1 to 21] and [Synthesis Examples 43 to 46], any amine intermediate selected from [Synthesis Examples 22 to 42], or a salt thereof.

TABLE 1

| Compound No | Structural Formula | NMR/MS |
|---|---|---|
| A1 | | 1H NMR (400 MHz, DMSO-d6) δ 10.67 (s, 1H), 9.57 (s, 1H), 8.97 (s, 1H), 8.67-8.47 (m, 2H), 7.98-7.67 (m, 5H), 7.46-7.32 (m, 2H), 7.28 (dd, J = 10.3, 6.3 Hz, 1H), 7.25-7.11 (m, 3H), 4.70-4.60 (m, 1H), 3.59 (s, 3H), 3.22 (dd, J = 14.0, 4.6 Hz, 1H), 3.06 (dd, J = 14.0, 9.8 Hz, 1H), 1.21 (s, 9H); MS (ESI) m/z 735[M + H]+. |

TABLE 1-continued

| Compound No | Structural Formula | NMR/MS |
|---|---|---|
| A2 | 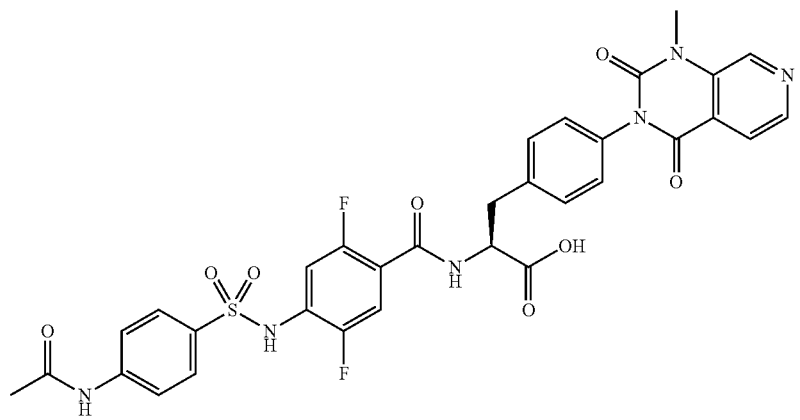 [SMILES: CC(=O)Nc1ccc(S(=O)(=O)Nc2cc(F)c(C(=O)N[C@@H](Cc3ccc(-n4c(=O)c5ccncc5n(C)c4=O)cc3)C(=O)O)cc2F)cc1] | 1H NMR (400 MHz, DMSO-d6) δ 10.67 (s, 1H), 10.34 (s, 1H), 8.97 (s, 1H), 8.63-8.51 (m, 2H), 7.89 (d, J = 4.9 Hz, 1H), 7.75 (m, 4H), 7.41-7.33 (m, 2H), 7.28 (dd, J = 10.2, 6.4 Hz, 1H), 7.25-7.13 (m, 3H), 4.62 (ddd, J = 10.1, 7.9, 4.7 Hz, 1H), 3.60 (s, 3H), 3.23 (dd, J = 14.0, 4.7 Hz, 1H), 3.06 (dd, J = 14.0, 9.8 Hz, 1H), 2.06 (s, 3H); MS (ESI) m/z 693 (M + H)+; MS (ESI) m/z 693[M + H]+. |
| A3 | 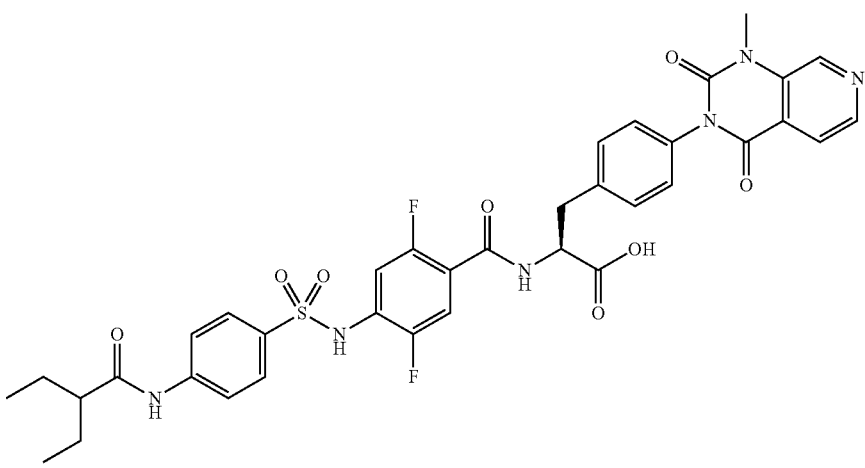 [SMILES: CCC(CC)C(=O)Nc1ccc(S(=O)(=O)Nc2cc(F)c(C(=O)N[C@@H](Cc3ccc(-n4c(=O)c5ccncc5n(C)c4=O)cc3)C(=O)O)cc2F)cc1] | 1H NMR (400 MHz, DMSO-d6) δ 12.91 (s, 1H), 10.70 (s, 1H), 10.28 (s, 1H), 8.97 (s, 1H), 8.62-8.50 (m, 2H), 7.88 (d, J = 5.0 Hz, 1H), 7.85-7.72 (m, 4H), 7.36 (d, J = 8.3 Hz, 2H), 7.29 (dd, J = 10.3, 6.4 Hz, 1H), 7.26-7.14 (m, 3H), 4.69-4.55 (m, 1H), 3.59 (s, 3H), 3.22 (dd, J = 14.0, 4.7 Hz, 1H), 3.06 (dd, J = 14.0, 9.8 Hz, 1H), 2.29-2.17 (m, 1H), 1.62-1.37 (m, 4H), 0.83 (t, J = 7.4 Hz, 6H); MS (ESI) m/z 749[M + H]+. |
| A4 | 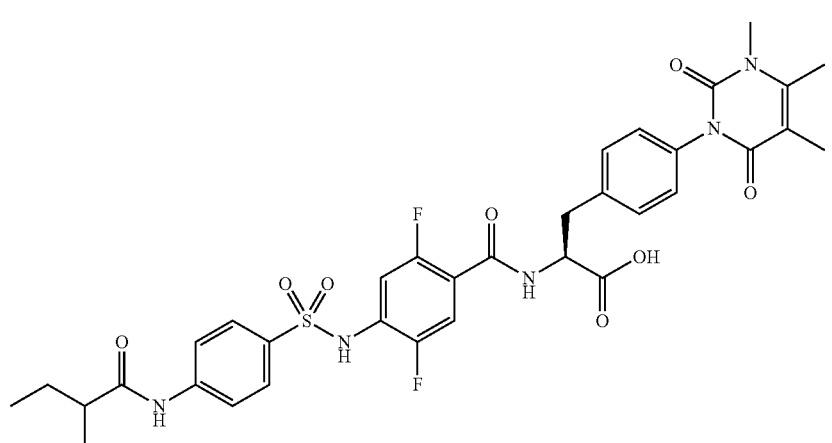 | 1H NMR (400 MHz, DMSO-d6) δ 12.89 (s, 1H), 10.69 (s, 1H), 10.28 (s, 1H), 8.55 (dd, J = 8.0, 2.7 Hz, 1H), 7.87-7.71 (m, 4H), 7.38-7.25 (m, 3H), 7.19 (dd, J = 11.3, 6.3 Hz, 1H), 7.06 (d, J = 8.3 Hz, 2H), 4.66-4.53 (m, 1H), 3.35 (s, 3H), 3.19 (dd, J = 14.1, 4.6 Hz, 1H), 3.04 (dd, J = 14.0, 9.7 Hz, 1H), 2.31 (s, 3H), 2.29-2.19 (m, 1H), 1.89 (s, 3H), 1.64-1.37 (m, 4H), 0.83 (t, J = 7.4 Hz, 6H); MS (ESI) m/z 726[M + H]+. |

TABLE 1-continued

| Compound No | Structural Formula | NMR/MS |
|---|---|---|
| A5 | | 1H NMR (400 MHz, DMSO-d6) δ 10.58 (s, 1H), 8.97 (s, 1H), 8.73 (s, 1H), 8.61-8.49 (m, 2H), 7.88 (d, J = 5.0 Hz, 1H), 7.66 (d, J = 8.9 Hz, 2H), 7.50 (d, J = 8.9 Hz, 2H), 7.37 (d, J = 8.3 Hz, 2H), 7.28 (dd, J = 10.3, 6.4 Hz, 1H), 7.24-7.13 (m, 3H), 6.17 (s, 1H), 4.66-4.57 (m, 1H), 3.60 (s, 3H), 3.22 (dd, J = 14.0, 4.5 Hz, 1H), 3.06 (dd, J = 14.0, 9.9 Hz, 1H), 1.27 (s, 9H); MS (ESI) m/z 750[M + H]+. |
| A6 | | 1H NMR (400 MHz, DMSO-d6) δ 12.92 (s, 1H), 10.70 (s, 1H), 10.44 (s, 1H), 8.97 (s, 1H), 8.64-8.43 (m, 3H), 8.37-8.17 (m, 1H), 7.88 (d, J = 4.9 Hz, 1H), 7.77 (m, 4H), 7.44-7.34 (m, 2H), 7.28 (dd, J = 10.3, 6.3 Hz, 1H), 7.24-7.15 (m, 3H), 4.69-4.55 (m, 1H), 3.60 (s, 3H), 3.34 (d, J = 12.6 Hz, 2H), 3.23 (dd, J = 14.0, 4.6 Hz, 1H), 3.06 (dd, J = 14.0, 9.8 Hz, 1H), 3.00-2.85 (m, 2H), 2.71-2.59 (m, 1H), 2.03-1.90 (m, 2H), 1.86-1.70 (m, 2H); MS (ESI) m/z 762[M + H]+. |
| A7 | | 1H NMR (400 MHz, DMSO-d6) δ 10.87 (s, 1H), 10.74 (s, 1H), 8.96 (s, 1H), 8.89-8.78 (m, 2H), 8.60 (dd, J = 8.0, 2.6 Hz, 1H), 8.54 (d, J = 5.0 Hz, 1H), 7.97 (d, J = 8.9 Hz, 2H), 7.92-7.79 (m, 5H), 7.37 (d, J = 8.4 Hz, 2H), 7.29 (dd, J = 10.2, 6.3 Hz, 1H), 7.25-7.17 (m, 3H), 4.68-4.55 (m, 1H), 3.59 (s, 3H), 3.23 (dd, J = 14.0, 4.6 Hz, 1H), 3.06 (dd, J = 14.0, 9.9 Hz, 1H); MS (ESI) m/z 756[M + H]+. |

TABLE 1-continued

| Compound No | Structural Formula | NMR/MS |
|---|---|---|
| A8 | | 1H NMR (400 MHz, DMSO-d6) δ 10.66 (s, 1H), 9.57 (s, 1H), 8.56 (dd, J = 7.8, 2.7 Hz, 1H), 7.85 (d, J = 8.9 Hz, 2H), 7.74 (d, J = 8.9 Hz, 2H), 7.35-7.25 (m, 3H), 7.18 (dd, J = 11.2, 6.3 Hz, 1H), 7.06 (d, J = 8.3 Hz, 2H), 4.62-4.55 (m, 1H), 3.35 (s, 3H), 3.19 (dd, J = 14.1, 4.6 Hz, 1H), 3.04 (dd, J = 14.1, 9.7 Hz, 1H), 2.31 (s, 3H), 1.89 (s, 3H), 1.21 (s, 9H); MS (ESI) m/z 712[M + H]+. |
| A9 | | 1H NMR (400 MHz, DMSO-d6) δ 11.16 (s, 1H), 10.80 (s, 1H), 8.97 (s, 1H), 8.61 (dd, J = 7.9, 2.6 Hz, 1H), 8.55 (d, J = 5.0 Hz, 1H), 7.88 (d, J = 5.0 Hz, 1H), 7.45 (d, J = 4.3 Hz, 1H), 7.38 (d, J = 8.4 Hz, 2H), 7.32 (dd, J = 10.3, 6.3 Hz, 1H), 7.28-7.19 (m, 3H), 6.79 (d, J = 4.3 Hz, 1H), 4.69-4.56 (m, 1H), 3.60 (s, 3H), 3.23 (dd, J = 14.0, 4.6 Hz, 1H), 3.07 (dd, J = 14.0, 9.7 Hz, 1H), 1.21 (s, 9H); MS (ESI) m/z 741[M + H]+. |
| A10 | | 1H NMR (400 MHz, DMSO-d6) δ 11.17 (s, 1H), 10.80 (s, 1H), 8.59 (dd, J = 7.9, 2.7 Hz, 1H), 7.45 (d, J = 4.3 Hz, 1H), 7.41-7.28 (m, 3H), 7.24 (dd, J = 11.3, 6.3 Hz, 1H), 7.12-6.99 (m, 2H), 6.79 (d, J = 4.3 Hz, 1H), 4.60 (ddd, J = 9.7, 7.7, 4.6 Hz, 1H), 3.36 (s, 3H), 3.20 (dd, J = 14.0, 4.5 Hz, 1H), 3.05 (dd, J = 14.0, 9.7 Hz, 1H), 2.31 (s, 3H), 1.89 (s, 3H), 1.21 (s, 9H); MS (ESI) m/z 718[M + H]+. |

TABLE 1-continued

| Compound No | Structural Formula | NMR/MS |
|---|---|---|
| A11 | | 1H NMR (400 MHz, DMSO-d6) δ 12.89 (s, 1H), 11.02 (s, 1H), 9.82 (s, 1H), 8.62 (dd, J = 8.0, 2.5 Hz, 1H), 7.92 (d, J = 1.7 Hz, 1H), 7.78 (d, J = 1.7 Hz, 1H), 7.42-7.30 (m, 3H), 7.25 (dd, J = 11.1, 6.2 Hz, 1H), 7.07 (d, J = 7.9 Hz, 2H), 4.66-4.55 (m, 1H), 3.36 (s, 3H), 3.21 (dd, J = 14.1, 4.6 Hz, 1H), 3.05 (dd, J = 14.1, 9.8 Hz, 1H), 2.31 (s, 3H), 1.89 (s, 3H), 1.18 (s, 9H); MS (ESI) m/z 718[M + H]+. |
| A12 | | 1H NMR (400 MHz, DMSO-d6) δ 10.77 (s, 1H), 9.24 (s, 1H), 8.90 (s, 1H), 8.56 (dd, J = 7.9, 2.4 Hz, 1H), 8.48 (d, J = 4.9 Hz, 1H), 7.82 (d, J = 4.9 Hz, 1H), 7.76-7.70 (m, 1H), 7.62 (dd, J = 9.8, 2.1 Hz, 1H), 7.56 (dd, J = 8.5, 2.1 Hz, 1H), 7.30 (d, J = 8.3 Hz, 2H), 7.24 (dd, J = 10.2, 6.3 Hz, 1H), 7.20-7.11 (m, 3H), 4.61-4.52 (m, 1H), 3.53 (s, 3H), 3.16 (dd, J = 14.1, 4.6 Hz, 1H), 3.00 (dd, J = 14.0, 9.9 Hz, 1H), 1.15 (s, 9H); MS (ESI) m/z 753[M + H]+. |
| A13 | | 1H NMR (400 MHz, DMSO-d6) δ 10.84 (s, 1H), 9.31 (s, 1H), 8.61 (dd, J = 7.9, 2.5 Hz, 1H), 7.84-7.77 (m, 1H), 7.69 (dd, J = 9.8, 2.1 Hz, 1H), 7.63 (dd, J = 8.4, 2.1 Hz, 1H), 7.35-7.28 (m, 3H), 7.23 (dd, J = 11.0, 6.3 Hz, 1H), 7.07 (d, J = 8.3 Hz, 2H), 4.64-4.55 (m, 1H), 3.36 (s, 3H), 3.20 (dd, J = 14.0, 4.6 Hz, 1H), 3.05 (dd, J = 14.0, 9.8 Hz, 1H), 2.31 (s, 3H), 1.90 (s, 3H), 1.22 (s, 9H); MS (ESI) m/z 730[M + H]+. |

TABLE 1-continued
| Compound No | Structural Formula | NMR/MS |
|---|---|---|
| A14 | 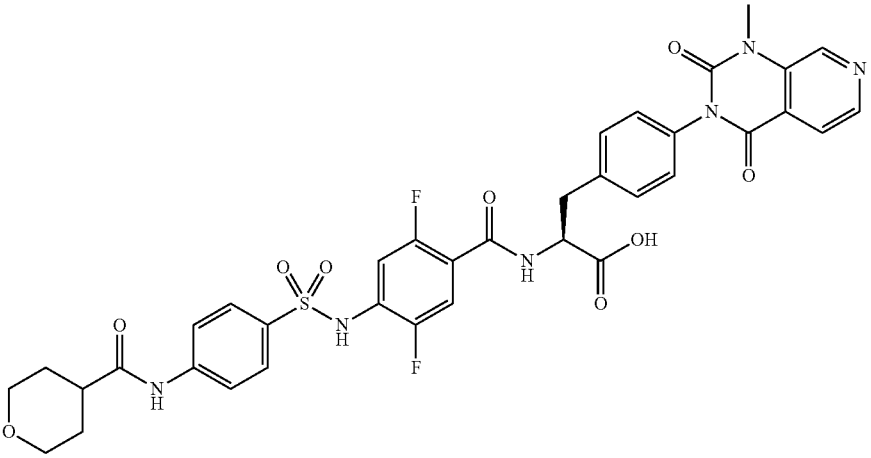 [SMILES: Cn1c(=O)n(-c2ccc(C[C@H](NC(=O)c3cc(F)c(NS(=O)(=O)c4ccc(NC(=O)C5CCOCC5)cc4)cc3F)C(=O)O)cc2)c(=O)c2ccncc21] | 1H NMR (400 MHz, DMSO-d6) δ 10.67 (s, 1H), 10.30 (s, 1H), 8.97 (s, 1H), 8.63-8.49 (m, 2H), 7.89 (d, J = 5.0 Hz, 1H), 7.82-7.70 (m, 4H), 7.41-7.33 (m, 2H), 7.28 (dd, J = 10.3, 6.3 Hz, 1H), 7.24-7.13 (m, 3H), 4.66-4.57 (m, 1H), 3.93-3.85 (m, 2H), 3.60 (s, 3H), 3.33 (td, J = 11.5, 2.7 Hz, 2H), 3.22 (dd, J = 14.0, 4.6 Hz, 1H), 3.06 (dd, J = 14.0, 9.8 Hz, 1H), 2.66-2.54 (m, 1H), 1.76-1.53 (m, 4H); MS (ESI) m/z 763[M + H]+. |
| A15 | 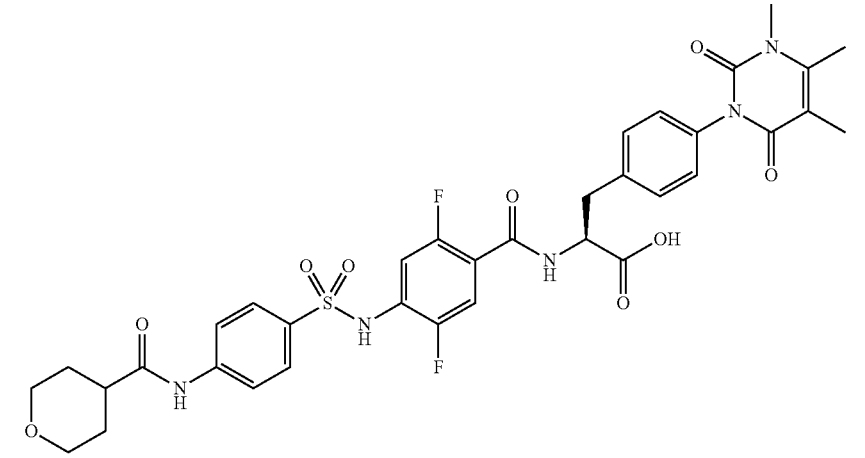 [SMILES: Cc1c(C)n(C)c(=O)n(-c2ccc(C[C@H](NC(=O)c3cc(F)c(NS(=O)(=O)c4ccc(NC(=O)C5CCOCC5)cc4)cc3F)C(=O)O)cc2)c1=O] | 1H NMR (400 MHz, DMSO-d6) δ 12.92 (s, 1H), 10.67 (s, 1H), 10.30 (s, 1H), 8.56 (dd, J = 7.8, 2.6 Hz, 1H), 7.83-7.68 (m, 4H), 7.36-7.24 (m, 3H), 7.18 (dd, J = 11.3, 6.3 Hz, 1H), 7.10-7.01 (m, 2H), 4.64-4.54 (m, 1H), 3.97-3.82 (m, 2H), 3.42-3.30 (m, 5H), 3.24-3.13 (m, 1H), 3.04 (dd, J = 13.8, 9.9 Hz, 1H), 2.64-2.55 (m, 1H), 2.31 (s, 3H), 1.89 (s, 3H), 1.77-1.57 (m, 4H); MS (ESI) m/z 740[M + H]+. |
| A16 | 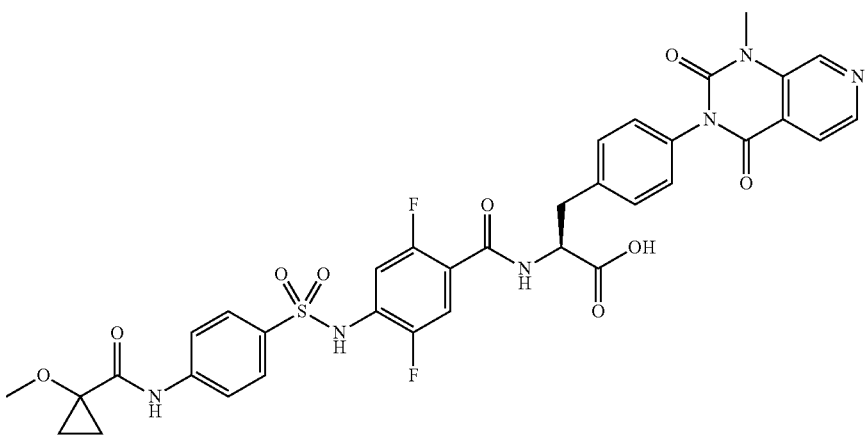 [SMILES: COC1(C(=O)Nc2ccc(S(=O)(=O)Nc3cc(F)c(C(=O)N[C@@H](Cc4ccc(-n5c(=O)c6ccncc6n(C)c5=O)cc4)C(=O)O)cc3F)cc2)CC1] | 1H NMR (400 MHz, DMSO-d6) δ 10.70 (s, 1H), 10.33 (s, 1H), 8.97 (s, 1H), 8.64-8.49 (m, 2H), 8.01-7.91 (m, 2H), 7.88 (d, J = 5.0 Hz, 1H), 7.80-7.70 (m, 2H), 7.36 (d, J = 8.3 Hz, 2H), 7.29 (dd, J = 10.3, 6.3 Hz, 1H), 7.24-7.13 (m, 3H), 4.69-4.56 (m, 1H), 3.59 (s, 3H), 3.31 (s, 3H), 3.27-3.18 (m, 1H), 3.13-3.01 (m, 1H), 1.20-1.10 (m, 4H); MS (ESI) m/z 749[M + H]+. |

TABLE 1-continued

| Compound No | Structural Formula | NMR/MS |
|---|---|---|
| A17 | | 1H NMR (400 MHz, DMSO-d6) δ 10.71 (s, 1H), 10.34 (s, 1H), 8.57 (dd, J = 7.9, 2.6 Hz, 1H), 7.99-7.88 (m, 2H), 7.83-7.72 (m, 2H), 7.36-7.25 (m, 3H), 7.20 (dd, J = 11.2, 6.2 Hz, 1H), 7.11-7.03 (m, 2H), 4.66-4.55 (m, 1H), 3.36 (s, 3H), 3.32 (s, 3H), 3.25-3.16 (m, 1H), 3.09-3.00 (m, 1H), 2.31 (s, 3H), 1.90 (s, 3H), 1.22-1.12 (m, 4H); MS (ESI) m/z 726[M + H]+. |
| A18 | | 1H NMR (400 MHz, DMSO-d6) δ 10.66 (s, 1H), 9.59 (s, 1H), 8.97 (s, 1H), 8.63-8.52 (m, 2H), 7.89 (d, J = 5.0 Hz, 1H), 7.83 (d, J = 8.9 Hz, 2H), 7.74 (d, J = 8.9 Hz, 2H), 7.37 (d, J = 8.4 Hz, 2H), 7.28 (dd, J = 10.3, 6.3 Hz, 1H), 7.25-7.14 (m, 3H), 4.67-4.59 (m, 1H), 3.60 (s, 3H), 3.49 (s, 2H), 3.22 (dd, J = 14.1, 4.6 Hz, 1H), 3.06 (dd, J = 14.1, 9.8 Hz, 1H), 1.13 (s, 6H); MS (ESI) m/z 751[M + H]+. |
| A19 | | 1H NMR (400 MHz, DMSO-d6) δ 10.85 (s, 1H), 9.80 (s, 1H), 8.94 (d, J = 2.4 Hz, 1H), 8.57 (dd, J = 7.9, 2.7 Hz, 1H), 8.35 (dd, J = 8.7, 2.5 Hz, 1H), 7.97 (d, J = 8.7 Hz, 1H), 7.39-7.21 (m, 4H), 7.14-7.02 (m, 2H), 4.69-4.52 (m, 1H), 3.36 (s, 3H), 3.20 (dd, J = 14.1, 4.6 Hz, 1H), 3.05 (dd, J = 14.1, 9.7 Hz, 1H), 2.31 (d, J = 1.0 Hz, 3H), 1.89 (d, J = 0.9 Hz, 3H), 1.23 (s, 9H).; MS (ESI) m/z 713[M + H]+ |

TABLE 1-continued
| Compound No | Structural Formula | NMR/MS |
|---|---|---|
| A20 | 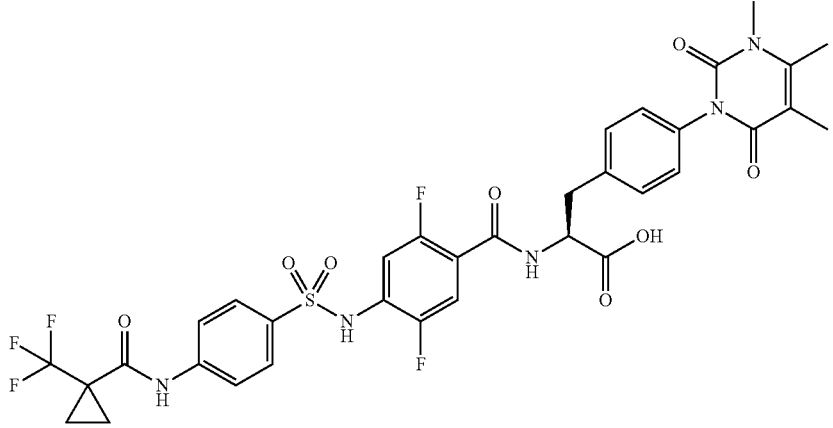 [SMILES: Cc1c(C)n(C)c(=O)n(-c2ccc(C[C@H](NC(=O)c3cc(F)c(NS(=O)(=O)c4ccc(NC(=O)C5(C(F)(F)F)CC5)cc4)cc3F)C(=O)O)cc2)c1=O] | 1H NMR (400 MHz, DMSO-d6) δ 10.71 (s, 1H), 10.09 (s, 1H), 8.56 (dd, J = 7.8, 2.6 Hz, 1H), 7.83-7.75 (m, 4H), 7.34-7.25 (m, 3H), 7.18 (dd, J = 11.2, 6.3 Hz, 1H), 7.06 (d, J = 8.0 Hz, 2H), 4.62-4.55 (m, 1H), 3.36 (s, 3H), 3.19 (dd, J = 14.1, 4.6 Hz, 1H), 3.04 (dd, J = 14.1, 9.8 Hz, 1H), 2.31 (s, 3H), 1.89 (s, 3H), 1.51-1.46 (m, 2H), 1.34-1.27 (m, 2H); MS (ESI) m/z 764[M + H]+. |
| A21 | 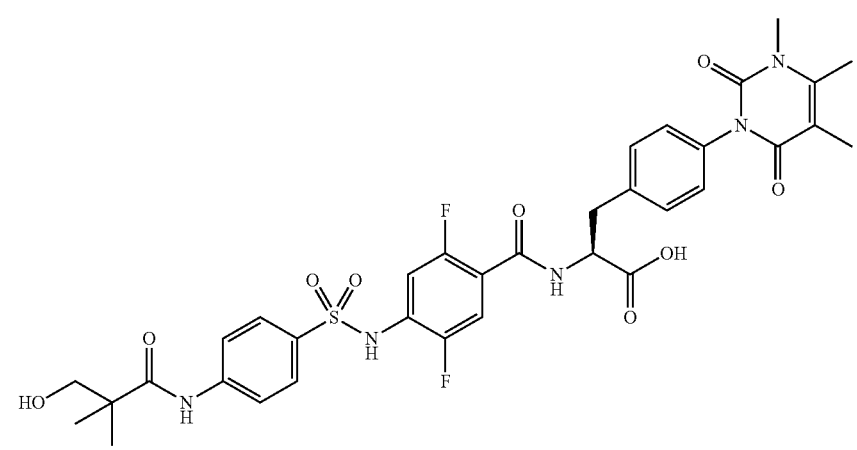 [SMILES: Cc1c(C)n(C)c(=O)n(-c2ccc(C[C@H](NC(=O)c3cc(F)c(NS(=O)(=O)c4ccc(NC(=O)C(C)(C)CO)cc4)cc3F)C(=O)O)cc2)c1=O] | 1H NMR (400 MHz, DMSO-d6) δ 10.66 (s, 1H), 9.59 (s, 1H), 8.57 (dd, J = 8.0, 2.6 Hz, 1H), 7.83 (d, J = 8.9 Hz, 2H), 7.74 (d, J = 8.9 Hz, 2H), 7.34-7.25 (m, 3H), 7.18 (dd, J = 11.2, 6.3 Hz, 1H), 7.06 (d, J = 8.3 Hz, 2H), 4.63-4.55 (m, 1H), 3.50 (s, 2H), 3.36 (s, 3H), 3.23-3.14 (m, 1H), 3.04 (dd, J = 14.1, 9.7 Hz, 1H), 2.31 (s, 3H), 1.89 (s, 3H), 1.13 (s, 6H); MS (ESI) m/z 728 [M + H]+. |
| A22 | 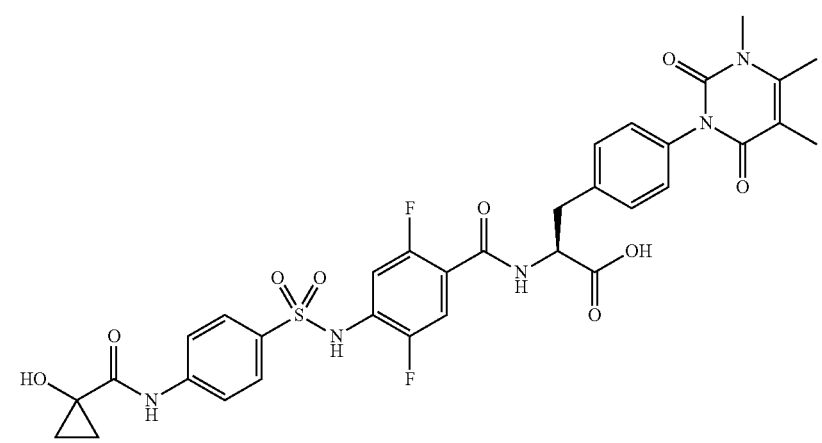 [SMILES: Cc1c(C)n(C)c(=O)n(-c2ccc(C[C@H](NC(=O)c3cc(F)c(NS(=O)(=O)c4ccc(NC(=O)C5(O)CC5)cc4)cc3F)C(=O)O)cc2)c1=O] | 1H NMR (400 MHz, DMSO-d6) δ 10.68 (s, 1H), 10.23 (s, 1H), 8.62-8.51 (m, 1H), 8.00-7.90 (m, 2H), 7.80-7.70 (m, 2H), 7.37-7.24 (m, 3H), 7.18 (dd, J = 11.2, 6.2 Hz, 1H), 7.06 (d, J = 8.1 Hz, 2H), 4.69-4.50 (m, 1H), 3.36 (s, 3H), 3.23-3.14 (m, 1H), 3.09-2.99 (m, 1H), 2.31 (s, 3H), 1.89 (s, 3H), 1.19-1.11 (m, 2H), 1.03-0.95 (m, 2H); MS (ESI) m/z 712[M + H]+. |

TABLE 1-continued

| Compound No | Structural Formula | NMR/MS |
|---|---|---|
| A23 | | 1H NMR (400 MHz, DMSO-d6) δ 10.68 (s, 1H), 10.23 (s, 1H), 8.97 (s, 1H), 8.63-8.50 (m, 2H), 8.00-7.92 (m, 2H), 7.89 (d, J = 4.9 Hz, 1H), 7.78-7.72 (m, 2H), 7.41-7.33 (m, 2H), 7.28 (dd, J = 10.3, 6.4 Hz, 1H), 7.25-7.14 (m, 3H), 4.68-4.56 (m, 1H), 3.60 (s, 3H), 3.27-3.18 (m, 1H), 3.13-3.00 (m, 1H), 1.20-1.11 (m, 2H), 1.04-0.94 (m, 2H); MS (ESI) m/z 735 [M + H]+. |
| A24 | | 1H NMR (400 MHz, DMSO-d6) δ 10.71 (s, 1H), 10.09 (s, 1H), 8.97 (s, 1H), 8.61-8.53 (m, 2H), 7.88 (d, J = 5.0 Hz, 1H), 7.84-7.74 (m, 4H), 7.36 (d, J = 7.9 Hz, 2H), 7.28 (dd, J = 10.4, 6.2 Hz, 1H), 7.25-7.15 (m, 3H), 4.66-4.58 (m, 1H), 3.59 (s, 3H), 3.26-3.18 (m, 1H), 3.06 (dd, J = 14.3, 10.0 Hz, 1H), 1.51-1.46 (m, 2H), 1.35-1.28 (m, 2H); MS (ESI) m/z 787[M + H]+. |
| A25 | | 1H NMR (400 MHz, DMSO-d6) δ 10.82 (s, 1H), 10.36 (s, 1H), 8.66 (d, J = 2.5 Hz, 1H), 8.61 (dd, J = 7.8, 2.5 Hz, 1H), 8.27-8.20 (m, 1H), 8.15 (dd, J = 9.0, 2.6 Hz, 1H), 7.31 (dd, J = 9.3, 6.1 Hz, 3H), 7.25 (dd, J = 10.9, 6.2 Hz, 1H), 7.12-7.00 (m, 2H), 4.60 (ddd, J = 9.7, 7.8, 4.6 Hz, 1H), 3.35 (s, 3H), 3.20 (dd, J = 14.2, 4.6 Hz, 1H), 3.04 (dd, J = 14.1, 9.8 Hz, 1H), 2.31 (s, 3H), 1.89 (s, 3H), 1.23 (s, 9H); MS (ESI) m/z 713[M + H]+. |

TABLE 1-continued

| Compound No | Structural Formula | NMR/MS |
|---|---|---|
| A26 | 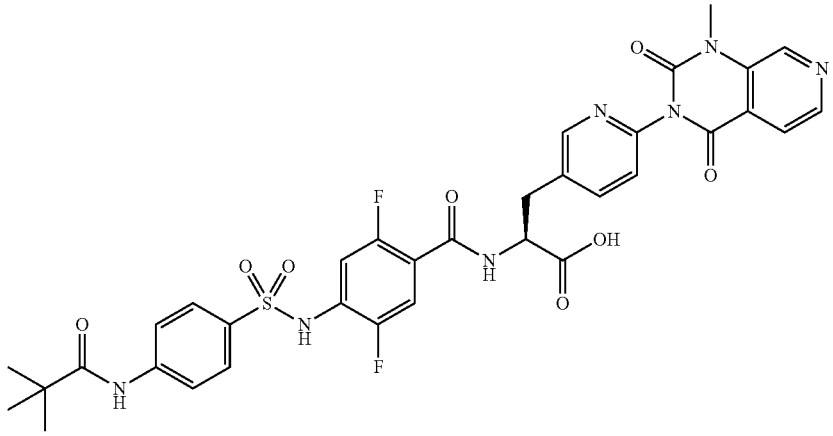 [SMILES: Cn1c(=O)n(-c2ccc(C[C@H](NC(=O)c3cc(F)c(NS(=O)(=O)c4ccc(NC(=O)C(C)(C)C)cc4)cc3F)C(=O)O)cn2)c(=O)c2ccncc21] | 1H NMR (400 MHz, DMSO-d6) δ 10.67 (s, 1H), 9.57 (s, 1H), 8.99 (s, 1H), 8.67 (dd, J = 8.2, 2.2 Hz, 1H), 8.57 (d, J = 5.0 Hz, 1H), 8.47 (d, J = 2.3 Hz, 1H), 8.02-7.88 (m, 2H), 7.88-7.81 (m, 2H), 7.81-7.69 (m, 2H), 7.40 (d, J = 8.1 Hz, 1H), 7.26 (dd, J = 10.2, 6.3 Hz, 1H), 7.18 (dd, J = 11.1, 6.3 Hz, 1H), 4.72-4.65 (m, 1H), 3.60 (s, 3H), 3.29 (dd, J = 14.1, 4.6 Hz, 1H), 3.09 (dd, J = 14.1, 10.1 Hz, 1H), 1.21 (s, 9H); MS (ESI) m/z 736[M + H]+. |
| A27 | 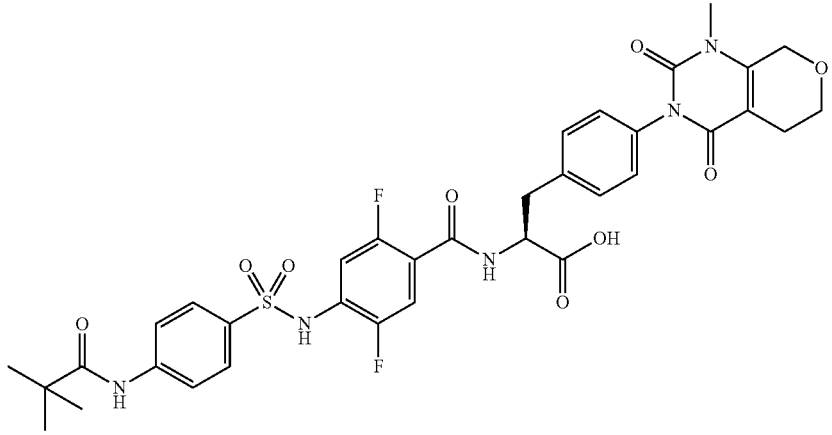 [SMILES: Cn1c2c(c(=O)n(-c3ccc(C[C@H](NC(=O)c4cc(F)c(NS(=O)(=O)c5ccc(NC(=O)C(C)(C)C)cc5)cc4F)C(=O)O)cc3)c1=O)CCOC2] | 1H NMR (400 MHz, DMSO-d6) δ 10.66 (s, 1H), 9.57 (s, 1H), 8.56 (dd, J = 7.9, 2.6 Hz, 1H), 7.88-7.82 (m, 2H), 7.78-7.71 (m, 2H), 7.36-7.24 (m, 3H), 7.18 (dd, J = 11.2, 6.3 Hz, 1H), 7.13-7.06 (m, 2H), 4.66-4.53 (m, 1H), 3.79 (t, J = 5.5 Hz, 2H), 3.22-3.17 (m, 5H), 3.04 (dd, J = 14.1, 9.7 Hz, 2H), 2.32 (dd, J = 6.5, 4.5 Hz, 2H), 1.21 (s, 9H); MS (ESI) m/z 740[M + H]+. |
| A28 | 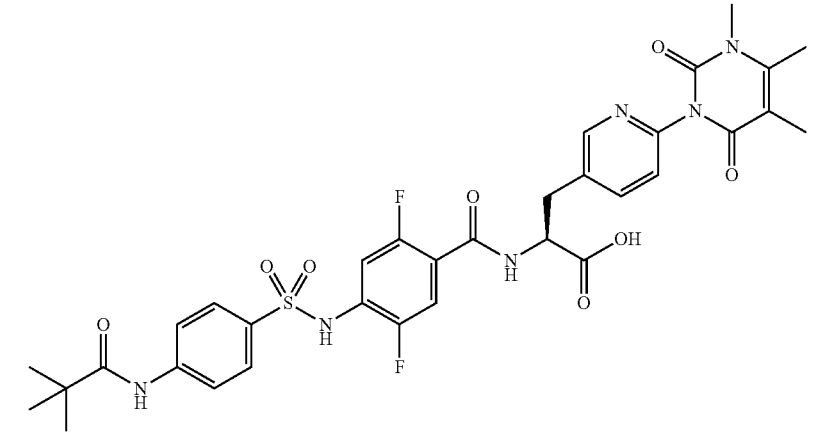 [SMILES: Cc1c(C)n(C)c(=O)n(-c2ccc(C[C@H](NC(=O)c3cc(F)c(NS(=O)(=O)c4ccc(NC(=O)C(C)(C)C)cc4)cc3F)C(=O)O)cn2)c1=O] | 1H NMR (400 MHz, DMSO-d6) δ 10.71-10.63 (m, 1H), 9.57 (s, 1H), 8.65 (dd, J = 8.1, 2.3 Hz, 1H), 8.41 (d, J = 2.3 Hz, 1H), 7.89-7.80 (m, 3H), 7.80-7.70 (m, 2H), 7.32-7.22 (m, 2H), 7.18 (dd, J = 11.2, 6.3 Hz, 1H), 4.70-4.59 (m, 1H), 3.36 (s, 3H), 3.25 (dd, J = 14.1, 4.7 Hz, 1H), 3.06 (dd, J = 14.1, 10.0 Hz, 1H), 2.32 (d, J = 1.0 Hz, 3H), 1.89 (d, J = 0.9 Hz, 3H), 1.21 (s, 9H); MS (ESI) m/z 713[M + H]+. |

TABLE 1-continued

| Compound No | Structural Formula | NMR/MS |
|---|---|---|
| A29 | 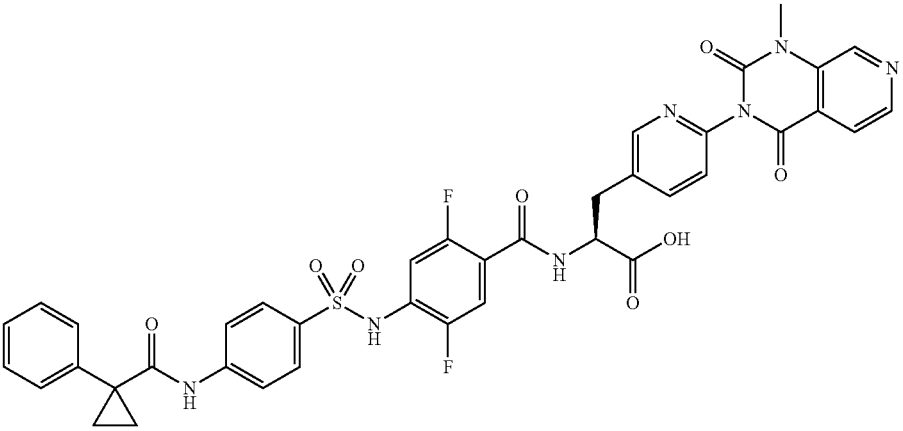 [SMILES: Cn1c(=O)n(-c2ccc(C[C@H](NC(=O)c3cc(F)c(NS(=O)(=O)c4ccc(NC(=O)C5(c6ccccc6)CC5)cc4)cc3F)C(=O)O)cn2)c(=O)c2ccncc21] | 1H NMR (400 MHz, DMSO-d6) δ 10.67 (s, 1H), 9.54 (s, 1H), 8.99 (s, 1H), 8.66 (dd, J = 8.0, 2.3 Hz, 1H), 8.57 (d, J = 4.9 Hz, 1H), 8.46 (d, J = 2.3 Hz, 1H), 7.95-7.86 (m, 2H), 7.83-7.64 (m, 4H), 7.44-7.30 (m, 5H), 7.29-7.21 (m, 2H), 7.17 (dd, J = 11.1, 6.3 Hz, 1H), 4.74-4.62 (m, 1H), 3.60 (s, 3H), 3.29 (dd, J = 14.2, 4.7 Hz, 1H), 3.09 (dd, J = 14.2, 10.1 Hz, 1H), 1.49-1.41 (m, 2H), 1.18-1.08 (m, 2H); MS (ESI) m/z 796[M + H]+. |
| A30 | 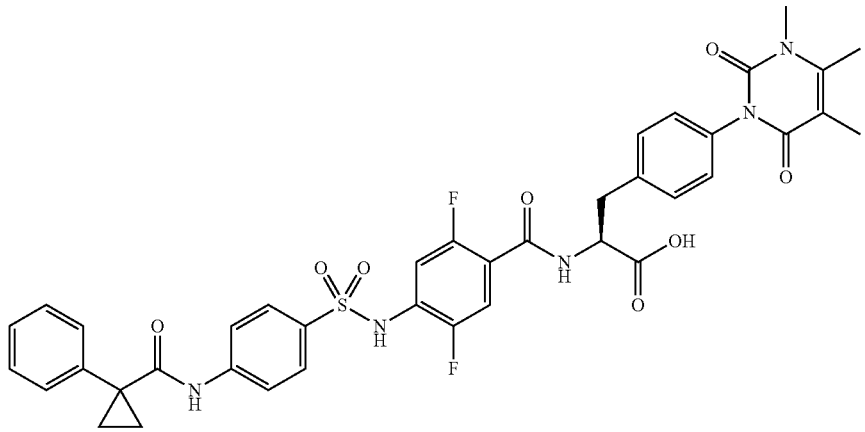 [SMILES: Cc1c(C)n(C)c(=O)n(-c2ccc(C[C@H](NC(=O)c3cc(F)c(NS(=O)(=O)c4ccc(NC(=O)C5(c6ccccc6)CC5)cc4)cc3F)C(=O)O)cc2)c1=O] | 1H NMR (400 MHz, DMSO-d6) δ 10.66 (s, 1H), 9.54 (s, 1H), 8.55 (dd, J = 7.9, 2.7 Hz, 1H), 7.79-7.68 (m, 4H), 7.43-7.23 (m, 8H), 7.16 (dd, J = 11.2, 6.3 Hz, 1H), 7.10-7.03 (m, 2H), 4.64-4.53 (m, 1H), 3.36 (s, 3H), 3.19 (dd, J = 14.1, 4.6 Hz, 1H), 3.04 (dd, J = 14.1, 9.7 Hz, 1H), 2.31 (s, 3H), 1.89 (s, 3H), 1.49-1.41 (m, 2H), 1.17-1.08 (m, 2H); MS (ESI) m/z 772[M + H]+. |
| A31 | 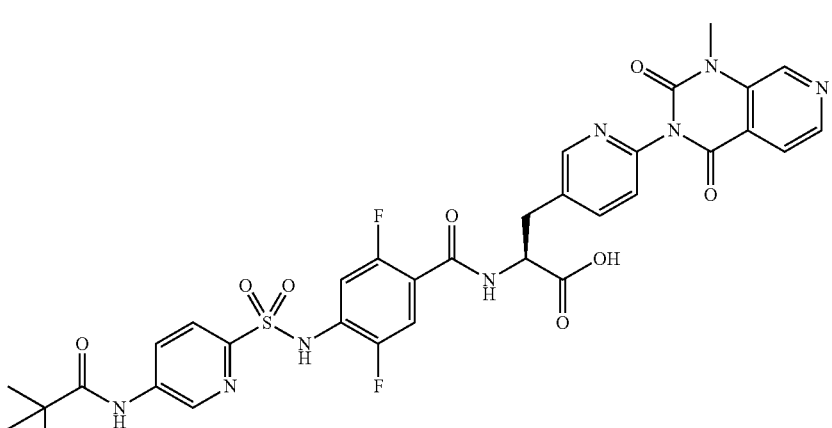 | 1H NMR (400 MHz, DMSO-d6) δ 10.86 (s, 1H), 9.80 (s, 1H), 8.99 (s, 1H), 8.94 (d, J = 2.5 Hz, 1H), 8.68 (dd, J = 8.1, 2.3 Hz, 1H), 8.57 (d, J = 5.0 Hz, 1H), 8.47 (d, J = 2.3 Hz, 1H), 8.35 (dd, J = 8.7, 2.5 Hz, 1H), 7.97 (d, J = 8.7 Hz, 1H), 7.95-7.87 (m, 2H), 7.41 (d, J = 8.1 Hz, 1H), 7.33-7.23 (m, 2H), 4.75-4.63 (m, 1H), 3.60 (s, 3H), 3.30 (dd, J = 14.1, 4.7 Hz, 1H), 3.10 (dd, J = 14.1, 10.2 Hz, 1H), 1.23 (s, 9H); MS (ESI) m/z 737[M + H]+. |

| Compound No | Structural Formula | NMR/MS |
|---|---|---|
| A32 | | 1H NMR (400 MHz, DMSO-d6) δ 10.85 (s, 1H), 9.80 (s, 1H), 8.93 (d, J = 2.4 Hz, 1H), 8.66 (dd, J = 8.0, 2.3 Hz, 1H), 8.42 (d, J = 2.3 Hz, 1H), 8.35 (dd, J = 8.7, 2.5 Hz, 1H), 7.97 (d, J = 8.7 Hz, 1H), 7.83 (dd, J = 8.1, 2.4 Hz, 1H), 7.33-7.21 (m, 3H), 4.70-4.61 (m, 1H), 336 (s, 3H), 3.26 (dd, J = 14.1, 4.7 Hz, 1H), 3.07 (dd, J = 14.1, 10.1 Hz, 1H), 2.32 (s, 3H), 1.89 (s, 3H), 1.23 (s, 9H); MS (ESI) m/z 714[M + H]+. |
| A33 | | 1H NMR (400 MHz, DMSO-d6) δ 10.60 (s, 1H), 9.50 (s, 1H), 8.49 (dd, J = 7.9, 2.7 Hz, 1H), 7.78 (d, J = 8.9 Hz, 2H), 7.68 (d, J = 8.9 Hz, 2H), 7.32-7.16 (m, 3H), 7.11 (dd, J = 11.2, 6.3 Hz, 1H), 7.03 (d, J = 8.3 Hz, 2H), 4.57-4.48 (m, 1H), 4.24-4.17 (m, 2H), 3.80 (t, J = 5.5 Hz, 2H), 3.23 (s, 3H), 3.17-3.09 (m, 1H), 3.01-2.94 (m, 1H), 2.69-2.62 (m, 2H), 1.15 (s, 9H); MS (ESI) m/z 740[M + H]+. |
| A34 | | 1H NMR (400 MHz, DMSO-d6) δ 11.01 (s, 1H), 8.60 (dd, J = 7.9, 2.5 Hz, 7.97 (d, J = 8.6 Hz, 2H), 7.69 (d, J = 8.6 Hz, 2H), 7.56 (dd, J = 9.5, 2.6 Hz, 1H), 7.47 (d, J = 2.5 Hz, 1H), 7.40-7.23 (m, 4H), 7.10-7.03 (m, 2H), 6.49 (d, J = 9.5 Hz, 1H), 4.67-4.54 (m, 1H), 3.91 (dd, J = 11.2, 3.9 Hz, 2H), 3.42-3.30 (m, 5H), 3.19 (dd, J = 14.0, 4.6 Hz, 1H), 3.04 (dd, J = 14.0, 9.7 Hz, 1H), 2.64-2.54 (m, 1H), 2.30 (s, 3H), 1.88 (s, 3H), 1.71-1.52 (m, 4H); MS (ESI) m/z 790[M + H]+. |

TABLE 1-continued

| Compound No | Structural Formula | NMR/MS |
|---|---|---|
| A35 | | 1H NMR (400 MHz, DMSO-d6) δ 10.73 (s, 1H), 8.51 (dd, J = 7.9, 2.6 Hz, 1H), 7.76 (d, J = 8.6 Hz, 2H), 7.47 (d, J = 8.6 Hz, 2H), 7.27-7.19 (m, 3H), 7.11 (dd, J = 11.0, 6.3 Hz, 1H), 6.99 (d, J = 8.3 Hz, 2H), 4.57-4.50 (m, 1H), 3.35-3.22 (m, 3H), 3.17-3.10 (m, 1H), 3.06 (s, 3H), 3.03-2.94 (m, 1H), 2.24 (s, 3H), 1.82 (s, 3H), 0.88 (s, 9H); MS (ESI) m/z 726[M + H]+. |
| A36 | | 1H NMR (400 MHz, DMSO-d6) δ 10.67 (s, 1H), 9.57 (s, 1H), 8.58 (dd, J = 7.8, 2.6 Hz, 1H), 8.54 (s, 1H), 7.86 (d, J = 9.0 Hz, 2H), 7.75 (d, J = 8.9 Hz, 2H), 7.36 (d, J = 8.3 Hz, 2H), 7.32-7.24 (m, 2H), 7.24-7.14 (m, 3H), 4.66-4.58 (m, 1H), 3.93 (s, 3H), 3.55 (s, 3H), 3.23 (dd, J = 14.1, 4.6 Hz, 1H), 3.06 (dd, J = 14.0, 9.8 Hz, 1H), 1.21 (s, 9H); MS (ESI) m/z 765[M + H]+. |
| A37 | | 1H NMR (400 MHz, DMSO-d6) δ 10.66 (s, 1H), 9.57 (s, 1H), 8.56 (dd, J = 8.0, 2.6 Hz, 1H), 7.96-7.80 (m, 2H), 7.82-7.71 (m, 2H), 7.73-7.61 (m, 1H), 7.42-7.23 (m, 3H), 7.18 (dd, J = 11.2, 6.3 Hz, 1H), 7.13-7.00 (m, 2H), 4.71-4.58 (m, 1H), 3.27 (s, 3H), 3.20 (dd, J = 14.1, 4.6 Hz, 1H), 3.04 (dd, J = 14.1, 9.7 Hz, 1H), 1.81 (s, 3H), 1.21 (s, 9H); MS (ESI) m/z 698[M + H]+. |

TABLE 1-continued
| Compound No | Structural Formula | NMR/MS |
|---|---|---|
| A38 | 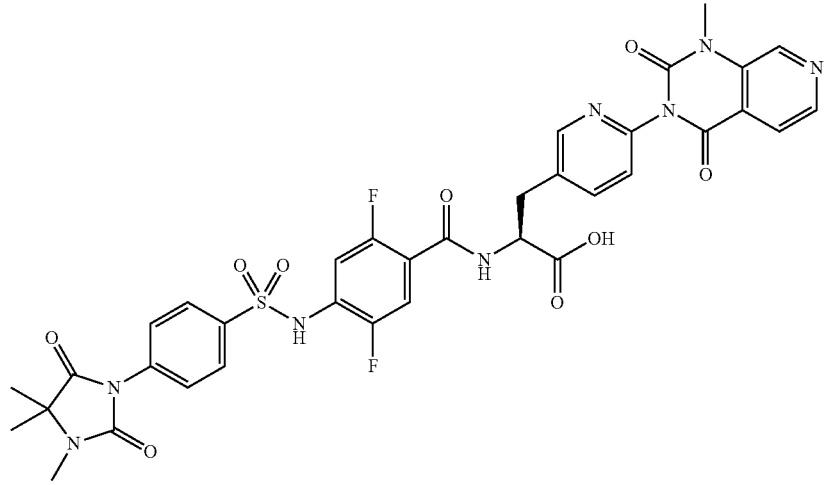 [SMILES: CN1C(=O)N(c2ccc(S(=O)(=O)Nc3cc(F)c(C(=O)N[C@@H](Cc4ccc(-n5c(=O)c6ccncc6n(C)c5=O)nc4)C(=O)O)cc3F)cc2)C(=O)C1(C)C] | 1H NMR (400 MHz, DMSO-d6) δ 10.90 (s, 1H), 8.99 (s, 1H), 8.70 (dd, J = 8.2, 2.1 Hz, 1H), 8.57 (d, J = 5.0 Hz, 1H), 8.46 (d, J = 2.3 Hz, 1H), 8.01-7.82 (m, 4H), 7.73-7.64 (m, 2H), 7.40 (d, J = 8.1 Hz, 1H), 7.35-7.16 (m, 2H), 4.76-4.55 (m, 1H), 3.60 (s, 3H), 3.33-3.23 (m, 1H), 3.09 (dd, J = 14.1, 10.1 Hz, 1H), 2.86 (s, 3H), 1.41 (s, 6H); MS (ESI) m/z 777[M + H]+. |
| A39 | 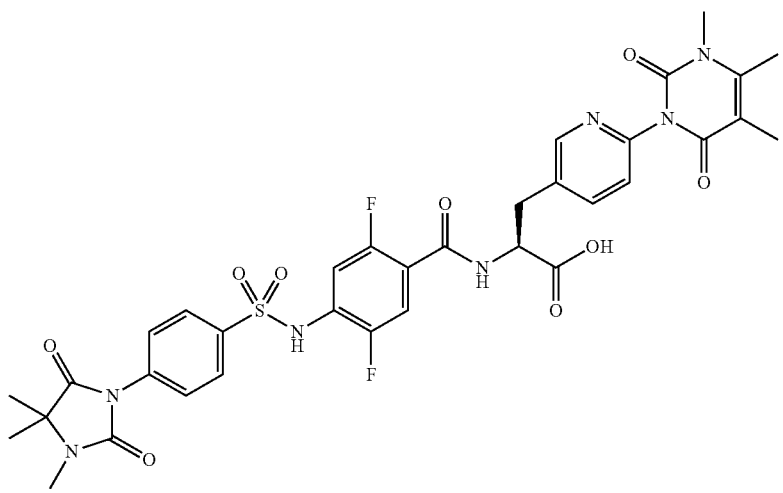 | 1H NMR (400 MHz, DMSO-d6) δ 10.90 (s, 1H), 8.60 (dd, J = 8.0, 2.5 Hz, 1H), 7.95 (s, 2H), 7.68 (d, J = 8.7 Hz, 2H), 7.37-7.27 (m, 3H), 7.23 (dd, J = 11.1, 6.3 Hz, 1H), 7.06 (d, J = 8.3 Hz, 2H), 4.64-4.53 (m, 1H), 3.36 (s, 3H), 3.19 (dd, J = 14.1, 4.6 Hz, 1H), 3.04 (dd, J = 14.1, 9.7 Hz, 1H), 2.87 (s, 3H), 2.31 (s, 3H), 1.89 (s, 3H), 1.42 (s, 6H); MS (ESI) m/z 753 (M + H)+. |
| A40 | 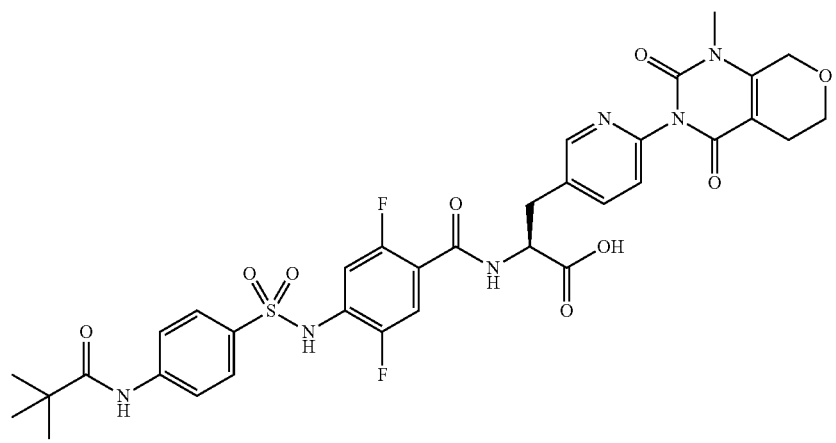 [SMILES: Cn1c2c(c(=O)n(-c3ccc(C[C@H](NC(=O)c4cc(F)c(NS(=O)(=O)c5ccc(NC(=O)C(C)(C)C)cc5)cc4F)C(=O)O)cn3)c1=O)CCOC2] | 1H NMR (400 MHz, DMSO-d6) δ 10.67 (s, 1H), 9.57 (s, 1H), 8.65 (dd, J = 8.1, 2.3 Hz, 1H), 8.43 (d, J = 2.2 Hz, 1H), 7.86-7.83 (m, 3H), 7.78-7.70 (m, 2H), 7.31-7.22 (m, 2H), 7.18 (dd, J = 11.2, 6.3 Hz, 1H), 4.71-4.56 (m, 3H), 3.79 (t, J = 5.5 Hz, 2H), 3.26 (dd, J = 14.2, 4.6 Hz, 2H), 3.20 (s, 3H), 3.07 (dd, J = 14.2, 10.0 Hz, 2H), 2.37-2.27 (m, 2H), 1.21 (s, 9H); MS (ESI) m/z 741[M + H]+. |

TABLE 1-continued

| Compound No | Structural Formula | NMR/MS |
|---|---|---|
| A41 | | 1H NMR (400 MHz, DMSO-d6) δ 10.68 (brs, 1H), 10.44-10.14 (m, 1H), 9.58 (s, 1H), 8.58 (dd, J = 7.9, 2.6 Hz, 1H), 7.86 (d, J = 8.9 Hz, 2H), 7.75 (d, J = 8.9 Hz, 2H), 7.36 (d, J = 8.4 Hz, 2H), 7.29 (dd, J = 10.3, 6.3 Hz, 1H), 7.18 (dd, J = 11.2, 6.3 Hz, 1H), 7.11 (d, J = 8.3 Hz, 2H), 4.66-4.56 (m, 1H), 4.42-2.54 (m, 14H), 1.22 (s, 9H).; MS (ESI) m/z 753[M + H]+ |
| A42 | | 1H NMR (400 MHz, DMSO-d6) δ 10.60 (s, 1H), 9.50 (s, 1H), 8.50 (dd, J = 7.8, 2.6 Hz, 1H), 7.92-7.73 (m, 2H), 7.73-7.53 (m, 3H), 7.42-7.16 (m, 3H), 7.11 (dd, J = 11.2, 6.3 Hz, 1H), 7.06-6.89 (m, 2H), 5.67 (d, J = 7.9 Hz, 1H), 4.62-4.52 (m, 1H), 3.23 (s, 3H), 3.12 (dd, J = 14.0, 4.6 Hz, 1H), 2.97 (dd, J = 14.0, 9.7 Hz, 1H), 1.15 (s, 9H); MS (ESI) m/z 684[M + H]+. |
| A43 | | 1H NMR (400 MHz, DMSO-d6) δ 10.60 (s, 1H), 9.50 (s, 1H), 8.50 (dd, J = 8.0, 2.6 Hz, 1H), 7.99 (s, 1H), 7.88-7.72 (m, 2H), 7.72-7.57 (m, 2H), 7.33-7.17 (m, 3H), 7.17-7.10 (m, 1H), 7.10-7.03 (m, 2H), 4.61-4.52 (m, 1H), 3.79 (s, 3H), 3.35 (s, 3H), 3.14 (dd, J = 14.0, 4.6 Hz, 1H), 2.98 (dd, J = 14.1, 9.8 Hz, 1H), 1.14 (s, 9H); MS (ESI) m/z 738[M + H]+. |

TABLE 1-continued
| Compound No | Structural Formula | NMR/MS |
|---|---|---|
| A44 | 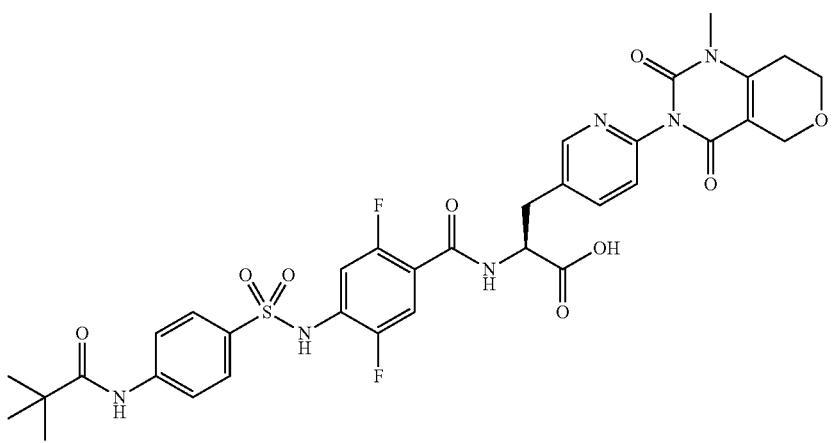 [SMILES: Cn1c2c(c(=O)n(-c3ccc(C[C@H](NC(=O)c4cc(F)c(NS(=O)(=O)c5ccc(NC(=O)C(C)(C)C)cc5)cc4F)C(=O)O)cn3)c1=O)COCC2] | 1H NMR (400 MHz, DMSO-d6) δ 10.67 (s, 1H), 9.57 (s, 1H), 8.65 (dd, J = 7.7, 2.2 Hz, 1H), 8.42 (d, J = 2.3 Hz, 1H), 7.89-7.80 (m, 3H), 7.75 (d, J = 8.9 Hz, 2H), 7.31-7.22 (m, 2H), 7.17 (dd, J = 11.2, 6.3 Hz, 1H), 4.69-4.60 (m, 1H), 4.32-4.22 (m, 2H), 3.88 (t, J = 5.6 Hz, 2H), 3.33-3.22 (m, 4H), 3.12-3.02 (m, 1H), 2.76-2.70 (m, 2H), 1.21 (s, 9H); MS (ESI) m/z 741[M + H]+. |
| A45 | 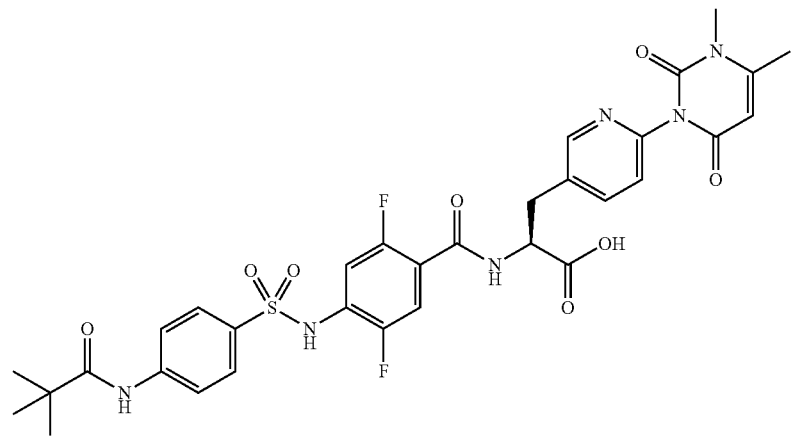 [SMILES: Cc1cc(=O)n(-c2ccc(C[C@H](NC(=O)c3cc(F)c(NS(=O)(=O)c4ccc(NC(=O)C(C)(C)C)cc4)cc3F)C(=O)O)cn2)c(=O)n1C] | 1H NMR (400 MHz, DMSO-d6) δ 10.66 (s, 1H), 9.57 (s, 1H), 8.65 (dd, J = 8.0, 2.2 Hz, 1H), 8.42 (d, J = 2.3 Hz, 1H), 7.89-7.79 (m, 3H), 7.80-7.70 (m, 2H), 7.29-7.21 (m, 2H), 7.18 (dd, J = 11.2, 6.2 Hz, 1H), 5.73 (s, 1H), 4.69-4.58 (m, 1H), 3.31 (s, 3H), 3.19 (dd, J = 14.1, 4.6 Hz, 1H), 3.06 (dd, J = 14.1, 10.0 Hz, 1H), 2.31 (s, 3H), 1.22 (s, 9H); MS (ESI) 699[M + H]+. |
| A46 | 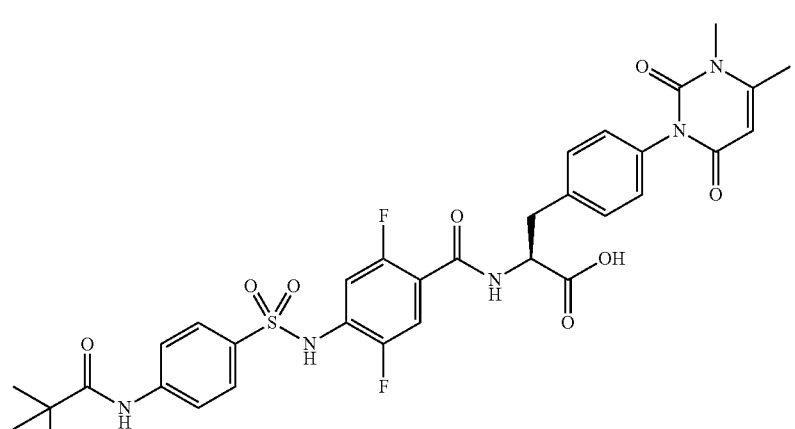 | 1H NMR (400 MHz, DMSO-d6) δ 10.66 (s, 1H), 9.57 (s, 1H), 8.56 (dd, J = 7.9, 2.6 Hz, 1H), 7.91-7.81 (m, 2H), 7.78-7.70 (m, 2H), 7.37-7.24 (m, 3H), 7.18 (dd, J = 11.2, 6.3 Hz, 1H), 7.11-7.03 (m, 2H), 5.71 (d, J = 1.1 Hz, 1H), 4.61-4.56 (m, 1H), 3.31 (s, 3H), 3.19 (dd, J = 14.1, 4.6 Hz, 1H), 3.04 (dd, J = 14.0, 9.7 Hz, 1H), 2.29 (d, J = 0.9 Hz, 3H), 1.21 (s, 9H); MS (ESI) m/z 698 [M + H]+. |

TABLE 1-continued

| Compound No | Structural Formula | NMR/MS |
|---|---|---|
| A47 | 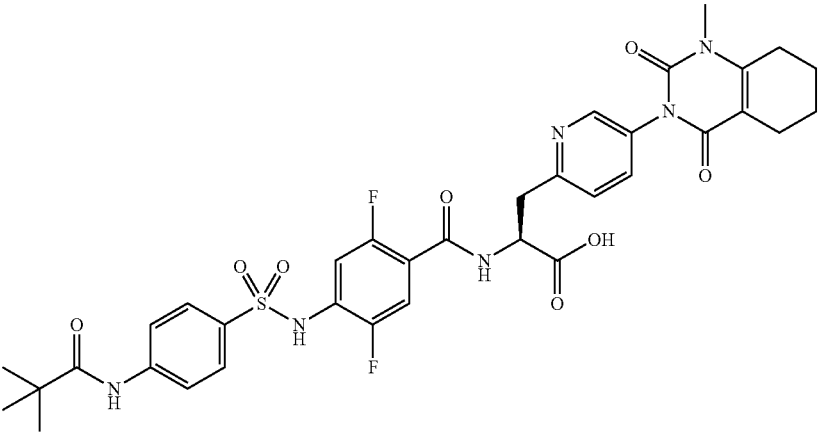 [SMILES: Cn1c2c(c(=O)n(-c3ccc(C[C@H](NC(=O)c4cc(F)c(NS(=O)(=O)c5ccc(NC(=O)C(C)(C)C)cc5)cc4F)C(=O)O)nc3)c1=O)CCCC2] | 1H NMR (400 MHz, DMSO-d6) δ 10.68 (s, 1H), 9.56 (s, 1H), 8.69 (dd, J = 7.8, 3.8 Hz, 1H), 8.34 (d, J = 2.4 Hz, 1H), 7.85 (d, J = 9.0 Hz, 2H), 7.74 (d, J = 8.9 Hz, 2H), 7.64 (dd, J = 8.2, 2.5 Hz, 1H), 7.41 (d, J = 8.2 Hz, 1H), 7.38-7.31 (m, 1H), 7.19 (dd, J = 11.4, 6.3 Hz, 1H), 4.91-4.81 (m, 1H), 3.38-3.21 (m, 5H), 2.69-2.59 (m, 2H), 2.28 (t, J = 6.1 Hz, 2H), 1.84-1.71 (m, 2H), 1.69-1.53 (m, 2H), 1.21 (s, 9H); MS (ESI) m/z 739[M + H]+. |
| A48 | 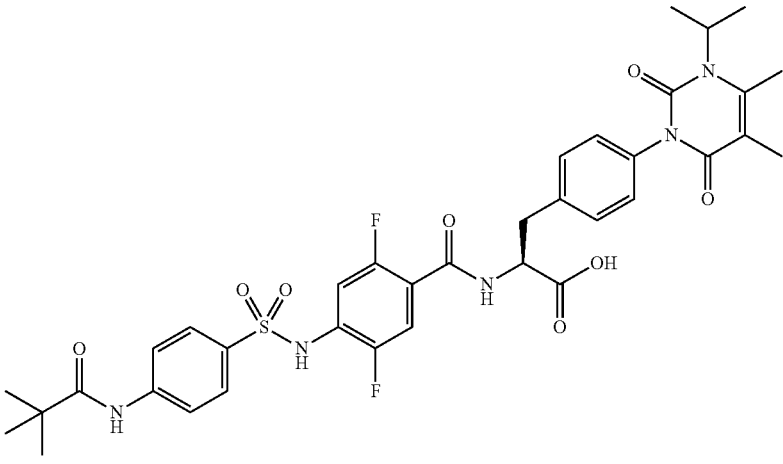 [SMILES: Cc1c(C)n(C(C)C)c(=O)n(-c2ccc(C[C@H](NC(=O)c3cc(F)c(NS(=O)(=O)c4ccc(NC(=O)C(C)(C)C)cc4)cc3F)C(=O)O)cc2)c1=O] | 1H NMR (400 MHz, DMSO-d6) δ 10.66 (s, 1H), 9.56 (s, 1H), 8.55 (dd, J = 7.7, 2.6 Hz, 1H), 7.89-7.80 (m, 2H), 7.80-7.70 (m, 2H), 7.36-7.24 (m, 3H), 7.18 (dd, J = 11.2, 6.3 Hz, 1H), 7.09-7.01 (m, 2H), 4.66-4.54 (m, 1H), 4.54-4.42 (m, 1H), 3.24-3.14 (m, 1H), 3.08-2.98 (m, 1H), 2.31 (s, 3H), 1.89 (d, J = 0.9 Hz, 3H), 1.42 (d, J = 6.6 Hz, 6H), 1.21 (s, 9H); MS (ESI) m/z 740[M + H]+. |
| A49 | 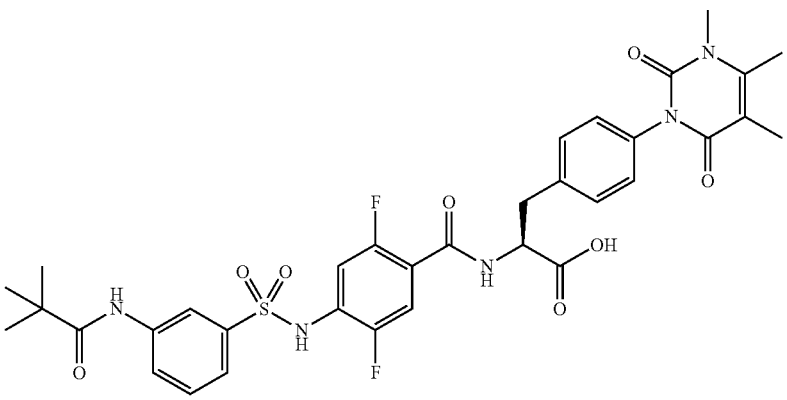 [SMILES: Cc1c(C)n(C)c(=O)n(-c2ccc(C[C@H](NC(=O)c3cc(F)c(NS(=O)(=O)c4cccc(NC(=O)C(C)(C)C)c4)cc3F)C(=O)O)cc2)c1=O] | 1H NMR (400 MHz, DMSO-d6) δ 10.83 (s, 1H), 9.56 (s, 1H), 8.57 (dd, J = 7.9, 2.7 Hz, 1H), 8.29 (s, 1H), 7.92 (d, J = 8.1 Hz, 1H), 7.57-7.42 (m, 2H), 7.37-7.27 (m, 3H), 7.18 (dd, J = 11.2, 6.2 Hz, 1H), 7.07 (d, J = 8.3 Hz, 2H), 4.65-4.55 (m, 1H), 3.36 (s, 3H), 3.20 (dd, J = 14.0, 4.6 Hz, 1H), 3.05 (dd, J = 14.1, 9.7 Hz, 1H), 2.31 (s, 3H), 1.90 (s, 3H), 1.22 (s, 9H); MS (ESI) m/z 712[M + H]+. |

TABLE 1-continued

| Compound No | Structural Formula | NMR/MS |
|---|---|---|
| A50 | | 1H NMR (400 MHz, DMSO-d6) δ 10.83 (s, 1H), 9.56 (s, 1H), 8.66 (dd, J = 8.1, 2.4 Hz, 1H), 8.42 (d, J = 2.3 Hz, 1H), 8.29 (s, 1H), 7.92 (d, J = 8.1 Hz, 1H), 7.83 (dd, J = 8.1, 2.4 Hz, 1H), 7.55-7.43 (m, 2H), 7.36-7.22 (m, 2H), 7.18 (dd, J = 11.1, 6.3 Hz, 1H), 4.70-4.61 (m, 1H), 3.36 (s, 3H), 3.26 (dd, J = 14.1, 4.7 Hz, 1H), 3.07 (dd, J = 14.2, 10.1 Hz, 1H), 2.33 (s, 3H), 1.89 (s, 3H), 1.23 (s, 9H); MS (ESI) m/z 713[M + H]+. |
| A51 | | 1H NMR (400 MHz, DMSO-d6) δ 10.67 (s, 1H), 9.57 (s, 1H), 8.57 (dd, J = 8.0, 2.6 Hz, 1H), 7.96-7.80 (m, 2H), 7.80-7.61 (m, 2H), 7.43-7.25 (m, 3H), 7.18 (dd, J = 11.2, 6.3 Hz, 1H), 7.13-6.99 (m, 2H), 4.69-4.56 (m, 1H), 4.30 (s, 2H), 3.37 (s, 3H), 3.19 (dd, J = 14.2, 4.7 Hz, 1H), 3.04 (dd, J = 14.0, 9.7 Hz, 1H), 2.39 (s, 3H), 1.21 (d, J = 2.4 Hz, 9H); MS (ESI) m/z 728[M + H]+. |
| A52 | | 1H NMR (400 MHz, DMSO-d6) δ 10.66 (s, 1H), 9.57 (s, 1H), 8.64 (dd, J = 8.1, 2.3 Hz, 1H), 8.41 (d, J = 2.3 Hz, 1H), 7.88-7.79 (m, 3H), 7.78-7.71 (m, 2H), 7.26 (dd, J = 10.7, 7.0 Hz, 2H), 7.18 (dd, J = 11.1, 6.2 Hz, 1H), 4.67-4.62 (m, 1H), 3.30 (s, 3H), 3.25 (dd, J = 14.2, 4.6 Hz, 1H), 3.06 (dd, J = 14.2, 10.0 Hz, 1H), 2.71-2.59 (m, 3H), 2.25 (t, J = 5.9 Hz, 2H), 1.77-1.72 (m, 2H), 1.63-1.59 (m, 2H), 1.21 (s, 9H); MS (ESI) m/z 739[M + H]+. |

TABLE 1-continued
| Compound No | Structural Formula | NMR/MS |
|---|---|---|
| A53 | 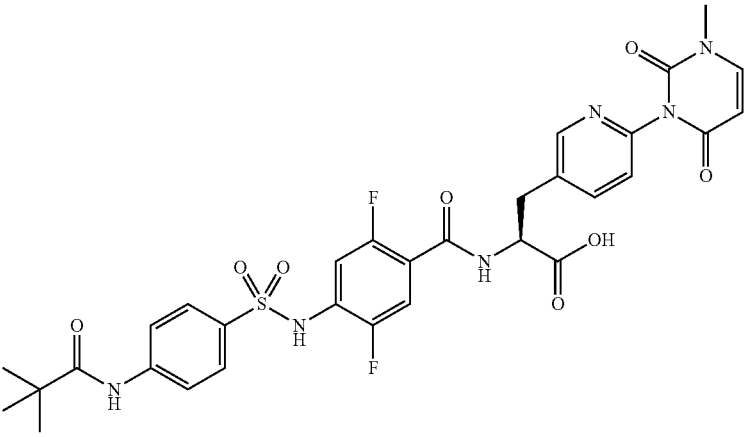 | 1H NMR (400 MHz, DMSO-d6) δ 10.66 (s, 1H), 9.57 (s, 1H), 8.65 (dd, J = 8.0, 2.2 Hz, 1H), 8.43 (d, J = 2.3 Hz, 1H), 7.88-7.81 (m, 3H), 7.79 (d, J = 7.9 Hz, 1H), 7.74 (d, J = 8.9 Hz, 2H), 7.30-7.22 (m, 2H), 7.17 (dd, J = 11.2, 6.3 Hz, 1H), 5.76 (d, J = 7.9 Hz, 1H), 4.66-4.61 (m, 1H), 3.30 (s, 3H), 3.25 (dd, J = 14.1, 4.6 Hz, 1H), 3.10-3.02 (m, 1H), 1.21 (s, 9H); MS (ESI) m/z 685 [M + H]+. |
| A54 | 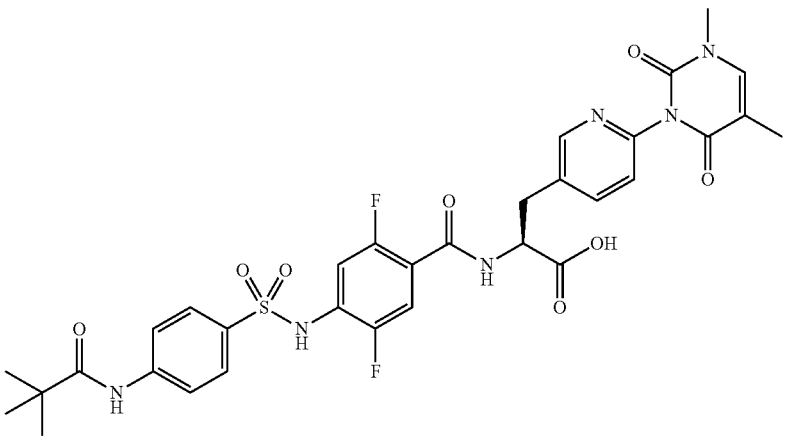 [SMILES: Cc1cn(C)c(=O)n(-c2ccc(C[C@H](NC(=O)c3cc(F)c(NS(=O)(=O)c4ccc(NC(=O)C(C)(C)C)cc4)cc3F)C(=O)O)cn2)c1=O] | 1H NMR (400 MHz, DMSO-d6) δ 10.68 (s, 1H), 9.58 (s, 1H), 8.66 (dd, J = 8.0, 2.3 Hz, 1H), 8.43 (d, J = 2.3 Hz, 1H), 7.85 (m, 3H), 7.80-7.72 (m, 2H), 7.70 (d, J = 1.4 Hz, 1H), 7.36-7.22 (m, 2H), 7.18 (dd, J = 11.2, 6.2 Hz, 1H), 4.72-4.63 (m, 1H), 3.28 (s, 3H), 3.24 (d, J = 4.6 Hz, 1H), 3.07 (dd, J = 14.2, 10.1 Hz, 1H), 1.82 (s, 3H), 1.22 (s, 9H); MS (ESI) m/z 699[M + H]+. |
| A55 | 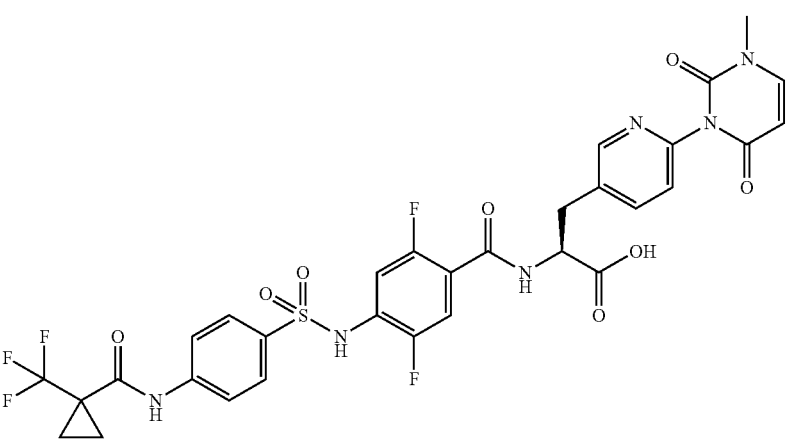 [SMILES: Cn1ccc(=O)n(-c2ccc(C[C@H](NC(=O)c3cc(F)c(NS(=O)(=O)c4ccc(NC(=O)C5(C(F)(F)F)CC5)cc4)cc3F)C(=O)O)cn2)c1=O] | 1H NMR(400 MHz, DMSO-d6): δ 12.98 (s, 1H), 10.71 (s, 1H), 10.09 (d, J = 2.5 Hz, 1H), 8.66 (d, J = 7.9 Hz, 1H), 8.43 (t, J = 2f.5 Hz, 1H), 7.92-7.71 (m, 5H), 7.35-7.11 (m, 3H), 5.77 (dd, J = 7.9, 2.4 Hz, 1H), 4.68-4.61 (m, 1H), 3.36-3.18 (m, 4H), 3.07 (t, J = 12.2 Hz, 1H), 1.50 (s, 2H), 1.37-1.27 (m, 2H); MS (ESI) m/z 737[M + H]+. |

TABLE 1-continued
| Compound No | Structural Formula | NMR/MS |
|---|---|---|
| A56 | 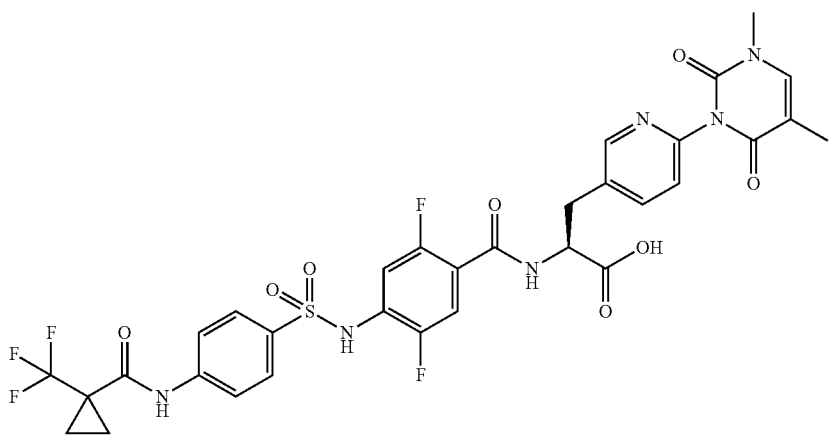 [SMILES: Cc1cn(C)c(=O)n(-c2ccc(C[C@H](NC(=O)c3cc(F)c(NS(=O)(=O)c4ccc(NC(=O)C5(C(F)(F)F)CC5)cc4)cc3F)C(=O)O)cn2)c1=O] | 1H NMR(400 MHz, DMSO-d6): δ 12.98 (s, 1H), 10.71 (s, 1H), 10.09 (s, 1H), 8.65 (dd, J = 7.9, 2.2 Hz, 1H), 8.42 (d, J = 2.2 Hz, 1H), 7.88-7.74 (m, 5H), 7.69 (d, J = 1.4 Hz, 1H), 7.30-7.23 (m, 2H), 7.18 (dd, J = 11.1, 6.3 Hz, 1H), 4.67-4.62 (m, 1H), 3.28-3.23 (m, 4H), 3.07 (dd, J = 14.2, 10.1 Hz, 1H), 1.54-1.45 (m, 2H), 1.36-1.27 (m, 2H); MS (ESI) m/z 751[M + H]+. |
| A57 | 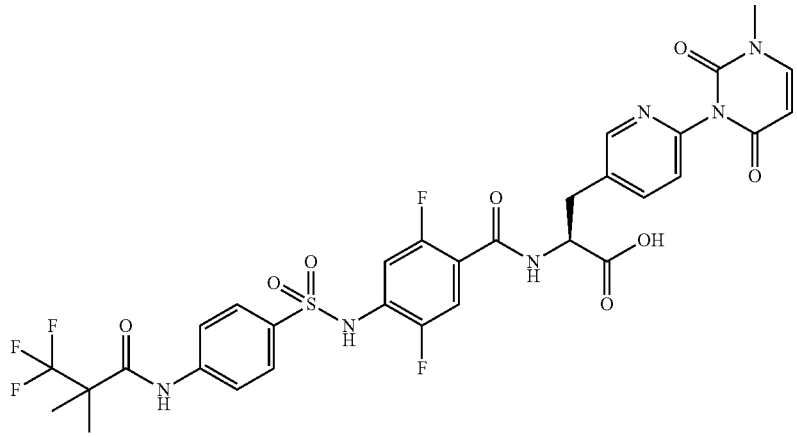 [SMILES: Cn1ccc(=O)n(-c2ccc(C[C@H](NC(=O)c3cc(F)c(NS(=O)(=O)c4ccc(NC(=O)C(C)(C)C(F)(F)F)cc4)cc3F)C(=O)O)cn2)c1=O] | 1H NMR(400 MHz, DMSO-d6): δ 12.98 (s, 1H), 10.71 (s, 1H), 9.85 (s, 1H), 8.66 (dd, J = 8.0, 2.3 Hz, 1H), 8.43 (d, J = 2.3 Hz, 1H), 7.88-7.73 (m, 6H), 7.31-7.22 (m, 2H), 7.18 (dd, J = 11.1, 6.2 Hz, 1H), 5.79-5.73 (m, 1H), 4.70-4.59 (m, 1H), 3.30 (s, 3H), 3.25 (dd, J = 14.2, 4.7 Hz, 1H), 3.07 (dd, J = 14.1, 10.1 Hz, 1H), 1.49 (s, 6H); MS (ESI) m/z 739[M + H]+. |
| A58 | 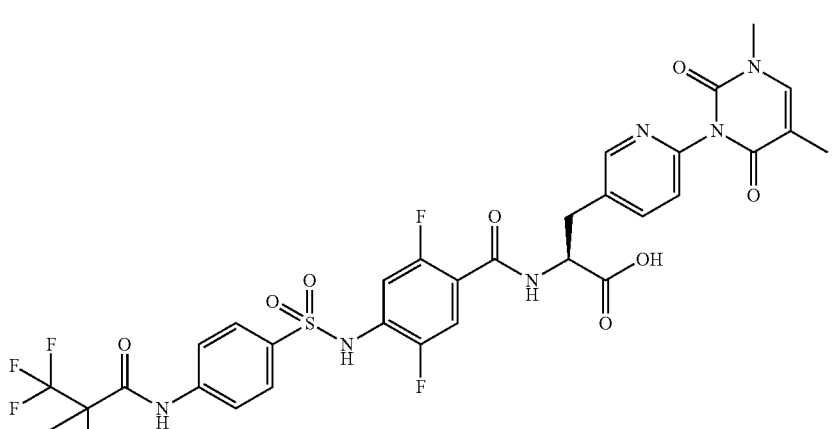 | 1H NMR(400 MHz, DMSO-d6): δ 12.97 (s, 1H), 10.71 (s, 1H), 9.85 (s, 1H), 8.65 (dd, J = 8.0, 2.3 Hz, 1H), 8.42 (d, J = 2.3 Hz, 1H), 7.88-7.75 (m, 5H), 7.69 (d, J = 1.5 Hz, 1H), 7.31-7.23 (m, 2H), 7.18 (dd, J = 11.1, 6.3 Hz, 1H), 4.67-4.62 (m, 1H), 3.28-3.23 (m, 4H), 3.07 (dd, J = 14.2, 10.0 Hz, 1H), 1.82 (d, J = 1.2 Hz, 3H), 1.49 (s, 6H); MS (ESI) m/z 753[M + H]+. |

TABLE 1-continued
| Compound No | Structural Formula | NMR/MS |
|---|---|---|
| A59 | 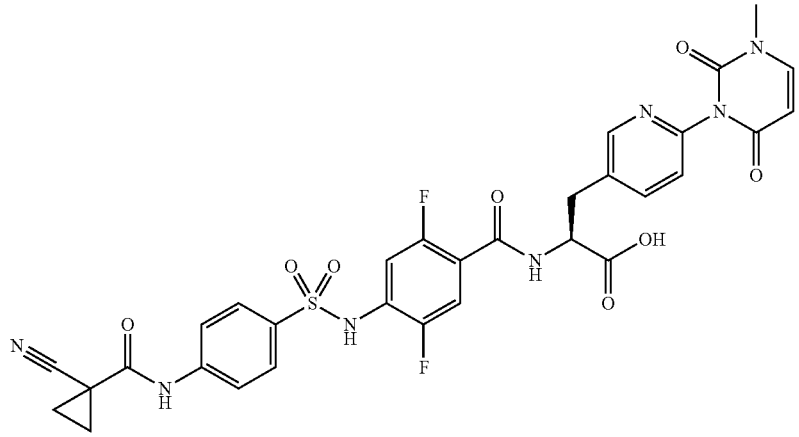 [SMILES: Cn1ccc(=O)n(-c2ccc(C[C@H](NC(=O)c3cc(F)c(NS(=O)(=O)c4ccc(NC(=O)C5(C#N)CC5)cc4)cc3F)C(=O)O)cn2)c1=O] | 1H NMR (400 MHz, DMSO-d6) δ 10.65 (s, 1H), 10.31 (s, 1H), 8.59 (dd, J = 7.9, 2.1 Hz, 1H), 8.36 (d, J = 2.3 Hz, 1H), 7.77 (dd, J = 8.1, 2.3 Hz, 1H), 7.74-7.53 (m, 5H), 7.37-6.98 (m, 3H), 5.70 (d, J = 7.9 Hz, 1H), 4.70-4.45 (m, 1H), 3.24 (s, 1H), 3.00 (dd, J = 14.1, 10.2 Hz, 1H), 2.01 (s, 3H), 1.63 (s, 4H); MS (ESI) m/z 694[M + H]+. |
| A60 | 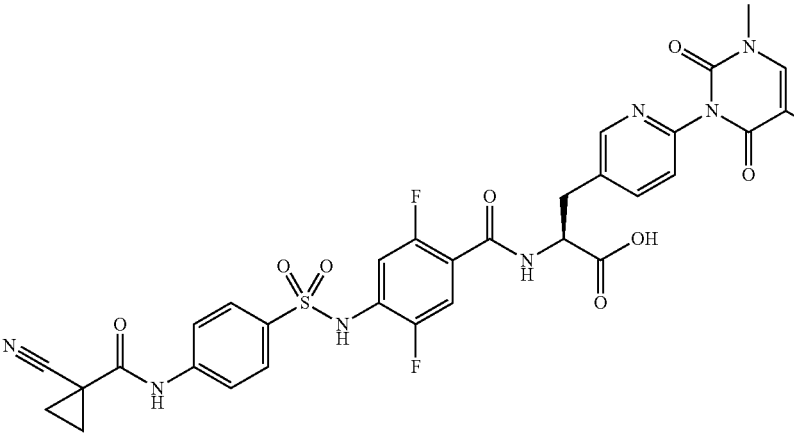 | 1H NMR (400 MHz, DMSO-d6) δ 10.66 (s, 1H), 10.31 (s, 1H), 8.59 (dd, J = 8.0, 2.3 Hz, 1H), 8.36 (d, J = 2.3 Hz, 1H), 7.77 (dd, J = 8.2, 2.4 Hz, 1H), 7.74-7.55 (m, 5H), 7.34-7.04 (m, 3H), 4.71-4.47 (m, 1H), 3.21 (s, 3H), 3.17 (d, J = 4.6 Hz, 1H), 3.00 (dd, J = 14.2, 10.1 Hz, 1H), 1.75 (s, 3H), 1.63 (s, 4H); MS (ESI) m/z 708[M + H]+. |
| A61 | 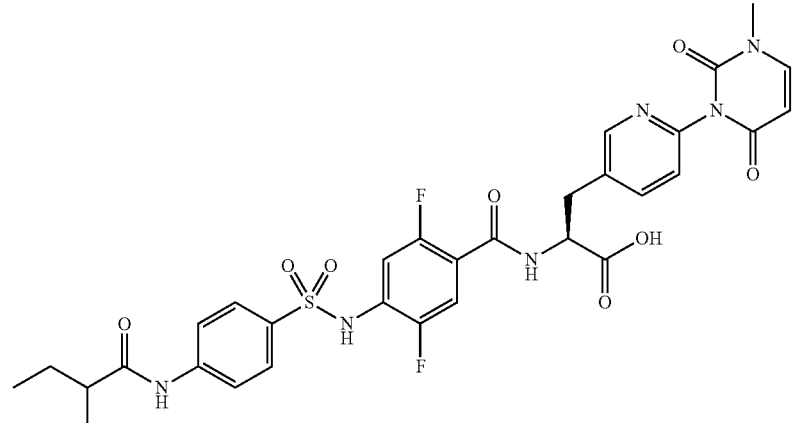 | 1H NMR (400 MHz, DMSO-d6) δ 12.97 (s, 1H), 10.70 (s, 1H), 10.43-10.16 (m, 1H), 8.65 (d, J = 7.6 Hz, 1H), 8.43 (s, 1H), 8.00-7.65 (m, 6H), 7.43-7.11 (m, 3H), 5.76 (dd, J = 8.0, 2.0 Hz, 1H), 4.76-4.47 (m, 1H), 3.34-3.20 (m, 4H), 3.15-2.99 (m, 1H), 2.31-2.13 (m, 1H), 1.70-1.32 (m, 4H), 1.03-0.58 (m, 6H); MS (ESI) m/z 699[M + H]+. |

TABLE 1-continued

| Compound No | Structural Formula | NMR/MS |
|---|---|---|
| A62 | | MS (ESI) m/z 701[M + H]+. |
| A63 | | MS (ESI) m/z 715[M + H]+. |
| A64 | | 1H NMR (400 MHz, DMSO-d6) δ 10.66 (s, 1H), 10.27 (s, 1H), 8.65 (dd, J = 8.0, 2.3 Hz, 1H), 8.43 (d, J = 2.3 Hz, 1H), 7.96-7.53 (m, 6H), 7.40-7.04 (m, 3H), 5.76 (d, J = 7.9 Hz, 1H), 4.64 (ddd, J = 10.1, 8.0, 4.7 Hz, 1H), 3.31 (s, 3H), 3.25 (dd, J = 14.2, 4.7 Hz, 1H), 3.07 (dd, J = 14.1, 10.0 Hz, 1H), 2.90-2.64 (m, 1H), 1.98-1.42 (m, 8H); MS (ESI) m/z 697[M + H]+. |

TABLE 1-continued
| Compound No | Structural Formula | NMR/MS |
|---|---|---|
| A65 | 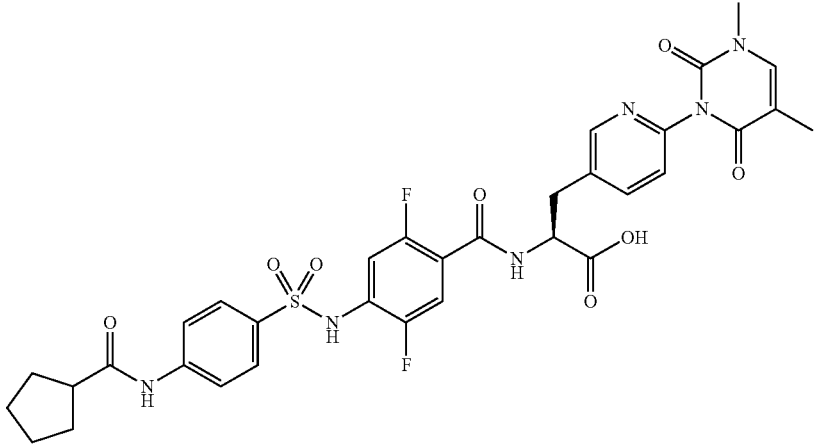 [SMILES: Cc1cn(C)c(=O)n(-c2ccc(C[C@H](NC(=O)c3cc(F)c(NS(=O)(=O)c4ccc(NC(=O)C5CCCC5)cc4)cc3F)C(=O)O)cn2)c1=O] | 1H NMR (400 MHz, DMSO-d6) δ 10.66 (s, 1H), 10.27 (s, 1H), 8.65 (dd, J = 7.9, 2.3 Hz, 1H), 8.42 (d, J = 2.3 Hz, 1H), 7.97-7.66 (m, 6H), 7.40-6.97 (m, 3H), 4.79-4.53 (m, 1H), 3.28 (s, 3H), 3.24 (d, J = 4.6 Hz, 1H), 3.18-2.99 (m, 1H), 2.90-2.71 (m, 1H), 1.96-1.40 (m, 11H); MS (ESI) m/z 711[M + H]+. |
| A66 | 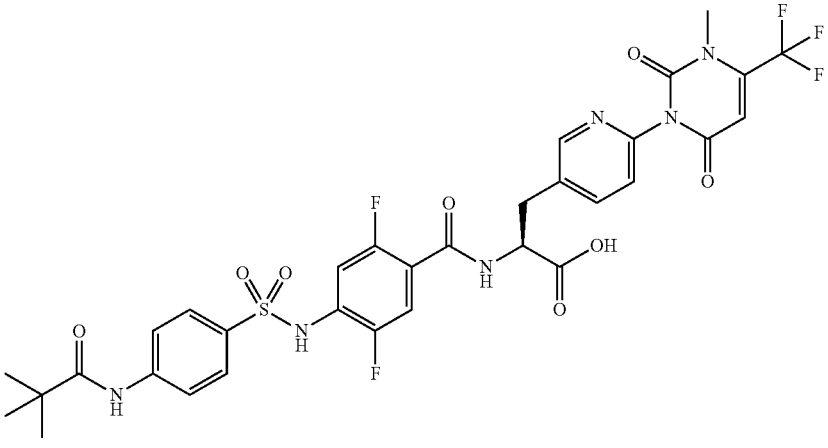 [SMILES: Cn1c(C(F)(F)F)cc(=O)n(-c2ccc(C[C@H](NC(=O)c3cc(F)c(NS(=O)(=O)c4ccc(NC(=O)C(C)(C)C)cc4)cc3F)C(=O)O)cn2)c1=O] | MS (ESI) m/z 753[M + H]+ |
| A67 | 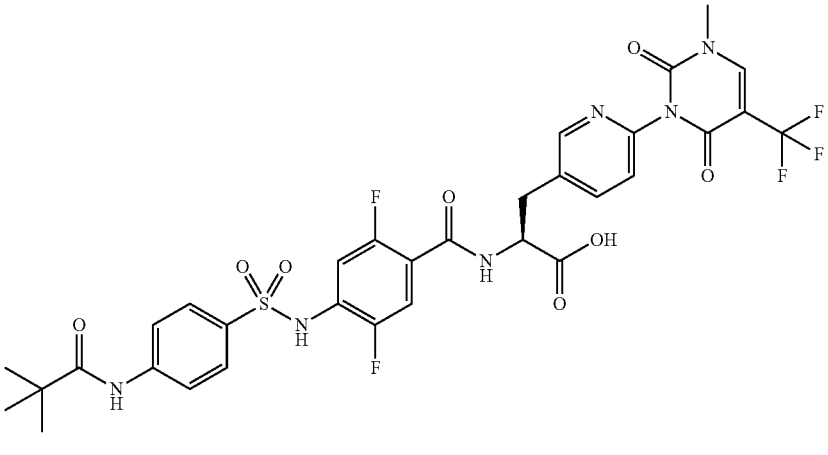 [SMILES: Cn1cc(C(F)(F)F)c(=O)n(-c2ccc(C[C@H](NC(=O)c3cc(F)c(NS(=O)(=O)c4ccc(NC(=O)C(C)(C)C)cc4)cc3F)C(=O)O)cn2)c1=O] | 1H NMR (400 MHz, DMSO-d6) δ 10.67 (s, 1H), 9.56 (s, 1H), 8.65 (dd, J = 8.1, 2.3 Hz, 1H), 8.57 (d, J = 1.1 Hz, 1H), 8.45 (d, J = 2.3 Hz, 1H), 7.95-7.79 (m, 3H), 7.78-7.65 (m, 2H), 7.36 (d, J = 8.1 Hz, 1H), 7.25 (dd, J = 10.2, 6.3 Hz, 1H), 7.17 (dd, J = 11.1, 6.2 Hz, 1H), 4.65 (td, J = 9.1, 4.7 Hz, 1H), 3.39 (s, 3H), 3.27 (dd, J = 14.1, 4.8 Hz, 1H), 3.12-3.05 (m, 1H), 1.21 (s, 9H)); MS (ESI) m/z 753[M + H]+. |

TABLE 1-continued

| Compound No | Structural Formula | NMR/MS |
|---|---|---|
| A68 | | 1H NMR (400 MHz, DMSO-d6) δ 10.89 (s, 1H), 10.73 (s, 1H), 8.70-8.63 (m, 1H), 8.43 (d, J = 2.3 Hz, 1H), 7.84 (dd, J = 8.2, 2.4 Hz, 1H), 7.84-7.71 (m, 4H), 7.70 (d, J = 1.3 Hz, 1H), 7.30-7.24 (m, 2H), 7.19 (dd, J = 11.2, 6.3 Hz, 1H), 4.68-4.61 (m, 1H), 3.33-3.04 (m, 5H), 1.82 (s, 3H), 1.29 (s, 9H); MS (ESI) m/z 723[M + H]+. |
| A69 | | 1H NMR (400 MHz, DMSO-d6) δ 10.68 (s, 1H), 9.56 (s, 1H), 8.70 (dd, J = 7.9, 3.8 Hz, 1H), 8.37 (s, 1H), 7.89-7.81 (m, 2H), 7.79-7.72 (m, 2H), 7.70 (d, J = 1.3 Hz, 1H), 7.69-7.62 (m, 1H), 7.47-7.38 (m, 1H), 7.34 (dd, J = 10.3, 6.4 Hz, 1H), 7.19 (dd, J = 11.4, 6.3 Hz, 1H), 4.86 (td, J = 8.1, 4.9 Hz, 1H), 3.43-3.15 (m, 5H), 1.83 (d, J = 1.2 Hz, 3H), 1.21 (s, 9H); MS (ESI) m/z 699[M + H]+. |
| A70 | | 1H NMR (400 MHz, DMSO-d6) δ 10.68 (s, 1H), 9.56 (s, 1H), 8.70 (dd, J = 7.8, 3.7 Hz, 1H), 8.38 (s, 1H), 7.88-7.82 (m, 2H), 7.80 (d, J = 7.9 Hz, 1H), 7.77-7.71 (m, 2H), 7.71-7.63 (m, 1H), 7.46-7.39 (m, 1H), 7.34 (dd, J = 10.4, 6.4 Hz, 1H), 7.19 (dd, J = 11.4, 6.2 Hz, 1H), 5.80 (d, J = 7.9 Hz, 1H), 4.86 (td, J = 8.2, 5.0 Hz, 1H), 3.41-3.13 (m, 5H), 1.21 (s, 9H); MS (ESI) m/z 685[M + H]+. |

TABLE 1-continued

| Compound No | Structural Formula | NMR/MS |
|---|---|---|
| A71 | 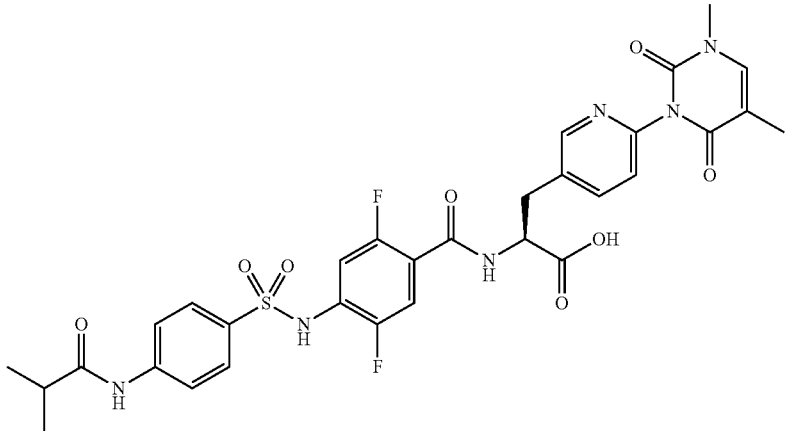 [SMILES: Cc1cn(C)c(=O)n(-c2ccc(C[C@H](NC(=O)c3cc(F)c(NS(=O)(=O)c4ccc(NC(=O)C(C)C)cc4)cc3F)C(=O)O)cn2)c1=O] | 1H NMR (400 MHz, DMSO-d6) δ 10.67 (s, 1H), 10.23 (s, 1H), 8.65 (dd, J = 7.9, 2.3 Hz, 1H), 8.42 (d, J = 2.3 Hz, 1H), 7.84 (dd, J = 8.1, 2.4 Hz, 1H), 7.81-7.72 (m, 4H), 7.69 (d, J = 1.3 Hz, 1H), 7.31-7.21 (m, 2H), 7.17 (dd, J = 11.2, 6.3 Hz, 1H), 4.68-4.60 (m, 1H), 3.31-3.20 (m, 4H), 3.07 (dd, J = 14.1, 10.0 Hz, 1H), 2.62-2.53 (m, 1H), 1.82 (s, 3H), 1.09 (d, J = 6.8 Hz, 6H); MS (ESI) m/z 685[M + H]+. |
| A72 | 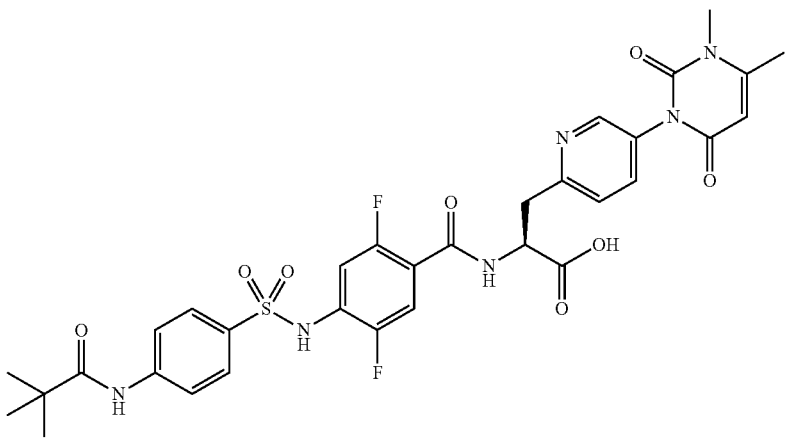 [SMILES: Cc1cc(=O)n(-c2ccc(C[C@H](NC(=O)c3cc(F)c(NS(=O)(=O)c4ccc(NC(=O)C(C)(C)C)cc4)cc3F)C(=O)O)nc2)c(=O)n1C] | 1H NMR (400 MHz, DMSO-d6) δ 10.68 (s, 1H), 9.56 (s, 1H), 8.69 (dd, J = 7.8, 3.6 Hz, 1H), 8.33 (d, J = 2.4 Hz, 1H), 7.87-7.82 (m, 2H), 7.77-7.71 (m, 2H), 7.62 (dd, J = 8.2, 2.5 Hz, 1H), 7.40 (d, J = 8.2 Hz, 1H), 7.34 (dd, J = 10.3, 6.3 Hz, 1H), 7.19 (dd, J = 11.5, 6.3 Hz, 1H), 5.76 (s, 1H), 4.91-4.79 (m, 1H), 3.36-3.17 (m, 5H), 2.31 (s, 3H), 1.21 (s, 9H); MS (ESI) m/z 699 [M + H]+. |
| A73 | 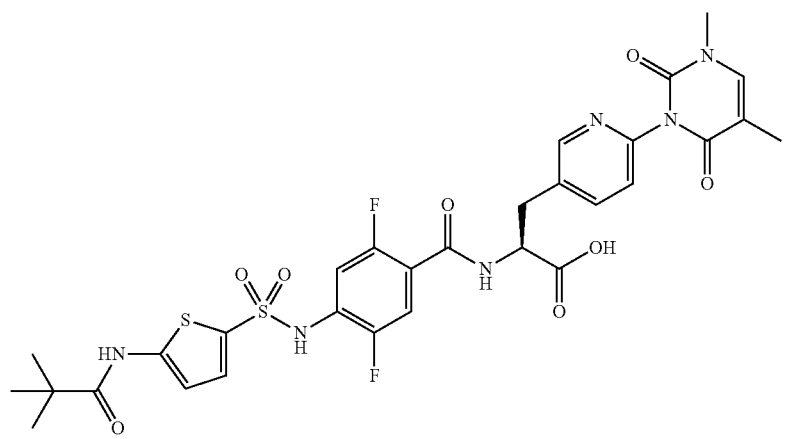 [SMILES: Cc1cn(C)c(=O)n(-c2ccc(C[C@H](NC(=O)c3cc(F)c(NS(=O)(=O)c4ccc(NC(=O)C(C)(C)C)s4)cc3F)C(=O)O)cn2)c1=O] | 1H NMR (400 MHz, DMSO-d6) δ 11.16 (s, 1H), 10.80 (s, 1H), 8.68 (d, J = 8.4 Hz, 1H), 8.43 (d, J = 2.4 Hz, 1H), 7.84 (dd, J = 8.0, 2.3 Hz, 1H), 7.69 (d, J = 1.3 Hz, 1H), 7.45 (d, J = 4.3 Hz, 1H), 7.39-7.15 (m, 3H), 6.79 (d, J = 4.3 Hz, 1H), 4.76-4.54 (m, 1H), 3.28 (s, 3H), 3.26-3.02 (m, 2H), 1.82 (d, J = 1.2 Hz, 3H), 1.21 (s, 9H); MS (ESI) m/z 705[M + H]+. |

TABLE 1-continued
| Compound No | Structural Formula | NMR/MS |
|---|---|---|
| A74 | 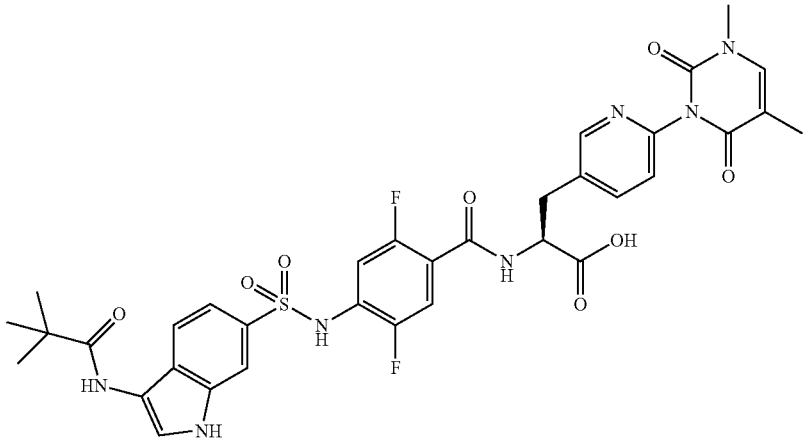 [SMILES: Cc1cn(C)c(=O)n(-c2ccc(C[C@H](NC(=O)c3cc(F)c(NS(=O)(=O)c4ccc5c(NC(=O)C(C)(C)C)c[nH]c5c4)cc3F)C(=O)O)cn2)c1=O] | 1H NMR(400 MHz, DMSO-d6): δ 12.97 (s, 1H), 11.41 (d, J = 2.7 Hz, 1H), 10.65 (s, 1H), 9.14 (s, 1H), 8.62 (dd, J = 8.1, 2.2 Hz, 1H), 8.41 (d, J = 2.3 Hz, 1H), 7.90-7.76 (m, 4H), 7.70 (d, J = 1.5 Hz, 1H), 7.43 (dd, J = 8.5, 1.7 Hz, 1H), 7.31-7.15 (m, 3H), 4.65-4.59 (m, 1H), 3.28-3.21 (m, 4H), 3.05 (dd, J = 14.1, 10.0 Hz, 1H), 1.82 (d, J = 1.2 Hz, 3H), 1.26 (s, 9H); MS (ESI) m/z 738 [M + H]+. |
| A75 | 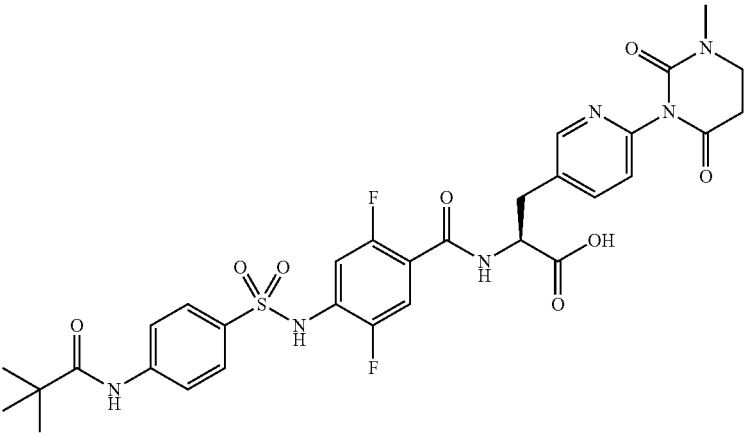 [SMILES: CN1CCC(=O)N(c2ccc(C[C@H](NC(=O)c3cc(F)c(NS(=O)(=O)c4ccc(NC(=O)C(C)(C)C)cc4)cc3F)C(=O)O)cn2)C1=O] | MS (ESI) m/z 687[M + H]+ |
| A76 | 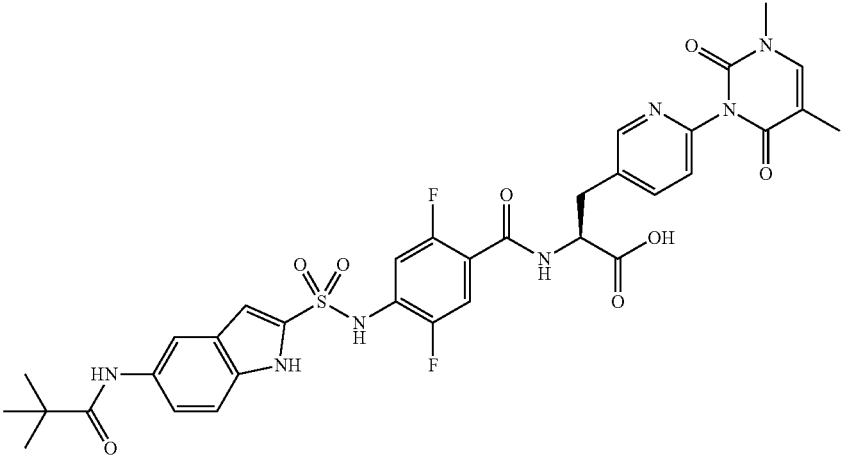 [SMILES: Cc1cn(C)c(=O)n(-c2ccc(C[C@H](NC(=O)c3cc(F)c(NS(=O)(=O)c4cc5cc(NC(=O)C(C)(C)C)ccc5[nH]4)cc3F)C(=O)O)cn2)c1=O] | 1H NMR (400 MHz, DMSO-d6) δ 12.01 (d, J = 3.2 Hz, 1H), 10.65 (s, 1H), 9.24 (s, 1H), 8.54 (dd, J = 7.9, 2.7 Hz, 1H), 8.41 (d, J = 2.3 Hz, 1H), 8.10-7.99 (m, 2H), 7.82 (dd, J = 8.2, 2.4 Hz, 1H), 7.69 (d, J = 1.2 Hz, 1H), 7.42-7.28 (m, 2H), 7.30-7.13 (m, 3H), 4.67-4.57 (m, 1H), 3.28-3.17 (m, 4H), 3.09-3.00 (m, 1H), 1.82 (s, 3H), 1.24 (s, 9H); MS (ESI) m/z 738[M + H]+. |

TABLE 1-continued

| Compound No | Structural Formula | NMR/MS |
|---|---|---|
| A77 | (structure shown) | 1H NMR (400 MHz, DMSO-d6) δ 11.98 (d, J = 3.0 Hz, 1H), 10.64 (s, 1H), 9.21 (s, 1H), 8.55 (dd, J = 8.0, 2.5 Hz, 1H), 8.41 (d, J = 2.3 Hz, 1H), 8.05 (d, J = 3.0 Hz, 1H), 7.98 (d, J = 1.7 Hz, 1H), 7.82 (dd, J = 8.1, 2.3 Hz, 1H), 7.73 (d, J = 8.7 Hz, 1H), 7.69 (d, J = 1.3 Hz, 1H), 7.33 (dd, J = 8.7, 1.9 Hz, 1H), 7.29-7.14 (m, 3H), 4.66-4.56 (m, 1H), 3.30-3.18 (m, 4H), 3.05 (dd, J = 14.1, 9.9 Hz, 1H), 1.81 (s, 3H), 1.23 (s, 9H); MS (ESI) m/z 738 [M + H]+. |

EXAMPLE 4

Isopropyl (2S)-2-[[4-(2,2-dimethylpropanoylamino)phenyl]sulfonylamino]-2,5-difluoro-benzoyl]amino]-3-[4-(1-methyl-2,4-dioxo-pyrido[3,4-d]pyrimidin-3-yl)phenyl]propanoate (P1)

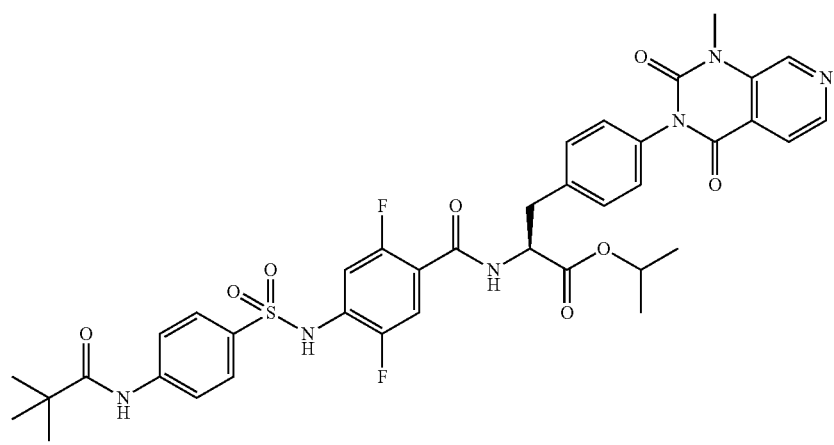 [SMILES: CC(C)OC(=O)[C@H](Cc1ccc(-n2c(=O)c3ccncc3n(C)c2=O)cc1)NC(=O)c1cc(F)c(NS(=O)(=O)c2ccc(NC(=O)C(C)(C)C)cc2)cc1F]

A 1,4-dioxane solution (1.0 ml) and concentrated sulfuric acid (0.005 ml) were added to an isopropyl alcohol solution (1.0 ml) of A1 (7.0 mg, 0.0095 mmol), and the mixture was stirred at 60° C. overnight. After the reaction solution was cooled to room temperature and was concentrated under reduced pressure, the residue was subjected to reverse phase HPLC using ODS as a packing material and was purified in the same method as in (step 1) in [Synthesis Example 4] to give the title compound (4.9 mg, 66%).

Each of the compounds (P2 to P120) shown in Table 2 can be synthesized in the same method as in the compound in [Example 4] by using: any of the sulfonamide derivatives selected from A1 to A77; and a corresponding alcohol (methanol, ethanol, n-propyl alcohol, isopropyl alcohol, n-butyl alcohol, isobutyl alcohol, cyclopropylmethyl alcohol, tetrahydro-4-pyranol, n-pentyl alcohol, isopentyl alcohol, 3-pentyl alcohol, or cyclohexyl alcohol).

EXAMPLE 5

Isobutyl (2S)-2-[2,5-difluoro-4-[(4-pivalamidophenyl)sulfonamido]benzamido]-3-[6-(3-methyl-2,6-dioxotetrahydropyrimidin-1(2H)-yl)pyridin-3-yl]propanoate (P121)

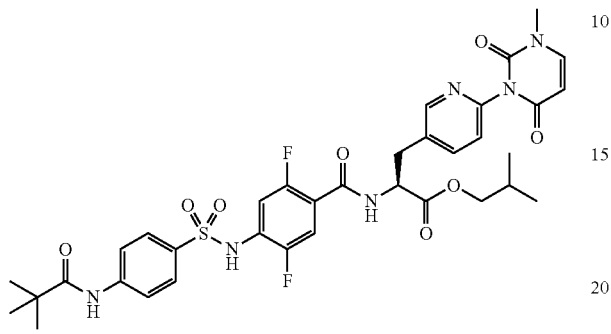

A catalytic amount of 5% rhodium carbon was added to a methanol solution of P74 (25.1 mg, 0.034 mmol) to cause a reaction to proceed at 60° C. and 60 bar. The solvent was evaporated under reduced pressure, the residue was subjected to reverse phase HPLC using ODS as a packing material, for elution with a mixed solution of water and acetonitrile containing 0.1% (v/v) of trifluoroacetic acid, and the targeted fraction was freeze-dried to give the title compound (23.6 mg, 0.034 mmol).

| Compound No. | Structural Formula | NMR/MS |
|---|---|---|
| P1 | 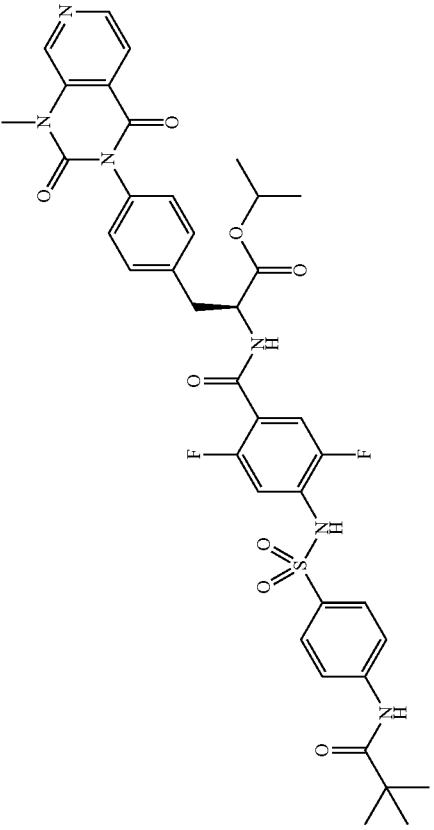 | MS (ESI) m/z 777 [M + H]+. |
| P2 | 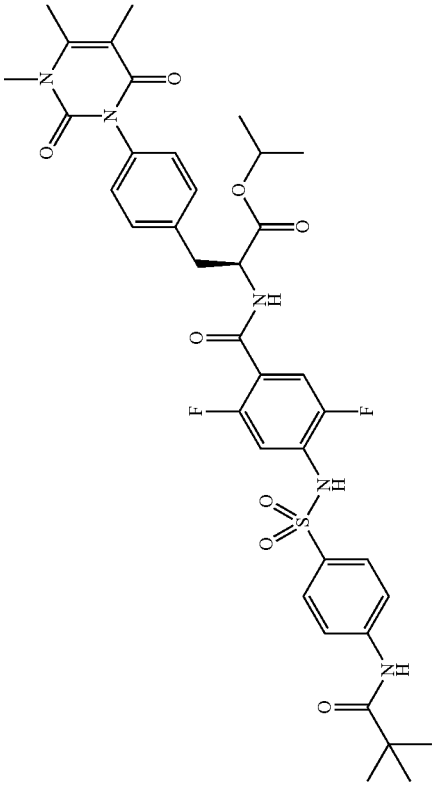 | 1H NMR (400 MHz, DMSO-d6) δ 10.67 (s, 1H), 9.57 (s, 1H), 8.71 (dd, J = 7.3, 1.9 Hz, 1H), 7.86 (d, J = 9.0 Hz, 2H), 7.75 (d, J = 8.9 Hz, 2H), 7.35-7.24 (m, 3H), 7.19 (dd, J = 11.1, 6.3 Hz, 1H), 7.07 (d, J = 8.3 Hz, 2H), 4.95-4.82 (m, 1H), 4.62-4.51 (m, 1H), 3.36 (s, 3H), 3.16-3.00 (m, 2H), 2.31 (s, 3H), 1.89 (s, 3H), 1.21 (s, 9H), 1.18 (d, J = 6.3 Hz, 3H), 1.12 (d, J = 6.2 Hz, 3H); MS (ES) m/z 754 [M + H]+. |

| Compound No. | Structural Formula | NMR/MS |
|---|---|---|
| P3 | | 1H NMR (400 MHz, DMSO-d6) δ 11.17 (s, 1H), 10.81 (s, 1H), 8.97 (s, 1H), 8.76 (dd, J = 7.5, 2.0 Hz, 1H), 8.55 (d, J = 5.0 Hz, 1H), 7.89 (dd, J = 4.9, 0.7 Hz, 1H), 7.46 (d, J = 4.3 Hz, 1H), 7.41-7.17 (m, 6H), 6.80 (d, J = 4.3 Hz, 1H), 4.96-4.83 (m, 1H), 4.66-4.53 (m, 1H), 3.60 (s, 3H), 3.20-3.05 (m, 2H), 1.21 (s, 9H), 1.19 (d, J = 6.3 Hz, 3H), 1.13 (d, J = 6.2 Hz, 3H); MS (ESI) m/z 783 [M + H]+. |
| P4 | | 1H NMR (400 MHz, DMSO-d6) δ 11.17 (s, 1H), 10.80 (s, 1H), 8.74 (dd, J = 7.5, 2.1 Hz, 1H), 7.46 (d, J = 4.3 Hz, 1H), 7.39-7.29 (m, 3H), 7.25 (dd, J = 11.2, 6.3 Hz, 1H), 7.07 (d, J = 8.3 Hz, 2H), 6.80 (d, J = 4.3 Hz, 1H), 4.94-4.83 (m, 1H), 4.63-4.50 (m, 1H), 3.36 (s, 3H), 3.20-3.02 (m, 2H), 2.31 (s, 3H), 1.89 (d, J = 0.9 Hz, 3H), 1.21 (s, 9H), 1.18 (d, J = 6.2 Hz, 3H), 1.12 (d, J = 6.2 Hz, 3H); MS (ESI) m/z 760 [M + H]+. |

-continued

| Compound No. | Structural Formula | NMR/MS |
|---|---|---|
| P5 | | 1H NMR (400 MHz, DMSO-d6) δ 11.03 (s, 1H), 9.83 (s, 1H), 8.78 (dd, J = 7.4, 2.0 Hz, 1H), 7.92 (d, J = 1.7 Hz, 1H), 7.79 (d, J = 1.8 Hz, 1H), 7.39-7.29 (m, 3H), 7.25 (dd, J = 11.0, 6.2 Hz, 1H), 7.08 (d, J = 8.3 Hz, 2H), 4.95-4.83 (m, 1H), 4.64-4.52 (m, 1H), 3.36 (s, 3H), 3.19-3.01 (m, 2H), 2.31 (d, J = 0.9 Hz, 3H), 1.89 (d, J = 0.8 Hz, 3H), 1.18 (s, 12H), 1.13 (d, J = 6.2 Hz, 3H); MS (ESI) m/z 760 [M + H]+. |
| P6 | | 1H NMR (400 MHz, DMSO-d6) δ 10.86 (s, 1H), 9.32 (s, 1H), 8.98 (s, 1H), 8.56 (d, J = 7.5, 1.9 Hz, 1H), 7.92-7.86 (m, 1H), 7.85-7.77 (m, 1H), 7.70 (dd, J = 9.9, 2.1 Hz, 1H), 7.64 (dd, J = 8.5, 2.1 Hz, 1H), 7.40-7.34 (m, 2H), 7.32 (dd, J = 10.2, 6.2 Hz, 1H), 7.28-7.18 (m, 3H), 4.96-4.86 (m, 1H), 4.65-4.55 (m, 1H), 3.60 (s, 3H), 3.20-3.04 (m, 2H), 1.25-1.17 (m, 12H), 1.14 (d, J = 6.3 Hz, 3H); MS (ESI) m/z 795 [M + H]+. |

| Compound No. | Structural Formula | NMR/MS |
|---|---|---|
| P7 | | 1H NMR (400 MHz, DMSO-d6) δ 10.85 (s, 1H), 9.32 (s, 1H), 8.76 (dd, J = 7.5, 1.9 Hz, 1H), 7.86-7.78 (m, 1H), 7.70 (dd, J = 9.9, 2.1 Hz, 1H), 7.64 (dd, J = 8.5, 2.1 Hz, 1H), 7.37-7.28 (m, 3H), 7.24 (dd, J = 10.9, 6.3 Hz, 1H), 7.08 (d, J = 8.3 Hz, 2H), 4.95-4.84 (m, 1H), 4.61-4.55 (m, 1H), 3.47-3.30 (m, 3H), 3.20-3.01 (m, 2H), 2.31 (s, 3H), 1.90 (s, 3H), 1.23 (s, 9H), 1.19 (d, J = 6.2 Hz, 3H), 1.13 (d, J = 6.2 Hz, 3H); MS (ESI) m/z 772 [M + H]+. |
| P8 | | 1H NMR (400 MHz, DMSO-d6) δ 10.68 (s, 1H), 10.31 (s, 1H), 8.97 (s, 1H), 8.73 (dd, J = 7.4, 2.0 Hz, 1H), 8.55 (d, J = 5.0 Hz, 1H), 7.92-7.85 (m, 1H), 7.82-7.73 (m, 4H), 7.36 (d, J = 8.4 Hz, 2H), 7.28 (dd, J = 10.2, 6.3 Hz, 1H), 7.25-7.15 (m, 3H), 4.89 (p, J = 6.2 Hz, 1H), 4.64-4.54 (m, 1H), 3.89 (dd, J = 10.6, 3.8 Hz, 2H), 3.60 (s, 3H), 3.39-3.29 (m, 2H), 3.19-3.03 (m, 2H), 2.66-2.54 (m, 1H), 1.77-1.56 (m, 4H), 1.18 (d, J = 6.2 Hz, 3H), 1.13 (d, J = 6.2 Hz, 3H); MS (ESI) m/z 805 [M + H]+. |

| Compound No. | Structural Formula | NMR/MS |
|---|---|---|
| P9 | (structure) | 1H NMR (400 MHz, DMSO-d6) δ 10.68 (s, 1H), 10.30 (s, 1H), 8.71 (dd, J = 7.5, 2.0 Hz, 1H), 7.82-7.72 (m, 4H), 7.36-7.24 (m, 3H), 7.18 (dd, J = 11.1, 6.3 Hz, 1H), 7.07 (d, J = 8.3 Hz, 2H), 4.93-4.84 (m, 1H), 4.61-4.50 (m, 1H), 3.95-3.84 (m, 2H), 3.38-3.28 (m, 5H), 3.16-3.01 (m, 2H), 2.65-2.56 (m, 1H), 2.31 (s, 3H), 1.89 (s, 3H), 1.75-1.57 (m, 4H), 1.18 (d, J = 6.2 Hz, 3H), 1.12 (d, J = 6.2 Hz, 3H); MS (ESI) m/z 782 [M + H]+. |
| P10 | (structure) | 1H NMR (400 MHz, DMSO-d6) δ 10.70 (s, 1H), 10.28 (s, 1H), 8.71 (dd, J = 7.4, 2.1 Hz, 1H), 7.85-7.74 (m, 4H), 7.35-7.26 (m, 3H), 7.20 (dd, J = 11.1, 6.3 Hz, 1H), 7.07 (d, J = 8.3 Hz, 2H), 4.97-4.80 (m, 1H), 4.61-4.51 (m, 1H), 3.36 (s, 3H), 3.17-3.00 (m, 2H), 2.31 (s, 3H), 2.29-2.19 (m, 1H), 1.89 (s, 3H), 1.64-1.37 (m, 4H), 1.18 (d, J = 6.2 Hz, 3H), 1.12 (d, J = 6.2 Hz, 3H), 0.83 (t, J = 7.4 Hz, 6H); MS (ESI) m/z 768 [M + H]+. |

| Compound No. | Structural Formula | NMR/MS |
|---|---|---|
| P11 | | MS (ESI) m/z 798 [M + H]+. |
| P12 | | 1H NMR (400 MHz, DMSO-d6) δ 10.67 (s, 1H), 9.60 (s, 1H), 8.97 (s, 1H), 8.74 (d, J = 7.4 Hz, 1H), 8.55 (d, J = 4.9 Hz, 1H), 7.89 (d, J = 5.0 Hz, 1H), 7.83 (d, J = 8.9 Hz, 2H), 7.75 (d, J = 9.0 Hz, 2H), 7.36 (d, J = 8.4 Hz, 2H), 7.28 (dd, J = 10.2, 6.3 Hz, 1H), 7.25-7.16 (m, 3H), 4.93-4.86 (m, 1H), 4.62-4.55 (m, 1H), 3.60 (s, 3H), 3.55-3.37 (m, 2H), 3.18-3.04 (m, 2H), 1.18 (d, J = 6.3 Hz, 3H), 1.16-1.07 (m, 9H); MS (ESI) m/z 793 [M + H]+. |

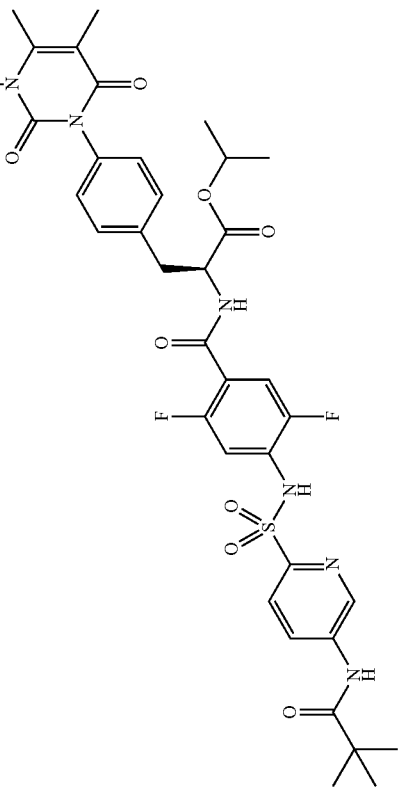

| Compound No. | Structural Formula | NMR/MS |
|---|---|---|
| P15 | | 1H NMR (400 MHz, DMSO-d6) δ 10.67 (s, 1H), 9.60 (s, 1H), 8.72 (d, J = 7.3 Hz, 1H), 7.83 (d, J = 8.8 Hz, 2H), 7.75 (d, J = 8.4 Hz, 2H), 7.34-7.23 (m, 3H), 7.19 (dd, J = 11.0, 6.2 Hz, 1H), 7.07 (d, J = 7.9 Hz, 2H), 4.94-4.82 (m, 1H), 4.60-4.50 (m, 1H), 3.55-3.49 (m, 2H), 3.36 (s, 3H), 3.17-3.00 (m, 2H), 2.31 (s, 3H), 1.89 (s, 3H), 1.21-1.05 (m, 12H); MS (ESI) m/z 770 [M + H]+. |
| P16 | | 1H NMR (400 MHz, DMSO-d6) δ 10.72 (s, 1H), 10.10 (s, 1H), 8.97 (s, 1H), 8.74 (dd, J = 7.4, 2.0 Hz, 1H), 8.55 (d, J = 5.0 Hz, 1H), 7.89 (dd, J = 5.0, 0.7 Hz, 1H), 7.83-7.75 (m, 4H), 7.39-7.33 (m, 2H), 7.29 (dd, J = 10.2, 6.3 Hz, 1H), 7.25-7.16 (m, 3H), 4.95-4.84 (m, 1H), 4.64-4.55 (m, 1H), 3.60 (s, 3H), 3.17-3.04 (m, 2H), 1.53-1.44 (m, 2H), 1.34-1.28 (m, 2H), 1.18 (d, J = 6.2 Hz, 3H), 1.12 (d, J = 6.2 Hz, 3H); MS (ESI) m/z 829 [M + H]+. |

-continued
| Compound No. | Structural Formula | NMR/MS |
|---|---|---|
| P17 | 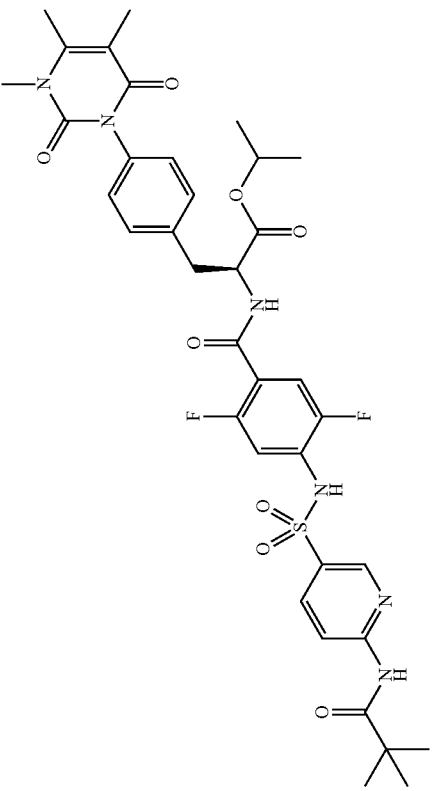 | 1H NMR (400 MHz, DMSO-d6) δ 10.83 (s, 1H), 10.36 (s, 1H), 8.76 (dd, J = 7.7, 1.9 Hz, 1H), 8.67 (dd, J = 2.6, 0.8 Hz, 1H), 8.24 (dd, J = 8.9, 0.8 Hz, 1H), 8.16 (dd, J = 9.0, 2.5 Hz, 1H), 7.37-7.20 (m, 4H), 7.07 (d, J = 8.3 Hz, 2H), 4.97-4.82 (m, 1H), 4.64-4.51 (m, 1H), 3.36 (s, 3H), 3.13 (dd, J = 14.0, 6.0 Hz, 1H), 3.06 (dd, J = 14.0, 9.1 Hz, 1H), 2.34-2.27 (m, 3H), 1.89 (d, J = 0.9 Hz, 3H), 1.23 (s, 9H), 1.18 (d, J = 6.2 Hz, 3H), 1.13 (d, J = 6.2 Hz, 3H); MS (ESI) m/z 755 [M + H]+. |
| P18 | | MS (ESI) m/z 778 [M + H]+. |

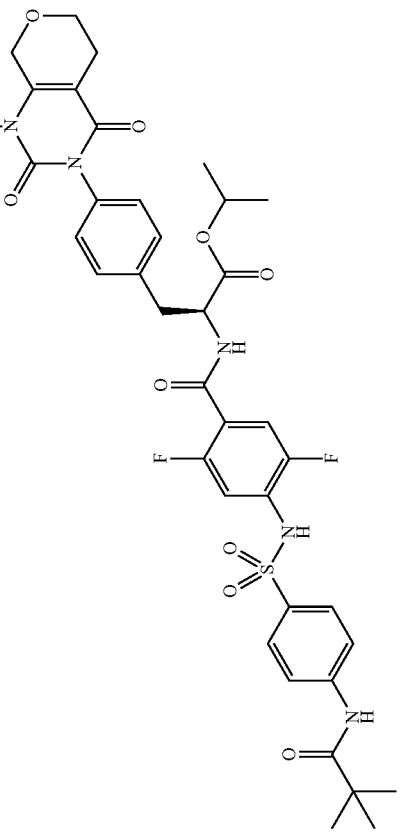

| Compound No. | Structural Formula | NMR/MS |
|---|---|---|
| P21 | 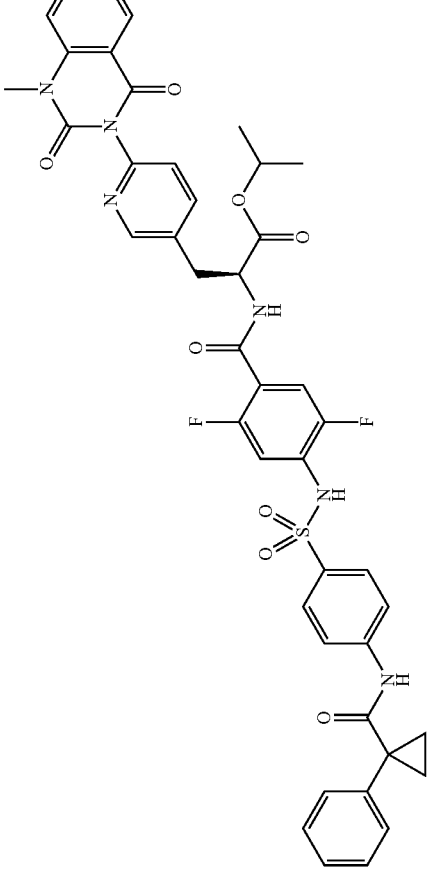 | 1H NMR (400 MHz, DMSO-d6) δ 10.69 (s, 1H), 9.55 (s, 1H), 9.00 (s, 1H), 8.80 (dd, J = 7.7, 1.8 Hz, 1H), 8.57 (d, J = 5.0 Hz, 1H), 8.47 (d, J = 2.2 Hz, 1H), 7.97-7.87 (m, 2H), 7.82-7.68 (m, 4H), 7.41 (d, J = 8.1 Hz, 1H), 7.39-7.31 (m, 4H), 7.30-7.23 (m, 2H), 7.18 (dd, J = 11.1, 6.3 Hz, 1H), 4.97-4.85 (m, 1H), 4.70-4.61 (m, 1H), 3.60 (s, 3H), 3.22 (dd, J = 14.0, 6.0 Hz, 1H), 3.12 (dd, J = 14.0, 9.4 Hz, 1H), 1.49-1.41 (m, 2H), 1.18 (d, J = 6.2 Hz, 3H), 1.16-1.09 (m, 5H); MS (ESI) m/z 738 [M + H]+. |
| P22 | 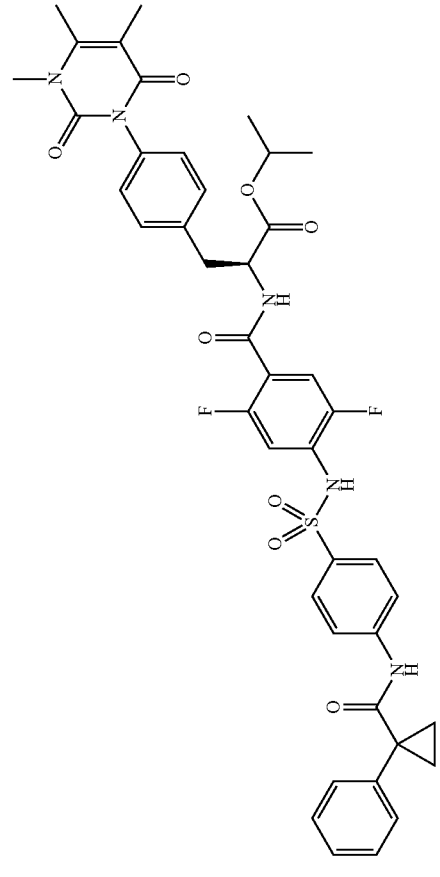 | 1H NMR (400 MHz, DMSO-d6) δ 10.67 (s, 1H), 9.55 (s, 1H), 8.70 (dd, J = 7.5, 2.1 Hz, 1H), 7.80-7.69 (m, 4H), 7.43-7.23 (m, 8H), 7.17 (dd, J = 11.1, 6.3 Hz, 2H), 7.07 (d, J = 8.3 Hz, 1H), 4.96-4.82 (m, 1H), 4.63-4.50 (m, 1H), 3.36 (s, 3H), 3.18-2.99 (m, 2H), 2.31 (s, 3H), 1.89 (s, 3H), 1.49-1.40 (m, 2H), 1.18 (d, J = 6.3 Hz, 3H), 1.16-1.09 (m, 5H); MS (ESI) m/z 814 [M + H]+. |

-continued

| Compound No. | Structural Formula | NMR/MS |
|---|---|---|
| P23 | | 1H NMR (400 MHz, DMSO-d6) δ 10.87 (s, 1H), 9.81 (s, 1H), 8.99 (s, 1H), 8.94 (d, J = 2.4 Hz, 1H), 8.83 (dd, J = 7.6, 1.8 Hz, 1H), 8.57 (d, J = 5.0 Hz, 1H), 8.47 (d, J = 2.3 Hz, 1H), 8.35 (dd, J = 8.7, 2.4 Hz, 1H), 7.98 (d, J = 8.7 Hz, 1H), 7.96-7.87 (m, 2H), 7.41 (d, J = 8.1 Hz, 1H), 7.34-7.24 (m, 2H), 4.98-4.86 (m, 1H), 4.72-4.61 (m, 1H), 3.60 (s, 3H), 3.23 (dd, J = 14.0, 6.0 Hz, 1H), 3.13 (dd, J = 14.0, 9.4 Hz, 1H), 1.23 (s, 9H), 1.19 (d, J = 6.2 Hz, 3H), 1.14 (d, J = 6.2 Hz, 3H); MS (ESI) m/z 779 [M + H]+. |
| P24 | | 1H NMR (400 MHz, DMSO-d6) δ 10.86 (s, 1H), 9.81 (s, 1H), 8.94 (d, J = 2.5 Hz, 1H), 8.81 (dd, J = 7.7, 1.8 Hz, 1H), 8.42 (d, J = 2.3 Hz, 1H), 8.35 (dd, J = 8.7, 2.5 Hz, 1H), 7.98 (d, J = 8.7 Hz, 1H), 7.85 (dd, J = 8.1, 2.4 Hz, 1H), 7.35-7.19 (m, 3H), 4.98-4.85 (m, 1H), 4.70-4.57 (m, 1H), 3.36 (s, 3H), 3.20 (dd, J = 14.1, 5.8 Hz, 1H), 3.10 (dd, J = 14.1, 9.4 Hz, 1H), 2.32 (s, 3H), 1.89 (d, J = 0.9 Hz, 3H), 1.24 (s, 9H), 1.18 (d, J = 6.2 Hz, 3H), 1.13 (d, J = 6.2 Hz, 3H); MS (ESI) m/z 756 [M + H]+. |

| Compound No. | Structural Formula | NMR/MS |
|---|---|---|
| P25 | 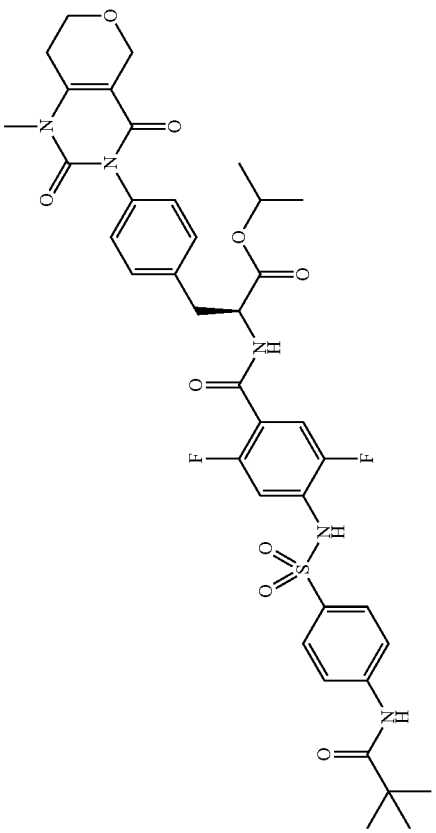 | 1H NMR (400 MHz, DMSO-d6) δ 10.68 (s, 1H), 9.58 (s, 1H), 8.72 (d, J = 7.5 Hz, 1H), 7.86 (d, J = 9.0 Hz, 2H), 7.76 (d, J = 8.9 Hz, 2H), 7.35-7.26 (m, 3H), 7.19 (dd, J = 11.1, 6.3 Hz, 1H), 7.11 (d, J = 8.3 Hz, 2H), 4.93-4.85 (m, 1H), 4.60-4.53 (m, 1H), 4.30-4.26 (m, 2H), 3.88 (t, J = 5.5 Hz, 2H), 3.30 (s, 3H), 3.18-3.03 (m, 2H), 2.76-2.69 (m, 2H), 1.22 (s, 9H), 1.18 (d, J = 6.3 Hz, 3H), 1.12 (d, J = 6.2 Hz, 3H); MS (ESI) m/z 782 [M + H]+. |
| P26 | 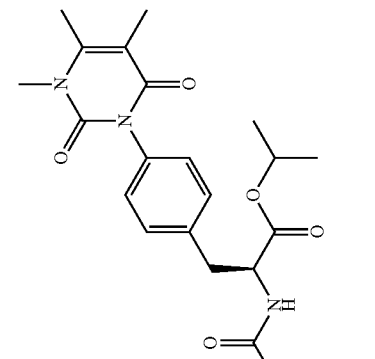 | 1H NMR (400 MHz, DMSO-d6) δ 10.81 (s, 1H), 8.74 (dd, J = 7.5, 2.1 Hz, 1H), 7.84 (d, J = 8.6 Hz, 2H), 7.54 (d, J = 8.6 Hz, 2H), 7.36-7.25 (m, 3H), 7.19 (dd, J = 10.9, 6.2 Hz, 1H), 7.07 (d, J = 8.3 Hz, 2H), 4.94-4.86 (m, 1H), 4.61-4.52 (m, 1H), 3.36 (s, 3H), 3.18-3.04 (m, 5H), 2.31 (s, 3H), 1.90 (s, 3H), 1.19 (d, J = 6.2 Hz, 3H), 1.13 (d, J = 6.2 Hz, 3H), 0.96 (s, 9H); MS (ESI) m/z 768 [M + H]+. |

| Compound No. | Structural Formula | NMR/MS |
|---|---|---|
| P27 | | 1H NMR (400 MHz, DMSO-d6) δ 10.92 (s, 1H), 8.99 (s, 1H), 8.84 (dd, J = 7.6, 1.7 Hz, 1H), 8.57 (d, J = 5.0 Hz, 1H), 8.46 (d, J = 2.3 Hz, 1H), 8.01-7.87 (m, 4H), 7.73-7.64 (m, 2H), 7.41 (d, J = 8.0 Hz, 1H), 7.32-7.20 (m, 2H), 5.00-4.82 (m, 1H), 4.72-4.61 (m, 1H), 3.22 (dd, J = 14.0, 5.9 Hz, 1H), 3.12 (dd, J = 14.0, 9.4 Hz, 1H), 2.87 (s, 3H), 1.41 (s, 6H), 1.18 (d, J = 6.2 Hz, 3H), 1.13 (d, J = 6.2 Hz, 3H); MS (ESI) m/z 819 [M + H]+. |
| P28 | | 1H NMR (400 MHz, DMSO-d6) δ 10.91 (s, 1H), 8.75 (dd, J = 7.5, 1.9 Hz, 1H), 8.03-7.87 (m, 2H), 7.75-7.62 (m, 2H), 7.35-7.27 (m, 3H), 7.24 (dd, J = 10.9, 6.2 Hz, 1H), 7.11-6.99 (m, 2H), 4.98-4.80 (m, 1H), 4.61-4.51 (m, 1H), 3.36 (s, 3H), 3.18-2.98 (m, 2H), 2.87 (s, 3H), 2.31 (s, 3H), 1.89 (s, 3H), 1.42 (s, 6H), 1.18 (d, J = 6.2 Hz, 3H), 1.12 (d, J = 6.2 Hz, 3H); MS (ESI) m/z 795 [M + H]+. |

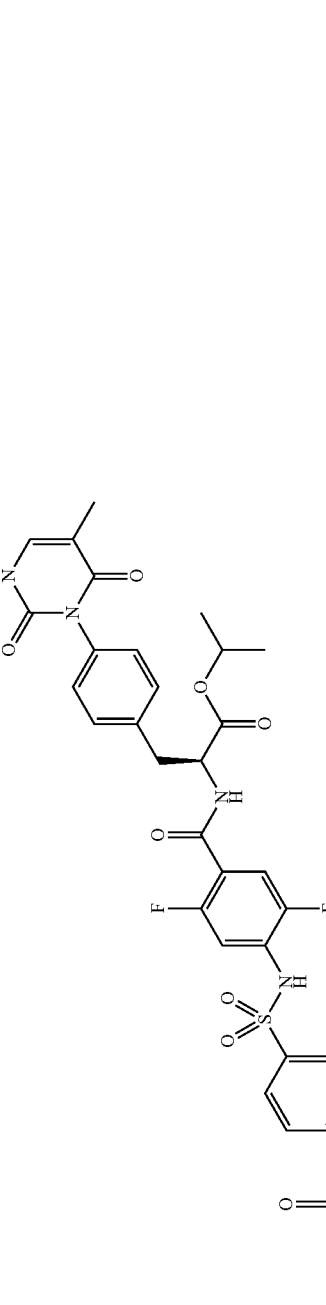

| Compound No. | Structural Formula | NMR/MS |
|---|---|---|
| P31 | | MS (ESI) m/z 783 [M + H]+. |
| P32 | | 1H NMR (400 MHz, DMSO-d6) δ 10.68 (s, 1H), 9.57 (s, 1H), 8.79 (dd, J = 7.7, 1.8 Hz, 1H), 8.42 (d, J = 2.2 Hz, 1H), 7.92-7.81 (m, 3H), 7.75 (d, J = 8.9 Hz, 2H), 7.32-7.22 (m, 2H), 7.18 (dd, J = 11.1, 6.3 Hz, 1H), 4.94-4.85 (m, 1H), 4.67-4.59 (m, 1H), 4.34-4.22 (m, 2H), 3.88 (t, J = 5.5 Hz, 2H), 3.30 (s, 3H), 3.23-3.14 (m, 1H), 3.14-3.05 (m, 1H), 2.78-2.69 (m, 2H), 1.22 (s, 9H), 1.17 (d, J = 6.2 Hz, 3H), 1.12 (d, J = 6.2 Hz, 3H); MS (ESI) m/z 783 [M + H]+. |

-continued
| Compound No. | Structural Formula | NMR/MS |
|---|---|---|
| P33 | 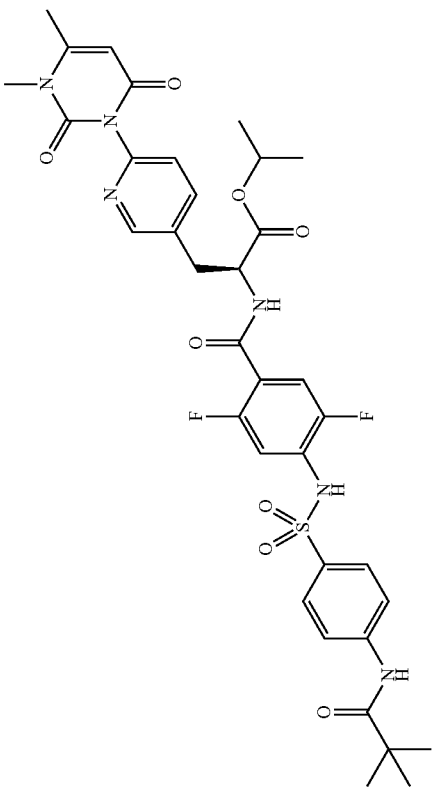 | MS (ESI) m/z 741 [M + H]+. |
| P34 | 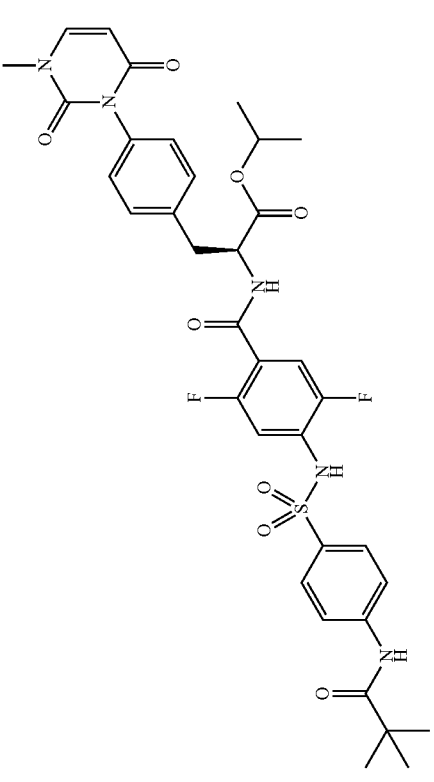 | MS (ESI) m/z 726 [M + H]+. |

| Compound No. | Structural Formula | NMR/MS |
|---|---|---|
| P35 | | MS (ESI) m/z 740 [M + H]+. |
| P36 | | 1H NMR (400 MHz, DMSO-d6) δ 10.69 (s, 1H), 9.57 (s, 1H), 8.80 (dd, J = 7.5, 3.2 Hz, 1H), 8.33 (d, J = 2.1 Hz, 1H), 7.85 (d, J = 9.0 Hz, 2H), 7.75 (d, J = 8.9 Hz, 2H), 7.63 (dd, J = 8.2, 2.5 Hz, 1H), 7.41 (d, J = 8.2 Hz, 1H), 7.34 (dd, J = 10.3, 6.3 Hz, 1H), 7.20 (dd, J = 11.3, 6.3 Hz, 1H), 4.92-4.81 (m, 2H), 3.32 (s, 3H), 3.29-3.24 (m, 2H), 2.67-2.61 (m, 2H), 2.31-2.25 (m, 2H), 1.80-1.71 (m, 2H), 1.65-1.57 (m, 2H), 1.21 (s, 9H), 1.15 (d, J = 6.2 Hz, 3H), 1.10 (d, J = 6.2 Hz, 3H); MS (ESI) m/z 781 [M + H]+. |

| Compound No. | Structural Formula | NMR/MS |
|---|---|---|
| P37 | 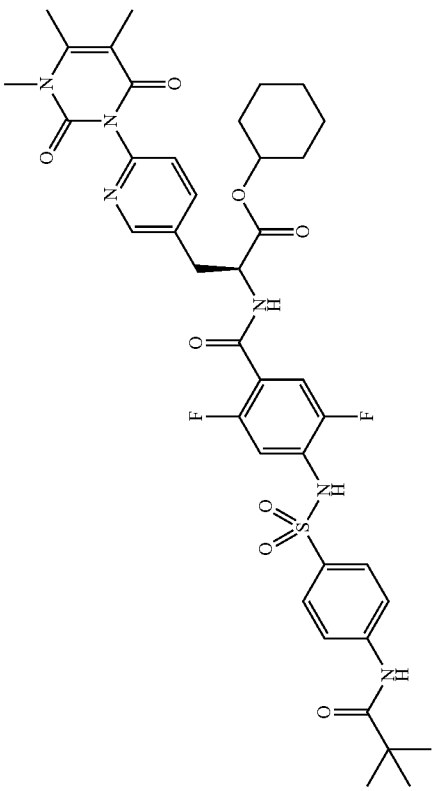 | 1H NMR (400 MHz, DMSO-d6) δ 10.68 (s, 1H), 9.57 (s, 1H), 8.79 (dd, J = 7.6, 1.9 Hz, 1H), 8.41 (s, 1H), 7.89-7.82 (m, 3H), 7.80-7.64 (m, 2H), 7.32-7.22 (m, 2H), 7.18 (dd, J = 11.1, 6.3 Hz, 1H), 4.80-4.58 (m, 2H), 3.36 (s, 3H), 3.21 (dd, J = 14.1, 5.6 Hz, 1H), 3.09 (dd, J = 14.1, 9.6 Hz, 1H), 2.32 (s, 3H), 1.89 (s, 3H), 1.81-1.52 (m, 4H), 1.52-1.24 (m, 6H), 1.21 (s, 9H); MS (ESI) m/z 795 [M + H]+. |
| P38 | 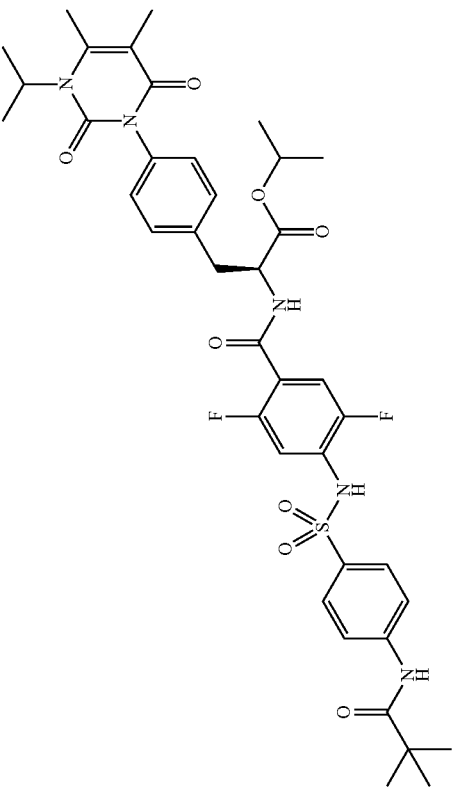 | 1H NMR (400 MHz, DMSO-d6) δ 10.66 (s, 1H), 9.57 (s, 1H), 8.76-8.65 (m, 1H), 7.89-7.81 (m, 2H), 7.80-7.70 (m, 2H), 7.34-7.23 (m, 3H), 7.18 (dd, J = 11.1, 6.3 Hz, 1H), 7.10-7.02 (m, 2H), 4.95-4.85 (m, 1H), 4.62-4.44 (m, 2H), 3.19-2.99 (m, 2H), 2.31 (s, 3H), 1.89 (d, J = 0.9 Hz, 3H), 1.42 (d, J = 6.7 Hz, 6H), 1.21 (s, 9H), 1.19 (d, J = 6.2 Hz, 3H), 1.14 (d, J = 6.2 Hz, 3H); MS (ESI) m/z 782 [M + H]+. |

-continued
| Compound No. | Structural Formula | NMR/MS |
|---|---|---|
| P39 | 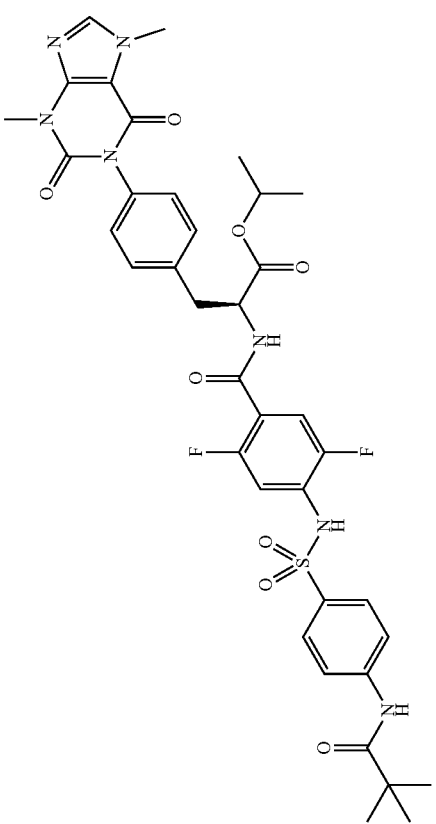 | 1H NMR (400 MHz, DMSO-d6) δ 10.68 (s, 1H), 9.58 (s, 1H), 8.72 (dd, J = 7.5, 2.0 Hz, 1H), 8.07 (s, 1H), 7.86 (d, J = 8.9 Hz, 2H), 7.76 (d, J = 8.9 Hz, 2H), 7.38-7.25 (m, 3H), 7.25-7.11 (m, 3H), 4.94-4.85 (m, 1H), 4.62-4.55 (m, 1H), 3.86 (s, 3H), 3.68-3.02 (m, 5H), 1.28-1.17 (m, 12H), 1.14 (d, J = 6.2 Hz, 3H); MS (ESI) m/z 780 [M + H]+. |
| P40 | 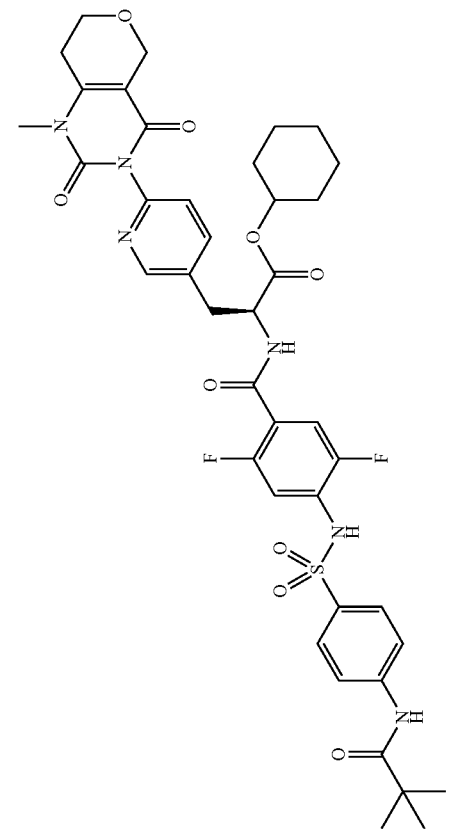 | 1H NMR (400 MHz, DMSO-d6) δ 10.68 (s, 1H), 9.57 (s, 1H), 8.79 (d, J = 8.7 Hz, 1H), 8.43 (d, J = 2.3 Hz, 1H), 7.92-7.81 (m, 3H), 7.75 (d, J = 8.9 Hz, 2H), 7.32-7.22 (m, 2H), 7.18 (dd, J = 11.1, 6.3 Hz, 1H), 4.73-4.62 (m, 2H), 4.28 (s, 2H), 3.88 (t, J = 5.6 Hz, 2H), 3.30 (s, 3H), 3.21 (dd, J = 14.0, 5.6 Hz, 1H), 3.10 (dd, J = 14.1, 9.6 Hz, 1H), 2.77-2.70 (m, 2H), 1.79-1.14 (m, 19H); MS (ESI) m/z 823. [M + H]+. |

| Compound No. | Structural Formula | NMR/MS |
|---|---|---|
| P41 | 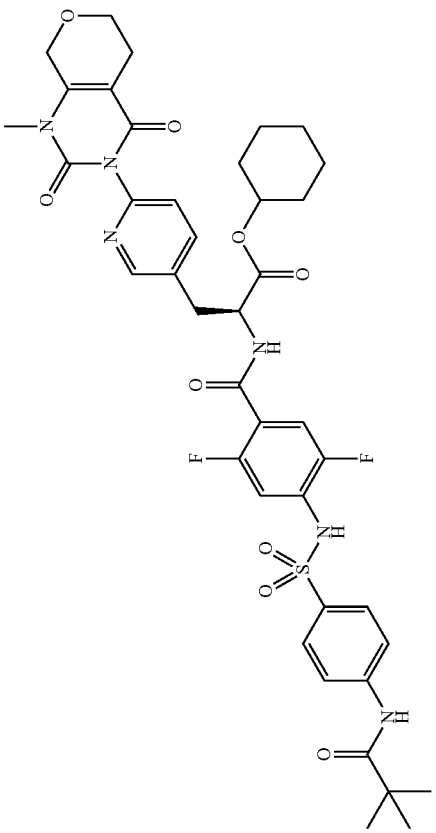 | MS (ESI) m/z 823 [M + H]+. |
| P42 | 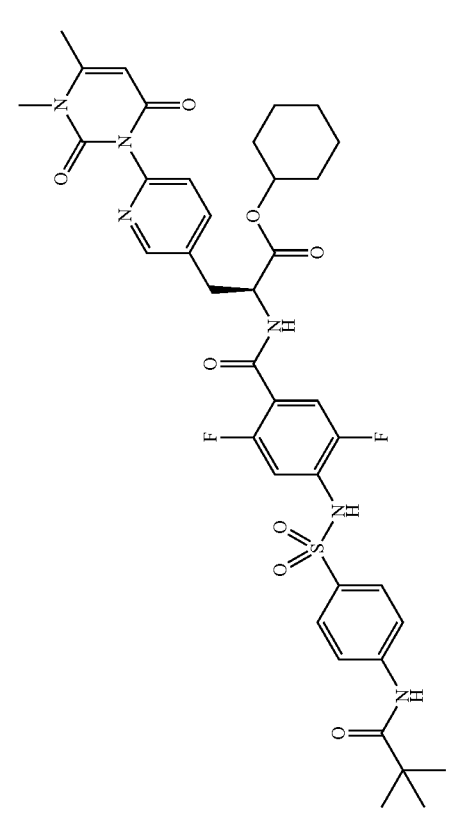 | MS (ESI) m/z 781 [M + H]+. |

| Compound No. | Structural Formula | NMR/MS |
|---|---|---|
| P43 | 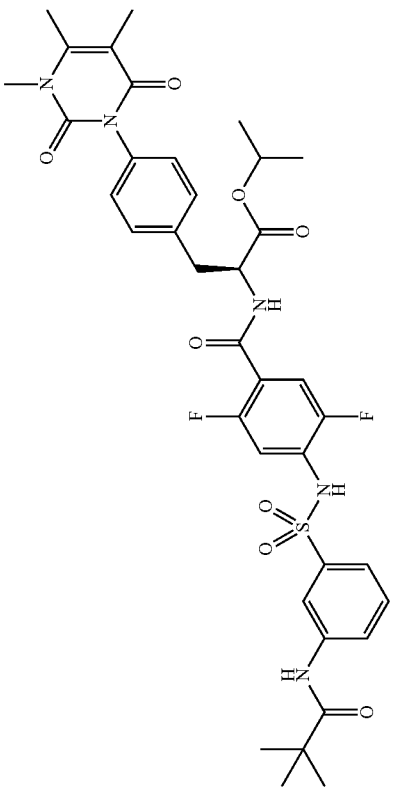 | 1H NMR (400 MHz, DMSO-d6) δ 10.84 (s, 1H), 9.56 (s, 1H), 8.72 (dd, J = 7.5, 2.1 Hz, 1H), 8.33-8.27 (m, 1H), 7.91 (d, J = 8.0 Hz, 1H), 7.55-7.43 (m, 2H), 7.35-7.26 (m, 3H), 7.18 (dd, J = 11.0, 6.3 Hz, 1H), 7.07 (d, J = 8.3 Hz, 2H), 4.94-4.83 (m, 1H), 4.61-4.51 (m, 1H), 3.36 (s, 3H), 3.17-3.00 (m, 2H), 2.31 (s, 3H), 1.89 (s, 3H), 1.22 (s, 9H), 1.18 (d, J = 6.2 Hz, 3H), 1.12 (d, J = 6.2 Hz, 3H); MS (ESI) m/z 754 [M + H]+. |
| P44 | 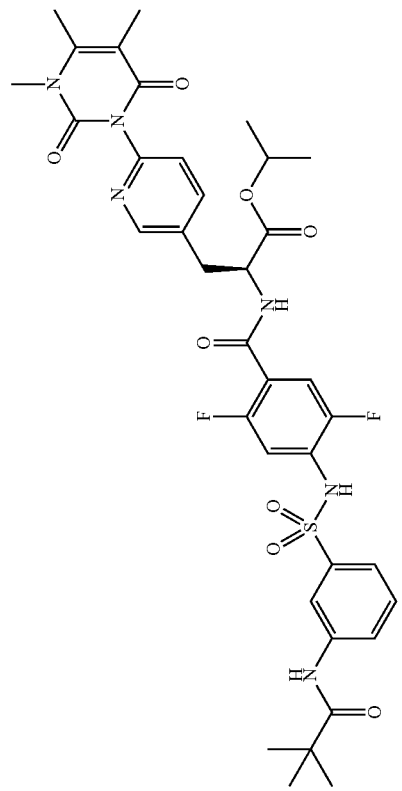 | 1H NMR (400 MHz, DMSO-d6) δ 10.84 (s, 1H), 9.56 (s, 1H), 8.80 (d, J = 7.2 Hz, 1H), 8.41 (d, J = 2.3 Hz, 1H), 8.30 (s, 1H), 7.91 (d, J = 8.0 Hz, 1H), 7.84 (dd, J = 8.1, 2.4 Hz, 1H), 7.53-7.45 (m, 2H), 7.30-7.23 (m, 2H), 7.18 (dd, J = 11.0, 6.3 Hz, 1H), 4.93-4.86 (m, 1H), 4.66-4.59 (m, 1H), 3.36 (s, 3H), 3.24-3.05 (m, 2H), 2.32 (s, 3H), 1.89 (s, 3H), 1.22 (s, 9H), 1.18 (d, J = 6.2 Hz, 3H), 1.13 (d, J = 6.2 Hz, 3H); MS (ESI) m/z 755 [M + H]+. |

-continued

| Compound No. | Structural Formula | NMR/MS |
|---|---|---|
| P45 | | 1H NMR (400 MHz, DMSO-d6) δ 10.70 (s, 1H), 9.58 (s, 1H), 9.00 (s, 1H), 8.84 (dd, J = 7.8, 1.8 Hz, 1H), 8.58 (d, J = 5.0 Hz, 1H), 8.47 (d, J = 2.3 Hz, 1H), 7.94-7.82 (m, 4H), 7.76 (d, J = 8.9 Hz, 2H), 7.41 (d, J = 8.1 Hz, 1H), 7.28 (dd, J = 10.2, 6.3 Hz, 1H), 7.20 (dd, J = 11.2, 6.3 Hz, 1H), 4.78-4.72 (m, 1H), 3.67 (s, 3H), 3.61 (s, 3H), 3.32-3.24 (m, 1H), 3.12 (dd, J = 14.1, 10.1 Hz, 1H), 1.22 (s, 9H); MS (ESI) m/z 750 [M + H]+. |
| P46 | | 1H NMR (400 MHz, DMSO-d6) δ 10.69 (s, 1H), 9.58 (s, 1H), 8.82 (dd, J = 7.8, 1.9 Hz, 1H), 8.42 (d, J = 2.3 Hz, 1H), 7.92-7.81 (m, 3H), 7.76 (d, J = 8.9 Hz, 2H), 7.33-7.23 (m, 2H), 7.19 (dd, J = 11.1, 6.3 Hz, 1H), 4.75-4.68 (m, 1H), 3.66 (s, 3H), 3.36 (s, 3H), 3.24 (dd, J = 14.1, 5.1 Hz, 1H), 3.14-3.05 (m, 1H), 2.33 (s, 3H), 1.89 (s, 3H), 1.22 (s, 9H); MS (ESI) m/z 727 [M + H]+. |

| Compound No. | Structural Formula | NMR/MS |
|---|---|---|
| P47 | 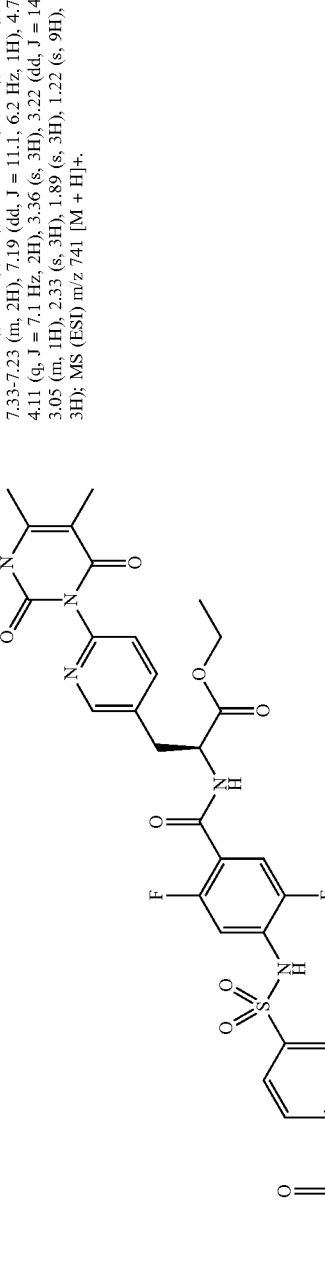 | 1H NMR (400 MHz, DMSO-d6) δ 10.69 (s, 1H), 9.58 (s, 1H), 8.82 (d, J = 7.7 Hz, 1H), 8.42 (s, 1H), 7.92-7.81 (m, 3H), 7.76 (d, J = 8.6 Hz, 2H), 7.33-7.23 (m, 2H), 7.19 (dd, J = 11.1, 6.2 Hz, 1H), 4.72-4.64 (m, 1H), 4.11 (q, J = 7.1 Hz, 2H), 3.36 (s, 3H), 3.22 (dd, J = 14.0, 5.6 Hz, 1H), 3.14-3.05 (m, 1H), 2.33 (s, 3H), 1.89 (s, 3H), 1.22 (s, 9H), 1.16 (t, J = 7.1 Hz, 3H); MS (ESI) m/z 741 [M + H]+. |
| P48 | 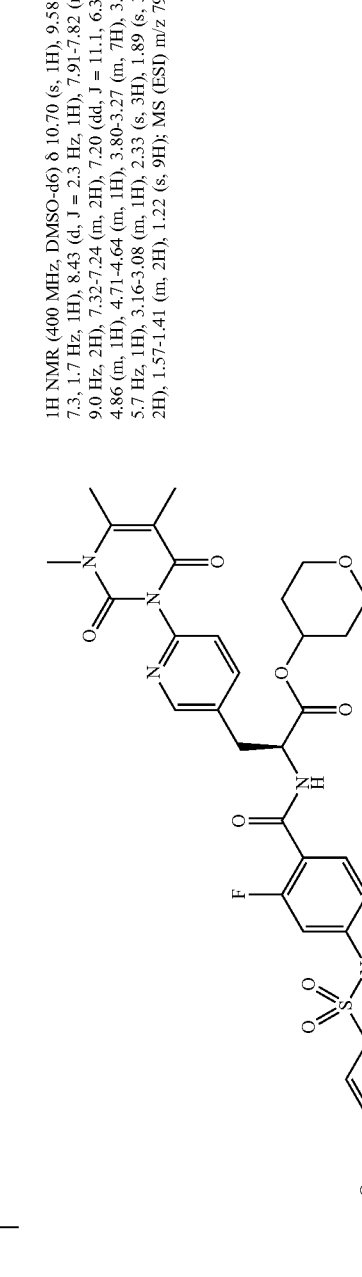 | 1H NMR (400 MHz, DMSO-d6) δ 10.70 (s, 1H), 9.58 (s, 1H), 8.85 (dd, J = 7.3, 1.7 Hz, 1H), 8.43 (d, J = 2.3 Hz, 1H), 7.91-7.82 (m, 3H), 7.76 (d, J = 9.0 Hz, 2H), 7.32-7.24 (m, 2H), 7.20 (dd, J = 11.1, 6.3 Hz, 1H), 4.94-4.86 (m, 1H), 4.71-4.64 (m, 1H), 3.80-3.27 (m, 7H), 3.23 (dd, J = 14.1, 5.7 Hz, 1H), 3.16-3.08 (m, 1H), 2.33 (s, 3H), 1.89 (s, 3H), 1.86-1.72 (m, 2H), 1.57-1.41 (m, 2H), 1.22 (s, 9H); MS (ESI) m/z 797 [M + H]+. |

| Compound No. | Structural Formula | NMR/MS |
|---|---|---|
| P49 | | 1H NMR (400 MHz, DMSO-d6) δ 10.70 (s, 1H), 9.58 (s, 1H), 9.00 (s, 1H), 8.84 (dd, J = 7.7, 1.8 Hz, 1H), 8.58 (d, J = 5.0 Hz, 1H), 8.47 (d, J = 2.3 Hz, 1H), 7.95-7.82 (m, 4H), 7.76 (d, J = 8.9 Hz, 2H), 7.42 (d, J = 8.0 Hz, 1H), 7.28 (dd, J = 10.2, 6.3 Hz, 1H), 7.20 (dd, J = 11.1, 6.3 Hz, 1H), 4.74-4.67 (m, 1H), 4.11 (q, J = 7.1 Hz, 2H), 3.61 (s, 3H), 3.25 (dd, J = 14.0, 5.7 Hz, 1H), 3.17-3.09 (m, 1H), 1.22 (s, 9H), 1.17 (t, J = 7.1 Hz, 3H); MS (ESI) m/z 764 [M + H]+ |
| P50 | | 1H NMR (400 MHz, DMSO-d6) δ 10.69 (s, 1H), 9.58 (s, 1H), 9.00 (s, 1H), 8.82 (dd, J = 7.7, 1.8 Hz, 1H), 8.58 (d, J = 5.0 Hz, 1H), 8.47 (d, J = 2.3 Hz, 1H), 7.97-7.81 (m, 4H), 7.76 (d, J = 8.9 Hz, 2H), 7.41 (d, J = 8.1 Hz, 1H), 7.30-7.24 (m, 1H), 7.20 (dd, J = 11.1, 6.3 Hz, 1H), 4.76-4.65 (m, 2H), 3.61 (s, 3H), 3.25 (dd, J = 14.1, 5.7 Hz, 1H), 3.17-3.07 (m, 1H), 1.82-1.16 (m, 19H); MS (ESI) m/z 818 [M + H]+. |

| Compound No. | Structural Formula | NMR/MS |
|---|---|---|
| P51 | | MS (ESI) m/z 713 [M + H]+. |
| P52 | | 1H NMR (400 MHz, DMSO-d6) δ 10.68 (s, 1H), 9.57 (s, 1H), 8.81 (d, J = 7.7 Hz, 1H), 8.42 (d, J = 2.5 Hz, 1H), 7.93-7.79 (m, 3H), 7.80-7.70 (m, 2H), 7.30-7.31 (m, 2H), 7.18 (dd, J = 11.1, 6.2 Hz, 1H), 5.73 (s, 1H), 4.73-4.60 (m, 1H), 4.10 (q, J = 7.1 Hz, 2H), 3.32 (s, 3H), 3.21 (dd, J = 14.2, 5.6 Hz, 1H), 3.09 (dd, J = 14.4, 9.9 Hz, 1H), 2.31 (s, 3H), 1.22 (s, 9H), 1.15 (d, J = 7.1 Hz, 3H); MS (ESI) m/z 727 [M + H]+. |

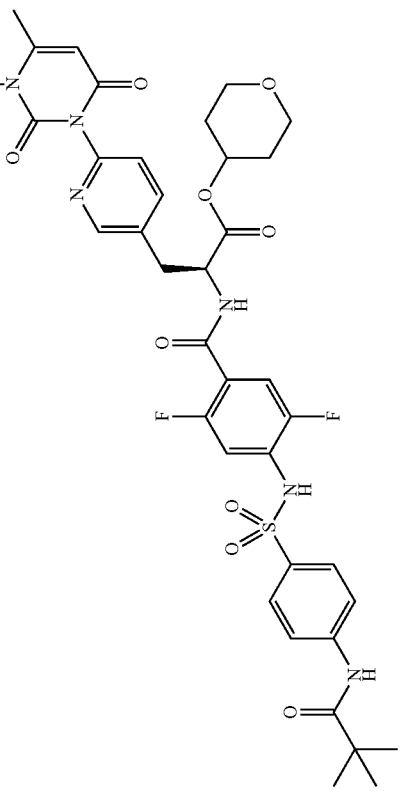
| Compound No. | Structural Formula | NMR/MS |
|---|---|---|
| P53 | | MS (ESI) m/z 783 [M + H]+. |
| P54 | | 1H NMR (400 MHz, DMSO-d6) δ 10.70 (s, 1H), 9.57 (s, 1H), 8.99 (s, 1H), 8.86 (d, J = 6.9 Hz, 1H), 8.57 (d, J = 5.0 Hz, 1H), 8.48 (d, J = 2.3 Hz, 1H), 7.98-7.80 (m, 4H), 7.76 (d, J = 8.9 Hz, 2H), 7.41 (d, J = 8.1 Hz, 1H), 7.27 (dd, J = 10.2, 6.3 Hz, 1H), 7.20 (dd, J = 11.1, 6.3 Hz, 1H), 4.94-4.86 (m, 1H), 4.74-4.66 (m, 1H), 3.78-3.67 (m, 2H), 3.60 (s, 3H), 3.53-3.09 (m, 4H), 1.85-1.72 (m, 2H), 1.56-1.40 (m, 2H), 1.21 (s, 9H); MS (ESI) m/z 820 [M + H]+. |

-continued
| Compound No. | Structural Formula | NMR/MS |
|---|---|---|
| P55 | 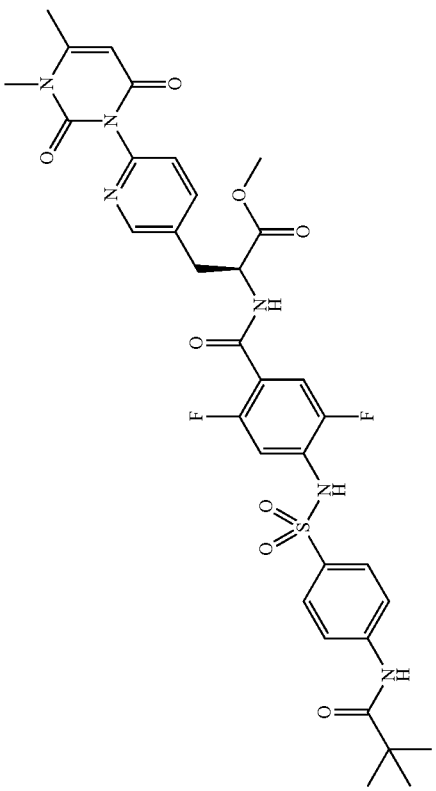 | MS (ESI) m/z 726 [M + H]+. |
| P56 | 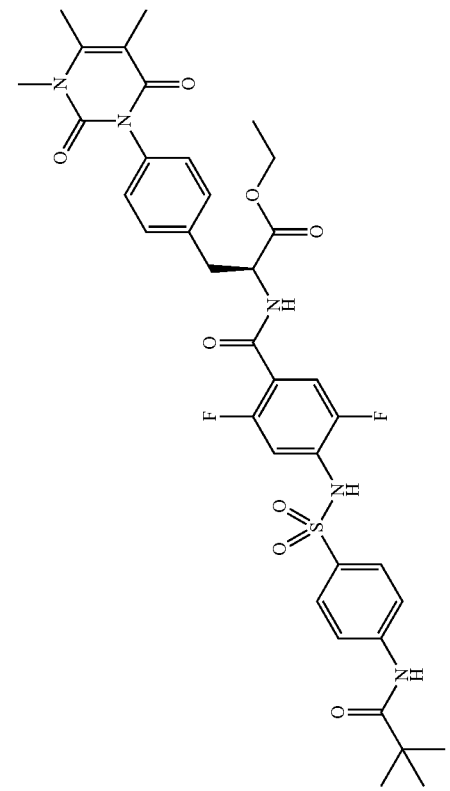 | MS (ESI) m/z 740 [M + H]+. |

-continued
| Compound No. | Structural Formula | NMR/MS |
|---|---|---|
| P57 | 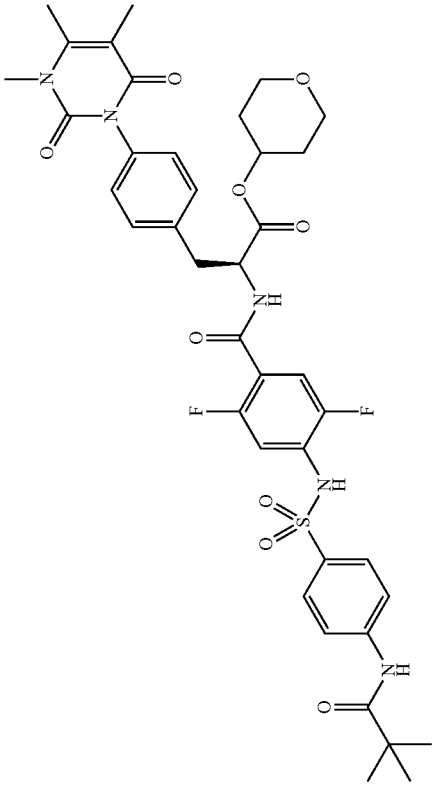 | MS (ESI) m/z 794 [M + H]+. |
| P58 | 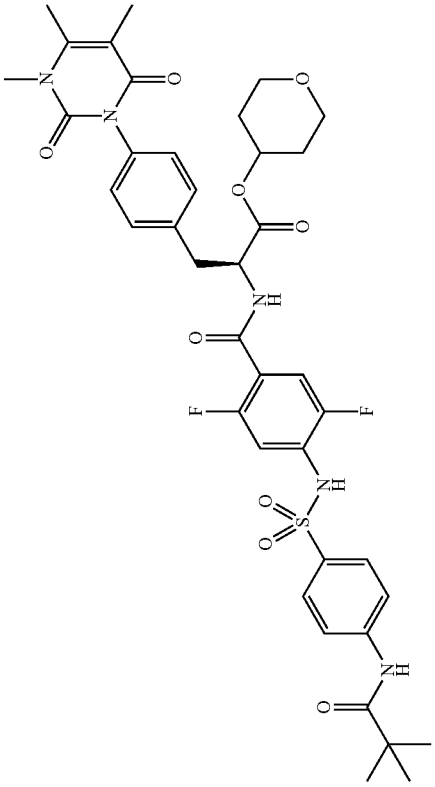 | MS (ESI) m/z 796 [M + H]+. |

-continued
| Compound No. | Structural Formula | NMR/MS |
|---|---|---|
| P59 | 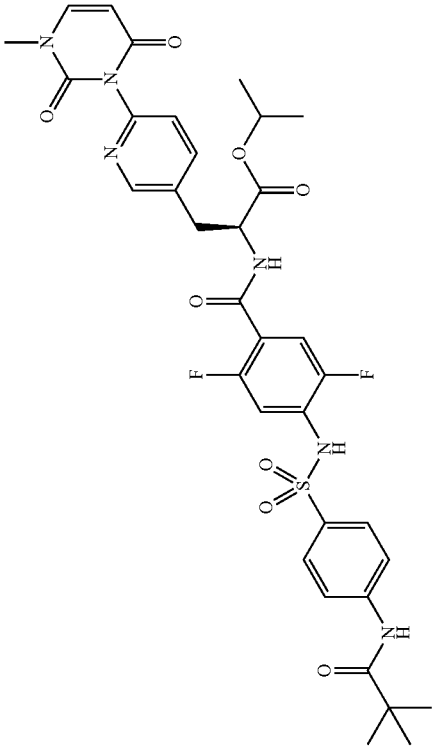 | 1H NMR (400 MHz, DMSO-d6) δ 10.68 (s, 1H), 9.57 (s, 1H), 8.79 (dd, J = 7.6, 1.8 Hz, 1H), 8.48-8.33 (m, 1H), 7.90-7.83 (m, 3H), 7.81-7.72 (m, 3H), 7.32-7.21 (m, 2H), 7.18 (dd, J = 11.1, 6.3 Hz, 1H), 5.76 (d, J = 7.9 Hz, 1H), 4.97-4.81 (m, 1H), 4.62 (ddd, J = 9.3, 7.5, 5.9 Hz, 1H), 3.31 (s, 3H), 3.19 (dd, J = 14.1, 5.9 Hz, 1H), 3.09 (dd, J = 14.1, 9.3 Hz, 1H), 1.22 (s, 9H), 1.17 (d, J = 6.2 Hz, 3H), 1.12 (d, J = 6.2 Hz, 3H); MS (ESI) m/z 727 [M + H]+. |
| P60 | 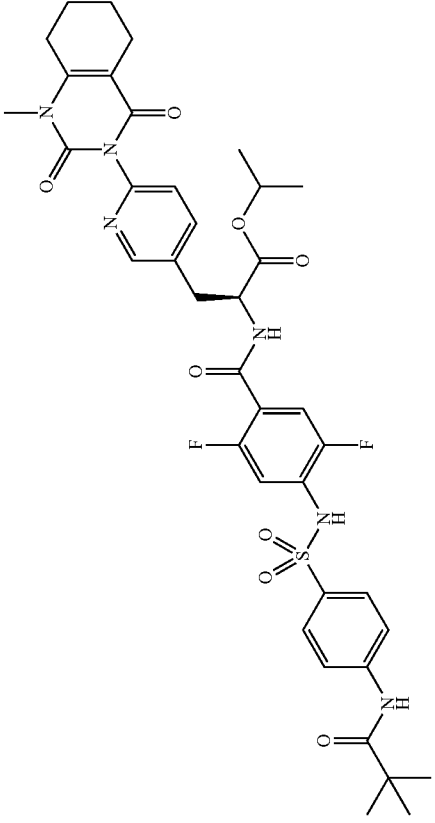 | MS (ESI) m/z 781 [M + H]+. |

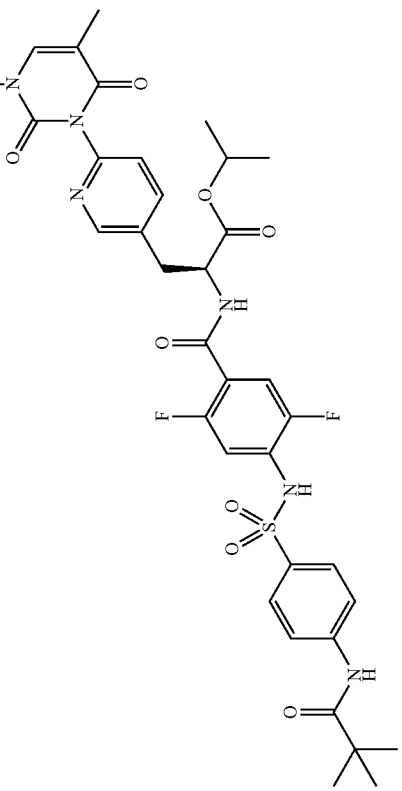
| Compound No. | Structural Formula | NMR/MS |
|---|---|---|
| P61 | | MS (ESI) m/z 741 [M + H]+. |
| P62 | | 1H NMR (400 MHz, DMSO-d6) δ 10.68 (s, 1H), 9.57 (s, 1H), 8.77-8.67 (m, 1H), 7.86 (d, J = 8.9 Hz, 2H), 7.75 (d, J = 8.9 Hz, 2H), 7.37-7.24 (m, 3H), 7.19 (dd, J = 11.0, 6.1 Hz, 1H), 7.11-7.04 (m, 2H), 4.95-4.82 (m, 1H), 4.63-4.49 (m, 1H), 4.30 (s, 2H), 3.37 (s, 3H), 3.20-2.98 (m, 2H), 2.39 (d, J = 4.5 Hz, 3H), 1.22 (s, 9H), 1.18 (d, J = 6.2 Hz, 3H), 1.12 (dd, J = 6.3, 2.6 Hz, 3H); MS (ESI) m/z 770 [M + H]+. |

-continued
| Compound No. | Structural Formula | NMR/MS |
|---|---|---|
| P63 | 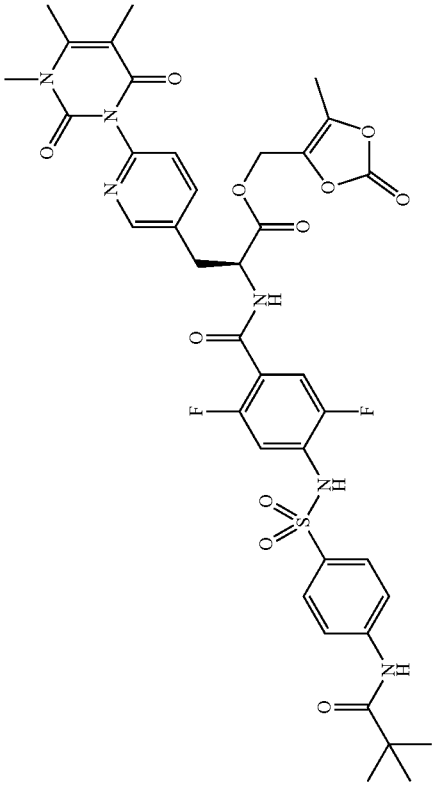 | 1H NMR (400 MHz, DMSO-d6) δ 10.69 (s, 1H), 9.57 (s, 1H), 8.87 (d, J = 8.3 Hz, 1H), 8.41 (d, J = 2.3 Hz, 1H), 7.89-7.80 (m, 3H), 7.75 (d, J = 8.9 Hz, 2H), 7.29-7.21 (m, 2H), 7.18 (dd, J = 11.1, 6.3 Hz, 1H), 5.03 (s, 2H), 4.75-4.68 (m, 1H), 3.36 (s, 3H), 3.27-3.21 (m, 1H), 3.14-3.05 (m, 1H), 2.32 (s, 3H), 2.15 (s, 3H), 1.89 (s, 3H), 1.21 (s, 9H); MS (ESI) m/z 825 [M + H]+. |
| P64 | 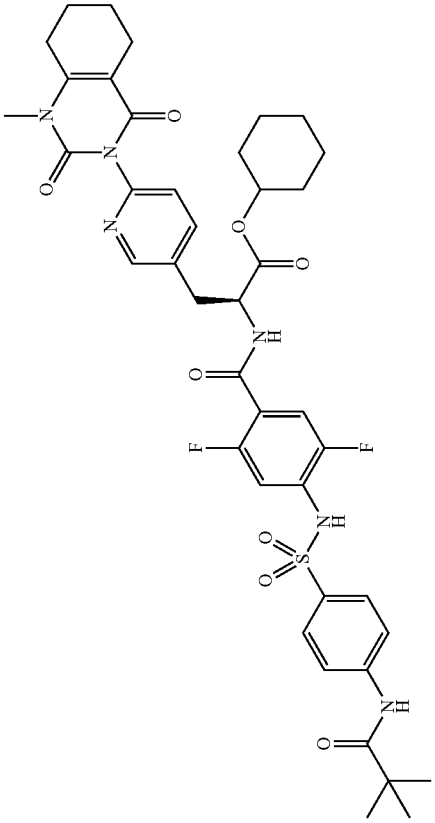 | MS (ESI) m/z 821 [M + H]+. |

-continued

| Compound No. | Structural Formula | NMR/MS |
|---|---|---|
| P65 | | 1H NMR (400 MHz, DMSO-d6) δ 10.68 (s, 1H), 9.57 (s, 1H), 8.83 (d, J = 7.6 Hz, 1H), 8.43 (d, J = 2.3 Hz, 1H), 7.92-7.81 (m, 3H), 7.78-7.71 (m, 2H), 7.31-7.13 (m, 3H), 4.88-4.78 (m, 1H), 4.74-4.62 (m, 1H), 3.36 (s, 3H), 3.28-3.20 (m, 1H), 3.17-3.06 (m, 1H), 2.33 (d, 3H), 2.30-2.17 (m, 2H), 1.89 (s, 3H), 1.87-1.78 (m, 1H), 1.71-1.59 (m, 2H), 1.21 (s, 9H), 1.18-1.03 (m, 2H), 0.86 (s, 3H), 0.83 (s, 3H), 0.78 (s, 3H); MS (ESI) m/z 849 [M + H]+. |
| P66 | | 1H NMR (400 MHz, DMSO-d6) δ 10.68 (s, 1H), 9.57 (s, 1H), 8.80 (d, J = 7.4 Hz, 1H), 8.41 (d, J = 2.3 Hz, 1H), 7.90-7.79 (m, 3H), 7.75 (d, J = 8.7 Hz, 2H), 7.30-7.12 (m, 3H), 4.73-4.51 (m, 2H), 3.36 (s, 3H), 3.26-3.15 (m, 1H), 3.15-3.04 (m, 1H), 2.32 (s, 3H), 1.96-1.76 (m, 5H), 1.70-1.54 (m, 2H), 1.51-1.24 (m, 2H), 1.21 (s, 9H), 1.08-0.88 (m, 3H), 0.86 (d, J = 6.4 Hz, 3H), 0.78 (d, J = 7.0 Hz, 3H), 0.67 (d, J = 6.8 Hz, 3H); MS (ESI) m/z 851 [M + H]+. |

| Compound No. | Structural Formula | NMR/MS |
|---|---|---|
| P67 | 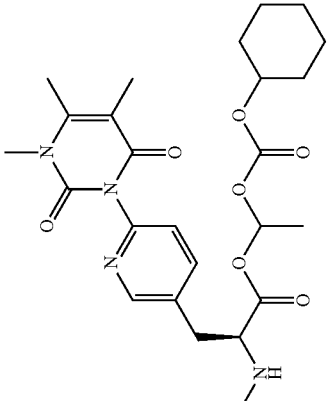 | 1H NMR (400 MHz, DMSO-d6) δ 10.69 (s, 1H), 9.57 (s, 1H), 8.90-8.82 (m, 1H), 8.47-8.39 (m, 1H), 7.92-7.81 (m, 3H), 7.75 (d, J = 8.9 Hz, 2H), 7.30-7.11 (m, 3H), 6.72-6.60 (m, 1H), 4.76-4.67 (m, 1H), 4.58-4.47 (m, 1H), 3.36 (s, 3H), 3.24-3.17 (m, 1H), 3.16-3.01 (m, 1H), 2.32 (s, 3H), 1.89 (s, 3H), 1.86-1.12 (m, 22H); MS (ESI) m/z 883 [M + H]+. |
| P68 | 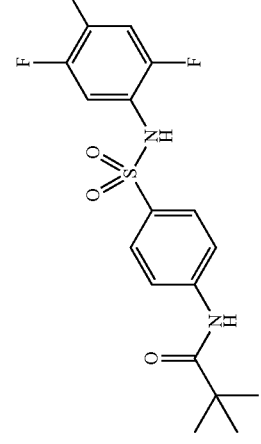 | 1H NMR (400 MHz, DMSO-d6) δ 10.68 (s, 1H), 9.57 (s, 1H), 8.81 (dd, J = 7.8, 1.8 Hz, 1H), 8.43 (d, J = 2.3 Hz, 1H), 7.89-7.82 (m, 3H), 7.81-7.71 (m, 3H), 7.34-7.22 (m, 2H), 7.18 (dd, J = 11.1, 6.3 Hz, 1H), 5.76 (d, J = 7.9 Hz, 1H), 4.70-4.62 (m, 1H), 4.09 (q, J = 7.1 Hz, 2H), 3.31 (s, 3H), 3.25-3.16 (m, 1H), 3.14-3.04 (m, 1H), 1.22 (s, 9H), 1.15 (t, J = 7.1 Hz, 3H); MS (ESI) m/z 713 [M + H]+. |

-continued
| Compound No. | Structural Formula | NMR/MS |
|---|---|---|
| P69 | 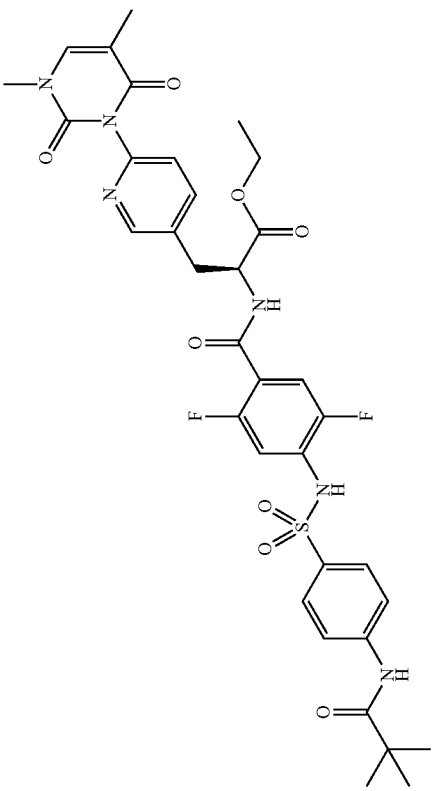 | 1H NMR (400 MHz, DMSO-d6) δ 10.68 (s, 1H), 9.57 (s, 1H), 8.82 (d, J = 7.6 Hz, 1H), 8.43 (s, 1H), 8.01-7.79 (m, 3H), 7.79-7.72 (m, 2H), 7.70 (s, 1H), 7.27 (dd, J = 9.0, 7.3 Hz, 2H), 7.19 (dd, J = 11.1, 6.2 Hz, 1H), 4.70-4.62 (m, 1H), 4.10 (q, J = 7.1 Hz, 2H), 3.28 (s, 3H), 3.22 (dd, J = 14.1, 5.7 Hz, 1H), 3.10 (dd, J = 14.0, 9.7 Hz, 1H), 1.82 (s, 3H), 1.22 (s, 9H), 1.15 (t, J = 7.2 Hz, 3H); MS (ESI) m/z 727 [M + H]+. |
| P70 | 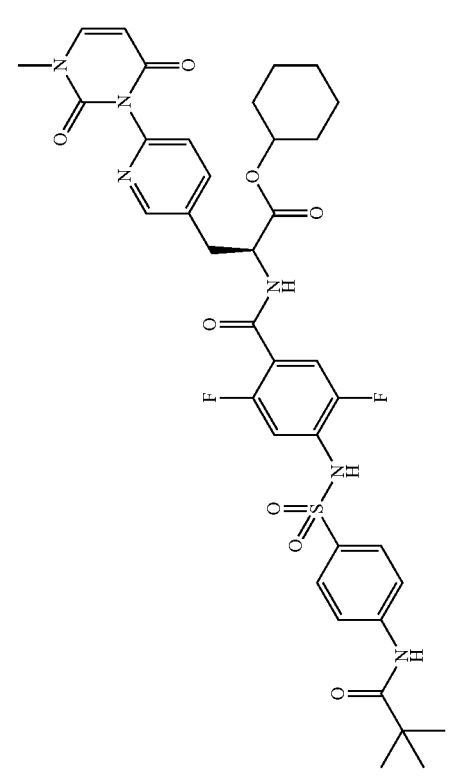 | MS (ESI) m/z 767 [M + H]+ |

| Compound No. | Structural Formula | NMR/MS |
|---|---|---|
| P71 | (structure) | 1H NMR (400 MHz, DMSO-d6) δ 10.68 (s, 1H), 9.57 (s, 1H), 8.80 (dd, J = 7.6, 1.7 Hz, 1H), 8.42 (d, J = 2.3 Hz, 1H), 7.97-7.81 (m, 3H), 7.81-7.72 (m, 2H), 7.72-7.62 (m, 1H), 7.34-7.12 (m, 3H), 4.83-4.56 (m, 2H), 3.28 (s, 3H), 3.21 (dd, J = 14.1, 5.6 Hz, 1H), 3.10 (dd, J = 14.1, 9.6 Hz, 1H), 1.82 (d, J = 1.2 Hz, 3H), 1.80-1.23 (m, 10H), 1.21 (s, 9H); MS (ESI) m/z 781 [M + H]+. |
| P72 | (structure) | MS (ESI) m/z 769 [M + H]+. |

| Compound No. | Structural Formula | NMR/MS |
|---|---|---|
| P73 | | 1H NMR (400 MHz, DMSO-d6) δ 10.69 (s, 1H), 9.57 (s, 1H), 8.82 (d, J = 7.8 Hz, 1H), 8.43 (dd, J = 2.3, 0.8 Hz, 1H), 7.91-7.81 (m, 3H), 7.79-7.72 (m, 2H), 7.70 (d, J = 1.4 Hz, 1H), 7.32-7.10 (m, 3H), 4.79-4.64 (m, 1H), 3.92-3.81 (m, 2H), 3.30-3.19 (m, 4H), 3.11 (dd, J = 14.1, 10.1 Hz, 1H), 1.90-1.78 (m, 4H), 1.22 (s, 9H), 0.87 (d, J = 6.7 Hz, 6H); MS (ESI) m/z 755 [M + H]+. |
| P74 | | 1H NMR (400 MHz, DMSO-d6) δ 10.68 (s, 1H), 9.53 (s, 1H), 8.70 (s, 1H), 8.43 (dd, J = 2.3, 0.8 Hz, 1H), 7.89-7.66 (m, 6H), 7.29 (dd J = 8.0, 0.7 Hz, 1H), 7.21 (dd, J = 10.5, 6.4 Hz, 1H), 7.17-7.07 (m, 1H), 5.76 (d, J = 7.9 Hz, 1H), 4.70 (ddd, J = 9.9, 7.7, 5.2 Hz, 1H), 3.93-3.79 (m, 2H), 3.31 (s, 3H), 3.24 (dd, J = 14.1, 5.3 Hz, 1H), 3.11 (dd, J = 14.1, 9.9 Hz, 1H), 1.90-1.77 (m, 1H), 1.21 (s, 9H), 0.86 (d, J = 6.7 Hz, 6H); MS (ESI) m/z 741 [M + H]+. |

-continued
| Compound No. | Structural Formula | NMR/MS |
|---|---|---|
| P75 | 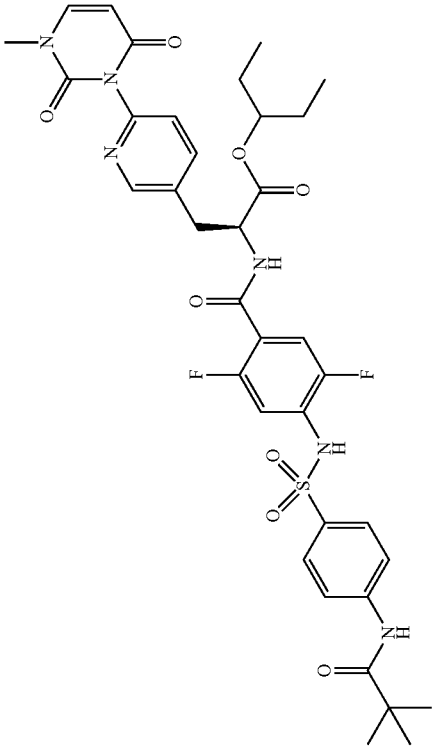 | MS (ESI) m/z 755 [M + H]+ |
| P76 | 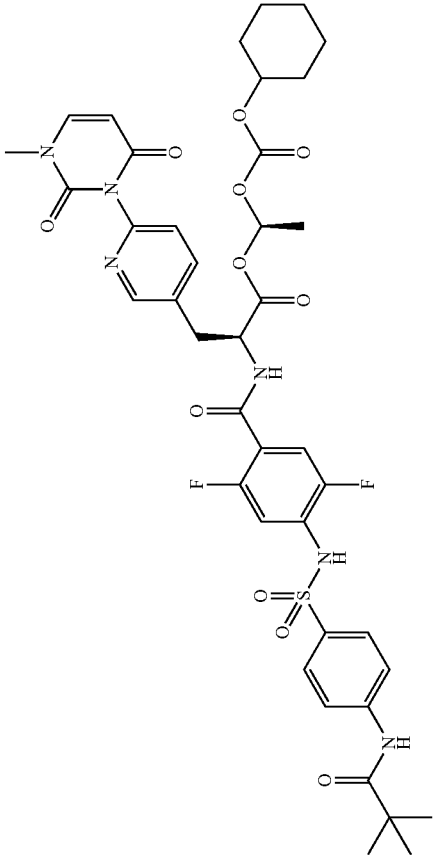 | MS (ESI) m/z 855 [M + H]+ |

| Compound No. | Structural Formula | NMR/MS |
|---|---|---|
| P77 | 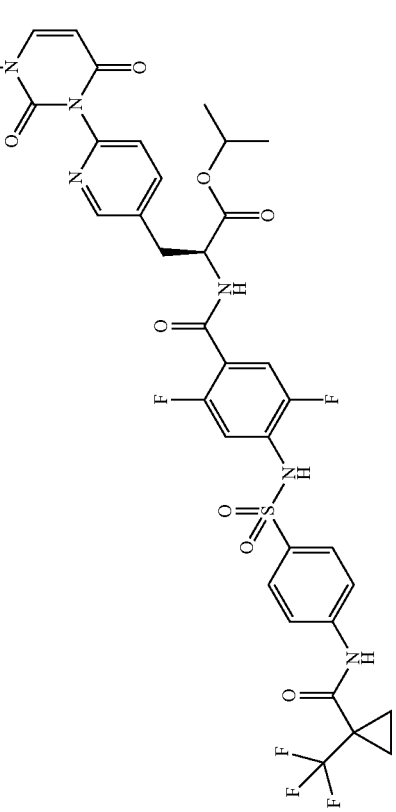 | MS (ESI) m/z 779 [M + H]+ |
| P78 | 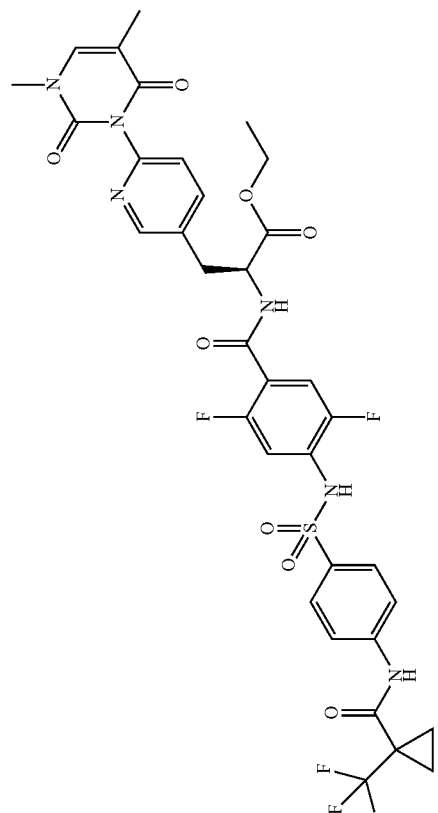 | MS (ESI) m/z 779 [M + H]+ |

-continued
| Compound No. | Structural Formula | NMR/MS |
|---|---|---|
| P79 | 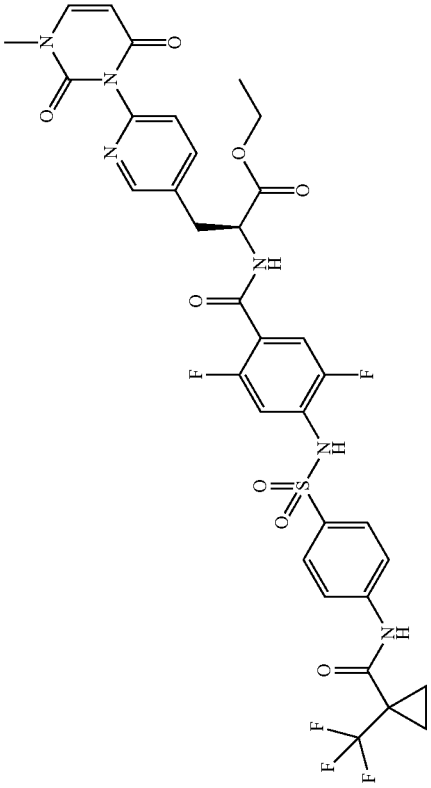 | MS (ESI) m/z 765 [M + H]+ |
| P80 | 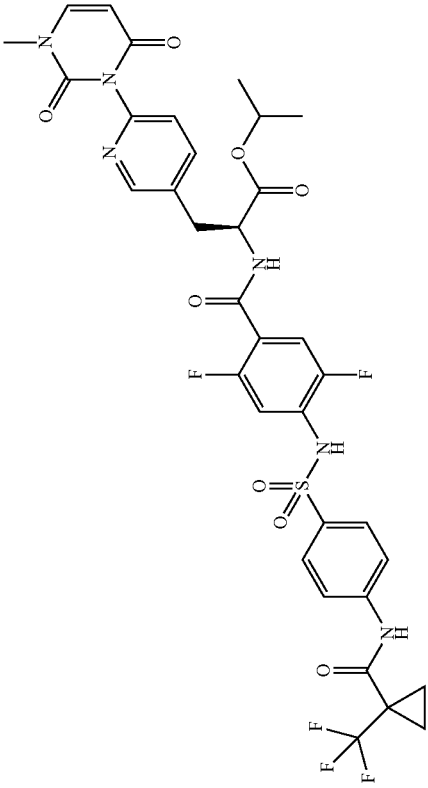 | MS (ESI) m/z 793 [M + H]+ |

-continued
| Compound No. | Structural Formula | NMR/MS |
|---|---|---|
| P81 | 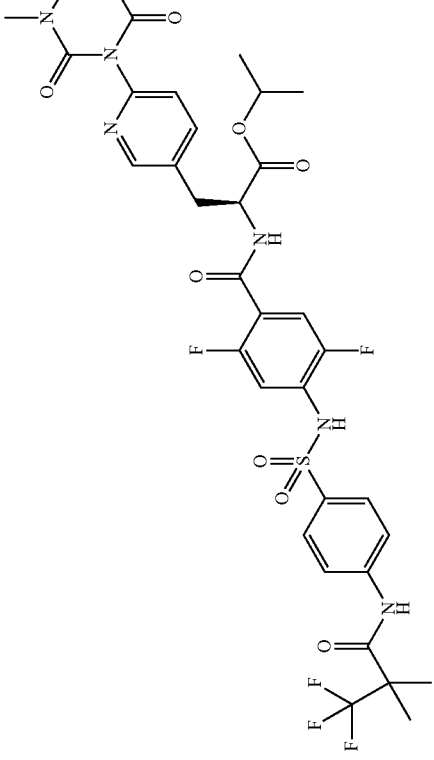 | MS (ESI) m/z 781 [M + H]+ |
| P82 | 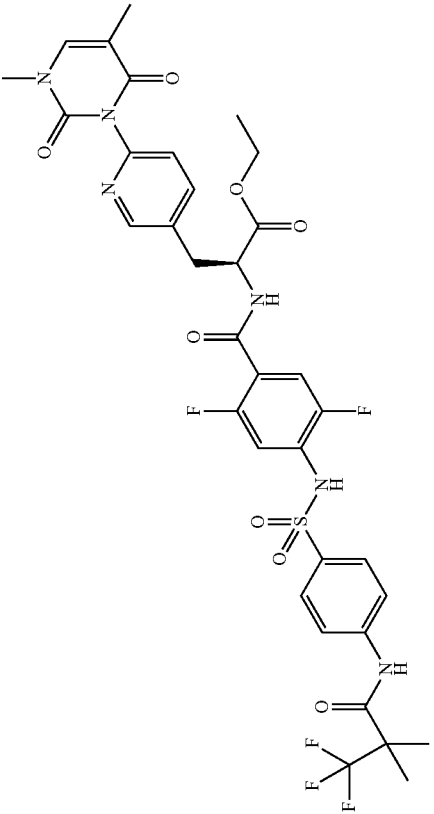 | MS (ESI) m/z 781 [M + H]+ |

| Compound No. | Structural Formula | NMR/MS |
|---|---|---|
| P83 | 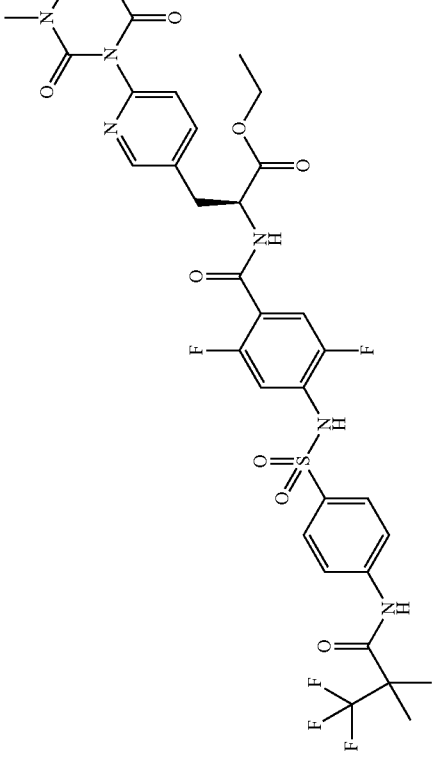 | MS (ESI) m/z 767 [M + H]+ |
| P84 | 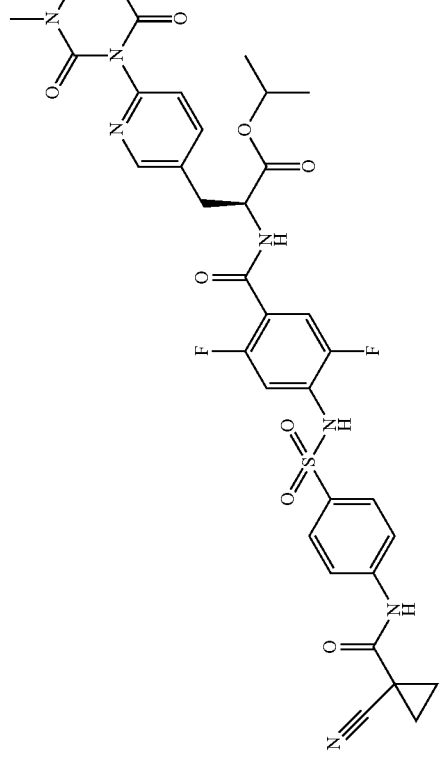 | MS (ESI) m/z 736 [M + H]+. |

| Compound No. | Structural Formula | NMR/MS |
|---|---|---|
| P85 | 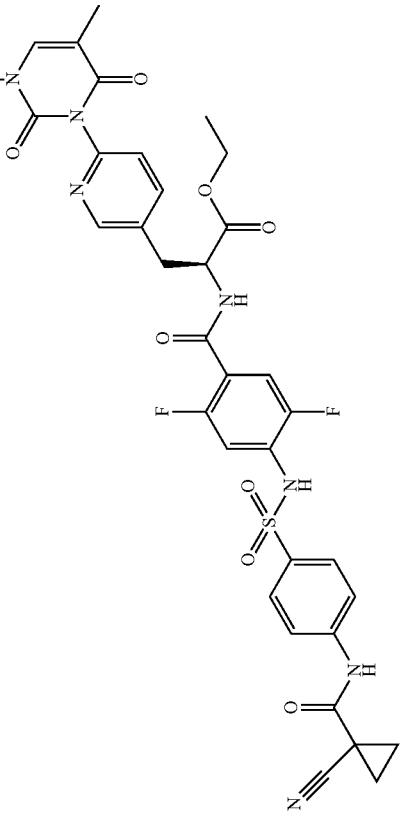 | MS (ESI) m/z 736 [M + H]+. |
| P86 | 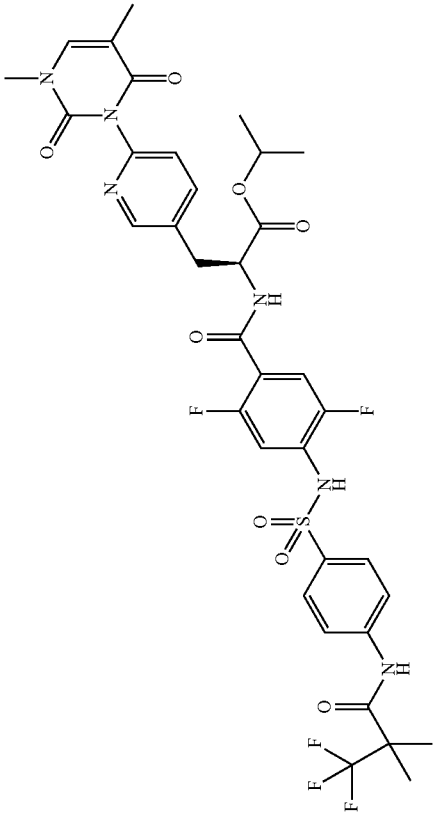 | MS (ESI) m/z 795 [M + H]+ |

-continued
| Compound No. | Structural Formula | NMR/MS |
|---|---|---|
| P87 | 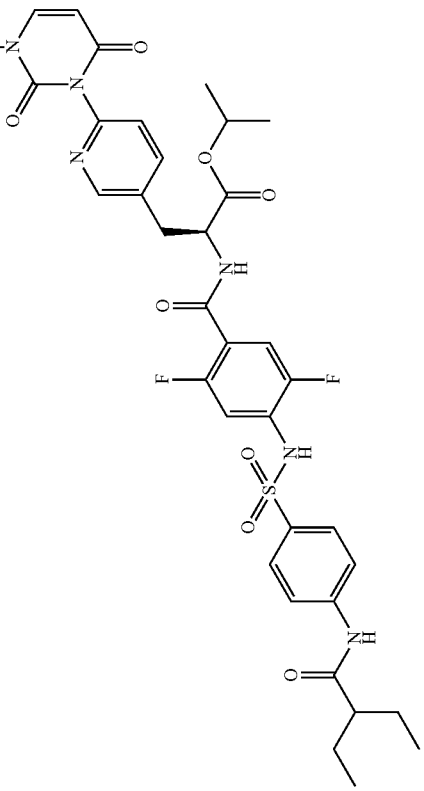 | MS (ESI) m/z 741 [M + H]+. |
| P88 | 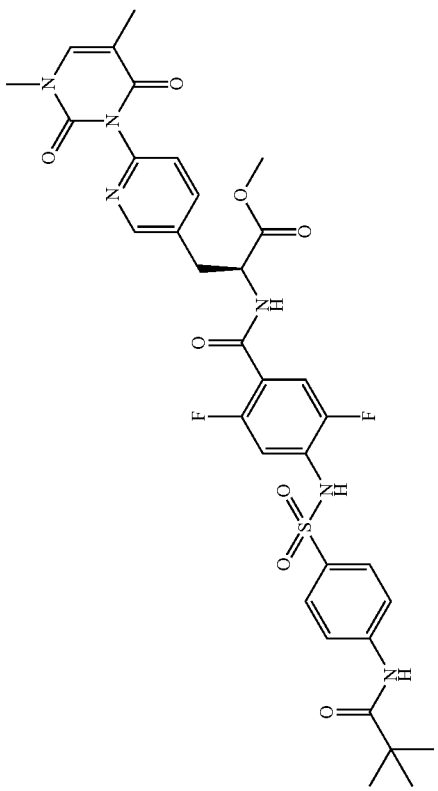 | MS (ESI) m/z 713 [M + H]+. |

-continued
| Compound No. | Structural Formula | NMR/MS |
|---|---|---|
| P89 | 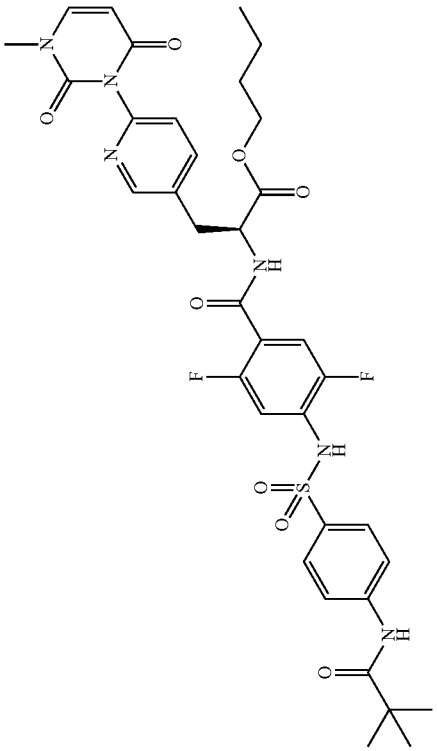 | MS (ESI) m/z 741 [M + H]+ |
| P90 | 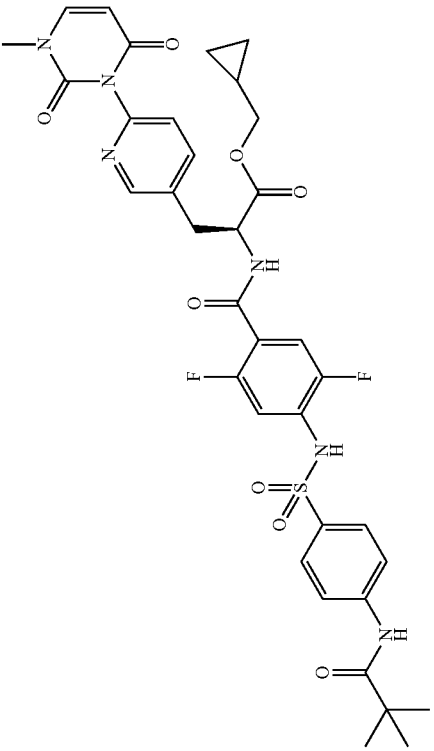 | MS (ESI) m/z 739 [M + H]+ |

-continued
| Compound No. | Structural Formula | NMR/MS |
|---|---|---|
| P91 | 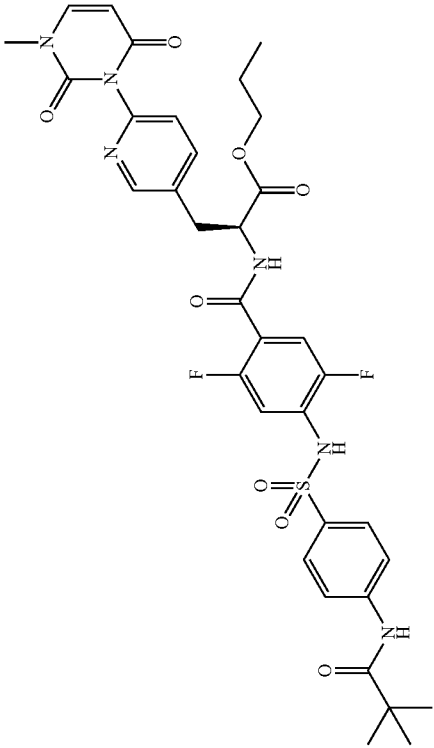 | MS (ESI) m/z 727 [M + H]+ |
| P92 | 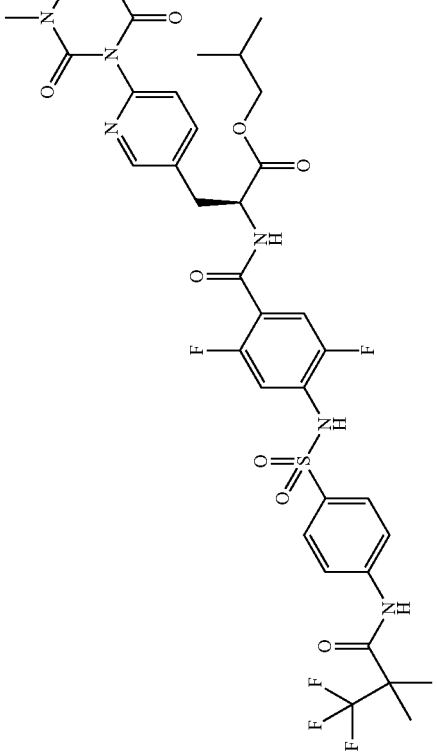 | MS (ESI) m/z 795 [M + H]+ |

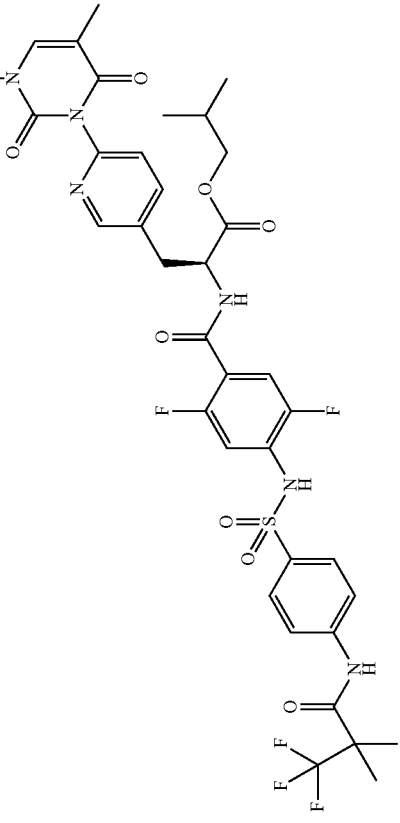
| Compound No. | Structural Formula | NMR/MS |
|---|---|---|
| P93 | | MS (ESI) m/z 809 [M + H]+ |
| P94 | | 1H NMR (400 MHz, DMSO-d6) δ 10.68 (s, 1H), 9.57 (s, 1H), 8.81 (dd, J = 7.9, 1.8 Hz, 1H), 8.42 (d, J = 2.3 Hz, 1H), 7.85 (dt, J = 7.9, 2.4 Hz, 3H), 7.80-7.71 (m, 2H), 7.69 (d, J = 1.4 Hz, 1H), 7.32-7.22 (m, 2H), 7.18 (dd, J = 11.1, 6.3 Hz, 1H), 4.74-4.63 (m, 1H), 4.12-4.01 (m, 2H), 3.28 (s, 3H), 3.23 (dd, J = 14.1, 5.3 Hz, 1H), 3.10 (dd, J = 14.1, 9.9 Hz, 1H), 1.82 (d, J = 1.1 Hz, 3H), 1.59-1.47 (m, 2H), 1.36-1.25 (m, 2H), 1.21 (s, 9H), 0.85 (t, J = 7.4 Hz, 3H); MS (ESI) m/z 755 [M + H]+. |

| Compound No. | Structural Formula | NMR/MS |
|---|---|---|
| P95 | 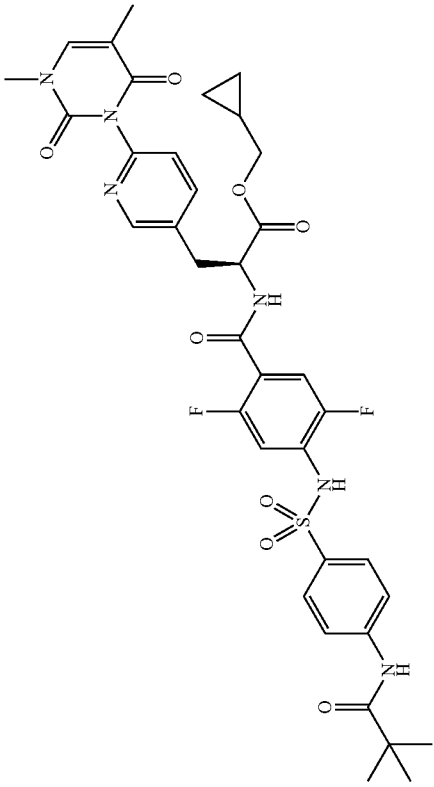 | 1H NMR (400 MHz, DMSO-d6) δ 10.44 (s, 1H), 9.33 (s, 1H), 8.57 (dd, J = 7.5, 2.0 Hz, 1H), 8.19 (d, J = 2.2 Hz, 1H), 7.66-7.57 (m, 3H), 7.54-7.48 (m, 2H), 7.45 (d, J = 1.4 Hz, 1H), 7.07-6.99 (m, 2H), 6.94 (dd, J = 11.1, 6.3 Hz, 1H), 4.53-4.40 (m, 1H), 3.73-3.61 (m, 2H), 3.04 (s, 3H), 3.02-2.92 (m, 1H), 2.92-2.82 (m, 1H), 1.57 (d, J = 1.1 Hz, 3H), 0.97 (s, 9H), 0.87-0.71 (m, 1H), 0.32-0.16 (m, 2H), 0.06-−0.05 (m, 1H), −0.06-−0.15 (m, 1H); MS (ESI) m/z 753 [M + H]+. |
| P96 | 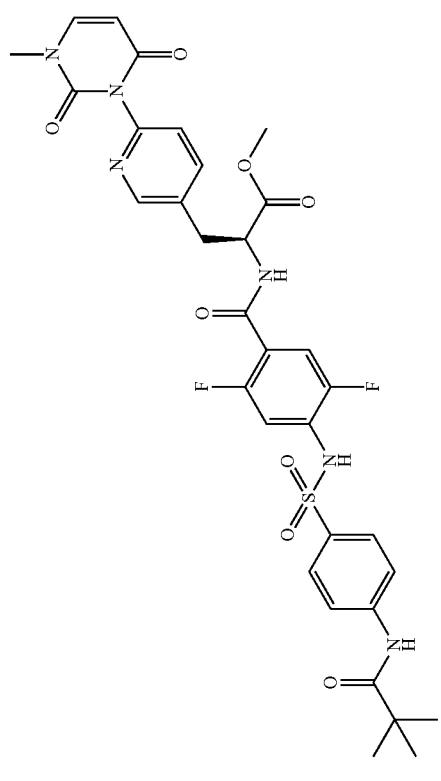 | MS (ESI) m/z 699 [M + H]+. |

-continued
| Compound No. | Structural Formula | NMR/MS |
|---|---|---|
| P97 | 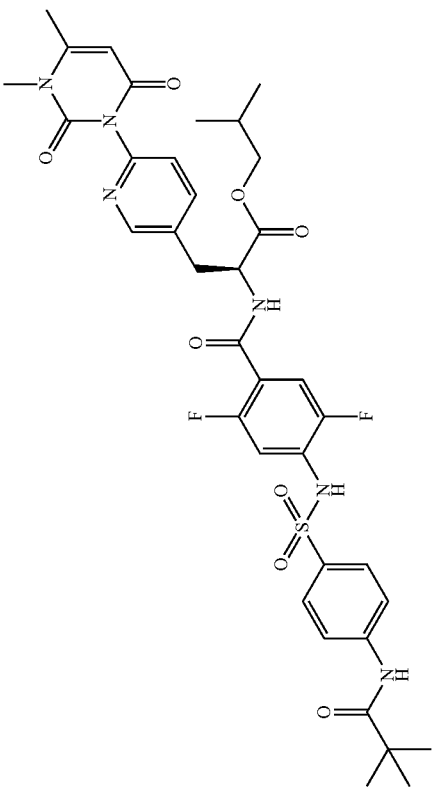 | 1H NMR (400 MHz, DMSO-d6) δ 10.68 (s, 1H), 9.57 (s, 1H), 8.81 (d, J = 7.8 Hz, 1H), 8.42 (dd, J = 2.4, 0.8 Hz, 1H), 7.92-7.80 (m, 3H), 7.80-7.70 (m, 2H), 7.32-7.11 (m, 3H), 5.73 (d, J = 1.0 Hz, 1H), 4.71 (ddd, J = 10.1, 7.7, 5.1 Hz, 1H), 3.92-3.79 (m, 2H), 3.31 (s, 3H), 3.24 (dd, J = 14.1, 5.2 Hz, 1H), 3.10 (dd, J = 14.2, 10.1 Hz, 1H), 2.31 (d, J = 0.9 Hz, 3H), 1.85 (hept, J = 6.6 Hz, 1H), 1.22 (s, 9H), 0.86 (d, J = 6.7 Hz, 6H); MS (ESI) m/z 755 [M + H]+. |
| P98 | | MS (ESI) m/z 741 [M + H]+. |

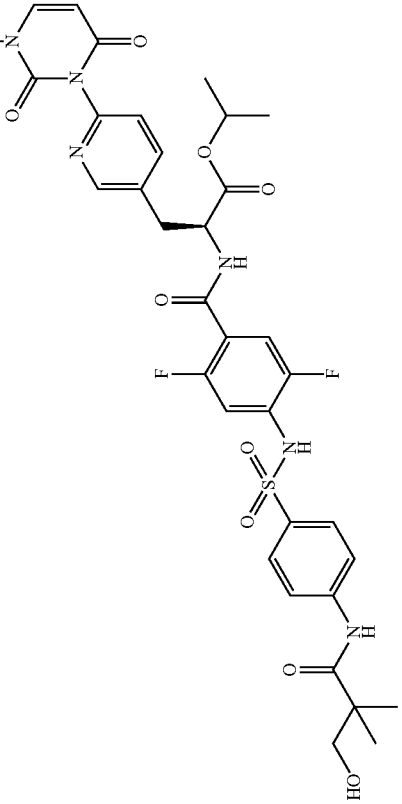

| Compound No. | Structural Formula | NMR/MS |
|---|---|---|
| P101 | 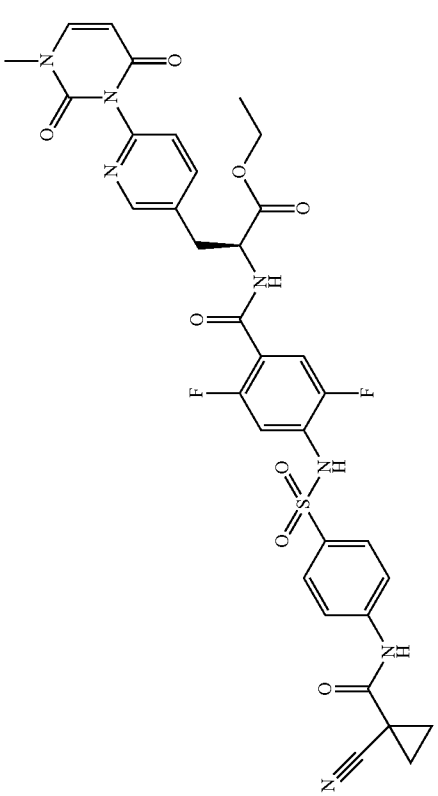 | MS (ESI) m/z 722 [M + H]+. |
| P102 | 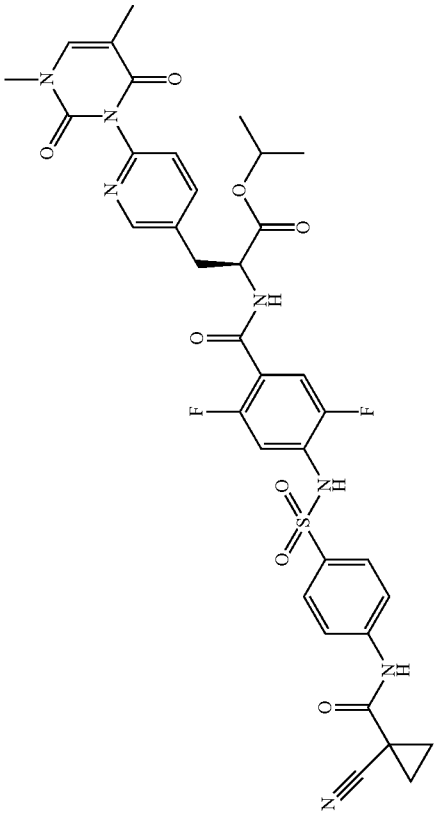 | MS (ESI) m/z 750 [M + H]+. |

-continued
| Compound No. | Structural Formula | NMR/MS |
|---|---|---|
| P103 | 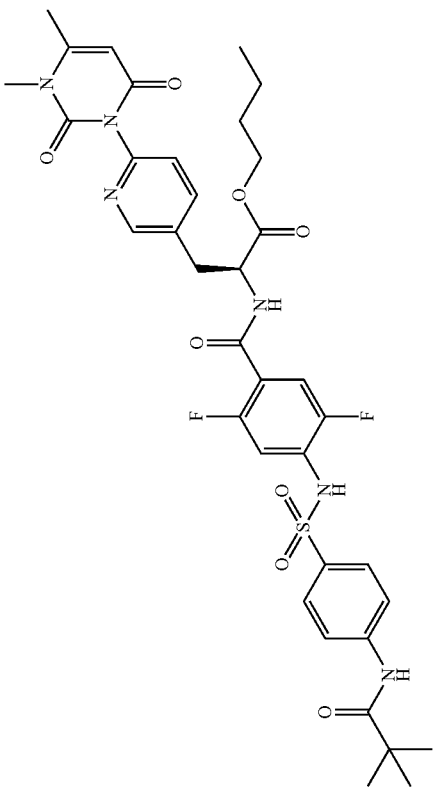 | MS (ESI) m/z 755 [M + H]+. |
| P104 | 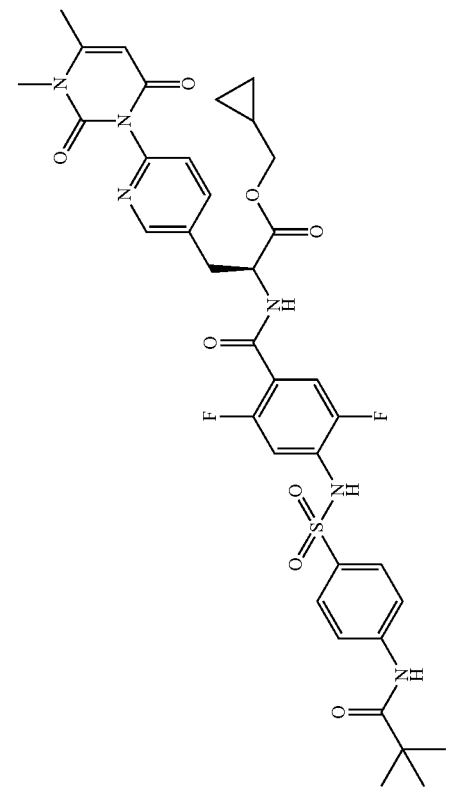 | MS (ESI) m/z 753 [M + H]+. |

-continued
| Compound No. | Structural Formula | NMR/MS |
|---|---|---|
| P105 | 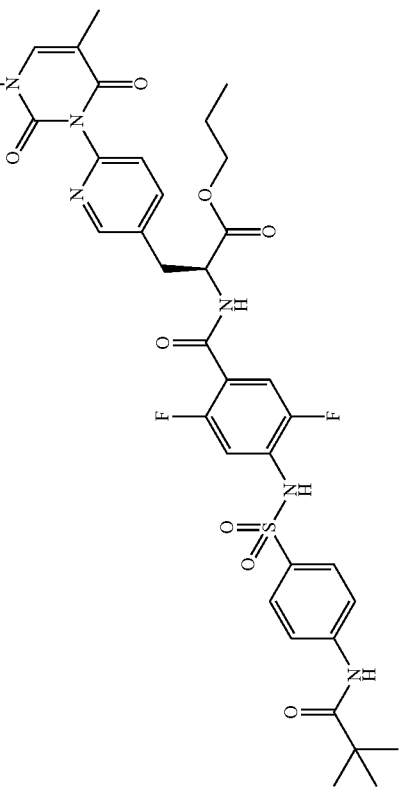 | MS (ESI) m/z 741 [M + H]+ |
| P106 | 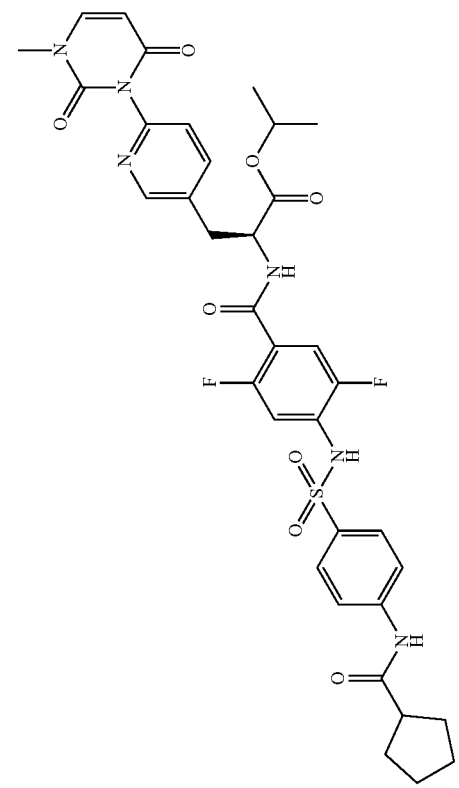 | MS (ESI) m/z 739 [M + H]+. |

-continued
| Compound No. | Structural Formula | NMR/MS |
|---|---|---|
| P107 | 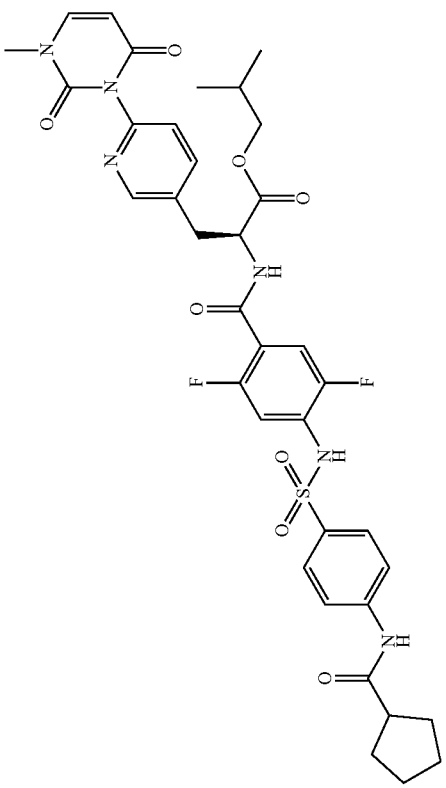 | MS (ESI) m/z 753 [M + H]+. |
| P108 | 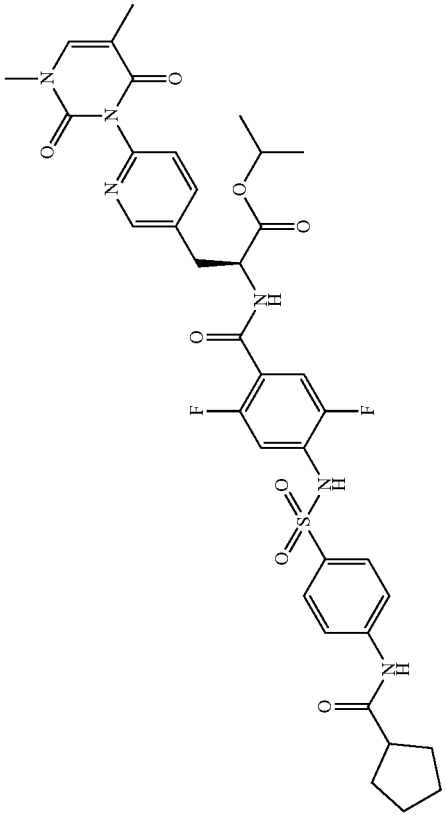 | MS (ESI) m/z 753 [M + H]+. |

| Compound No. | Structural Formula | NMR/MS |
|---|---|---|
| P109 | 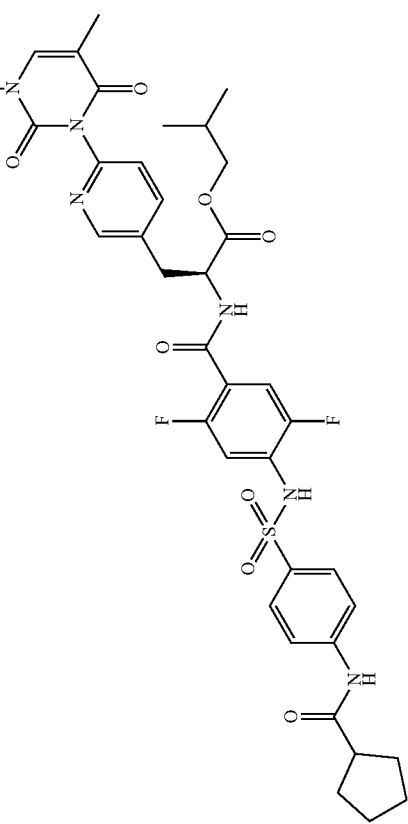 | MS (ESI) m/z 767 [M + H]+. |
| P110 | 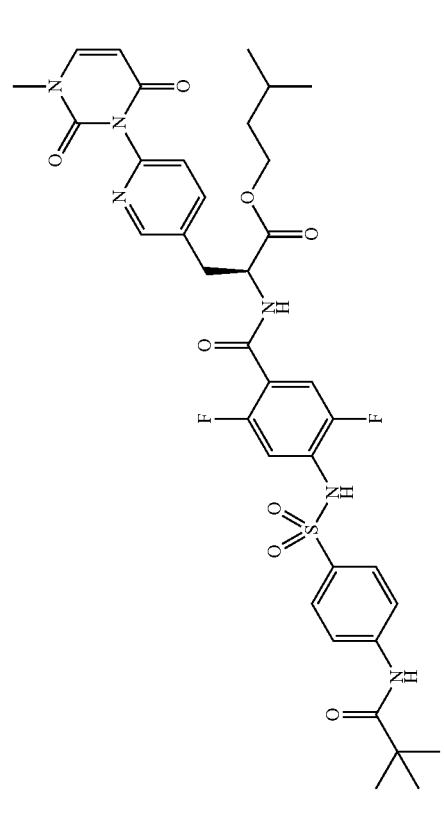 | MS (ESI) m/z 755 [M + H]+. |

| Compound No. | Structural Formula | NMR/MS |
|---|---|---|
| P111 | 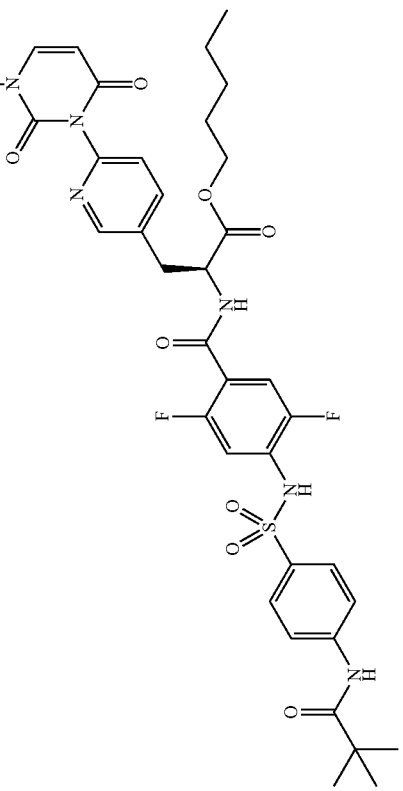 | MS (ESI) m/z 755 [M + H]+. |
| P112 | 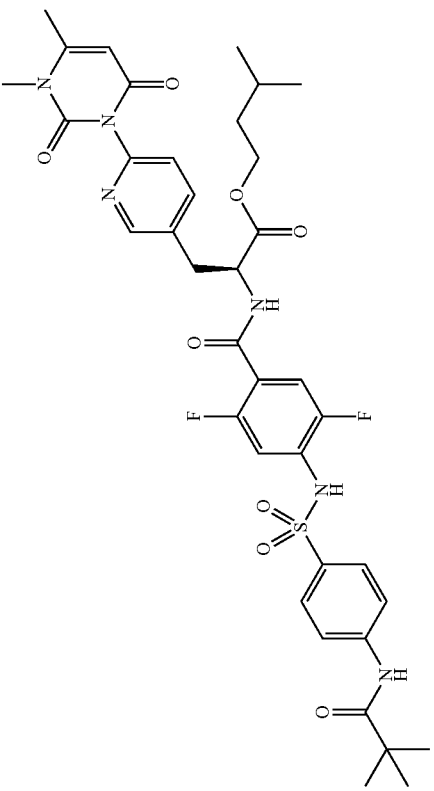 | MS (ESI) m/z 769 [M + H]+. |

-continued
| Compound No. | Structural Formula | NMR/MS |
|---|---|---|
| P113 | 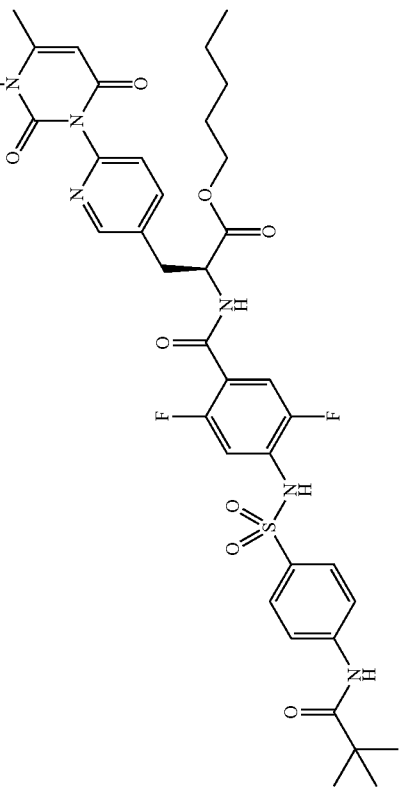 | MS (ESI) m/z 769 [M + H]+. |
| P114 | | 1H NMR (400 MHz, DMSO-d6) δ 10.68 (s, 1H), 9.57 (s, 1H), 8.80 (dd, J = 7.9, 1.8 Hz, 1H), 8.42 (d, J = 2.3 Hz, 1H), 7.88-7.80 (m, 3H), 7.75 (d, J = 8.9 Hz, 2H), 7.69 (s, 1H), 7.29-7.13 (m, 3H), 4.90-4.53 (m, 1H), 4.09 (t, J = 6.6 Hz, 2H), 3.31-3.17 (m, 4H), 3.09 (dd, J = 14.2, 10.0 Hz, 1H), 1.82 (s, 3H), 1.65-1.56 (m, 1H), 1.47-1.36 (m, 2H), 1.21 (s, 9H), 0.85 (d, J = 6.6 Hz, 6H); MS (ESI) m/z 769 [M + H]+. |

-continued
| Compound No. | Structural Formula | NMR/MS |
|---|---|---|
| P115 | 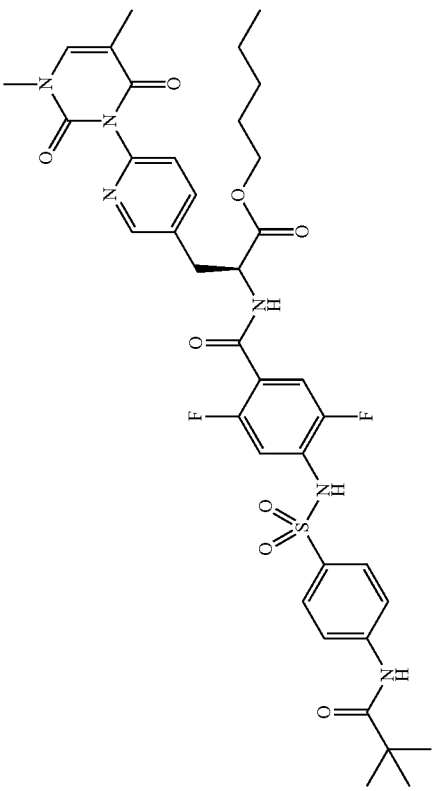 | 1H NMR (400 MHz, DMSO-d6) δ 10.68 (s, 1H), 9.57 (s, 1H), 8.80 (d, J = 7.9 Hz, 1H), 8.42 (d, J = 2.3 Hz, 1H), 7.89-7.81 (m, 3H), 7.75 (d, J = 8.9 Hz, 2H), 7.69 (d, J = 1.2 Hz, 1H), 7.30-7.21 (m, 2H), 7.18 (dd, J = 11.1, 6.3 Hz, 1H), 4.72-4.62 (m, 1H), 4.08-4.00 (m, 2H), 3.29-3.18 (m, 4H), 3.13-3.04 (m, 1H), 1.82 (s, 3H), 1.59-1.49 (m, 2H), 1.31-1.13 (m, 13H), 0.84-0.77 (m, 3H); MS (ESI) m/z 769 [M + H]+ |
| P116 | 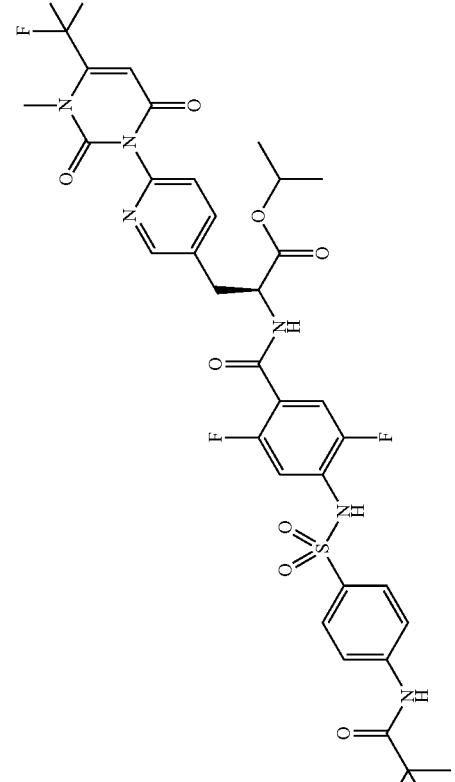 | MS (ESI) m/z 795 [M + H]+ |

-continued
| Compound No. | Structural Formula | NMR/MS |
|---|---|---|
| P117 | 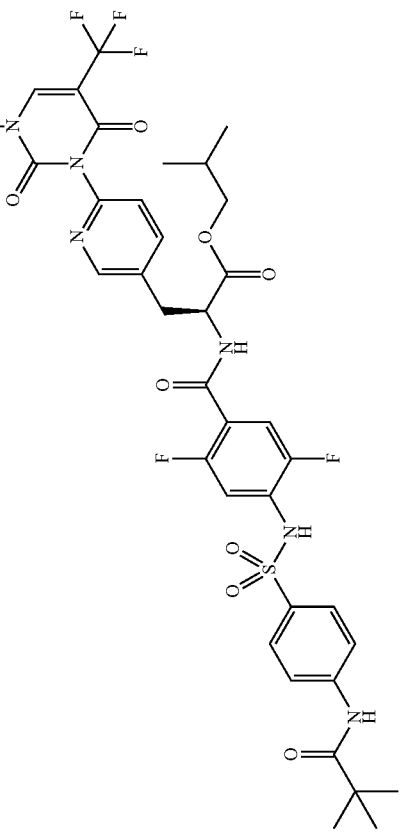 | MS (ESI) m/z 809 [M + H]+. |
| P118 | 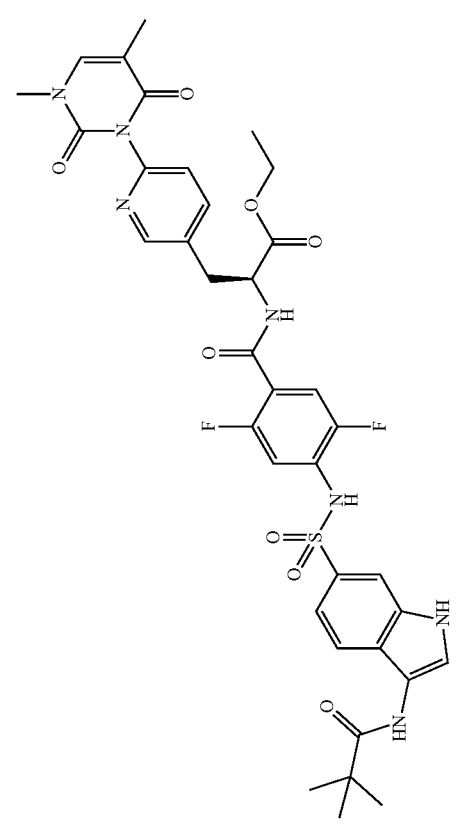 | MS (ESI) m/z 766 [M + H]+ |

| Compound No. | Structural Formula | NMR/MS |
|---|---|---|
| P119 | | MS (ESI) m/z 771 [M + H]+. |
| P120 | | 1H NMR (400 MHz, DMSO-d6) δ 11.99 (d, J = 3.0, 1H), 10.66 (s, 1H), 9.22 (s, 1H), 8.73 (d, J = 7.7 Hz, 1H), 8.42 (d, J = 2.0 Hz, 1H), 8.07 (d, J = 3.0 Hz, 1H), 7.98 (d, J = 1.5 Hz, 1H), 7.84 (dd, J = 8.1, 2.4 Hz, 1H), 7.76-7.66 (m, 2H), 7.34 (dd, J = 8.8, 1.9 Hz, 1H), 7.30-7.21 (m, 2H), 7.17 (dd, J = 10.4, 6.3 Hz, 1H), 4.72-4.64 (m, 1H), 3.90-3.78 (m, 2H), 3.50-3.18 (m, 4H), 3.13-3.04 (m, 1H), 1.88-1.76 (m, 4H), 1.24-1.12 (m, 9H), 0.85 (d, J = 6.7 Hz, 6H); MS (ESI) m/z 794 [M + H]+ |

| Compound No. | Structural Formula | NMR/MS |
|---|---|---|
| P121 | 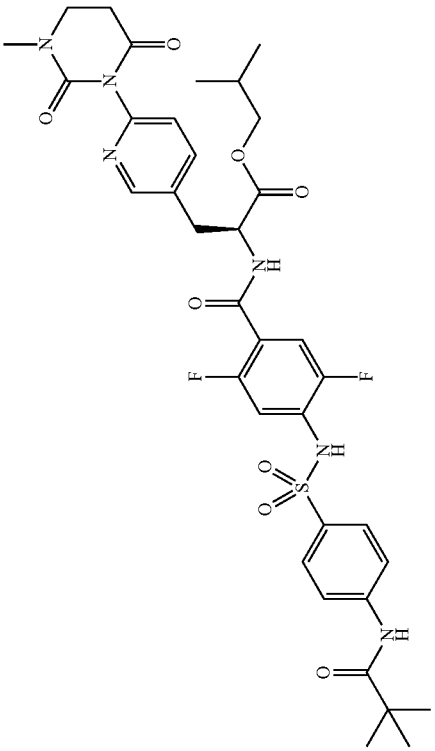 | 1H NMR (400 MHz, DMSO-d6) δ 10.68 (s, 1H), 9.57 (s, 1H), 8.80 (d, J = 7.6 Hz, 1H), 8.40-8.33 (m, 1H), 7.89-7.82 (m, 2H), 7.81-7.72 (m, 3H), 7.27-7.13 (m, 3H), 4.68 (ddd, J = 10.0, 7.7, 5.2 Hz, 1H), 3.91-3.80 (m, 2H), 3.50 (t, 2H), 3.22 (s, 3H), 2.82 (t, J = 6.8 Hz, 2H), 1.93-1.75 (m, 1H), 1.22 (s, 9H), 0.85 (d, J = 6.7 Hz, 6H); MS (ESI) m/z 743 [M + H]+. |

(1) VCAM-1/α4β1 Integrin Binding Inhibitory Activity Evaluation Test

Each test substance was measured in terms of an ability to inhibit the VCAM-1 binding of a human T cell line, namely, a cell line Jurkat, which is known to express α4β1 integrin.

A solution of recombinant human VCAM-1/Fc (R&D Systems, Inc.) (1 µg/mL) diluted with a buffer A (carbonate buffer, pH 9.6) was placed in an amount of 50 µL/well in a 96-well microtiter plate, followed by incubation at 4° C. overnight. After the plate was washed with PBS once, 150 µL/well of Block Ace (Snow Brand Milk Products Co., Ltd.) was added, followed by incubation at room temperature for 2 hours. After removal, the plate was washed with PBS once.

Then, 100 µL of the Jurkat cells ($2 \times 10^6$ cells/mL) and 100 µL of the test substance at each of various concentrations diluted with a binding buffer (DMEM containing 40 mM HEPES, 0.2% BSA, and 4 mM $MnCl_2$) were added to the plate coated with the VCAM-1/Fc ($5 \times 10^5$ cells/well), followed by incubation at 30° C. for 15 to 60 minutes. After the cells were bound to the wells, the plate was washed with PBS to remove unbound cells. A buffer C (PBS containing 1.5% Triton X-100) was added in an amount 50 µL/well to the plate to lyse the bound Jurkat cells. After 30 µL of a substrate buffer (Promega, CytoTox 96 Non-Radioactive Cytotoxicity Assay) was added to 30 µL of the cell lysate, a reaction was allowed to proceed at room temperature in the dark for 30 minutes. After 30 µL of a stop solution (Promega, CytoTox 96 Non-Radioactive Cytotoxicity Assay) was added to each, and then an absorbance at 490 nm was measured using a plate reader. The absorbance obtained here represents a detection result of an activity of lactate dehydrogenase (LDH) eluted in the supernatant of each well, that is, the absorbance is proportional to the number of Jurkat cells bound to the VCAM-1 and thus remaining on the plate. The test was performed in duplicate. Provided that the absorbance of a well containing no test substance was 100%, a cell binding rate with the test substance at each of the various concentrations was figured out, and a concentration $IC_{50}$ which brought about 50% binding inhibition was calculated. The obtained results are all shown in Tables 3.

TEST EXAMPLE 2

(2) MAdCAM-1/α4β7 Integrin Binding Inhibitory Activity Evaluation Test

Each test substance was measured in terms of an ability to inhibit the MAdCAM-1 binding of a human B cell line, namely, a cell line RPMI-8866, which is known to express α4β7 integrin.

A solution of recombinant mouse MAdCAM-1/Fc (R&D Systems, Inc.) (0.75 µg/mL) diluted with a buffer A (carbonate buffer, pH 9.6) was added in an amount of 50 µL/well to a 96-well microtiter plate, followed by incubation at 4° C. overnight. After the plate was washed with PBS once, 150 µL/well of Block Ace (Snow Brand Milk Products Co., Ltd.) was added, followed by incubation at room temperature for 2 hours. After removal, the plate was washed with PBS once.

Then, 100 µL of the RPMI-8866 cells ($2 \times 10^6$ cells/mL) and 100 µL of the test substance at each of various concentrations diluted with a binding buffer (DMEM containing 40 mM HEPES, 0.2% BSA, and 4 mM $MnCl_2$) were added on the plate coated with the MAdCAM-1/Fc ($5 \times 10^5$ cells/well), followed by incubation at 30° C. for 15 to 60 minutes. After the cells were bound to the wells, the plate was washed with PBS to remove unbound cells. A buffer C (PBS containing 1.5% Triton X-100) in an amount 50 µL/well was added to the plate to lyse the bound RPMI-8866 cells. After 30 µL of a substrate buffer (Promega, CytoTox 96 Non-Radioactive Cytotoxicity Assay) was added to 30 µL of the cell lysate, a reaction was allowed to proceed at room temperature in the dark for 30 minutes. After 30 µL of a stop solution (Promega, CytoTox 96 Non-Radioactive Cytotoxicity Assay) was added to each, and then an absorbance at 490 nm was measured using a plate reader. The absorbance obtained here represents a detection result of an activity of lactate dehydrogenase (LDH) eluted in the supernatant of each well, that is, the absorbance is proportional to the number of RPMI-8866 cells bound to the MAdCAM-1 and thus remaining on the plate. The test was performed in duplicate. Provided that the absorbance of the well containing no test substance was 100%, a cell binding rate with the test substance at each of the various concentrations was figured out, and a concentration $IC_{50}$ which brought about 50% binding inhibition was calculated. The obtained results are all shown in Tables 3.

TEST EXAMPLE 3

(3) MAdCAM-1/α4β7 Integrin Binding Inhibitory Activity Evaluation Test in Presence of Serum (1)

Each test substance was measured in terms of an ability to inhibit the MAdCAM-1 binding of a human B cell line, namely, a cell line RPMI-8866, which is known to express α4β7 integrin.

A solution of recombinant mouse MAdCAM-1/Fc (R&D Systems, Inc.) (1 µg/mL) diluted with a buffer A (carbonate buffer, pH 9.6) was added in an amount of 50 µL/well to a 96-well microtiter plate, followed by incubation at 4° C. overnight. After the plate was washed with PBS once, 150 µL/well of Block Ace (Snow Brand Milk Products Co., Ltd.) was added, followed by incubation at room temperature for 2 hours. After removal, the plate was washed with PBS once.

Then, 100 µL of the RPMI-8866 cells ($2 \times 106$ cells/mL) and 100 of the test substance at each of various concentrations diluted with a binding buffer (DMEM containing 40 mM HEPES, 0.2% BSA, and 4 mM $MnCl_2$) were added to the plate coated with the MAdCAM-1/Fc ($5 \times 10^5$ cells/well) such that 50% human serum was contained at the final concentration. Then, incubation was allowed to proceed at 30° C. for 15 to 60 minutes. After the cells were bound to the wells, the plate was washed with PBS to remove unbound cells. A buffer C (PBS containing 1.5% Triton X-100) was added in an amount 50 µL/well to the plate to lyse the bound RPMI-8866 cells. After 30 µL of a substrate buffer (Promega, CytoTox 96 Non-Radioactive Cytotoxicity Assay) was added to 30 µL of the cell lysate, a reaction was allowed to proceed at room temperature in the dark for 30 minutes. After 30 µL of a stop solution (Promega, CytoTox 96 Non-Radioactive Cytotoxicity Assay) was added to each, and then an absorbance at 490 nm was measured using a plate reader. The absorbance obtained here represents a detection result of an activity of lactate dehydrogenase (LDH) eluted in the supernatant of each well, that is, the absorbance is proportional to the number of RPMI-8866 cells bound to the MAdCAM-1 and thus remaining on the plate. The test was performed in duplicate. Provided that the absorbance of the well containing no test substance was 100%, a cell binding rate with the test substance at each of the various concentrations was figured out, and a concentration $IC_{50}$ which brought about 50% binding inhibition was calculated. The obtained results are all shown in Tables 3.

TABLE 3

| Compound No. | α4β7 IC50 (nM) | α4β1 IC50 (nM) | α4β7 Serum Added IC50 (nM) |
| --- | --- | --- | --- |
| A1 | 0.26 | 440 | 10 |
| A2 | 1.2 | 1100 | 36 |
| A3 | 0.72 | 2400 | 10 |
| A4 | 0.85 | 2500 | 16 |
| A5 | 2.3 | 2000 | 70 |

TABLE 3-continued

| Compound No. | α4β7 IC50 (nM) | α4β1 IC50 (nM) | α4β7 Serum Added IC50 (nM) |
|---|---|---|---|
| A6 | 2.4 | 890 | 14 |
| A7 | 0.36 | 2000 | 28 |
| A8 | 0.33 | 1600 | 3.7 |
| A9 | 0.41 | 160 | 4.5 |
| A10 | 0.38 | 400 | 10 |
| A11 | 2.0 | 3200 | 38 |
| A12 | 0.45 | 1200 | 61 |
| A13 | 0.93 | 1800 | 22 |
| A14 | 0.38 | 550 | 12 |
| A15 | 0.93 | 950 | 14 |
| A16 | 0.52 | 1200 | 44 |
| A17 | 0.55 | 1300 | 67 |
| A18 | 0.36 | 720 | 9.0 |
| A19 | 0.39 | 370 | 4.6 |
| A20 | 0.25 | 850 | 17 |
| A21 | 0.34 | 680 | 7.2 |
| A22 | 0.98 | 830 | 25 |
| A23 | 1.0 | 820 | 32 |
| A24 | 0.30 | 1400 | 15 |
| A25 | 1.1 | 2300 | 48 |
| A26 | 0.23 | 4600 | 6.4 |
| A27 | 0.36 | 910 | 2.4 |
| A28 | 0.56 | 3600 | 4.4 |
| A29 | 0.95 | 12000 | 54 |
| A30 | 0.57 | 2700 | 43 |
| A31 | 0.71 | 1900 | 5.0 |
| A32 | 0.62 | 4400 | 3.0 |
| A33 | 0.45 | 1000 | 1.7 |
| A34 | 3.4 | 3600 | 24 |
| A35 | 9.8 | 3800 | 600 |
| A36 | 0.94 | 1800 | 18 |
| A37 | 1.1 | 4100 | 6.6 |
| A38 | 5.2 | 4000 | 20 |
| A39 | 2.5 | 1200 | 21 |
| A40 | 0.74 | 2300 | 4.3 |
| A41 | 0.29 | 480 | 1.9 |
| A42 | 0.77 | 2500 | 9.8 |
| A43 | 0.42 | 1200 | 5.8 |
| A44 | 0.48 | 3400 | 2.6 |
| A45 | 1.6 | 10000 | 8.4 |
| A46 | 0.76 | 1800 | 7.6 |
| A47 | 0.74 | 4100 | 15 |
| A48 | 2.0 | 11000 | 22 |
| A49 | 2.9 | 1800 | 45 |
| A50 | 6.4 | 7100 | 63 |
| A51 | 3.1 | 5500 | 13 |
| A52 | 0.70 | 2200 | 4.9 |
| A53 | 2.0 | >31250 | 11 |
| A54 | 1.6 | 29000 | 8.4 |
| A55 | 2.2 | >31250 | 33 |
| A56 | 1.2 | 19000 | 19 |
| A57 | 2.0 | 25000 | 14 |
| A58 | 1.3 | 14000 | 12 |
| A59 | 3.3 | >31250 | 93 |
| A60 | 2.3 | 12000 | 52 |
| A61 | 6.9 | >31250 | 62 |
| A62 | 4.9 | >31250 | 22 |
| A63 | 2.4 | >31250 | 12 |
| A64 | 5.5 | >31250 | 89 |
| A65 | 3.3 | 21000 | 50 |
| A66 | 3.3 | 19000 | 25 |
| A67 | 1.9 | 19000 | 14 |
| A68 | 5.0 | 2300 | 33 |
| A69 | 1.8 | 13000 | 16 |
| A70 | 3.4 | 38000 | 33 |
| A71 | 3.2 | 15000 | 43 |
| A72 | 1.8 | 9300 | 28 |
| A73 | 2.2 | 21000 | 37 |
| A74 | 7.8 | 7400 | 50 |
| A75 | 4.0 | 32000 | 16 |
| A76 | 2.0 | 25000 | 14 |
| A77 | 3.6 | 7100 | 25 |

As a result of comparison between the results of Test Example (1) and the results of Test Example (2), it was found that the compounds of the present invention have selectivity with which the compounds have low effect on α4β1 while having high effect on α4β7. Having such a selectivity that a compound has low effect on α4β1 and high effect on α4β7 as mentioned above, the compound can greatly inhibit the action on α4β7, which is expressed specifically in the intestinal tract, while producing a small action on α4β1 that inhibits infiltration of lymphocytes circulating through the whole body, and therefore has an advantage in that the compound may possibly provide efficient treatment on diseases to be treated.

TEST EXAMPLE 4

(4) Mouse MAdCAM-1/α4β7 Integrin Binding Inhibitory Activity Evaluation Test in Whole Human Blood Each test substance was measured in terms of the binding inhibitory activity of T cell α4β7 integrin and MAdCAM-1 in human whole blood. Blood samples were obtained from healthy volunteers' blood donation.

A 4 mM $MnCl_2$ solution and each of dilutions of various test substances were added to human whole blood, followed by incubation for 10 minutes. Recombinant mouse MAdCAM-1/Fc (R&D Systems, Inc.) at 10 µg/mL was added to the resultant, and each test sample taken in a total amount of 50 µL was incubated for 30 minutes. Then, 950 µL of Lyse/Fix (BD Biosciences) was added to allow hemolysis and fixation to proceed at 37° C. for 10 minutes. After centrifugation for 5 minutes, the supernatant was removed and 600 µL of a RPMI-1640 medium supplemented with 10% inactivated fetal bovine serum (hereinafter referred to as the medium) was added, followed by centrifugation for 5 minutes, removal of the supernatant, and then washing. After the test sample was washed again with the medium, Rat Anti-Mouse MAdCAM-1 antibody (Southern Biotech) at 0.625 µg/mL was added, followed by incubation for 30 minutes or more. After the test sample was washed with the medium, 50 µg/mL Goat Anti-Rat IgG (H+L) Antibody, FITC (Life Technologies) was added, followed by incubation for 30 minutes or more. After the test sample was washed with the medium, 10 µg/mL PE Rat Anti-Mouse CD4 (BD Pharmigen) was added, followed by incubation for 30 minutes or more. After the test sample was washed with the medium, a ratio of MAdCAM-1 positive cells to CD4 positive cells was measured by using flow cytometry.

From independent test results using different blood samples of two to three persons, a MAdCAM-1 binding inhibiting rate of each test substance at each of various concentrations was obtained under the setting in which, among wells containing no test substances, a well containing no ligand was scored at 100% inhibition and a well containing ligand was scored at 0% inhibition, and then a concentration $IC_{50}$ which brought about 50% binding inhibition was calculated. The obtained results are shown in Table 4.

TABLE 4

| Compound No. | α 4β7 Inhibitory Activity in Whole Human Blood IC50 (nM) |
|---|---|
| A1 | 3.9 |
| A8 | 1.3 |

TABLE 4-continued

| Compound No. | α 4β7 Inhibitory Activity in Whole Human Blood IC50 (nM) |
|---|---|
| A26 | 2.4 |
| A28 | 1.2 |
| A32 | 1.9 |
| A37 | 3.3 |
| A40 | 2.3 |
| A42 | 2.2 |
| A44 | 1.0 |
| A45 | 1.3 |
| A46 | 1.6 |
| A53 | 1.8 |
| A54 | 1.3 |

TEST EXAMPLE 5

A mouse portal vein migration concentration of each test substance was measured and oral absorbability thereof was evaluated.

The test substance was dissolved or homogeneously suspended in a 0.5% (w/v) methylcellulose aqueous solution, and an oral cassette dosing of three compounds (3 mg/10 mL/kg) was conducted on female mice (BALB/cAnNCrl-Crlj, 7 to 9 weeks old) by using a stomach probe. About 30 minutes after administration, laparotomy was performed under isoflurane anesthesia, and about 0.2 mL of blood was collected from the portal vein using a syringe treated with DDVP (esterase inhibitor) and sodium heparin, and was stored on ice.

The collected blood was centrifuged at 18,000 g×3 minutes using a refrigerated centrifuge to obtain a plasma sample, the test substance was extracted with acetonitrile, and the plasma concentration was determined by LC/MS/MS.

The plasma concentration was the total concentration of the test substance and its active metabolite. The calculated plasma concentrations are shown in Table 5.

TABLE 5

| Compound | Plasma Concentration (nM) |
|---|---|
| P1 | 2.1 |
| P2 | 1.2 |
| P14 | 1.4 |
| P16 | 1.1 |
| P18 | 0.76 |
| P20 | 0.39 |
| P31 | 0.37 |
| P32 | 0.4 |
| P33 | 0.36 |
| P34 | 1.8 |
| P37 | 1.1 |
| P38 | 0.61 |
| P39 | 1.2 |
| P40 | 0.76 |
| P41 | 0.44 |
| P42 | 1.2 |

TEST EXAMPLE 6

Human MAdCAM-1/α4β7 Integrin Binding Inhibitory Activity Evaluation Test in Whole Human Blood Each test substance was measured in terms of the inhibitory activity of binding of T cell α4β7 integrin and MAdCAM-1 in human whole blood. Blood samples were obtained from healthy volunteers' blood donation.

A 4 mM $MnCl_2$ solution and each of dilutions of various test substances were added to human whole blood, followed by incubation for 10 minutes. Recombinant human MAdCAM-1/Fc (R&D Systems) at 10 μg/mL was added, and each test sample taken in a total amount of 50 μL was incubated for 30 minutes. Then, 950 μL of Lyse/Fix (BD Biosciences) was added to allow hemolysis and fixation to proceed at 37° C. for 10 minutes. After centrifugation for 5 minutes, the supernatant was removed and 600 μL of a RPMI-1640 medium supplemented with 10% inactivated fetal bovine serum (hereinafter referred to as the medium) was added, followed by centrifugation for 5 minutes, removal of the supernatant, and then washing. The test sample was washed again with the medium, and then 2.5 μg/mL Mouse Anti-MAdCAM-1 antibody (Invitrogen) was added, followed by incubation for 30 minutes or more. After the test sample was washed with the medium, 3.4 μg/mL Goat Anti-Mouse IgG H&L, FITC (Abcam) was added, followed by incubation for 30 minutes or more. After the test sample was washed with the medium, 0.15 μg/mL PE Rat Anti-Mouse CD4 (BD Pharmigen) was added, followed by incubation for 30 minutes or more. After the test sample was washed with the medium, a ratio of MAdCAM-1 positive cells to CD4 positive cells was measured by using flow cytometry.

From independent test results using different blood samples of two to three persons, a MAdCAM-1 binding inhibiting rate of each test substance at each of various concentrations was obtained under the setting in which, among wells containing no test substances, a well containing no ligand was scored at 100% inhibition and a well containing ligand was scored at 0% inhibition, and then a concentration $IC_{50}$ which brought about 50% binding inhibition was calculated. The obtained results are shown in Table 6.

TABLE 6

| Compound No. | α 4β7 Inhibitory Activity in Whole Human Blood IC50 (nM) |
|---|---|
| A45 | 1.5 |
| A53 | 2.9 |
| A54 | 2.0 |
| A56 | 5.4 |
| A58 | 5.1 |
| A63 | 4.8 |
| A67 | 5.7 |
| A75 | 5.6 |

TEST EXAMPLE 7

As a method for preparing mouse colitis model induced by transfer of IL-10$^{-/-}$ cells, used was the method described in J Crohns Colitis. 2013 December; 7 (11): e533-42.

Each test substance was suspended in a 0.5% methylcellulose aqueous solution to be contained at 30, 10, 3, or 1 mg/mL, and was orally administered with Terumo syringe (1 mL) and a metal probe for mouse in a dose of 10 ml per kilogram of animal body weight. The administration was performed three times per day for 14 days.

An intestinal tract weight as a medicinal effect indicator was measured by the following method. On the final necropsy day, the large intestine from the anus to just before the cecum was taken out, the content in the intestinal tract was washed away with physiological saline, the moisture was lightly removed, and the weight of the large intestine was measured. The inhibitory rate (%) in each of compound administered groups was figured out based on the average value of intestinal tract weights per group under the setting in which a colitis onset group was scored at 0% and a normal group was scored at 100%. The evaluation results of the inflammation inhibiting action using this evaluation system are presented in Table 7. All the compounds demonstrated a dose-dependent inhibitory effect.

TABLE 7

| Compound No. | Dose [mg/kg] | Inhibitory Rate (%) |
|---|---|---|
| P2 | 10 | 24.6 |
|  | 100 | 52.2 |
| P52 | 30 | 39.9 |
|  | 300 | 42.8 |
| P59 | 30 | 46.7 |
|  | 300 | 58.6 |
| P69 | 30 | 36.1 |
|  | 300 | 51.1 |
| P73 | 30 | 21.9 |
|  | 300 | 38.8 |
| P74 | 30 | 12.5 |
|  | 300 | 47.1 |
| P97 | 30 | 17.5 |
|  | 300 | 43.6 |

The invention claimed is:

1. A compound represented by the formula (I):

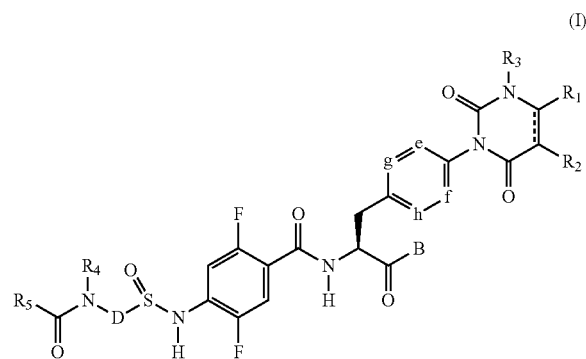

(I)

or a pharmaceutically acceptable salt thereof,
wherein:
  ═══ represents a single bond or double bond;
  e, f, g and h independently represent C—H or nitrogen;
  B represents hydroxy, $OC_{1-10}$ alkyl, O-heterocyclyl, O-cilexetilyl or O-medoxomilyl;
  D represents phenyl or heteroaryl, each optionally substituted with one or more substituents independently selected from the group consisting of halogen, lower alkyl, lower alkoxy and hydroxy;
  $R_1$ and $R_2$ each independently represent hydrogen, halogen, lower alkyl, lower alkenyl, lower alkoxy, lower alkoxy lower alkyl, halogeno lower alkyl, hydroxy or hydroxy lower alkyl; or
  $R_1$ and $R_2$, together with the carbon atoms to which they are attached, may form a fused phenyl, a fused $C_{4-7}$ cycloalkyl, a fused heteroaryl or a fused heterocyclyl, each optionally substituted with one or more substituents independently selected from the group consisting of lower alkyl, lower alkoxy, hydroxy lower alkyl, amino, lower alkylamino and lower alkylamino lower alkyl;
  $R_3$ represents lower alkyl;
  $R_4$ represents hydrogen or lower alkyl; and
  $R_5$ represents lower alkylamino or a group selected from the group consisting of lower alkyl, lower alkenyl, lower alkynyl, phenyl, heteroaryl and heterocyclyl, wherein the lower alkyl, lower alkenyl, lower alkynyl, phenyl, heteroaryl and heterocyclyl are each optionally substituted with one or more substituents independently selected from the group consisting of halogen, cyano, hydroxy, lower alkyl, lower alkoxy, trifluoromethyl, phenyl and heterocyclyl; or
  $R_4$ and $R_5$, together with the carbon atom and nitrogen atom to which they are attached, may form a fused heteroaryl or a fused heterocyclyl, each optionally substituted with one or more substituents selected from the group consisting of lower alkyl, lower alkoxy, hydroxy and heterocyclyl.

2. The compound according to claim 1, or a pharmaceutically acceptable salt thereof, wherein ═══ represents a double bond.

3. The compound according to claim 1, or a pharmaceutically acceptable salt thereof, wherein:
  e represents nitrogen; and
  f, g and h independently represent C—H.

4. The compound according to claim 1, or a pharmaceutically acceptable salt thereof, wherein B represents hydroxy or $OC_{1-6}$ alkyl.

5. The compound according to claim 1, or a pharmaceutically acceptable salt thereof, wherein B represents hydroxy, methoxy, ethoxy, isopropoxy or isobutoxy.

6. The compound according to claim 1, or a pharmaceutically acceptable salt thereof, wherein D represents phenyl, pyridinyl or thiophenyl, each optionally substituted.

7. The compound according to claim 1, or a pharmaceutically acceptable salt thereof, wherein $R_1$ and $R_2$ each independently represent hydrogen, lower alkyl or hydroxy lower alkyl.

8. The compound according to claim 1, or a pharmaceutically acceptable salt thereof, wherein:
  $R_1$ and $R_2$ each independently represent hydrogen, lower alkyl or hydroxy lower alkyl; or
  $R_1$ and $R_2$, together with the carbon atoms to which they are attached, may form a fused $C_{4-7}$ cycloalkyl, a fused heteroaryl or a fused heterocyclyl, each optionally substituted with one or more substituents independently selected from the group consisting of lower alkyl and lower alkoxy.

9. The compound according to claim 1, or a pharmaceutically acceptable salt thereof, wherein $R_1$ and $R_2$, together with the carbon atoms to which they are attached, form a fused phenyl, a fused C<sub>4-7</sub> cycloalkyl, a fused heteroaryl or a fused heterocyclyl, each optionally substituted.

10. The compound according to claim 1, or a pharmaceutically acceptable salt thereof, wherein R<sub>4</sub> represents hydrogen.

11. The compound according to claim 1, or a pharmaceutically acceptable salt thereof, wherein R<sub>5</sub> represents lower alkylamino or a group selected from the group consisting of lower alkyl and heterocyclyl, wherein the lower alkyl and heterocyclyl are each optionally substituted with one or more substituents independently selected from the group consisting of halogen, cyano, hydroxy, lower alkoxy, trifluoromethyl and phenyl.

12. The compound according to claim 1, or a pharmaceutically acceptable salt thereof, wherein:
   R<sub>1</sub> and R<sub>2</sub> each independently represent hydrogen, halogen, lower alkyl, lower alkenyl, lower alkoxy, lower alkoxy lower alkyl, hydroxy or hydroxy lower alkyl; or
   R<sub>1</sub> and R<sub>2</sub>, together with the carbon atoms to which they are attached, may form a fused phenyl, a fused C<sub>4-7</sub> cycloalkyl, a fused heteroaryl or a fused heterocyclyl, each optionally substituted; and
   R<sub>5</sub> represents lower alkylamino or a group selected from the group consisting of lower alkyl, lower alkenyl, phenyl, heteroaryl and heterocyclyl, wherein the lower alkyl, lower alkenyl, phenyl, heteroaryl and heterocyclyl are each optionally substituted.

13. The compound according to claim 1, or a pharmaceutically acceptable salt thereof, wherein:
   D represents 1,4-phenylene, optionally substituted with a halogen; or
   D represents

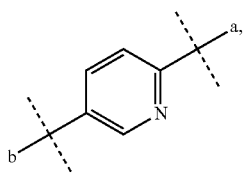

wherein a represents a bonding position with S, b represents a bonding position with N and e represents a nitrogen; or
   D represents

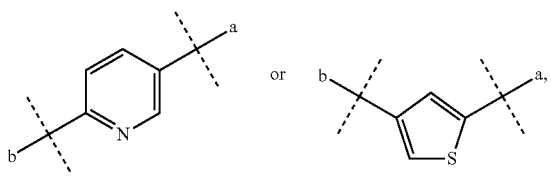

wherein a represents a bonding position with S and b represents a bonding position with N;
   R<sub>1</sub> and R<sub>2</sub> each independently represent hydrogen, lower alkyl, lower alkoxy or hydroxy lower alkyl; or
   R<sub>1</sub> and R<sub>2</sub>, together with the carbon atoms to which they are attached, may form a fused C<sub>4-7</sub> cycloalkyl, a fused heteroaryl or a fused heterocyclyl, each optionally substituted with a lower alkyl;
   R<sub>4</sub> represents hydrogen; and
   R<sub>5</sub> represents C<sub>2-5</sub> alkyl, optionally substituted with a substituent selected from the group consisting of halogen, hydroxy, lower alkoxy and phenyl; or
   R<sub>5</sub> represents heteroaryl or heterocyclyl containing at least one O ring heteroatom;
   with the provisos that (i) when R<sub>5</sub> represents heterocyclyl containing at least one O ring heteroatom, R<sub>1</sub> and R<sub>2</sub>, together with the carbon atoms to which they are attached, form a fused heteroaryl; and (ii) when R<sub>5</sub> represents C<sub>2-5</sub> alkyl substituted with hydroxy, R<sub>5</sub> represents —C(CH<sub>3</sub>)<sub>2</sub>CH<sub>2</sub>OH.

14. The compound according to claim 1, wherein the compound is represented by the following formula:

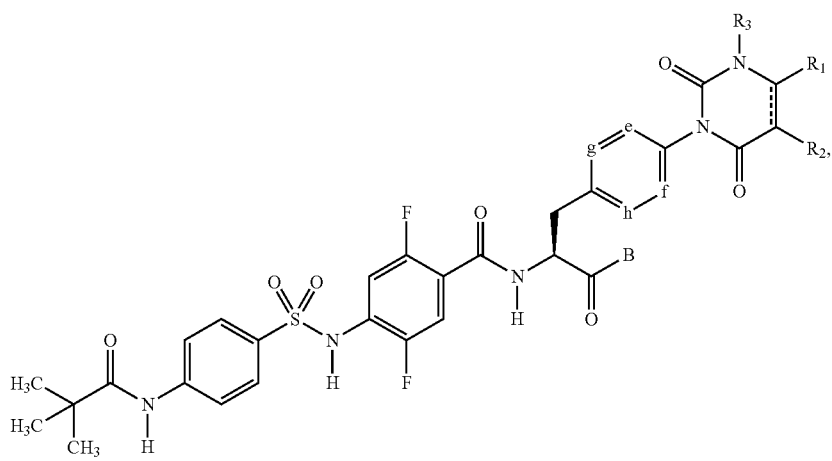

or a pharmaceutically acceptable salt thereof.

15. The compound according to claim 14, wherein the compound is represented by the following formula:
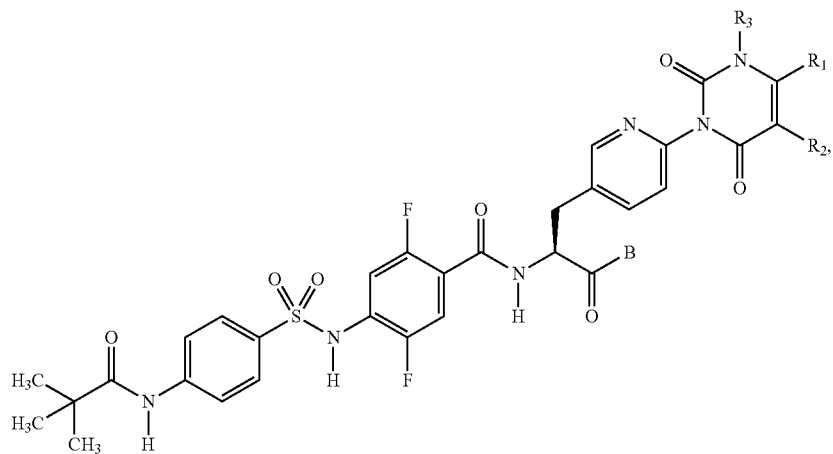
or a pharmaceutically acceptable salt thereof.
16. The compound according to claim 14, wherein the compound is represented by any one of the following formulas selected from the group consisting of:
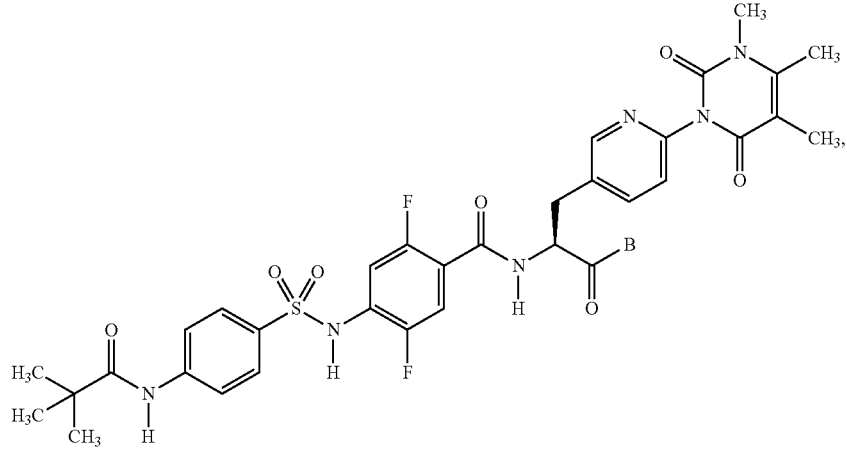
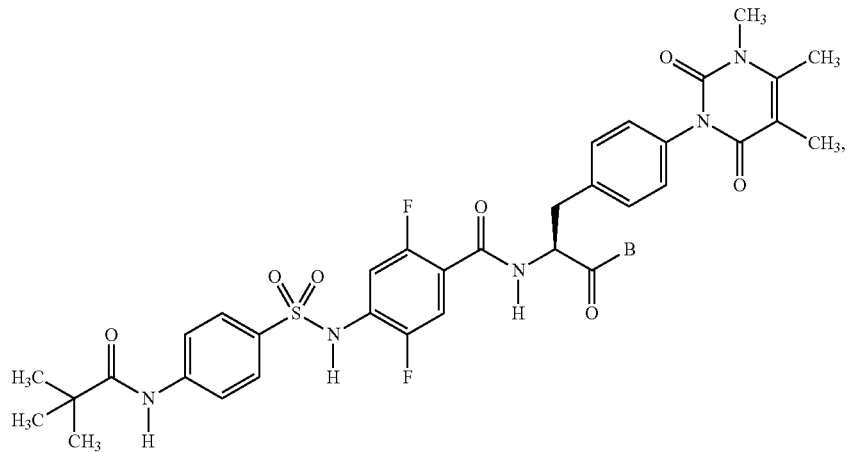

-continued
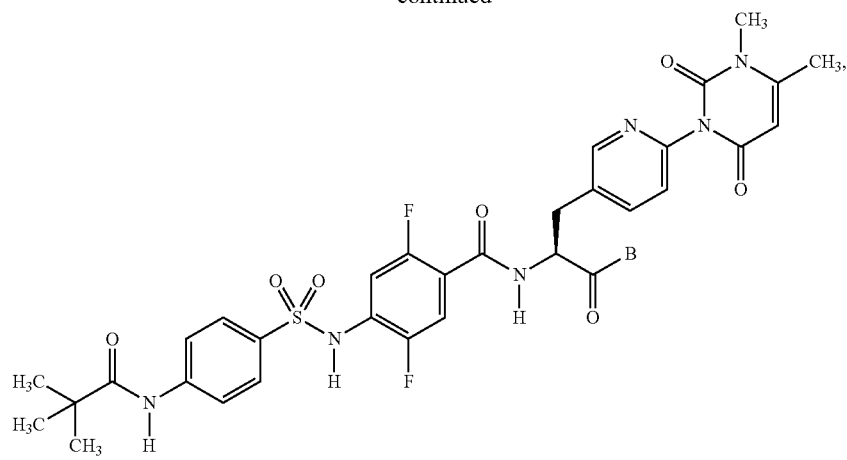
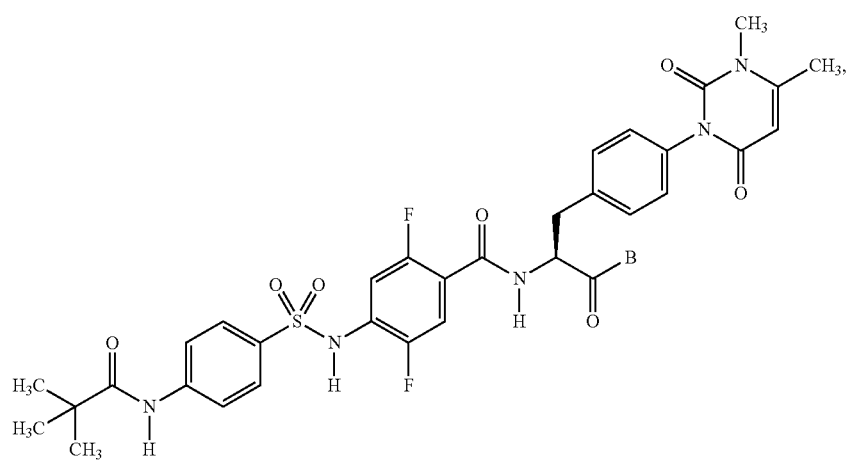
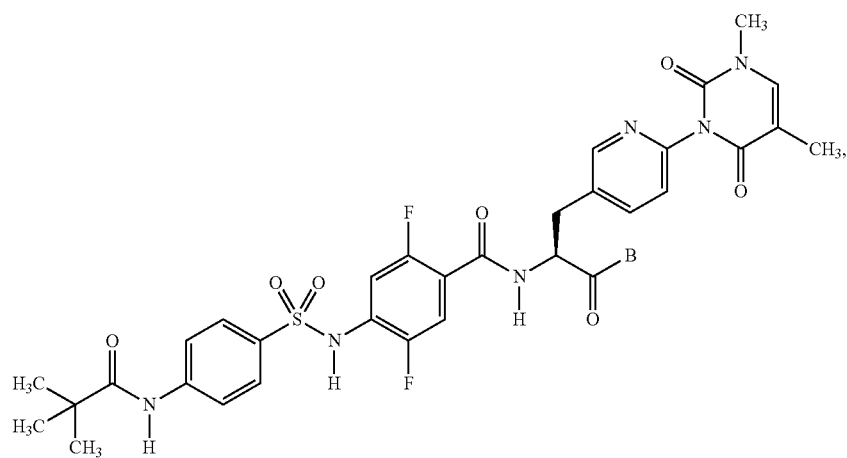

-continued
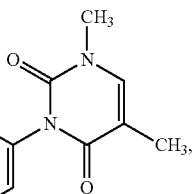
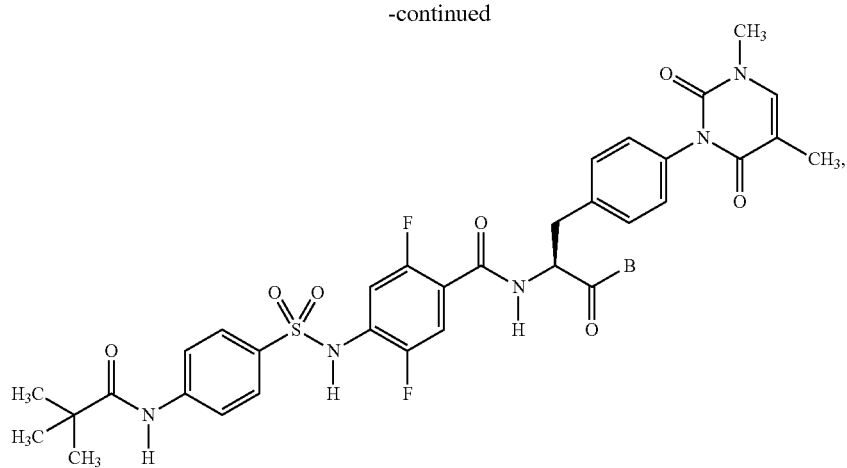
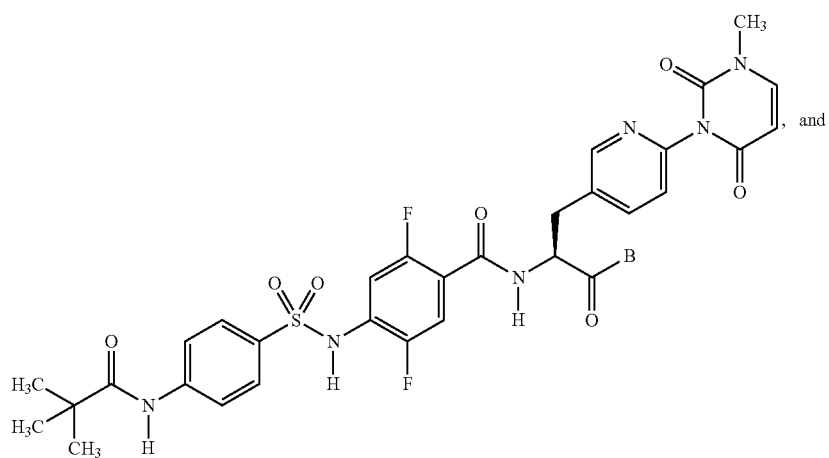
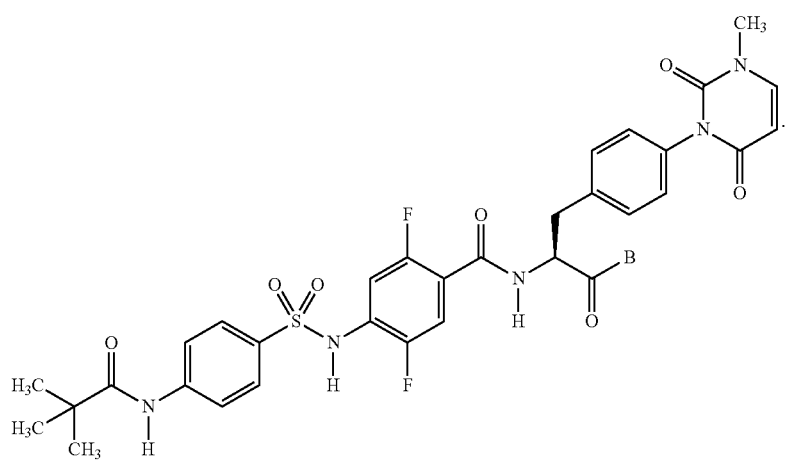
or a pharmaceutically acceptable salt thereof.

17. The compound according to claim 16, wherein the compound is represented by any one of the following formulas selected from the group consisting of:

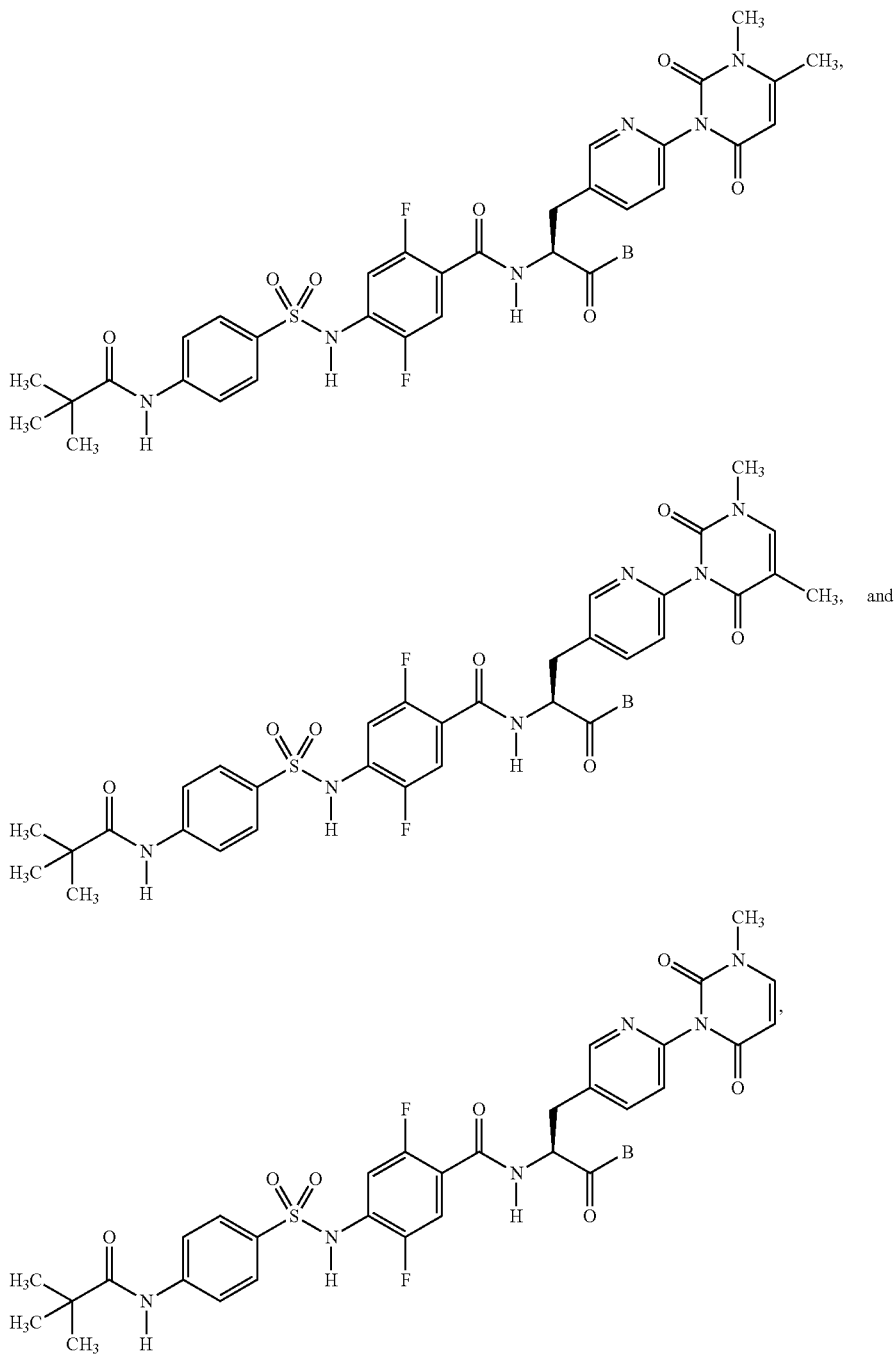

or a pharmaceutically acceptable salt thereof.

18. A pharmaceutical composition comprising a compound according to claim 1, or a pharmaceutically acceptable salt thereof, and a pharmaceutically acceptable carrier.

19. A method for inhibiting α4β7 integrin activity in a subject, comprising administering to a subject in need thereof a therapeutically effective amount of a compound according to claim 1, or a pharmaceutically acceptable salt thereof.

20. The method according to claim 19, wherein the subject has an inflammatory disease in which an α4β7 integrin-dependent adhesion process is involved selected from the group consisting of rheumatoid arthritis, inflammatory bowel disease, systemic lupus erythematosus, multiple sclerosis, Sjögren's syndrome, asthma, psoriasis, allergy, diabetes, cardiovascular disease, arteriosclerosis, restenosis, tumor growth, tumor metastasis, transplant rejection and human immunodeficiency virus infection.

* * * * *

UNITED STATES PATENT AND TRADEMARK OFFICE
CERTIFICATE OF CORRECTION

PATENT NO. : 10,562,898 B2
APPLICATION NO. : 16/075415
DATED : February 18, 2020
INVENTOR(S) : Munetaka Tokumasu et al.

Page 1 of 1

It is certified that error appears in the above-identified patent and that said Letters Patent is hereby corrected as shown below:

In the Claims

In Column 275, Claim 1, beginning at Line 35, please delete the following formula (I):

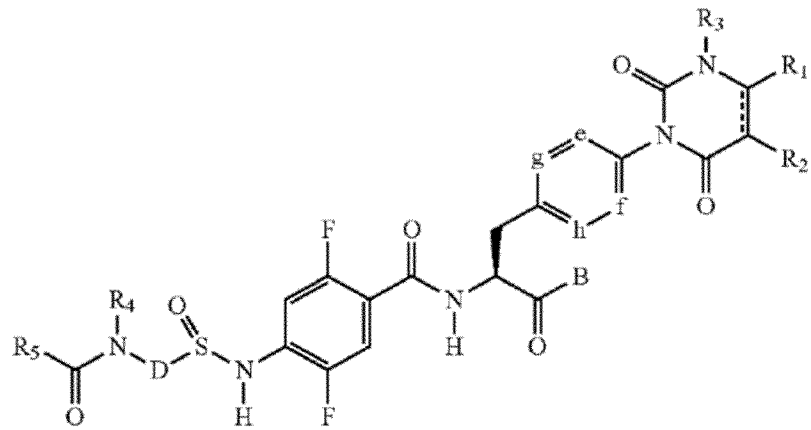

And insert the following formula (I) therefor:

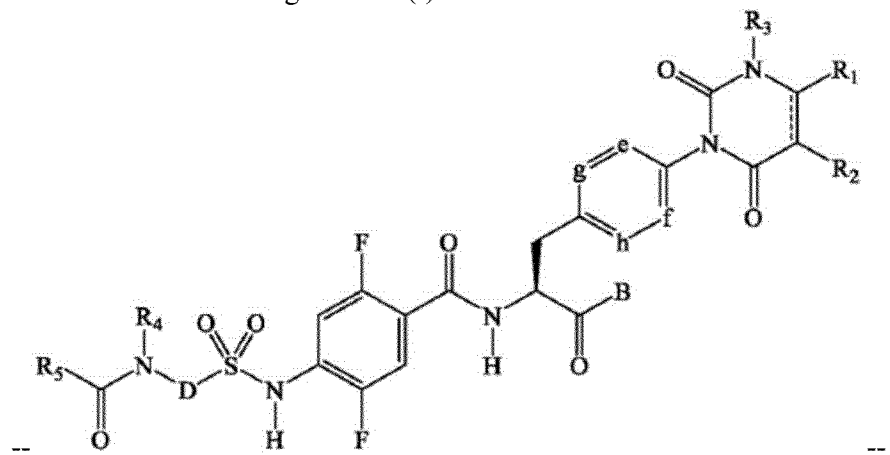

Signed and Sealed this
Twenty-ninth Day of October, 2024

Katherine Kelly Vidal
*Director of the United States Patent and Trademark Office*